(12) United States Patent
Rajopadhye et al.

(10) Patent No.: US 7,052,673 B2
(45) Date of Patent: May 30, 2006

(54) PHARMACEUTICALS FOR THE IMAGING OF ANGIOGENIC DISORDERS

(75) Inventors: Milind Rajopadhye, Westford, MA (US); D. Scott Edwards, Burlington, MA (US); John A. Barrett, Groton, MA (US); Alan P. Carpenter, Jr., Carlisle, MA (US); Thomas D Harris, Samel, NH (US); Stuart D Heminway, Wellesley, MA (US); Shuang Liu, West Lafayette, IN (US); Singh R Prahlad, Arlington, MA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 134 days.

(21) Appl. No.: 10/622,246

(22) Filed: Jul. 18, 2003

(65) Prior Publication Data

US 2006/0003926 A1  Jan. 5, 2006

Related U.S. Application Data

(60) Division of application No. 10/342,081, filed on Jan. 14, 2003, now Pat. No. 6,800,273, which is a division of application No. 09/599,295, filed on Jun. 21, 2000, now Pat. No. 6,537,520, which is a continuation-in-part of application No. 09/281,474, filed on Mar. 30, 1999.

(60) Provisional application No. 60/080,150, filed on Mar. 31, 1998, provisional application No. 60/112,715, filed on Dec. 18, 1998.

(51) Int. Cl.
 *A61K 51/00* (2006.01)
 *A61M 36/14* (2006.01)

(52) U.S. Cl. .................. 424/1.69; 424/1.11; 424/1.65; 206/223; 206/569; 206/570; 534/14; 514/14

(58) Field of Classification Search ............... 424/1.11, 424/1.65, 1.69, 9.1; 206/223, 569, 570; 534/7, 534/10–16; 514/2; 530/300
See application file for complete search history.

(56) References Cited

U.S. PATENT DOCUMENTS

| | | |
|---|---|---|
| 4,248,802 A | 2/1981 | Kuntz |
| 4,472,509 A | 9/1984 | Gansow et al. |
| 4,536,387 A | 8/1985 | Sakamoto et al. |
| 4,859,777 A | 8/1989 | Toner |
| 4,988,827 A | 1/1991 | Bergstein et al. |
| 5,021,236 A | 6/1991 | Gries et al. |
| 5,064,956 A | 11/1991 | Kruper et al. |
| 5,087,440 A | 2/1992 | Cacheris et al. |
| 5,155,215 A | 10/1992 | Ranney |
| 5,281,704 A | 1/1994 | Love et al. |
| 5,342,757 A | 8/1994 | Garin-Chesa et al. |
| 5,350,837 A | 9/1994 | Bridger et al. |
| 5,376,356 A | 12/1994 | Morgan, Jr. |
| 5,382,654 A | 1/1995 | Lyle et al. |
| 5,395,609 A | 3/1995 | Stuttle |
| 5,403,713 A | 4/1995 | Bevilacqua et al. |
| 5,412,148 A | 5/1995 | Keana |
| 5,417,959 A | 5/1995 | Wallace |
| 5,520,904 A | 5/1996 | Nosco et al. |
| 5,556,939 A | 9/1996 | Flanagan et al. |
| 5,567,411 A | 10/1996 | Keana et al. |
| 5,595,723 A | 1/1997 | Quay .......................... 424/9.5 |
| 5,650,134 A | 7/1997 | Albert et al. |
| 5,659,013 A | 8/1997 | Senger et al. |
| 5,659,041 A | 8/1997 | Pollak et al. |
| 5,660,827 A | 8/1997 | Thorpe et al. |
| 5,679,810 A | 10/1997 | Love et al. |
| 5,739,789 A | 4/1998 | Kronhamn ................... 342/465 |
| 5,744,120 A | 4/1998 | Edwards .................... 424/1.69 |
| 5,750,088 A | 5/1998 | Sworin et al. ............. 424/1.69 |
| 5,760,028 A | 6/1998 | Jadhav et al. |
| 5,760,191 A | 6/1998 | Snow et al. |
| 5,766,591 A | 6/1998 | Brooks et al. |
| 5,767,071 A | 6/1998 | Palladino et al. ............. 514/11 |
| 5,770,565 A | 6/1998 | Cheng et al. .................. 514/11 |
| 5,776,427 A | 7/1998 | Thorpe et al. |
| 5,780,426 A | 7/1998 | Palladino et al. .............. 514/9 |
| 5,801,228 A | 9/1998 | Hollister et al. |
| 5,804,161 A | 9/1998 | Long et al. |
| 5,855,866 A | 1/1999 | Thorpe et al. |
| 5,863,538 A | 1/1999 | Thorpe et al. |
| 6,040,311 A | 3/2000 | Duggan et al. |
| 6,051,207 A | 4/2000 | Klaveness et al. |

(Continued)

FOREIGN PATENT DOCUMENTS

AU    5314694    7/1994

(Continued)

OTHER PUBLICATIONS

Ashton, et al., *J. Org. Chem.*, 1996, 61, 903-908.

(Continued)

*Primary Examiner*—Dameron L. Jones
(74) *Attorney, Agent, or Firm*—Woodcock Washburn LLP

(57) ABSTRACT

The present invention describes novel compounds of the formula:

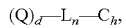

useful for the diagnosis and treatment of cancer, methods of imaging tumors in a patient, and methods of treating cancer in a patient. The present invention also provides novel compounds useful for monitoring therapeutic angiogenesis treatment and destruction of new angiogenic vasculature. The pharmaceuticals are comprised of a targeting moiety that binds to a receptor that is upregulated during angiogenesis, an optional linking group, and a therapeutically effective radioisotope or diagnostically effective imageable moiety. The imageable moiety is a gamma ray or positron emitting radioisotope, a magnetic resonance imaging contrast agent, an X-ray contrast agent, or an ultrasound contrast agent.

22 Claims, No Drawings

U.S. PATENT DOCUMENTS

| | | | |
|---|---|---|---|
| 6,051,230 A | 4/2000 | Thorpe et al. | |
| 6,056,973 A | 5/2000 | Allen et al. | |
| 6,143,274 A | 11/2000 | Tweedle et al. | |
| 6,342,219 B1 | 1/2002 | Thorpe et al. | 424/145.1 |
| 6,537,520 B1* | 3/2003 | Rajopadhye et al. | 424/1.69 |
| 6,800,273 B1* | 10/2004 | Rajopadhye et al. | 424/1.69 |
| 2002/0132774 A1 | 9/2002 | Klagsbrun et al. | 514/12 |
| 2002/0147136 A1 | 10/2002 | Von Wronski et al. | 514/8 |

FOREIGN PATENT DOCUMENTS

| | | |
|---|---|---|
| CA | 2 113 245 | 6/1988 |
| CA | 2 039 259 | 10/1991 |
| CA | 2 156 620 | 10/1994 |
| CA | 2 232 315 | 4/1997 |
| DE | 4 311 023 | 10/1994 |
| DE | 19 536 781 | 3/1997 |
| DE | 19 536 785 | 3/1997 |
| DE | 19 725 368 | 12/1998 |
| EP | 0 107 734 | 7/1987 |
| EP | 0 359 347 | 3/1990 |
| EP | 0 436 005 | 10/1991 |
| EP | 0 606 683 | 7/1994 |
| EP | 0 727 225 | 8/1996 |
| WO | WO 81/01145 | 4/1981 |
| WO | WO 90/93801 | 4/1990 |
| WO | WO 90/05539 | 5/1990 |
| WO | WO 09/12585 | 11/1990 |
| WO | WO 90/13300 | 11/1990 |
| WO | WO 91/01144 | 2/1991 |
| WO | WO 91/14460 | 10/1991 |
| WO | WO 91/15244 | 10/1991 |
| WO | WO 92/12729 | 8/1992 |
| WO | WO 92/17215 | 10/1992 |
| WO | WO 92/19646 | 11/1992 |
| WO | WO 93/08210 | 4/1993 |
| WO | WO 93/17715 | 9/1993 |
| WO | WO 93/23074 | 11/1993 |
| WO | WO 94/05328 | 4/1994 |
| WO | WO 94/11499 | 5/1994 |
| WO | WO 94/22496 | 10/1994 |
| WO | WO 94/22497 | 10/1994 |
| WO | WO 94/22910 | 10/1994 |
| WO | WO 95/25593 | 9/1995 |
| WO | WO 96/00574 | 1/1996 |
| WO | WO 96/01653 | 1/1996 |
| WO | WO 96/31243 | 10/1996 |
| WO | WO 96/41803 | 12/1996 |
| WO | WO 97/08145 | 3/1997 |
| WO | WO 97/16474 | 5/1997 |
| WO | WO 97/18207 | 5/1997 |
| WO | WO 97/23480 | 7/1997 |
| WO | WO 09/14220 | 4/1998 |
| WO | WO 98/16256 | 4/1998 |
| WO | WO 98/47541 | 10/1998 |
| WO | WO 99/06049 | 2/1999 |
| WO | WO 99/13329 | 3/1999 |
| WO | WO 99/40947 | 8/1999 |
| WO | WO 99/58162 | 11/1999 |
| WO | WO 02/04030 | 1/2002 |

OTHER PUBLICATIONS

Bakker, et al., *Life Sci.*, 1991, 49, 1583-1591.
Barcelona, E.S., "Cilengitide/oncolytic angiogenesis inhibitor integrin alphavbeta3, alphabeta5 antagonist," *Drugs of the Future*, 2000, 7(25), 674-678.
Batt, et al., *J. Med. Chem.*, 2000, 43, 41-58.
Bevilacqua, et al., *Proc. Natl. Acad. Sci.*, 1987, 84, 9238-9242.
Bousquet, et al., *Radiology*, 1988, 166, 693.
Brechbiel, M., et al., *Bioconjugate Chem.*, 1991, 2, 187.
Brechbiel, M., et al., *J. chem.. Soc. Perkins Trans.*, 1992, 1, 1175.
Burke, P.A., et al., "Combined modality radioimmunotherapy/promise and peril," *Am. Can. Soc.*, Feb. 15, 2002, Suppl. 4(94), 1320-1331.
Burris, et al., *Clin. Can. Res.*, 1995, 1, 1623-1634.
Burrows, et al., *J. of Controlled Release*, Jan. 1994, 28(1), 195-202.
Burrows, et al., *Cancer Res.*, 1992, 52, 5954-5962.
Burrows, et al., *Proc. Nat. Acad. Sci. USA*, 1993, 90, 8996-9000.
Clauss, et al., *J. of Biological Chem.*, 1990, 265(12), 7078-7083.
DeGrado, et al., *J. Org. Chem.*, 45, 1295-1300.
Denekamp, J., et al., *Br. J. Cancer*, 1982, 45, 136-139.
Denekamp, J., et al., *Br. J. Cancer*, 1982, 46, 711-720.
Denekamp, J., *Acta Radiologica Oncology*, 1984, 23 Fasc. 4, 217-225.
Denekamp, J., *Cancer Meta. Rev.*, 1990, 9, 267-282.
DeNardo, et al., *Cancer Biotherapy & Radiopharm.*, Feb. 2000, 15(1), 71-79.
DiZio, et al., *Bioconjugate Chem.*, 1991, 2, 353-366.
Dvorak, et al., *Cancer Cells*, 1991, 3, 77-85.
Folkman, J., *Nature Medicine*, 1995, 1, 27-31.
Friedlander, et al., *Science*, 1995, 270, 1500-1502.
Ghose, et al., *Meth. Enzymology*, 1983, 93, 280-333.
Hagemeier, H.-H., et al., *Int. J. Cancer*, 1986, 38, 481-488.
Henry, T., et al., *J. Amer. College Cardiology* 1998, 31, 65A.
Horton, et al., *Int. J. Biochem. Cell Biol.*, May 1997, 29(5), 721-725.
Hu, et al., *Oncology Res.*, 1994, 6(7), 321-327.
Hubbrich, et al., *Liebigs Ann. Chem.*, 1979, 776-783.
Kennel, et al., *Nuclear Med. & Biol.*, 1998, 25, 241-246.
Kerr, etal., *Anticancer Res.*, Mar./Apr. 1999, 19(2A), 958-958.
Knowles, et al., *Analytical Biochemistry*, 1987, 160-440-443.
Krenning, et al., *Digestion*, 1996, 57, 57-61.
Krenning, et al., *Eur. J. Nucl. Med.*, 1993, 20, 716-731.
Liu, S., et al., "90Y and 177LU labeling of a dota-conjugated vitorneclin receptor antagonist useful for tumor therapy," *Bioconjugate Chemistry, Am. Chem. Soc.*, Jul. 2001, 4(12), 559-568.
Liu, et al., *Inorg. Chem.*, 1999, 38(6), 1326-1335.
Manning, et al., *Tet Lett.*, 1997, 53, 11937-11952.
Margerstadt, et al., *Magn, Reson. Med.*, 1986, 3, 808.
Molema, et al., *Biochemical pharm.*, 1998, 55, 1939-1945.
Mueller, et al., *Proc. Natl. Acad Sci. USA*, 1992, 89, 11832-11836.
Nucl. Med., Proceeding of the 42nd Annual Meeting, May 1995, 36(5), No. 287, 71P.
Olson, et al., *Int. J. Cancer*, 1997, 73, 865-870.
O'Reilly, et al., *Cell*, 1994, 79, 315-328.
Orlando, et al., *J. of Biological Chem.*, Oct. 1991, 266(29), 19543-19550.
Runge, et al., *Radiology*, 1988, 166, 835.
Seillke, et al., *Drugs*, 1999, 58(3), 391-396.
Sipkins, et al., *Nature Medicine*, May 1998, 4(5), 623-626.
Takeshima, S., et al., *J. Clin. Invest.*, 1994, 93, 662-670.
Thorpe, et al., *Breast Cancer Res. & Treat.*, 1995, 36(2), 237-251.
Van Waes, et al., *Intn'l J. Oncology*, 2000, 16, 1189-1195.
Wellicome, et al., *J. Immunol.*, 1990, 144(7), 2558-2565.
Deshpande, S., et al., *J. Nucl. Med.*, 1990, 31, 473.

O'Reilly, et al., *Cell*, 1997, 88, 277-285.
Senger, et al., *Proc. Natl. Acad. Sci. USA*, 1997, 94, 13612-13617.
Srivatsa, et al., *Cardiovascular Res.*, 1997, 36, 408-428.
Bundgaard, H., "Design and Applications of Prodrugs," Krogsgaard-Larsen, P., et al. (Eds.), *A Textbook of Drug Design and Development*, 1991, 113-191.
Bundgard, H., "(C) Means to enhance penetration; (1) Prodrugs as a means to improve the delivery of peptide drugs," Advanced Drug Delivery Reviews, 1992, 8, 1-38.
Burrows, F.J., et al., "Up-regulation of endoglin on vascular endothelial cells in human solid tumors: implications for diagnosis and therapy," *Clin. Can. Res.*, 1995, 1, 1623-1634.
Chen, A.Y., et al., "DNA topoisomeerase I-targeting drugs as radiation sensitizers," *Oncology.*, Oct. 1999, 13(10) *Suppl.* 5, 39-46.
Cheung, S.T., et al., "N-methylamino acids in peptide synthesis. V. The synthesis of N-tert-butyloxycarbonyl,N-methylamino acids by N-methylation," *Ca. J. Chem.*, 1977, 55, 906-910.
Chou, T.-C., et al., "Quantitative analysis of dose-effect relationships: the combines effects of multiple drugs or enzyme inhibitors," *Adv. Enzyme Regul.*, 1984, 22, 27-55.
Choy, H., "Taxanes in combined-modality therapy for solid tumors," *Oncology*, Oct. 1999, 13(10) *Suppl.* 5, 23-38.
Corbett, J.W., et al., "Solid-phase synthesis of a selective $\alpha_v\beta_3$ integrin antagonist library," *Biorg. Med. Chem. Lett.*, 1997. 7(11), 1271-1376.
Cosic, I., et al., "In vitro inhibition of the actions of basic FGF by a novel 16 amino acid peptide," *Mol. And Cell. Biochem.*, 1994, 130, 1-9.
Dougher, A.M., et al., "identification of a heparin binding peptide on the extracellular domain of the KDR VEGF receptor," *Growth Factors*, 1997, 14, 257-268.
Friedlander, M., et al., "Definition of two angiogenic pathways by distrinct $\alpha_v$ integrins," *Science*, 1995, 270, 1500-1502.
Friedinger, R.M., et al., "Synthesis of 9-fluorenylmethyloxycarbonyl-protected N-alkyl amino acids by reduction of oxazolidinones," *J. Org. Chem.*, 1983, 48, 77-81.
Gho, Y.S., et al., "Development of antiangiogenin peptide using a phage-displayed peptide library," *Cancer Res.*, Sep. 1, 1997, 57, 3733-3740.
Haubner, R., et al., "Stereoisomeric peptide libraries and peptidomimetics for designing selective inhibitors of the $\alpha_v\beta_3$ integrin for a new cancer therapy," *Angew. Chem. Int. Ed. Engl.*, 1997, 36, 1374-1389.
Herscher, L.L., et al., "Principles of chemoradiation: theoretical and practical considerations," *Oncology.*, Oct. 1999, 13(10) *Suppl.* 5, 11-22.

Kakeya, N., et al., "Studies on prodrugs of cephalosporins. I. Synthesis and biological properties of glycyloxybenzoyloxymethyl and glycylaminobenzoyloxymethyl esters of 7β-[2-(2-aminothiazol-4-yl)-(Z)-2methoxyiminoscetamido]3-methyl-3-cephem-4-carboxylic acid," *Chem. Pharm. Bull.*, 1984, 32, 692-698.
Merrifield, R.B., "Solid phase peptide synthesis. I. The synthesis of a tetrapeptide," *J. Am. Chem. Soc.*, 1963, 85, 2149-2154.
Nielsen, N.M., et al., "Glycolamide esters as biolabile prodrugs of carboxylic acid agents: synthesis, stability, bioconversion, and physicochemical properties," Journal of Pharmaceutical Sciences, 1988, 77(4), 285-298.
Notari, R.E., "[24] Theory and pratices of prodrug kinetics,"Widder, K.J. et al. (Eds), *Methods in Enzymology, Drug anmd Enmzyme Targeting, Academic Press*, 1985, 42, 309-396.
Ortéga, N., et al. "Systemic activation of the vascular endothelial growth factor receptor KDR/flk-1 selectively triggers endothelial cells with an angiogenic phenotype," *Am. J. Pathol.*, Nov. 1997, 151(5), 1215-1224.
Ösapay, G., et al., "Synthesis of tyrocidine A: use of oxime resin for peptide chain assembly and cyclization," *Tetrahedron Letters*, 1990, 31,(43), 6121-6124.
Remington's Pharmaceutical Sciences, 17$^{th}$ Ed., *Mack Publishing Co., Easton, PA*, 1985, 1418.
Roberts, D.C., et al., "Unusual amino acids in peptide synthesis," *The Peptides*, 1983, 5(6), 341-449.
Rowinsky, E.K., "Novel radiation sensitizers targeting tissue hypoxia," *Oncology.*, Oct. 1999, 13(10) *Suppl.* 5, 61-70.
Soker, S., et al., "Inhibition of vascular enhothelial growth factor (VEGF)-induced endothelial cell proliferation by a peptide corresponding to the exon 7-encoded domain of VEGF$_{165}$"*J. Biol. Chem.*, 1997, 272(50), 31582-31588.
Stein, R., et al., "Assessment of combined radioimmunotherapy and chemotherapy for treatment of medullary thyroid cancer," *Clin. Cancer Res.*, Oct. 1999, 5, 3199s-3206s.
Stewart, et al., Solid Phase Peptide Synthesis, 2$^{nd}$ Ed., *Pierce Chem. Co., Rockford, IL*, 1984, p. 88.
Tran, T.-A., et al., "A novel RGD containing dodecapeptidomimetic which exhibits selective binding to the $\alpha_v\beta3$ receptor," *Bioorg. & Med. Chem. Lett.*, 1997, 7(8), 997-1002.
Yayon, A., et al., "Isolation of peptides that inhibit binding of basic fibroblast growth factor to its receptor from a random phage-epitope library," *Proc. Natl. Acad. Sci. USA*, Nov. 1993, 90, 10643-10647.
U.S. Appl. No. 60/013,360, filed Mar. 13, 1996, Edwards.

* cited by examiner

PHARMACEUTICALS FOR THE IMAGING OF ANGIOGENIC DISORDERS

CROSS-REFERENCE TO RELATED APPLICATIONS

This application is a divisional application of U.S. Ser. No. 10/342,081, filed Jan. 14, 2003, now U.S. Pat. No. 6,800,273, which is a divisional application of U.S. Ser. No. 09/599,295, filed Jun. 21, 2000, now U.S. Pat. No. 6,537,520, which is a continuation-in-part application of U.S. Ser. No. 09/281,474, filed Mar. 30, 1999, which claims the benefit of U.S. Ser. No. 60/080,150, filed Mar. 31, 1998 and Ser. No. 60/112,715, filed Dec. 18, 1998, all of which are incorporated herein by reference as if reproduced in their entireties.

FIELD OF THE INVENTION

The present invention provides novel pharmaceuticals useful for the diagnosis and treatment of cancer, methods of imaging tumors in a patient, and methods of treating cancer in a patient. The invention is also directed to novel pharmaceutical compositions and combination therapy comprising a compound of the invention or a pharmaceutically acceptable salt thereof, and at least one agent selected from the group consisting of a chemotherapeutic agent and a radiosensitizer agent. The present invention also provides novel pharmaceuticals useful for monitoring therapeutic angiogenesis treatment and destruction of new angiogenic vasculature. The pharmaceuticals are comprised of a targeting moiety that binds to a receptor that is upregulated during angiogenesis, an optional linking group, and a therapeutically effective radioisotope or diagnostically effective imageable moiety. The therapeutically effective radioisotope emits a particle or electron sufficient to be cytotoxic. The imageable moiety is a gamma ray or positron emitting radioisotope, a magnetic resonance imaging contrast agent, an X-ray contrast agent, or an ultrasound contrast agent.

BACKGROUND OF THE INVENTION

Cancer is a major public health concern in the United States and around the world. It is estimated that over 1 million new cases of invasive cancer will be diagnosed in the United States in 1998. The most prevalent forms of the disease are solid tumors of the lung, breast, prostate, colon and rectum. Cancer is typically diagnosed by a combination of in vitro tests and imaging procedures. The imaging procedures include X-ray computed tomography, magnetic resonance imaging, ultrasound imaging and radionuclide scintigraphy. Frequently, a contrast agent is administered to the patient to enhance the image obtained by X-ray CT, MRI and ultrasound, and the administration of a radiopharmaceutical that localizes in tumors is required for radionuclide scintigraphy.

Treatment of cancer typically involves the use of external beam radiation therapy and chemotherapy, either alone or in combination, depending on the type and extent of the disease. A number of chemotherapeutic agents are available, but generally they all suffer from a lack of specificity for tumors versus normal tissues, resulting in considerable side-effects. The effectiveness of these treatment modalities is also limited, as evidenced by the high mortality rates for a number of cancer types, especially the more prevalent solid tumor diseases. More effective and specific treatment means continue to be needed.

Despite the variety of imaging procedures available for the diagnosis of cancer, there remains a need for improved methods. In particular, methods that can better differentiate between cancer and other pathologic conditions or benign physiologic abnormalities are needed. One means of achieving this desired improvement would be to administer to the patient a metallopharmaceutical that localizes specifically in the tumor by binding to a receptor expressed only in tumors or expressed to a significantly greater extent in tumors than in other tissue. The location of the metallopharmaceutical could then be detected externally either by its imageable emission in the case of certain radiopharmaceuticals or by its effect on the relaxation rate of water in the immediate vicinity in the case of magnetic resonance imaging contrast agents.

This tumor specific metallopharmaceutical approach can also be used for the treatment of cancer when the metallopharmaceutical is comprised of a particle emitting radioisotope. The radioactive decay of the isotope at the site of the tumor results in sufficient ionizing radiation to be toxic to the tumor cells. The specificity of this approach for tumors minimizes the amount of normal tissue that is exposed to the cytotoxic agent and thus may provide more effective treatment with fewer side-effects.

Previous efforts to achieve these desired improvements in cancer imaging and treatment have centered on the use of radionuclide labeled monoclonal antibodies, antibody fragments and other proteins or polypeptides (i.e., molecular weight over 10,000 D) that bind to tumor cell surface receptors. The specificity of these radiopharmaceuticals is frequently very high, but they suffer from several disadvantages. First, because of their high molecular weight, they are generally cleared from the blood stream very slowly, resulting in a prolonged blood background in the images. Also, due to their molecular weight they do not extravasate readily at the site of the tumor and then only slowly diffuse through the extravascular space to the tumor cell surface. This results in a very limited amount of the radiopharmaceutical reaching the receptors and thus very low signal intensity in imaging and insufficient cytotoxic effect for treatment.

Alternative approaches to cancer imaging and therapy have involved the use of small molecules, such as peptides, that bind to tumor cell surface receptors. An $^{111}$In labeled somatostatin receptor binding peptide, $^{111}$In-DTPA-D-Phe[1]-octeotide, is in clinical use in many countries for imaging tumors that express the somatostatin receptor (Baker, et al., Life Sci., 1991, 49, 1583–91 and Krenning, et al., Eur. J. Nucl. Med., 1993, 20, 716–31). Higher doses of this radiopharmaceutical have been investigated for potential treatment of these types of cancer (Krenning, et al., *Digestion*, 1996, 57, 57–61). Several groups are investigating the use of Tc-99m labeled analogs of $^{111}$In-DTPA-D-Phe[1]-octeotide for imaging and Re-186 labeled analogs for therapy (Flanagan, et al., U.S. Pat. No. 5,556,939, Lyle, et al., U.S. Pat. No. 5,382,654, and Albert et al., U.S. Pat. No. 5,650,134).

Angiogenesis is the process by which new blood vessels are formed from pre-existing capillaries or post capillary venules; it is an important component of a variety of physiological processes including ovulation, embryonic development, wound repair, and collateral vascular generation in the myocardium. It is also central to a number of pathological conditions such as tumor growth and metastasis, diabetic retinopathy, and macular degeneration. The process begins with the activation of existing vascular endothelial cells in response to a variety of cytokines and growth factors. Tumor released cytokines or angiogenic factors stimulate vascular endothelial cells by interacting with specific cell surface receptors for the factors. The activated endothelial cells secrete enzymes that degrade the basement membrane of the vessels. The endothelial cells then proliferate and invade into the tumor tissue. The endothelial cells differentiate to form lumens, making new vessel offshoots of pre-existing vessels. The new blood vessels then provide nutrients to the tumor permitting further growth and a route for metastasis.

Under normal conditions, endothelial cell proliferation is a very slow process, but it increases for a short period of time during embryogenesis, ovulation and wound healing. This temporary increase in cell turnover is governed by a combination of a number of growth stimulatory factors and growth suppressing factors. In pathological angiogenesis, this normal balance is disrupted resulting in continued increased endothelial cell proliferation. Some of the pro-angiogenic factors that have been identified include basic fibroblast growth factor (bFGF), angiogenin, TGF-alpha, TGF-beta, and vascular endothelium growth factor (VEGF), while interferon-alpha, interferon-beta and thrombospondin are examples of angiogenesis suppressors.

The proliferation and migration of endothelial cells in the extracellular matrix is mediated by interaction with a variety of cell adhesion molecules (Folkman, J., Nature Medicine, 1995, 1, 27–31). Integrins are a diverse family of heterodimeric cell surface receptors by which endothelial cells attach to the extracellular matrix, each other and other cells. The integrin $\alpha_v\beta_3$ is a receptor for a wide variety of extracellular matrix proteins with an exposed tripeptide Arg-Gly-Asp moiety and mediates cellular adhesion to its ligands: vitronectin, fibronectin, and fibrinogen, among others. The integrin $\alpha_v\beta_3$ is minimally expressed on normal blood vessels, but is significantly upregulated on vascular cells within a variety of human tumors. The role of the $\alpha_v\beta_3$ receptors is to mediate the interaction of the endothelial cells and the extracellular matrix and facilitate the migration of the cells in the direction of the angiogenic signal, the tumor cell population. Angiogenesis induced by bFGF or TNF-alpha depend on the agency of the integrin $\alpha_v\beta_3$, while angiogenesis induced by VEGF depends on the integrin $\alpha_v\beta_5$ (Cheresh et. al., Science, 1995, 270, 1500–2). Induction of expression of the integrins $\alpha_1\beta_1$ and $\alpha_2\beta_1$ on the endothelial cell surface is another important mechanism by which VEGF promotes angiogenesis (Senger, et. al., Proc. Natl. Acad, Sci USA, 1997, 94, 13612–7).

Angiogenic factors interact with endothelial cell surface receptors such as the receptor tyrosine kinases EGFR, FGFR, PDGFR, Flk-1/KDR, Flt-1, Tek, Tie, neuropilin-1, endoglin, endosialin, and A×1. The receptors Flk-1/KDR, neuropilin-1, and Flt-1 recognize VEGF and these interactions play key roles in VEGF-induced angiogenesis. The Tie subfamily of receptor tyrosine kinases are also expressed prominently during blood vessel formation.

Because of the importance of angiogenesis to tumor growth and metastasis, a number of chemotherapeutic approaches are being developed to interfere with or prevent this process. One of these approaches, involves the use of anti-angiogenic proteins such as angiostatin and endostatin. Angiostatin is a 38 kDa fragment of plasminogen that has been shown in animal models to be a potent inhibitor of endothelial cell proliferation. (O'Reilly et. al., Cell, 1994, 79, 315–328) Endostatin is a 20 kDa C-terminal fragment of collagen XVIII that has also been shown to be a potent inhibitor. (O'Reilly et. al., Cell, 1997, 88, 277–285).

Systemic therapy with endostatin has been shown to result in strong anti-tumor activity in animal models. However, human clinical trials of these two chemotherapeutic agents of biological origin have been hampered by lack of availability.

Another approach to anti-angiogenic therapy is to use targeting moieties that interact with endothelial cell surface receptors expressed in the angiogenic vasculature to which are attached chemotherapeutic agents. Burrows and Thorpe (Proc. Nat. Acad. Sci, USA, 1993, 90, 8996–9000) described the use of an antibody-immunotoxin conjugate to eradicate tumors in a mouse model by destroying the tumor vasculature. The antibody was raised against an endothelial cell class II antigen of the major histocompatibility complex and was then conjugated with the cytotoxic agent, deglycosylated ricin A chain. The same group (Clin. Can. Res., 1995, 1, 1623–1634) investigated the use of antibodies raised against the endothelial cell surface receptor, endoglin, conjugated to deglycosylated ricin A chain. Both of these conjugates exhibited potent anti-tumor activity in mouse models. However, both still suffer drawbacks to routine human use. As with most antibodies or other large, foreign proteins, there is considerable risk of immunologic toxicity which could limit or preclude administration to humans. Also, while the vasculature targeting may improve the local concentration of the attached chemotherapeutic agents, the agents still must be cleaved from the antibody carrier and be transported or diffuse into the cells to be cytotoxic.

Thus, it is desirable to provide anti-angiogenic pharmaceuticals and tumor or new vasculature imaging agents which don't suffer from poor diffusion or transportation, possible immunologic toxicity, limited availability, and/or a lack of specificity.

There continues to be a need for more effective treatment options for patients with solid tumors. This is especially true in cases of metastatic cancer in which current standard chemotherapy and external beam radiation regimens only result in marginal survival improvements.

Although improvements in cytotoxic chemotherapeutics have been made in recent years, the toxicity of these compounds to normal tissues has continued to severely limit their utility in extending survival in patients with solid tumors. Recently developed combinations of different therapeutic modalities, such as external beam irradiation and chemotherapy (i.e. chemoradiation), has provided some incremental benefit to the control of tumor progression and quality of life. However, neither systemic chemotherapeutics nor external beam irradiation have acceptable therapeutic indices, and are often limited due to unacceptable toxicity to normal tissues. The concept of combined therapy of cancer using anti-angiogenesis drugs in combination with chemotherapeutics is not new. Further, the concept of combining targeted in-vivo radiotherapy using radiolabeled antibodies and antibody fragments with chemotherapy has been reported (Stein R, Juweid M, Zhang C, et al., Clin. Cancer Res., 5: 3199s–3206s, 1999. However, the combination of a angiogenesis-targeted therapeutic radiopharmaceutical which is targeted to receptors, which are then upregulated in the neovasculature of tumors, together with chemotherapy has not been described before. Therefore, there is a need for a combination of a therapeutic radiopharmaceutical, which is targeted to localize in the neovasculature of tumors, with chemotherapeutics or a radiosensitizer agent, or a pharmaceutically acceptable salt thereof, to provide additive or synergistic therapeutic response without unacceptable additive toxicity in the treatment of solid tumors.

The major advantage of combined chemotherapy and angiogenesis-targeted therapeutic radiopharmaceuticals, over each therapeutic modality alone, is improved tumor response without substantial increases in toxicity over either treatment alone. The advantage of using neovascular-specific radiopharmaceuticals, versus a tumor-cell targeted antibody, is that there is much lower systemic radiation exposure to the subject being treated.

Further, if the receptor targets for the radiopharmaceutical compounds, used in this method of treatment, are expressed on the luminal side of tumor vessels, there is no requirement that these compounds traverse the capillary bed and bind to the tumor itself.

Thus, it is desirable to provide a combination of angiogenesis-targeted therapeutic radiopharmaceuticals and a chemotherapeutics or a radiosensitizer agent, or a pharmaceutically acceptable salt thereof, which target the luminal side of the neovasculature of tumors, to provide a surprising, and enhanced degree of tumor suppression relative to each treatment modality alone without significant additive toxicity.

There is also a growing interest in therapeutic angiogenesis to improve blood flow in regions of the body that have become ischemic or poorly perfused. Several investigators are using growth factors administered locally to cause new vasculature to form either in the limbs or the heart. The growth factors VEGF and bFGF are the most common for this application. Recent publications include: Takeshita, S., et. al., J. Clin. Invest., 1994, 93, 662–670; and Schaper, W. and Schaper, J., Collateral Circulation:Heart, Brain, Kidney, Limbs, Kluwer Academic Publishers, Boston, 1993. The main applications that are under investigation in a number of laboratories are for improving cardiac blood flow and in improving peripheral vessal blood flow in the limbs. For example, Henry, T. et. al. (J. Amer. College Cardiology, 1998, 31, 65A) describe the use of recombinant human VEGF in patients for improving myocardial perfusion by therapeutic angiogenesis. Patients received infusions of rh VEGF and were monitored by nuclear perfusion imaging 30 and 60 days post treatment to determine improvement in myocardial perfusion. About 50% of patients showed improvement by nuclear perfusion imaging whereas 5/7 showed new collatoralization by angiography.

Thus, it is desirable to discover a method of monitoring improved cardiac blood flow which is targeted to new collatoral vessels themselves and not, as in nuclear perfusion imaging, a regional consequence of new collatoral vessels.

SUMMARY OF THE INVENTION

It is one object of the present invention to provide anti-angiogenic pharmaceuticals, comprised of a targeting moiety that binds to a receptor that is expressed in tumor neovasculature, an optional linking group, and a radioactive metal ion that emits ionizing radiation such as beta particles, alpha particles and Auger or Coster-Kronig electrons. The receptor binding compounds target the radioisotope to the tumor neovasculature. The beta or alpha-particle emitting radioisotope emits a cytotoxic amount of ionizing radiation which results in cell death. The penetrating ability of radiation obviates the requirement that the cytotoxic agent diffuse or be transported into the cell to be cytotoxic.

It is another object of the present invention to provide pharmaceuticals to treat rheumatoid arthritis. These pharmaceuticals comprise a targeting moiety that binds to a receptor that is upregulated during angiogenesis, an optional linking group, and a radioisotope that emits cytotoxic radiation (i.e., beta particles, alpha particles and Auger or Coster-Kronig electrons). In rheumatoid arthritis, the ingrowth of a highly vascularized pannus is caused by the excessive production of angiogenic factors by the infiltrating macrophages, immune cells, or inflammatory cells. Therefore, the radiopharmaceuticals of the present invention that emit cytotoxic radiation could be used to destroy the new angiogenic vasculature that results and thus treat the disease.

It is another object of the present invention to provide tumor imaging agents, comprised of targeting moiety that binds to a receptor that is upregulated during angiogenesis, an optional linking group, and an imageable moiety, such as a gamma ray or positron emitting radioisotope, a magnetic resonance imaging contrast agent, an X-ray contrast agent, or an ultrasound contrast agent.

It is another object of the present invention to provide imaging agents for monitoring the progress and results of therapeutic angiogenesis treatment. These agents comprise of targeting moiety that binds to a receptor that is upregulated during angiogenesis, an optional linking group, and an imageable moiety. Imaging agents of the present invention could be administered intravenously periodically after the administration of growth factors and imaging would be performed using standard techniques of the affected areas, heart or limbs, to monitor the progress and results of the therapeutic angiogenesis treatment (i.e., image the formation of new blood vessels).

It is another object of the present invention to provide compounds useful for preparing the pharmaceuticals of the present invention. These compounds are comprised of a peptide or peptidomimetic targeting moiety that binds to a receptor that is upregulated during angiogenesis, Q, an optional linking group, $L_n$, and a metal chelator or bonding moiety, $C_h$. The compounds may have one or more protecting groups attached to the metal chelator or bonding moiety. The protecting groups provide improved stability to the reagents for long-term storage and are removed either immediately prior to or concurrent with the synthesis of the radiopharmaceuticals. Alternatively, the compounds of the present invention are comprised of a peptide or peptidomimetic targeting moiety that binds to a receptor that is upregulated during angiogenesis, Q, an optional linking group, $L_n$, and a surfactant, $S_f$.

The pharmaceuticals of the present invention may be used for diagnostic and/or therapeutic purposes. Diagnostic radiopharmaceuticals of the present invention are pharmaceuticals comprised of a diagnostically useful radionuclide (i.e., a radioactive metal ion that has imageable gamma ray or positron emissions). Therapeutic radiopharmaceuticals of the present invention are pharmaceuticals comprised of a therapeutically useful radionuclide, a radioactive metal ion that emits ionizing radiation such as beta particles, alpha particles and Auger or Coster-Kronig electrons.

The pharmaceuticals comprising a gamma ray or positron emitting radioactive metal ion are useful for imaging tumors by gamma scintigraphy or positron emission tomography. The pharmaceuticals comprising a gamma ray or positron emitting radioactive metal ion are also useful for imaging therapeutic angiogenesis by gamma scintigraphy or positron emission tomography. The pharmaceuticals comprising a particle emitting radioactive metal ion are useful for treating cancer by delivering a cytotoxic dose of radiation to the tumors. The pharmaceuticals comprising a particle emitting radioactive metal ion are also useful for treating rheumatoid arthritis by destroying the formation of angiogenic vasculature. The pharmaceuticals comprising a paramagnetic metal ion are useful as magnetic resonance imaging contrast agents. The pharmaceuticals comprising one or more X-ray absorbing or "heavy" atoms of atomic number 20 or greater are useful as X-ray contrast agents. The pharmaceuticals comprising a microbubble of a biocompatible gas, a liquid carrier, and a surfactant microsphere, are useful as ultrasound contrast agents.

DETAILED DESCRIPTION OF THE INVENTION

[1] Thus, in a first embodiment, the present invention provides a novel compound, comprising: a targeting moiety and a chelator, wherein the targeting moiety is bound to the chelator, is a peptide or peptidomimetic, and binds to a receptor that is upregulated during angiogenesis and the compound has 0–1 linking groups between the targeting moiety and chelator.

[2] In a preferred embodiment, the targeting moiety is a peptide or a mimetic thereof and the receptor is selected from the group: EGFR, FGFR, PDGFR, Flk-1/KDR, Flt-1, Tek, Tie, neuropilin-1, endoglin, endosialin, A×1, $\alpha_v\beta_3$, $\alpha_v\beta_5$, $\alpha_5\beta_1\alpha_4\beta_1$, $\alpha_1\beta_1$, and $\alpha_2\beta_2$ and the linking group is present between the targeting moiety and chelator.

[3] In a more preferred embodiment, the receptor is the integrin $\alpha_v\beta_3$ and the compound is of the formula:

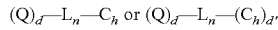

wherein, Q is a peptide independently selected from the group:

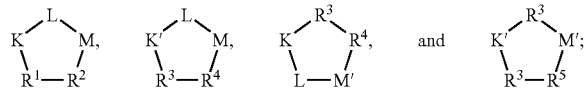

K is an L-amino acid independently selected at each occurrence from the group: arginine, citrulline, N-methylarginine, lysine, homolysine, 2-aminoethylcysteine, δ-N-2-imidazolinylornithine, δ-N-benzylcarbamoylornithine, and β-2-benzimidazolylacetyl-1,2-diaminopropionic acid;

K' is a D-amino acid independently selected at each occurrence from the group: arginine, citrulline, N-methylarginine, lysine, homolysine, 2-aminoethylcysteine, δ-N-2-imidazolinylornithine, δ-N-benzylcarbamoylornithine, and β-2-benzimidazolylacetyl-1,2-diaminopropionic acid;

L is independently selected at each occurrence from the group: glycine, L-alanine, and D-alanine;

M is L-aspartic acid;

M" is D-aspartic acid;

$R^1$ is an amino acid substituted with 0–1 bonds to $L_n$, independently selected at each occurrence from the group: glycine, L-valine, D-valine, alanine, leucine, isoleucine, norleucine, 2-aminobutyric acid, 2-aminohexanoic acid, tyrosine, phenylalanine, thienylalanine, phenylglycine, cyclohexylalanine, homophenylalanine, 1-naphthylalanine, lysine, serine, ornithine, 1,2-diaminobutyric acid, 1,2-diaminopropionic acid, cysteine, penicillamine, and methionine;

$R^2$ is an amino acid, substituted with 0–1 bonds to $L_n$, independently selected at each occurrence from the group: glycine, valine, alanine, leucine, isoleucine, norleucine, 2-aminobutyric acid, 2-aminohexanoic acid, tyrosine, L-phenylalanine, D-phenylalanine, thienylalanine, phenylglycine, biphenylglycine, cyclohexylalanine, homophenylalanine, L-1-naphthylalanine, D-1-naphthylalanine, lysine, serine, ornithine, 1,2-diaminobutyric acid, 1,2-diaminopropionic acid, cysteine, penicillamine, methionine, and 2-aminothiazole-4-acetic acid;

$R^3$ is an amino acid, substituted with 0–1 bonds to $L_n$, independently selected at each occurrence from the group: glycine, D-valine, D-alanine, D-leucine, D-isoleucine, D-norleucine, D-2-aminobutyric acid, D-2-aminohexanoic acid, D-tyrosine, D-phenylalanine, D-thienylalanine, D-phenylglycine, D-cyclohexylalanine, D-homophenylalanine, D-1-naphthylalanine, D-lysine, D-serine, D-ornithine, D-1,2-diaminobutyric acid, D-1,2-diaminopropionic acid, D-cysteine, D-penicillamine, and D-methionine;

$R^4$ is an amino acid, substituted with 0–1 bonds to $L_n$, independently selected at each occurrence from the group: glycine, D-valine, D-alanine, D-leucine, D-isoleucine, D-norleucine, D-2-aminobutyric acid, D-2-aminohexanoic acid, D-tyrosine, D-phenylalanine, D-thienylalanine, D-phenylglycine, D-cyclohexylalanine, D-homophenylalanine, D-1-naphthylalanine, D-lysine, D-serine, D-ornithine, D-1,2-diaminobutyric acid, D-1,2-diaminopropionic acid, D-cysteine, D-penicillamine, D-methionine, and 2-aminothiazole-4-acetic acid;

$R^5$ is an amino acid, substituted with 0–1 bonds to $L_n$, independently selected at each occurrence from the group: glycine, L-valine, L-alanine, L-leucine, L-isoleucine, L-norleucine, L-2-aminobutyric acid, L-2-aminohexanoic acid, L-tyrosine, L-phenylalanine, L-thienylalanine, L-phenylglycine, L-cyclohexylalanine, L-homophenylalanine, L-1-naphthylalanine, L-lysine, L-serine, L-ornithine, L-1,2-diaminobutyric acid, L-1,2-diaminopropionic acid, L-cysteine, L-penicillamine, L-methionine, and 2-aminothiazole-4-acetic acid;

provided that one of $R^1$, $R^2$, $R^3$, $R^4$, and $R^5$ in each Q is substituted with a bond to $L_n$, further provided that when $R^2$ is 2-aminothiazole-4-acetic acid, K is N-methylarginine, further provided that when $R^4$ is 2-aminothiazole-4-acetic acid, K and K' are N-methylarginine, and still further provided that when $R^5$ is 2-aminothiazole-4-acetic acid, K' is N-methylarginine;

d is selected from 1, 2, 3, 4, 5, 6, 7, 8, 9, and 10;

$L_n$ is a linking group having the formula:

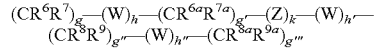

provided that g+h+g'+k+h'+g"+h"+g'" is other than 0;

W is independently selected at each occurrence from the group: O, S, NH, NHC(=O), C(=O)NH, C(=O), C(=O)O, OC(=O), NHC(=S)NH, NHC(=O)NH, SO$_2$, (OCH$_2$CH$_2$)$_s$, (CH$_2$CH$_2$O)$_{s'}$, (OCH$_2$CH$_2$)$_{s'''}$, (CH$_2$CH$_2$CH$_2$O)$_t$, and (aa)$_{t'}$;

aa is independently at each occurrence an amino acid;

Z is selected from the group: aryl substituted with 0–3 $R^{10}$, $C_{3-10}$ cycloalkyl substituted with 0–3 $R^{10}$, and a 5–10 membered heterocyclic ring system containing 1–4 heteroatoms independently selected from N, S, and O and substituted with 0–3 $R^{10}$;

$R^6$, $R^{6a}$, $R^7$, $R^{7a}$, $R^8$, $R^{8a}$, $R^9$ and $R^{9a}$ are independently selected at each occurrence from the group: H, =O, COOH, SO$_3$H, PO$_3$H, $C_1$–$C_5$ alkyl substituted with 0–3 $R^{10}$, aryl substituted with 0–3 $R^{10}$, benzyl substituted with 0–3 $R^{10}$, and $C_1$–$C_5$ alkoxy substituted with 0–3 $R^{10}$, NHC(=O)$R^{11}$, C(=O)NHR$^{11}$, NHC(=O)NHR$^{11}$, NHR$^{11}$, $R^{11}$, and a bond to $C_h$;

$R^{10}$ is independently selected at each occurrence from the group: a bond to $C_h$, COOR$^{11}$, OH, NHR$^{11}$, SO$_3$H, PO$_3$H, aryl substituted with 0–3 $R^{11}$, $C_{1-5}$ alkyl substituted with 0–1 $R^{12}$, $C_{1-5}$ alkoxy substituted with 0–1 $R^{12}$, and a 5–10 membered heterocyclic ring system containing 1–4 heteroatoms independently selected from N, S, and O and substituted with 0–3 $R^{11}$;

$R^{11}$ is independently selected at each occurrence from the group: H, aryl substituted with 0–1 $R^{12}$, a 5–10 membered heterocyclic ring system containing 1–4 heteroatoms independently selected from N, S, and O and substituted with 0–1 $R^{12}$, $C_{3-10}$ cycloalkyl substituted with 0–1 $R^{12}$, polyalkylene glycol substituted with 0–1 $R^{12}$, carbohydrate substituted with 0–1 $R^{12}$, cyclodextrin substituted with 0–1 $R^{12}$, amino acid substituted with 0–1 $R^{12}$, polycarboxyalkyl substituted with 0–1 $R^{12}$, polyazaalkyl substituted with 0–1 $R^{12}$, peptide substituted with 0–1 $R^{12}$, wherein the peptide is comprised of 2–10 amino acids, and a bond to $C_h$;

$R^{12}$ is a bond to $C_h$;

k is selected from 0, 1, and 2;

h is selected from 0, 1, and 2;

h' is selected from 0, 1, 2, 3, 4, and 5;

h'' is selected from 0, 1, 2, 3, 4, and 5;

g is selected from 0, 1, 2, 3, 4, 5, 6, 7, 8, 9, and 10;

g' is selected from 0, 1, 2, 3, 4, 5, 6, 7, 8, 9, and 10;

g'' is selected from 0, 1, 2, 3, 4, 5, 6, 7, 8, 9, and 10;

g''' is selected from 0, 1, 2, 3, 4, 5, 6, 7, 8, 9, and 10;

s is selected from 0, 1, 2, 3, 4, 5, 6, 7, 8, 9, and 10;

s' is selected from 0, 1, 2, 3, 4, 5, 6, 7, 8, 9, and 10;

s'' is selected from 0, 1, 2, 3, 4, 5, 6, 7, 8, 9, and 10;

t is selected from 0, 1, 2, 3, 4, 5, 6, 7, 8, 9, and 10;

t' is selected from 0, 1, 2, 3, 4, 5, 6, 7, 8, 9, and 10;

$C_h$ is a metal bonding unit having a formula selected from the group:

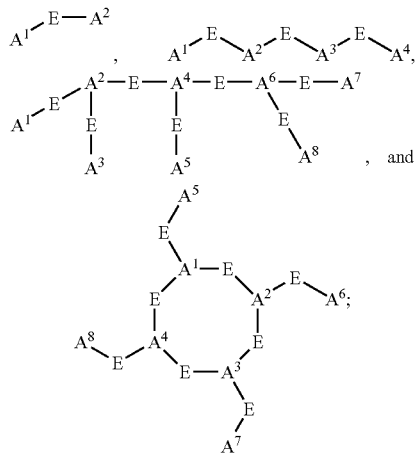

$A^1, A^2, A^3, A^4, A^5, A^6, A^7$, and $A^8$ are independently selected at each occurrence from the group: N, $NR^{13}$, $NR^{13}R^{14}$, S, SH, S(Pg), O, OH, $PR^{13}$, $PR^{13}R^{14}$, $P(O)R^{15}R^{16}$, and a bond to $L_n$;

E is a bond, CH, or a spacer group independently selected at each occurrence from the group: $C_1$–$C_{10}$ alkyl substituted with 0–3 $R^{17}$, aryl substituted with 0–3 $R^{17}$, $C_{3-10}$ cycloalkyl substituted with 0–3 $R^{17}$, heterocyclo-$C_{1-10}$ alkyl substituted with 0–3 $R^{17}$, wherein the heterocyclo group is a 5–10 membered heterocyclic ring system containing 1–4 heteroatoms independently selected from N, S, and O, $C_{6-10}$ aryl-$C_{1-10}$ alkyl substituted with 0–3 $R^{17}$, $C_{1-10}$ alkyl-$C_{6-10}$ aryl-substituted with 0–3 $R^{17}$, and a 5–10 membered heterocyclic ring system containing 1–4 heteroatoms independently selected from N, S, and O and substituted with 0–3 $R^{17}$;

$R^{13}$, and $R^{14}$ are each independently selected from the group: a bond to $L_n$, hydrogen, $C_1$–$C_{10}$ alkyl substituted with 0–3 $R^{17}$, aryl substituted with 0–3 $R^{17}$, $C_{1-10}$ cycloalkyl substituted with 0–3 $R^{17}$, heterocyclo-$C_{1-10}$ alkyl substituted with 0–3 $R^{17}$, wherein the heterocyclo group is a 5–10 membered heterocyclic ring system containing 1–4 heteroatoms independently selected from N, S, and O, $C_{6-10}$ aryl-$C_{1-10}$ alkyl substituted with 0–3 $R^{17}$, $C_{1-10}$ alkyl-$C_{6-10}$ aryl-substituted with 0–3 $R^{17}$, a 5–10 membered heterocyclic ring system containing 1–4 heteroatoms independently selected from N, S, and O and substituted with 0–3 $R^{17}$, and an electron, provided that when one of $R^{13}$ or $R^{14}$ is an electron, then the other is also an electron;

alternatively, $R^{13}$ and $R^{14}$ combine to form =$C(R^{20})(R^{21})$;

$R^{15}$ and $R^{16}$ are each independently selected from the group: a bond to $L_n$, —OH, $C_1$–$C_{10}$ alkyl substituted with 0–3 $R^{17}$, $C_1$–$C_{10}$ alkyl substituted with 0–3 $R^{17}$, aryl substituted with 0–3 $R^{17}$, $C_{3-10}$ cycloalkyl substituted with 0–3 $R^{17}$, heterocyclo-$C_{1-10}$ alkyl substituted with 0–3 $R^{17}$, wherein the heterocyclo group is a 5–10 membered heterocyclic ring system containing 1–4 heteroatoms independently selected from N, S, and O, $C_{6-10}$ aryl-$C_{1-10}$ alkyl substituted with 0–3 $R^{17}$, $C_{6-10}$ alkyl-$C_{6-10}$ aryl-substituted with 0–3 $R^{17}$, and a 5–10 membered heterocyclic ring system containing 1–4 heteroatoms independently selected from N, S, and O and substituted with 0–3 $R^{17}$;

$R^{17}$ is independently selected at each occurrence from the group: a bond to $L_n$, =O, F, Cl, Br, I, —$CF_3$, —CN, —$CO_2R^{18}$, —$C(=O)R^{18}$, —$C(=O)N(R^{18})_2$, —CHO, —$CH_2OR^{18}$, —$OC(=O)R^{18}$, —$OC(=O)OR^{18a}$, —$OR^{18}$, —$OC(=O)N(R^{18})_2$, —$NR^{19}C(=O)R^{18}$, —$NR^{19}C(=O)OR^{18a}$, —$NR^{19}C(=O)N(R^{18})_2$, —$NR^{19}SO_2N(R^{18})_2$, —$NR^{19}SO_2R^{18a}$, —$SO_3H$, —$SO_2R^{18a}$, —$SR^{18}$, —$S(=O)R^{18a}$, —$SO_2N(R^{18})_2$, —$N(R^{18})_2$, —$NHC(=S)NHR^{18}$, =$NOR^{18}$, $NO_2$, —$C(=O)NHOR^{18}$, —$C(=O)NHNR^{18}R^{18a}$, —$OCH_2CO_2H$, 2-(1-morpholino)ethoxy, $C_1$–$C_5$ alkyl, $C_2$–$C_4$ alkenyl, $C_3$–$C_6$ cycloalkyl, $C_3$–$C_6$ cycloalkylmethyl, $C_2$–$C_6$ alkoxyalkyl, aryl substituted with 0–2 $R^{18}$, and a 5–10 membered heterocyclic ring system containing 1–4 heteroatoms independently selected from N, S, and O;

$R^{18}$, $R^{18a}$ and $R^{19}$ are independently selected at each occurrence from the group: a bond to $L_n$, H, $C_1$–$C_6$ alkyl, phenyl, benzyl, $C_1$–$C_6$ alkoxy, halide, nitro, cyano, and trifluoromethyl;

Pg is a thiol protecting group;

$R^{20}$ and $R^{21}$ are independently selected from the group: H, $C_1$–$C_{10}$ alkyl, —CN, —$CO_2R^{25}$, —$C(=O)R^{25}$, —$C(=O)N(R^{25})_2$, $C_2$–$C_{10}$ 1-alkene substituted with 0–3 $R^{23}$, $C_2$–$C_{10}$ 1-alkyne substituted with 0–3 $R^{23}$, aryl substituted with 0–3 $R^{23}$, unsaturated 5–10 membered heterocyclic ring system containing 1–4 heteroatoms independently selected from N, S, and O and substituted with 0–3 $R^{23}$, and unsaturated $C_{3-10}$ carbocycle substituted with 0–3 $R^{23}$;

alternatively, $R^{20}$ and $R^{21}$, taken together with the divalent carbon radical to which they are attached form:

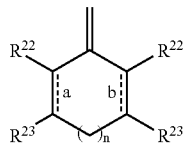

$R^{22}$ and $R^{23}$ are independently selected from the group: H, $R^{24}$, $C_1$–$C_{10}$ alkyl substituted with 0–3 $R^{24}$, $C_2$–$C_{10}$ alkenyl substituted with 0–3 $R^{24}$, $C_2$–$C_{10}$ alkynyl substituted with 0–3 $R^{24}$, aryl substituted with 0–3 $R^{24}$, a 5–10 membered heterocyclic ring system containing 1–4 heteroatoms independently selected from N, S, and O and substituted with 0–3 $R^{24}$, and $C_{3-10}$ carbocycle substituted with 0–3 $R^{24}$;

alternatively, $R^{22}$, $R^{23}$ taken together form a fused aromatic or a 5–10 membered heterocyclic ring system containing 1–4 heteroatoms independently selected from N, S, and O;

a and b indicate the positions of optional double bonds and n is 0 or 1;

$R^{24}$ is independently selected at each occurrence from the group: =O, F, Cl, Br, I, —$CF_3$, —CN, —$CO_2R^{25}$, —C(=O)$R^{25}$, —C(=O)N($R^{25}$)$_2$, —N($R^{25}$)$_3^+$, —$CH_2OR^{25}$, —OC(=O)$R^{25}$, —OC(=O)O$R^{25a}$, —O$R^{25}$, —OC(=O)N($R^{25}$)$_2$, —$NR^{26}$C(=O)$R^{25}$, —$NR^{26}$C(=O)O$R^{25a}$, —$NR^{26}$C(=O)N($R^{25}$)$_2$, —$NR^{26}SO_2$N($R^{25}$)$_2$, —$NR^{26}SO_2R^{25a}$, —$SO_3$H, —$SO_2R^{25a}$, —$SR^{25}$, —S(=O)$R^{25a}$, —$SO_2$N($R^{25}$)$_2$, —N($R^{25}$)$_2$, =NO$R^{25}$, —C(=O)NHO$R^{25}$, —$OCH_2CO_2$H, and 2-(1-morpholino)ethoxy; and, $R^{25}$, $R^{25a}$, and $R^{26}$ are each independently selected at each occurrence from the group: hydrogen and $C_1$–$C_6$ alkyl;

and a pharmaceutically acceptable salt thereof.

[4] In an even more preferred embodiment, the present invention provides a compound, wherein:

L is glycine;

$R^1$ is an amino acid, optionally substituted with a bond to $L_n$, independently selected at each occurrence from the group: L-valine, D-valine, alanine, leucine, isoleucine, norleucine, 2-aminobutyric acid, tyrosine, phenylalanine, phenylglycine, cyclohexylalanine, homophenylalanine, lysine, ornithine, 1,2-diaminobutyric acid, and 1,2-diaminopropionic acid;

$R^2$ is an amino acid, optionally substituted with a bond to $L_n$, independently selected at each occurrence from the group: valine, alanine, leucine, isoleucine, norleucine, 2-aminobutyric acid, tyrosine, L-phenylalanine, D-phenylalanine, thienylalanine, phenylglycine, biphenylglycine, cyclohexylalanine, homophenylalanine, L-1-naphthylalanine, D-1-naphthylalanine, lysine, ornithine, 1,2-diaminobutyric acid, 1,2-diaminopropionic acid, and 2-aminothiazole-4-acetic acid;

$R^3$ is an amino acid, optionally substituted with a bond to $L_n$, independently selected at each occurrence from the group: D-valine, D-alanine, D-leucine, D-isoleucine, D-norleucine, D-2-aminobutyric acid, D-tyrosine, D-phenylalanine, D-phenylglycine, D-cyclohexylalanine, D-homophenylalanine, D-lysine, D-serine, D-ornithine, D-1,2-diaminobutyric acid, and D-1,2-diaminopropionic acid;

$R^4$ is an amino acid, optionally substituted with a bond to $L_n$, independently selected at each occurrence from the group: D-valine, D-alanine, D-leucine, D-isoleucine, D-norleucine, D-2-aminobutyric acid, D-tyrosine, D-phenylalanine, D-thienylalanine, D-phenylglycine, D-cyclohexylalanine, D-homophenylalanine, D-1-naphthylalanine, D-lysine, D-ornithine, D-1,2-diaminobutyric acid, D-1,2-diaminopropionic acid, and 2-aminothiazole-4-acetic acid;

$R^5$ is an amino acid, optionally substituted with a bond to $L_n$, independently selected at each occurrence from the group: L-valine, L-alanine, L-leucine, L-isoleucine, L-norleucine, L-2-aminobutyric acid, L-tyrosine, L-phenylalanine, L-thienylalanine, L-phenylglycine, L-cyclohexylalanine, L-homophenylalanine, L-1-naphthylalanine, L-lysine, L-ornithine, L-1,2-diaminobutyric acid, L-1,2-diaminopropionic acid, and 2-aminothiazole-4-acetic acid;

d is selected from 1, 2, and 3;

W is independently selected at each occurrence from the group: O, NH, NHC(=O), C(=O)NH, C(=O), C(=O)O, OC(=O), NHC(=S)NH, NHC(=O)NH, $SO_2$, $(OCH_2CH_2)_s$, $(CH_2CH_2O)_{s'}$, $(OCH_2CH_2)_{s''}$, and $(CH_2CH_2CH_2O)_t$;

Z is selected from the group: aryl substituted with 0–1 $R^{10}$, $C_{3-10}$ cycloalkyl substituted with 0–1 $R^{10}$, and a 5–10 membered heterocyclic ring system containing 1–4 heteroatoms independently selected from N, S, and O and substituted with 0–1 $R^{10}$;

$R^6$, $R^{6a}$, $R^7$, $R^{7a}$, $R^8$, $R^{8a}$, $R^9$, and $R^{9a}$ are independently selected at each occurrence from the group: H, =O, COOH, $SO_3$H, $C_1$–$C_5$ alkyl substituted with 0–1 $R^{10}$, aryl substituted with 0–1 $R^{10}$, benzyl substituted with 0–1 $R^{10}$, and $C_1$–$C_5$ alkoxy substituted with 0–1 $R^{10}$, NHC(=O)$R^{11}$, C(=O)NH$R^{11}$, NHC(=O)NH$R^{11}$, NH$R^{11}$, $R^{11}$, and a bond to $C_h$;

$R^{10}$ is independently selected at each occurrence from the group: COO$R^{11}$, OH, NH$R^{11}$, $SO_3$H, aryl substituted with 0–1 $R^{11}$, a 5–10 membered heterocyclic ring system containing 1–4 heteroatoms independently selected from N, S, and O and substituted with 0–1 $R^{11}$, $C_1$–$C_5$ alkyl substituted with 0–1 $R^{12}$, $C_1$–$C_5$ alkoxy substituted with 0–1 $R^{12}$ and a bond to $C_h$;

$R^{11}$ is independently selected at each occurrence from the group: H, aryl substituted with 0–1 $R^{12}$, a 5–10 membered heterocyclic ring system containing 1–4 heteroatoms independently selected from N, S, and O and substituted with 0–1 $R^{12}$, polyalkylene glycol substituted with 0–1 $R^{12}$, carbohydrate substituted with 0–1 $R^{12}$, cyclodextrin substituted with 0–1 $R^{12}$ amino acid substituted with 0–1 $R^{12}$, and a bond to $C_h$;

k is 0 or 1;

h is 0 or 1;

h' is 0 or 1;

s is selected from 0, 1, 2, 3, 4, and 5;

s' is selected from 0, 1, 2, 3, 4, and 5;

s" is selected from 0, 1, 2, 3, 4, and 5;

t is selected from 0, 1, 2, 3, 4, and 5;

$A^1$, $A^2$, $A^3$, $A^4$, $A^5$, $A^6$, $A^7$, and $A^8$ are independently selected at each occurrence from the group: $NR^{13}$, $NR^{13}R^{14}$, S, SH, S(Pg), OH, and a bond to $L_n$;

E is a bond, CH, or a spacer group independently selected at each occurrence from the group: $C_1$–$C_{10}$ alkyl substituted with 0–3 $R^{17}$, aryl substituted with 0–3 $R^{17}$, $C_{3-10}$ cycloalkyl substituted with 0–3 $R^{17}$, and a 5–10 membered heterocyclic ring system containing 1–4 heteroatoms independently selected from N, S, and O and substituted with 0–3 $R^{17}$;

13

R$^{13}$, and R$^{14}$ are each independently selected from the group: a bond to L$_n$, hydrogen, C$_1$–C$_{10}$ alkyl substituted with 0–3 R$^{17}$, aryl substituted with 0–3 R$^{17}$, a 5–10 membered heterocyclic ring system containing 1–4 heteroatoms independently selected from N, S, and O and substituted with 0–3 R$^{17}$, and an electron, provided that when one of R$^{13}$ or R$^{14}$ is an electron, then the other is also an electron;

alternatively, R$^{13}$ and R$^{14}$ combine to form =C(R$^{20}$)(R$^{21}$);

R$^{17}$ is independently selected at each occurrence from the group: a bond to L$_n$, =O, F, Cl, Br, I, —CF$_3$, —CN, —CO$_2$R$^{18}$, —C(=O)R$^{18}$, —C(=O)N(R$^{18}$)$_2$, —CH$_2$OR$^{18}$, —OC(=O)R$^{18}$, —OC(=O)OR$^{18a}$, —OR$^{18}$, —OC(=O)N(R$^{18}$)$_2$, —NR$^{19}$C(=O)R$^{18}$, —NR$^{19}$C(=O)OR$^{18a}$, —NR$^{19}$C(=O)N(R$^{18}$)$_2$, —NR$^{19}$SO$_2$N(R$^{18}$)$_2$, —NR$^{19}$SO$_2$R$^{18a}$, —SO$_3$H, —SO$_2$R$^{18a}$, —S(=O)R$^{18a}$, —SO$_2$N(R$^{18}$)$_2$, —N(R$^{18}$)$_2$, —NHC(=S)NHR$^{18}$, =NOR$^{18}$, —C(=O)NHNR$^{18}$R$^{18a}$, —OCH$_2$CO$_2$H, and 2-(1-morpholino)ethoxy;

R$^{18}$, R$^{18a}$, and R$^{19}$ are independently selected at each occurrence from the group: a bond to L$_n$, H, and C$_1$–C$_6$ alkyl;

R$^{20}$ and R$^{21}$ are independently selected from the group: H, C$_1$–C$_5$ alkyl, —CO$_2$R$^{25}$, C$_2$–C$_5$ 1-alkene substituted with 0–3 R$^{23}$, C$_2$–C$_{51}$-alkyne substituted with 0–3 R$^{23}$, aryl substituted with 0–3 R$^{23}$, and unsaturated 5–10 membered heterocyclic ring system containing 1–4 heteroatoms independently selected from N, S, and O and substituted with 0–3 R$^{23}$;

alternatively, R$^{20}$ and R$^{21}$, taken together with the divalent carbon radical to which they are attached form:

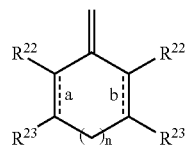

R$^{22}$ and R$^{23}$ are independently selected from the group: H, and R$^{24}$;

alternatively, R$^{22}$, R$^{23}$ taken together form a fused aromatic or a 5–10 membered heterocyclic ring system containing 1–4 heteroatoms independently selected from N, S, and O;

R$^{24}$ is independently selected at each occurrence from the group: —CO$_2$R$^{25}$, —C(=O)N(R$^{25}$)$_2$, —CH$_2$OR$^{25}$, —OC(=O)R$^{25}$, —OR$^{25}$, —SO$_3$H, —N(R$^{25}$)$_2$, and —OCH$_2$CO$_2$H; and, R$^{25}$ is independently selected at each occurrence from the group: H and C$_1$–C$_3$ alkyl.

[5] In a still more preferred embodiment, the present invention provides a compound, wherein:

Q is a peptide selected from the group:

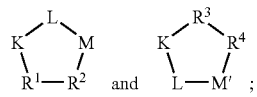

R$^1$ is L-valine, D-valine, D-lysine optionally substituted on the ε amino group with a bond to L$_n$ or L-lysine optionally substituted on the ε amino group with a bond to L$_n$;

14

R$^2$ is L-phenylalanine, D-phenylalanine, D-1-naphthylalanine, 2-aminothiazole-4-acetic acid, L-lysine optionally substituted on the ε amino group with a bond to L$_n$ or tyrosine, the tyrosine optionally substituted on the hydroxy group with a bond to L$_n$;

R$^3$ is D-valine, D-phenylalanine, or L-lysine optionally substituted on the ε amino group with a bond to L$_n$;

R$^4$ is D-phenylalanine, D-tyrosine substituted on the hydroxy group with a bond to L$_n$, or L-lysine optionally substituted on the ε amino group with a bond to L$_n$;

provided that one of R$^1$ and R$^2$ in each Q is substituted with a bond to L$_n$, and further provided that when R$^2$ is 2-aminothiazole-4-acetic acid, K is N-methylarginine;

d is 1 or 2;

W is independently selected at each occurrence from the group: NHC(=O), C(=O)NH, C(=O), (CH$_2$CH$_2$O)$_s$, and (CH$_2$CH$_2$CH$_2$O)$_t$;

R$^6$, R$^{6a}$, R$^7$, R$^{7a}$, R$^8$, R$^{8a}$, R$^9$, and R$^{9a}$ are independently selected at each occurrence from the group: H, NHC(=O)R$^{11}$, and a bond to C$_h$;

k is 0;

h" is selected from 0, 1, 2, and 3;

g is selected from 0, 1, 2, 3, 4, and 5;

g' is selected from 0, 1, 2, 3, 4, and 5;

g" is selected from 0, 1, 2, 3, 4, and 5;

g'" is selected from 0, 1, 2, 3, 4, and 5;

s' is 1 or 2;

t is 1 or 2;

C$_h$ is

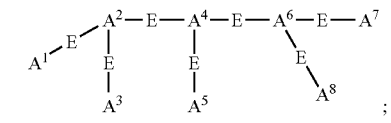

A$^1$ is selected from the group: OH, and a bond to L$_n$;

A$^2$, A$^4$, and A$^6$ are each N;

A$^3$, A$^5$, and A$^8$ are each OH;

A$^7$ is a bond to L$_n$ or NH-bond to L$_n$;

E is a C$_2$ alkyl substituted with 0–1 R$^{17}$;

R$^{17}$ is =O;

alternatively, C$_h$ is

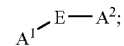

A$^1$ is NH$_2$ or N=C(R$^{20}$)(R$^{21}$);

E is a bond;

A$^2$ is NHR$^{13}$;

R$^{13}$ is a heterocycle substituted with R$^{17}$, the heterocycle being selected from pyridine and pyrimidine;

R$^{17}$ is selected from a bond to L$_n$, C(=O)NHR$^{18}$, and C(=O)R$^{18}$;

R$^{18}$ is a bond to L$_n$;

R$^{24}$ is selected from the group: —CO$_2$R$^{25}$, —OR$^{25}$, —SO$_3$H, and —N(R$^{25}$)$_2$;

R$^{25}$ is independently selected at each occurrence from the group: hydrogen and methyl;

alternatively, $C_h$ is

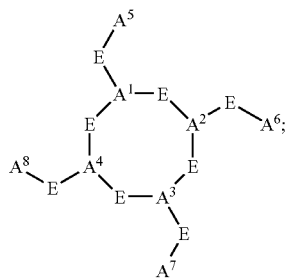

$A^1$, $A^2$, $A^3$, and $A^4$ are each N;
$A^5$, $A^6$, and $A^8$ are each OH;
$A^7$ is a bond to $L_n$;
E is a $C_2$ alkyl substituted with 0–1 $R^{17}$; and,
$R^{17}$ is =O.

[6] In another even more preferred embodiment, the present invention provides a compound selected from the group:

(a) cyclo{Arg-Gly-Asp-D-Tyr(N-[2-[[[5-[carbonyl]-2-pyridinyl]hydrazono]methyl]-benzenesulfonic acid]-3-aminopropyl-Val} [SEQ. ID NO.: 1];

(b) cyclo{Arg-Gly-Asp-D-Tyr((N-[2-[[[5-[carbonyl]-2-pyridinyl]hydrazono]methyl]-benzenesulfonic acid]-18-amino-14-amino-14-aza-4,7,10-oxy-15-oxo-octadecoyl)-3-aminopropyl)-Val} [SEQ. ID NO.: 2];

(c) [2-[carbonyl]-2-pyridinyl]hydrazono]methyl]-benzenesulfonic acid]-Glu(cyclo{D-Tyr(3-aminopropyl)-Val-Arg-Gly-Asp})-cyclo{D-Tyr(3-aminopropyl)-Val-Arg-Gly-Asp} [SEQ. ID NO.: 3];

(d) cyclo(Arg-Gly-Asp-D-Tyr-Lys([2-[[[5-[carbonyl]-2-pyridinyl]hydrazono]methyl]-benzenesulfonic acid])} [SEQ. ID NO.: 4];

(e) cyclo{Arg-Gly-Asp-D-Phe-Lys([2-[[[5-[carbonyl]-2-pyridinyl]hydrazono]methyl]-benzenesulfonic acid])} [SEQ. ID NO.: 5];

(f) [2-[[[5-[carbonyl]-2-pyridinyl]hydrazono]methyl]-benzenesulfonic acid]-Glu(cyclo{Lys-Arg-Gly-Asp-D-Phe})-cyclo{Lys-Arg-Gly-Asp-D-Phe} [SEQ. ID NO.: 6];

(g) [2-[[[5-[carbonyl]-2-pyridinyl]hydrazono]methyl]-benzenesulfonic acid]-Phe-Gly(cyclo{Lys-Arg-Gly-Asp-D-Phe})-cyclo{Lys-Arg-Asp-D-Phe} [SEQ. ID NO.: 7];

(h) cyclo{Arg-Gly-Asp-D-Nal-Lys([2-[[[5-[carbonyl]-2-pyridinyl]hydrazono]methyl]-benzenesulfonic acid])} [SEQ. ID NO.: 8];

(i) [2-[[[5-[carbonyl]-2-pyridinyl-hydrazono]methyl]-benzenesulfonic acid]-Gly(cyclo{Lys-Arg-Gly-Asp-D-Nal])-cyclo{Lys-Arg-Gly-Asp-D-Nal} [SEQ. ID NO.: 9];

(j) cyclo{Arg-Gly-Asp-Lys([2-[[[5-[carbonyl]-2-pyridinyl]hydrazono]methyl]-benzenesulfonic acid])-D-Val} [SEQ. ID NO.: 10];

(k) [2-[[[5-[carbonyl]-2-pyridinyl]hydrazono]methyl]-benzenesulfonic acid]-Glu(cyclo{Lys-D-Val-Arg-Gly-Asp})-cyclo{Lys-D-Val-Arg-Gly-Asp} [SEQ. ID NO.: 11];

(l) {cyclo(Arg-D-Val-D-Tyr(N-[2-[[[5-[carbonyl]-2-pyridinyl]hydrazono]methyl]-benzenesulfonic acid]-3-aminopropyl)-D-Asp-Gly} [SEQ. ID NO.: 12];

(m) cyclo{D-Lys([2-[[[5-[carbonyl]-2-pyridinyl]hydrazono]methyl]-benzenesulfonic acid])-D-Phe-D-Asp-Gly-Arg} [SEQ. ID NO.: 13];

(n) [2-[[[5-[carbonyl]-2-pyridinyl]hydrazono]methyl]-benzenesulfonic acid]-Glu(cyclo{D-Lys-D-Phe-D-Asp-Gly-Arg})-cyclo{D-Lys-D-Phe-D-Asp-Gly-Arg} [SEQ. ID NO.: 14];

(o) cyclo{D-Phe-D-Lys([2-[[[5-[carbonyl]-2-pyridinyl]hydrazono]methyl]-benzenesulfonic acid])-D-Asp-Gly-Arg} [SEQ. ID NO.: 15];

(p) cyclo{N-Me-Arg-Gly-Asp-ATA-D-Lys([2-[[[5-[carbonyl]-2-pyridinyl]hydrazono]methyl]-benzenesulfonic acid])} [SEQ. ID NO.: 16];

(q) cyclo{Cit-Gly-Asp-D-Phe-Lys([2-[[[5-[carbonyl]-2-pyridinyl]hydrazono]methyl]-benzenesulfonic acid])} [SEQ. ID NO.: 17];

(r) 2-(1,4,7,10-tetraaza-4,7,10-tris(carboxymethyl)-1-cyclododecyl)acetyl-Glu(cyclo{Lys-Arg-Gly-Asp-D-Phe})-cyclo{Lys-Arg-Gly-Asp-D-Phe} [SEQ. ID NO.: 18];

(s) cyclo{Arg-Gly-Asp-D-Phe-Lys(DTPA)} [SEQ. ID NO.: 19];

(t) cyclo{Arg-Gly-Asp-D-Phe-Lys}$_2$(DTPA) [SEQ. ID NO.: 20];

(u) Cyclo{Arg-Gly-Asp-D-Tyr(N-DTPA-3-aminopropyl)-Val} [SEQ. ID NO.: 21];

(v) cyclo{Orn(d-N-2-Imidazolinyl)-Gly-Asp-D-Tyr)N-[2-[[[5-[carbonyl]-2-pyridinyl]hydrazono]methyl]-benzenesulfonic acid]-3-aminopropyl)-Val} [SEQ. ID NO.: 22];

(w) cyclo{Lys-Gly-Asp-D-Tyr(N-[2-[[[5-[carbonyl]-2-pyridinyl]hydrazono]methyl]-benzenesulfonic acid]-3-aminopropyl)-Val} [SEQ. ID NO.: 23];

(x) cyclo[Cys(2-aminoethyl)-Gly-Asp-D-Tyr(N-2-[[[5-[carbonyl]-2-pyridinyl]hydrazono]methyl]-benzenesulfonic acid]-3-aminopropyl)-Val} [SEQ. ID NO.: 24];

(y) cyclo{HomoLys-Gly-Asp-D-Tyr(N-[2-[[[5-[carbonyl]-2-pyridinyl]hydrazono]methyl]-benzenesulfonic acid]-3-aminopropyl)-Val} [SEQ. ID NO.: 25];

(z) cyclo{Orn(d-N-Benzylcarbamoyl)-Gly-Asp-D-Tyr(N-[2-[[[5-[carbonyl]-2-pyridinyl]hydrazono]methyl]-benzenesulfonic acid]-3-aminopropyl)-Val} [SEQ. ID NO.: 26];

(aa) cyclo{Dap(b-(2-benzimidazolylacetyl))-Gly-Asp-D-Tyr(N-[2-[[[5-[carbonyl]-2-pyridinyl]hydrazono]methyl]-benzenesulfonic acid]-3-aminopropyl)-Val} [SEQ. ID NO.: 27];

(bb) cyclo{Orn(d-N-2-Imidazolinyl)-Gly-Asp-D-Phe-Lys(N-[2-[[[5-[carbonyl]-2-pyridinyl]hydrazono]methyl]-methyl]-benzenesulfonic acid])} [SEQ. ID NO.: 28];

(cc) cyclo{Orn(d-N-Benzylcarbamoyl)-Gly-Asp-D-Phe-Lys(N-[2-[[[5-[carbonyl]-2-pyridinyl]hydrazono]-methyl]-benzenesulfonic acid])} [SEQ. ID NO.: 29];

(dd) cyclo{Lys-D-Val-D-Tyr(N-[2-[[[5-[carbonyl]-2-pyridinyl]hydrazono]methyl]-benzenesulfonic acid]-3-aminopropyl)-D-Asp-Gly} [SEQ. ID NO.: 30];

(ee) cyclo{Orn(d-N-Benzylcarbamoyl)-D-Val-D-Tyr(N-[2-[[[]5-[carbonyl]-2-pyridinyl]hydrazono]methyl]-benzenesulfonic acid]-3-aminopropyl)-D-Asp-Gly} [SEQ. ID NO.: 31]; and, (ff) cyclo{Orn(d-N-2-Imidazolinyl)-D-Val-D-Tyr(N-[2-[[[5-[carbonyl]-2-pyridinyl]hydrazono]methyl]-benzenesulfonic acid]-3-aminopropyl)-D-Asp-Gly} [SEQ. ID NO.: 32];

or a pharmaceutically acceptable salt form thereof.

[7] In a further preferred embodiment, the present invention provides a kit comprising a compound of the present invention.

[8] In an even further preferred embodiment, the kit further comprises one or more ancillary ligands and a reducing agent.

[9] In a still further preferred embodiment, the ancillary ligands are tricine and TPPTS.

[10] In another still further preferred embodiment, the reducing agent is tin(II).

[11] In a second embodiment, the present invention provides a novel diagnostic or therapeutic metallopharmaceutical composition, comprising: a metal, a chelator capable of chelating the metal and a targeting moiety, wherein the targeting moiety is bound to the chelator, is a peptide or peptidomimetic and binds to a receptor that is upregulated during angiogenesis and the compound has 0–1 linking groups between the targeting moiety and chelator.

[12] In another preferred embodiment, the metallopharmaceutical is a diagnostic radiopharmaceutical, the metal is a radioisotope selected from the group: $^{99m}$Tc, $^{95}$Tc, $^{111}$In, $^{62}$Cu, $^{64}$Cu, $^{67}$Ga, and $^{68}$Ga, the targeting moiety is a peptide or a mimetic thereof and the receptor is selected from the group: EGFR, FGFR, PDGFR, Flk-1/KDR, Flt-1, Tek, Tie, neuropilin-1, endoglin, endosialin, A×1, $\alpha_v\beta_3$, $\alpha_v\beta_3$, $\alpha_v\beta_5$, $\alpha_5\beta_1$, $\alpha_4\beta_1$, and $\alpha_2\beta_2$ and the linking group is present between the targeting moiety and chelator.

[13] In another more preferred embodiment, the targeting moiety is a cyclic pentapeptide and the receptor is $\alpha_v\beta_3$.

[14] In another even more preferred embodiment, the radioisotope is $^{99m}$Tc or $^{95}$Tc, the radiopharmaceutical further comprises a first ancillary ligand and a second ancillary ligand capable of stabilizing the radiopharmaceutical.

[15] In another still more preferred embodiment, the radioisotope is $^{99m}$Tc.

[16] In another further preferred embodiment, the radiopharmaceutical is selected from the group:

$^{99m}$Tc(tricine)(TPPTS)(cyclo(Arg-Gly-Asp-D-Tyr(N-[[5-[carbonyl]-2-pyridinyl]diazenido]-3-aminopropyl)-Val)) [SEQ. ID NO.: 33];

$^{99m}$Tc(tricine)(TPPMS)(cyclo(Arg-D-Val-D-Tyr(N-[[5-[carbonyl]-2-pyridinyl]diazenido]-3-aminopropyl)-D-Asp-Gly)) [SEQ. ID NO.: 34];

$^{99m}$Tc(tricine)(TPPDS)(cyclo(Arg-D-Val-D-Tyr(N-[[5-[carbonyl]-2-pyridinyl]diazenido]-3-aminopropyl)-D-Asp-Gly)) [SEQ. ID NO.: 35];

$^{99m}$Tc(tricine)(TPPTS)(cyclo(Arg-D-Val-D-Tyr(N-[[5-[carbonyl]-2-pyridinyl]diazenido]-3-aminopropyl)-D-Asp-Gly)) [SEQ. ID NO.: 36];

$^{99m}$Tc(tricine)(TPPTS)(cyclo(Arg-Gly-Asp-D-Phe-Lys(N-[[5-[carbonyl]-2-pyridinyl]diazenido]))) [SEQ. ID NO.: 37];

$^{99m}$Tc(tricine)(TPPTS)(cyclo(Arg-Gly-Asp-D-Tyr-Lys(N-[[5-[carbonyl]-2-pyridinyl]diazenido]))) [SEQ. ID NO.: 38];

$^{99m}$Tc(tricine)(TPPTS)([2-[[[5-[carbonyl]-2-pyridinyl]hydrazono]methyl]-benzenesulfonic acid]-Phe-Glu (cyclo{Lys-Arg-Gly-Asp-D-Phe})-cyclo{Lys-Arg-Gly-Asp-D-Phe}) [SEQ. ID NO.: 39];

$^{99m}$Tc(tricine)(TPPTS)(cyclo{Arg-Gly-Asp-D-Nal-Lys([2-[[[5-[carbonyl]-2-pyridinyl]hydrazono]methyl]-benzenesulfonic acid])}) [SEQ. ID NO.: 40];

$^{99m}$Tc(tricine)(TPPTS)([2-[[[5-[carbonyl]-2-pyridinyl]-hydrazono]methyl]-benzenesulfonic acid]-Glu(cyclo{Lys-Arg-Gly-Asp-D-Nal})-cyclo{Lys-Arg-Gly-Asp-D-Nal}) [SEQ. ID NO.: 41];

$^{99m}$Tc(tricine)(TPPTS)(cyclo(Arg-Gly-Asp-D-Tyr((N-[[5-[carbonyl]-2-pyridinyl]diazenido]-18-amino-14-aza-4,7,10-oxy-15-oxo-octadecoyl)-3-aminopropyl)-Val)) [SEQ. ID NO.: 42];

$^{99m}$Tc(tricine)(TPPTS)(N-[[5-[carbonyl]-2-pyridinyl]-Glu (O-cyclo(Lys-Arg-Gly-Asp-D-Phe))-O-cyclo(Lys-Arg-Gly-Asp-D-Phe)) [SEQ. ID NO.: 43];

$^{99m}$Tc(tricine)(TPPTS)(N-[[5-[carbonyl]-2-pyridinyl]diazenido]-Gly(O-cyclo(D-Tyr(3-aminopropyl)-Val-Arg-Gly-Asp))-O-cyclo(D-Tyr(3-aminopropyl)-Val-Arg-Gly-Asp)) [SEQ. ID NO.: 44];

$^{99m}$Tc(tricine)(TPPTS)(cyclo(Arg-Gly-Asp-Lys(N-[[5-[carbonyl]-2-pyridinyl]diazenido])-D-Val)) [SEQ. ID NO.: 45];

$^{99m}$Tc(tricine)(TPPTS)(cyclo{D-Lys([2-[[[5-[carbonyl]-2-pyridinyl]hydrazono]methyl]-benzenesulfonic acid])-D-Phe-D-Asp-Gly-Arg}) [SEQ. ID NO.: 46];

$^{99m}$Tc(tricine)(TPPTS)(2-[[[5-[carbonyl]-2-pyridinyl]hydrazono]methyl]-benzenesulfonic acid]-Glu(cyclo{D-Lys-D-Phe-D-Asp-Gly-Arg})-cyclo{D-Lys-D-Phe-D-Asp-Gly-Arg}) [SEQ. ID NO.: 47];

$^{99m}$Tc(tricine)(TPPTS)(cyclo{D-Phe-D-Lys([2-[[[5-[carbonyl]-2-pyridinyl]hydrazono]methyl]-benzenesulfonic acid])-D-Asp-Gly-Arg}) [SEQ. ID NO.: 48];

$^{99m}$Tc(tricine)(TPPTS)(cyclo(N-Me-Arg-Gly-Asp-ATA-D-Lys(N-[[5-[carbonyl]-2-pyridinyl]diazenido]))) [SEQ. ID NO.: 49];

$^{99m}$Tc(tricine)(TPPTS)(cyclo{Cit-Gly-Asp-D-Phe-Lys([2-[[[5-[carbonyl]-2-pyridinyl]hydrazono]methyl]-benzenesulfonic acid])}) [SEQ. ID NO.: 50]; and, $^{99m}$Tc(tricine)(1,2,4-triazole)(cyclo(Arg-Gly-Asp-D-Tyr(N-[[5-[carbonyl]-2-pyridinyl]diazenido]-3-aminopropyl)-Val)) [SEQ. ID NO.: 51];

[17] In another even more preferred embodiment, the radioisotope is $^{111}$In.

[18] In another still more preferred embodiment, the radiopharmaceutical is selected from the group:

(DOTA-$^{111}$In)-Gly(cyclo{Lys-Arg-Gly-Asp-D-Phe})-cyclo{Lys-Arg-Gly-Asp-D-Phe} [SEQ. ID NO.: 52];

cyclo(Arg-Gly-Asp-D-Phe-Lys(DTPA-$^{111}$In)) [SEQ. ID NO.: 53]; and, cyclo(Arg-Gly-Asp-D-Phe-Lys)$_2$(DTPA-$^{111}$In) [SEQ. ID NO.: 54].

[19] In another preferred embodiment, the metallopharmaceutical is a therapeutic radiopharmaceutical, the metal is a radioisotope selected from the group: $^{33}$P, $^{125}$I, $^{186}$Re, $^{188}$Re, $^{153}$Sm, $^{166}$Ho, $^{177}$Lu, $^{149}$Pm, 90Y, $^{212}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{67}$CU, $^{105}$Rh, $^{111}$Ag, and $^{192}$Ir, the targeting moiety is a peptide or a mimetic thereof and the receptor is selected from the group: EGFR, FGFR, PDGFR, Flk-1/KDR, Flt-1, Tek, Tie, neuropilin-1, endoglin, endosialin, A×1, $\alpha_v\beta_3$, $\alpha_v\beta_3$, $\alpha_v\beta_5$, $\alpha_5\beta_1$, $\alpha_4\beta_1$, and $\alpha_2\beta_2$ and the linking group is present between the targeting moiety and chelator.

[20] In another more preferred embodiment, the targeting moiety is a cyclic pentapeptide and the receptor is $\alpha_v\beta_3$.

[21] In another even more preferred embodiment, the radioisotope is $^{153}$Sm.

[22] In another still more preferred embodiment, the radiopharmaceutical is selected from the group:

cyclo(Arg-Gly-Asp-D-Phe-Lys(DTPA-153Sm)') [SEQ. ID NO.: 55];

cyclo(Arg-Gly-Asp-D-Phe-Lys)$_2$(DTPA-153Sm) [SEQ. ID NO.: 56]; and, cyclo(Arg-Gly-Asp-D-Tyr(N-DTPA(153Sm)-3-aminopropyl)-Val) [SEQ. ID NO.: 57].

[23] In another even more preferred embodiment, the radioisotope is $^{177}$Lu.

[24] In another still more preferred embodiment, the radiopharmaceutical is selected from the group:

cyclo(Arg-Gly-Asp-D-Phe-Lys(DTPA-$^{177}$Lu)) [SEQ. ID NO.: 58];
(DOTA-$^{177}$Lu)-Glu(cyclo{Lys-Arg-Gly-Asp-D-Phe})-cyclo{Lys-Arg-Gly-Asp-D-Phe} [SEQ. ID NO.: 59];
cyclo(Arg-Gly-Asp-D-Phe-Lys)$_2$(DTPA-$^{177}$Lu) [SEQ. ID NO.: 60]; and,
cyclo(Arg-Gly-Asp-D-Tyr(N-DTPA($^{177}$Lu)-3-aminopropyl)-Val) [SEQ. ID NO.: 61].

[25] In another even more preferred embodiment, the radioisotope is 90Y.

[26] In another still more preferred embodiment, the radiopharmaceutical is:
(DOTA-$^{90}$Y)-Glu(cyclo{Lys-Arg-Gly-Asp-D-Phe})-cyclo{Lys-Arg-Gly-Asp-D-Phe} [SEQ. ID NO.: 62];

[27] In another preferred embodiment, the metallopharmaceutical is a MRI contrast agent, the metal is a paramagnetic metal ion selected from the group: Gd(III), Dy(III), Fe(III), and Mn(II), the targeting moiety is a peptide or a mimetic thereof and the receptor is selected from the group: EGFR, FGFR, PDGFR, Flk-1/KDR, Flt-1, Tek, Tie, neuropilin-1, endoglin, endosialin, A×1, $\alpha_v\beta_3$, $\alpha_v\beta_3$, $\alpha_v\beta_5$, $\alpha_5\beta_1$, $\alpha_4\beta_1$, $\alpha_1\beta_1$, and $\alpha_2\beta_2$ and the linking group is present between the targeting moiety and chelator.

[28] In another more preferred embodiment, the targeting moiety is a cyclic pentapeptide and the receptor is $\alpha_v\beta_3$.

[29] In another even more preferred embodiment, the metal ion is Gd(III).

[30] In another still more preferred embodiment, the contrast agent is:
cyclo(Arg-Gly-Asp-D-Tyr(N-DTPA(Gd(III))-3-aminopropyl)-Val) [SEQ. ID NO.: 63].

[31] In another preferred embodiment, the metallopharmaceutical is a X-ray contrast agent, the metal is selected from the group: Re, Sm, Ho, Lu, Pm, Y, Bi, Pd, Gd, La, Au, Au, Yb, Dy, Cu, Rh, Ag, and Ir, the targeting moiety is a cyclic pentapeptide, the receptor is $\alpha_v\beta_3$, and the linking group is present between the targeting moiety and chelator.

[32] In another even more preferred embodiment, the present invention provides a novel method of treating rheumatoid arthritis in a patient comprising: administering a therapeutic radiopharmaceutical of the present invention capable of localizing in new angiogenic vasculature to a patient by injection or infusion.

[33] In another even more preferred embodiment, the present invention provides a novel method of treating cancer in a patient comprising: administering to a patient in need thereof a therapeutic radiopharmaceutical of the present invention by injection or infusion.

[34] In another even more preferred embodiment, the present invention provides a novel method of imaging formation of new blood vessels in a patient comprising: (1) administering a diagnostic radiopharmaceutical, a MRI contrast agent, or a X-ray contrast agent of the present invention to a patient by injection or infusion; (2) imaging the area of the patient wherein the desired formation of new blood vessels is located.

[35] In another even more preferred embodiment, the present invention provides a novel method of imaging cancer in a patient comprising: (1) administering a diagnostic radiopharmaceutical of the present invention to a patient by injection or infusion; (2) imaging the patient using planar or SPECT gamma scintigraphy, or positron emission tomography.

[36] In another even more preferred embodiment, the present invention provides a novel method of imaging cancer in a patient comprising: (1) administering a MRI contrast agent of the present invention; and (2) imaging the patient using magnetic resonance imaging.

[37] In another even more preferred embodiment, the present invention provides a novel method of imaging cancer in a patient comprising: (1) administering a X-ray to contrast agent of the present invention; and (2) imaging the patient using X-ray computed tomography.

[38] In a third embodiment, the present invention provides a novel compound capable of being used in an ultrasound contrast composition, comprising: a targeting moiety and a surfactant, wherein the targeting moiety is bound to the surfactant, is a peptide or peptidomimetic, and binds to a receptor that is upregulated during angiogenesis and the compound has 0–1 linking groups between the targeting moiety and surfactant.

[39] In a preferred embodiment, the targeting moiety is a peptide or a mimetic thereof and the receptor is selected from the group: EGFR, FGFR, PDGFR, Flk-1/KDR, Flt-1, Tek, Tie, neuropilin-1, endoglin, endosialin, A×1, $\alpha_v\beta_3$, $\alpha_v\beta_3$, $\alpha_v\beta_5$, $\alpha_5\beta_1$, $\alpha_4\beta_1$, $\alpha_1\beta_1$, and $\alpha_2\beta_2$ and the linking group is present between the targeting moiety and surfactant.

[40] In a more preferred embodiment, the receptor is the integrin $\alpha_v\beta_3$ and the compound is of the formula:

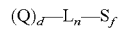

wherein, Q is a cyclic pentapeptide independently selected from the group:

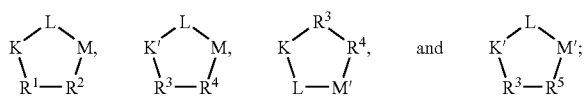

K is an L-amino acid independently selected at each occurrence from the group: arginine, citrulline, N-methylarginine, lysine, homolysine, 2-aminoethylcysteine, δ-N-2-imidazolinylornithine, δ-N-benzylcarbamoylornithine, and β-2-benzimidazolylacetyl-1,2-diaminopropionic acid;

K' is a D-amino acid independently selected at each occurrence from the group: arginine, citrulline, N-methylarginine, lysine, homolysine, 2-aminoethylcysteine, δ-N-2-imidazolinylornithine, δ-N-benzylcarbamoylornithine, and β-2-benzimidazolylacetyl-1,2-di aminopropionic acid;

L is independently selected at each occurrence from the group: glycine, L-alanine, and D-alanine;

M is L-aspartic acid;

M' is D-aspartic acid;

R$^1$ is an amino acid substituted with 0–1 bonds to L$_n$, independently selected at each occurrence from the group: glycine, L-valine, D-valine, alanine, leucine, isoleucine, norleucine, 2-aminobutyric acid, 2-aminohexanoic acid, tyrosine, phenylalanine, thienylalanine, phenylglycine, cyclohexylalanine, homophenylalanine, 1-naphthylalanine, lysine, serine, ornithine, 1,2-diaminobutyric acid, 1,2-diaminopropionic acid, cysteine, penicillamine, and methionine;

R$^2$ is an amino acid, substituted with 0–1 bonds to L$_n$, independently selected at each occurrence from the group: glycine, valine, alanine, leucine, isoleucine, norleucine, 2-aminobutyric acid, 2-aminohexanoic acid, tyrosine, L-phenylalanine, D-phenylalanine, thienylalanine, phenylglycine, biphenylglycine, cyclohexylalanine, homophenylalanine, L-1-naphthylalanine, D-1-naphthylalanine, lysine, serine, ornithine, 1,2-diaminobutyric acid, 1,2-diaminopropionic acid, cysteine, penicillamine, methionine, and 2-aminothiazole-4-acetic acid;

$R^3$ is an amino acid, substituted with 0–1 bonds to $L_n$, independently selected at each occurrence from the group: glycine, D-valine, D-alanine, D-leucine, D-isoleucine, D-norleucine, D-2-aminobutyric acid, D-2-aminohexanoic acid, D-tyrosine, D-phenylalanine, D-thienylalanine, D-phenylglycine, D-cyclohexylalanine, D-homophenylalanine, D-1-naphthylalanine, D-lysine, D-serine, D-ornithine, D-1,2-diaminobutyric acid, D-1,2-diaminopropionic acid, D-cysteine, D-penicillamine, and D-methionine;

$R^4$ is an amino acid, substituted with 0–1 bonds to $L_n$, independently selected at each occurrence from the group: glycine, D-valine, D-alanine, D-leucine, D-isoleucine, D-norleucine, D-2-aminobutyric acid, D-2-aminohexanoic acid, D-tyrosine, D-phenylalanine, D-thienylalanine, D-phenylglycine, D-cyclohexylalanine, D-homophenylalanine, D-1-naphthylalanine, D-lysine, D-serine, D-ornithine, D-1,2-diaminobutyric acid, D-1,2-diaminopropionic acid, D-cysteine, D-penicillamine, D-methionine, and 2-aminothiazole-4-acetic acid;

$R^5$ is an amino acid, substituted with 0–1 bonds to $L_n$, independently selected at each occurrence from the group: glycine, L-valine, L-alanine, L-leucine, L-isoleucine, L-norleucine, L-2-aminobutyric acid, L-2-aminohexanoic acid, L-tyrosine, L-phenylalanine, L-thienylalanine, L-phenylglycine, L-cyclohexylalanine, L-homophenylalanine, L-1-naphthylalanine, L-lysine, L-serine, L-ornithine, L-1,2-diaminobutyric acid, L-1,2-diaminopropionic acid, L-cysteine, L-penicillamine, L-methionine, and 2-aminothiazole-4-acetic acid;

provided that one of $R^1$, $R^2$, $R^3$, $R^4$, and $R^5$ in each Q is substituted with a bond to $L_n$, further provided that when $R^2$ is 2-aminothiazole-4-acetic acid, K is N-methylarginine, further provided that when $R^4$ is 2-aminothiazole-4-acetic acid, K and K' are N-methylarginine, and still further provided that when $R^5$ is 2-aminothiazole-4-acetic acid, K' is N-methylarginine;

d is selected from 1, 2, 3, 4, 5, 6, 7, 8, 9, and 10;

$S_f$ is a surfactant which is a lipid or a compound of the formula:

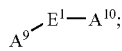

$A^9$ is selected from the group: OH and $OR^{27}$;
$A^{10}$ is $OR^{27}$;
$R^{27}$ is $C(=O)C_{1-20}$ alkyl;
$E^1$ is $C_{1-10}$ alkylene substituted with 1–3 $R^{28}$;
$R^{28}$ is independently selected at each occurrence from the group: $R^{30}$, $-PO_3H-R^{30}$, $=O$, $-CO_2R^{29}$, $-C(=O)R^{29}$, $-C(=O)N(R^{29})_2$, $-CH_2OR^{29}$, $-OR^{29}$, $-N(R^{29})_2$, $C_1-C_5$ alkyl, and $C_2-C_4$ alkenyl;
$R^{29}$ is independently selected at each occurrence from the group: $R^{30}$, H, $C_1-C_6$ alkyl, phenyl, benzyl, and trifluoromethyl;
$R^{30}$ is a bond to $L_n$;
$L_n$ is a linking group having the formula:

$(CR^6R^7)_g-(W)_h-(C^{6a}R^{7a})_{g'}-(Z)_k-(W)_{h'}-(CR^8R^9)_{g''}-(W)_{h''}-(CR^{8a}R^{9a})_{g'''}$

W is independently selected at each occurrence from the group: O, S, NH, NHC(=O), C(=O)NH, C(=O), C(=O)O, OC(=O), NHC(=S)NH, NHC(=O)NH, $SO_2$, $(OCH_2CH_2)_{20-200}$, $(CH_2CH_2O)_{20-200}$, $(OCH_2CH_2CH_2)_{20-200}$, $(CH_2CH_2CH_2O)_{20-200}$, and $(aa)_{t'}$;

aa is independently at each occurrence an amino acid;

Z is selected from the group: aryl substituted with 0–3 $R^{10}$, $C_{3-10}$ cycloalkyl substituted with 0–3 $R^{10}$, and a 5–10 membered heterocyclic ring system containing 1–4 heteroatoms independently selected from N, S, and O and substituted with 0–3 $R^{10}$;

$R^6$, $R^{6a}$, $R^7$, $R^{7a}$, $R^8$, $R^{8a}$, $R^9$ and $R^{9a}$ are independently selected at each occurrence from the group: H, =O, COOH, $SO_3H$, $PO_3H$, $C_1-C_5$ alkyl substituted with 0–3 $R^{10}$, aryl substituted with 0–3 $R^{10}$, benzyl substituted with 0–3 $R^{10}$, and $C_1-C_5$ alkoxy substituted with 0–3 $R^{10}$, $NHC(=O)R^{11}$, $C(=O)NHR^{11}$, $NHC(=O)NHR^{11}$, $NHR^{11}$, $R^{11}$, and a bond to $S_f$;

$R^{10}$ is independently selected at each occurrence from the group: a bond to $S_f$, $COOR^{11}$, OH, $NHR^{11}$, $SO_3H$, $PO_3H$, aryl substituted with 0–3 $R^{11}$, $C_{1-5}$ alkyl substituted with 0–1 $R^{12}$, $C_{1-5}$ alkoxy substituted with 0–1 $R^{12}$, and a 5–10 membered heterocyclic ring system containing 1–4 heteroatoms independently selected from N, S, and O and substituted with 0–3 $R^{11}$;

$R^{11}$ is independently selected at each occurrence from the group: H, aryl substituted with 0–1 $R^{12}$, a 5–10 membered heterocyclic ring system containing 1–4 heteroatoms independently selected from N, S, and O and substituted with 0–1 $R^{12}$, $C_{3-10}$ cycloalkyl substituted with 0–1 $R^{12}$ amino acid substituted with 0–1 $R^{12}$ and a bond to $S_f$;

$R^{12}$ is a bond to $S_f$;

k is selected from 0, 1, and 2;
h is selected from 0, 1, and 2;
h' is selected from 0, 1, 2, 3, 4, and 5;
h'' is selected from 0, 1, 2, 3, 4, and 5;
g is selected from 0, 1, 2, 3, 4, 5, 6, 7, 8, 9, and 10;
g' is selected from 0, 1, 2, 3, 4, 5, 6, 7, 8, 9, and 10;
g'' is selected from 0, 1, 2, 3, 4, 5, 6, 7, 8, 9, and 10;
g''' is selected from 0, 1, 2, 3, 4, 5, 6, 7, 8, 9, and 10;
t' is selected from 0, 1, 2, 3, 4, 5, 6, 7, 8, 9, and 10;
and a pharmaceutically acceptable salt thereof.

[41] In another even more preferred embodiment, the compound is of the formula:

$$Q-L_n-S_f$$

wherein, Q is a cyclic pentapeptide independently selected from the group:

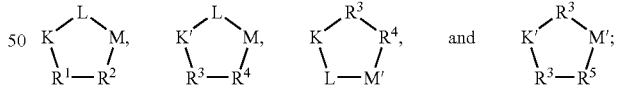

K is an L-amino acid independently selected at each occurrence from the group: arginine, citrulline, N-methylarginine, lysine, homolysine, 2-aminoethylcysteine, δ-N-2-imidazolinylornithine, δ-N-benzylcarbamoylornithine, and β-2-benzimidazolylacetyl-1,2-diaminopropionic acid;

K' is a D-amino acid independently selected at each occurrence from the group: arginine, citrulline, N-methylarginine, lysine, homolysine, 2-aminoethylcysteine, δ-N-2-imidazolinylornithine, δ-N-benzylcarbamoylornithine, and β-2-benzimidazolylacetyl-1,2-diaminopropionic acid;

L is independently selected at each occurrence from the group: glycine, L-alanine, and D-alanine;

M is L-aspartic acid;

M' is D-aspartic acid;

R$^1$ is an amino acid substituted with 0–1 bonds to L$_n$, independently selected at each occurrence from the group: glycine, L-valine, D-valine, alanine, leucine, isoleucine, norleucine, 2-aminobutyric acid, 2-aminohexanoic acid, tyrosine, phenylalanine, thienylalanine, phenylglycine, cyclohexylalanine, homophenylalanine, 1-naphthylalanine, lysine, serine, ornithine, 1,2-diaminobutyric acid, 1,2-diaminopropionic acid, cysteine, penicillamine, and methionine;

R$^2$ is an amino acid, substituted with 0–1 bonds to L$_n$, independently selected at each occurrence from the group: glycine, valine, alanine, leucine, isoleucine, norleucine, 2-aminobutyric acid, 2-aminohexanoic acid, tyrosine, L-phenylalanine, D-phenylalanine, thienylalanine, phenylglycine, biphenylglycine, cyclohexylalanine, homophenylalanine, L-1-naphthylalanine, D-1-naphthylalanine, lysine, serine, ornithine, 1,2-diaminobutyric acid, 1,2-diaminopropionic acid, cysteine, penicillamine, methionine, and 2-aminothiazole-4-acetic acid;

R$^3$ is an amino acid, substituted with 0–1 bonds to L$_n$, independently selected at each occurrence from the group: glycine, D-valine, D-alanine, D-leucine, D-isoleucine, D-norleucine, D-2-aminobutyric acid, D-2-aminohexanoic acid, D-tyrosine, D-phenylalanine, D-thienylalanine, D-phenylglycine, D-cyclohexylalanine, D-homophenylalanine, D-1-naphthylalanine, D-lysine, D-serine, D-ornithine, D-1,2-diaminobutyric acid, D-1,2-diaminopropionic acid, D-cysteine, D-penicillamine, and D-methionine;

R$^4$ is an amino acid, substituted with 0–1 bonds to L$_n$, independently selected at each occurrence from the group: glycine, D-valine, D-alanine, D-leucine, D-isoleucine, D-norleucine, D-2-aminobutyric acid, D-2-aminohexanoic acid, D-tyrosine, D-phenylalanine, D-thienylalanine, D-phenylglycine, D-cyclohexylalanine, D-homophenylalanine, D-1-naphthylalanine, D-lysine, D-serine, D-ornithine, D-1,2-diaminobutyric acid, D-1,2-diaminopropionic acid, D-cysteine, D-penicillamine, D-methionine, and 2-aminothiazole-4-acetic acid;

R$^5$ is an amino acid, substituted with 0–1 bonds to L$_n$, independently selected at each occurrence from the group: glycine, L-valine, L-alanine, L-leucine, L-isoleucine, L-norleucine, L-2-aminobutyric acid, L-2-aminohexanoic acid, L-tyrosine, L-phenylalanine, L-thienylalanine, L-phenylglycine, L-cyclohexylalanine, L-homophenylalanine, L-1-naphthylalanine, L-lysine, L-serine, L-ornithine, L-1,2-diaminobutyric acid, L-1,2-diaminopropionic acid, L-cysteine, L-penicillamine, L-methionine, and 2-aminothiazole-4-acetic acid;

provided that one of R$^1$, R$^2$, R$^3$, R$^4$, and R$^5$ in each Q is substituted with a bond to L$_n$, further provided that when R$^2$ is 2-aminothiazole-4-acetic acid, K is N-methylarginine, further provided that when R$^4$ is 2-aminothiazole-4-acetic acid, K and K' are N-methylarginine, and still further provided that when R$^5$ is 2-aminothiazole-4-acetic acid, K' is N-methylarginine;

S$_f$ is a surfactant which is a lipid or a compound of the formula:

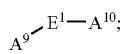

A$^9$ is OR$^{27}$;
A$^{10}$ is OR$^{27}$;
R$^{27}$ is C(=O)C$_{1-15}$ alkyl;
E$^1$ is C$_{1-4}$ alkylene substituted with 1–3 R$^{28}$;

R$^{28}$ is independently selected at each occurrence from the group: R$^{30}$, —PO$_3$H—R$^{30}$, =O, —CO$_2$R$^{29}$, —C(=O)R$^{29}$, —CH$_2$OR$^{29}$, —OR$^{29}$, and C$_1$–C$_5$ alkyl;

R$^{29}$ is independently selected at each occurrence from the group: R$^{30}$, H, C$_1$–C$_6$ alkyl, phenyl, and benzyl;

R$^{30}$ is a bond to L$_n$;

L$_n$ is a linking group having the formula:

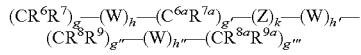

W is independently selected at each occurrence from the group: O, S, NH, NHC(=O), C(=O)NH, C(=O), C(=O)O, OC(=O), NHC(=S)NH, NHC(=O)NH, SO$_2$, (OCH$_2$CH$_2$)$_{20-200}$, (CH$_2$CH$_2$O)$_{20-200}$, (OCH$_2$CH$_2$CH$_2$)$_{20-200}$, (CH$_2$CH$_2$CH$_2$O)$_{20-200}$, and (aa)$_{t'}$;

aa is independently at each occurrence an amino acid;

Z is selected from the group: aryl substituted with 0–3 R$^{10}$, C$_{3-10}$ cycloalkyl substituted with 0–3 R$^{10}$, and a 5–10 membered heterocyclic ring system containing 1–4 heteroatoms independently selected from N, S, and O and substituted with 0–3 R$^{10}$;

R$^6$, R$^{6a}$, R$^7$, R$^{7a}$, R$^8$, R$^{8a}$, R$^9$ and R$^{9a}$ are independently selected at each occurrence from the group: H, =O, C$_1$–C$_5$ alkyl substituted with 0–3 R$^{10}$, and C$_1$–C$_5$ alkoxy substituted with 0–3 R$^{10}$, and a bond to S$_f$;

R$^{10}$ is independently selected at each occurrence from the group: a bond to S$_f$, COOR$^{11}$, OH, NHR$^{11}$, C$_{1-5}$ alkyl substituted with 0–1 R$^{12}$ and C$_{1-5}$ alkoxy substituted with 0–1 R$^{12}$;

R$^{11}$ is independently selected at each occurrence from the group: H, aryl substituted with 0–1 R$^{12}$, C$_{3-10}$ cycloalkyl substituted with 0–1 R$^{12}$ amino acid substituted with 0–1 R$^{12}$, and a bond to S$_f$;

R$^{12}$ is a bond to S$_f$;

k is selected from 0, 1, and 2;

h is selected from 0, 1, and 2;

h' is selected from 0, 1, 2, 3, 4, and 5;

h" is selected from 0, 1, 2, 3, 4, and 5;

g is selected from 0, 1, 2, 3, 4, and 5;

g' is selected from 0, 1, 2, 3, 4, and 5;

g" is selected from 0, 1, 2, 3, 4, and 5;

g'" is selected from 0, 1, 2, 3, 4, and 5;

s is selected from 0, 1, 2, 3, 4, and 5;

s' is selected from 0, 1, 2, 3, 4, and 5;

s" is selected from 0, 1, 2, 3, 4, and 5;

t is selected from 0, 1, 2, 3, 4, and 5;

t' is selected from 0, 1, 2, 3, 4, and 5;

and a pharmaceutically acceptable salt thereof.

[42] In another still more preferred embodiment, the present invention provides a compound selected from the group:

1-(1,2-Dipalmitoyl-sn-glycero-3-phosphoethanolamino)-12-(cyclo(Arg-Gly-Asp-D-Phe-Lys)-dodecane-1,12-dione [SEQ. ID NO.: 64];

1-(1,2-Dipalmitoyl-sn-glycero-3-phosphoethanolamino)-12-((ω-amino-PEG$_{3400}$-α-carbonyl)-cyclo(Arg-Gly-Asp-D-Phe-Lys))-dodecane-1,12-dione [SEQ. ID NO.: 65]; and, 1-(1,2-Dipalmitoyl-sn-glycero-3-phosphoethanolamino)-12-((ω-amino-PEG$_{3400}$-α-carbonyl)-Glu-(cyclo(Arg-Gly-Asp-D-Phe-Lys))$_2$)-Dodecane-1,12-dione [SEQ. ID NO.: 66].

[43] In another even more preferred embodiment, the present invention provides a novel ultrasound contrast agent composition, comprising:
(a) a compound comprising: a cyclic pentapeptide that binds to the integrin $\alpha_v\beta_3$, a surfactant and a linking group between the cyclicpentapeptide and the surfactant;
(b) a parenterally acceptable carrier; and,
(c) an echogenic gas.

[44] In another still more preferred embodiment, the ultrasound contrast agent further comprises: 1,2-dipalmitoyl-sn-glycero-3-phosphotidic acid, 1,2-dipalmitoyl-sn-glycero-3-phosphatidylcholine, and N-(methoxypolyethylene glycol 5000 carbamoyl)-1,2-dipalmitoyl-sn-glycero-3-phosphatidylethanolamine.

[45] In another further preferred embodiment, the echogenic gas is a $C_{2-5}$ perfluorocarbon.

[46] In another even more preferred embodiment, the present invention provides a method of imaging cancer in a patient comprising: (1) administering, by injection or infusion, a ultrasound contrast agent composition of the present invention to a patient; and (2) imaging the patient using sonography.

[47] In another even more preferred embodiment, the present invention provides a novel method of imaging formation of new blood vessels in a patient comprising: (1) administering, by injection or infusion, a ultrasound contrast agent composition of the present invention to a patient; (2) imaging the area of the patient wherein the desired formation of new blood vessels is located.

[48] In another even more preferred embodiment, the present invention provides a novel therapeutic radiopharmaceutical composition, comprising:
(a) a therapeutic radiopharmaceutical of the present invention; and,
(b) a parenterally acceptable carrier.

[49] In another even more preferred embodiment, the present invention provides a novel diagnostic radiopharmaceutical composition, comprising:
(a) a diagnostic radiopharmaceutical, a MRI contrast agent, or a X-ray contrast agent of the present invention; and,
(b) a parenterally acceptable carrier.

[50] In another even more preferred embodiment, the present invention provides a novel therapeutic radiopharmaceutical composition, comprising: a radiolabelled targeting moiety, wherein the targeting moiety is a compound Q and the radiolabel is a therapeutic isotope selected from the group: $^{35}S$, $^{32}P$, $^{125}I$, $^{131}I$, and $^{211}At$.

[51] In another further preferred embodiment, the present invention provides a novel therapeutic radiopharmaceutical composition, comprising: a radiolabelled targeting moiety, wherein the targeting moiety is a compound Q and the radiolabel is a therapeutic isotope which is $^{131}I$.

[52] In another preferred embodiment, the present invention provides a kit for treating cancer, comprising a compound of Embodiment 1, or a pharmaceutically acceptable salt thereof, and at least one agent selected from the group consisting of a chemotherapeutic agent and a radiosensitizer agent, or a pharmaceutically acceptable salt thereof, and a pharmaceutically acceptable carrier.

[53] In another preferred embodiment, the present invention provides a kit according to Embodiment 52 wherein said kit comprises a plurality of separate containers, wherein at least one of said containers contains a compound of Embodiment 1, or a pharmaceutically acceptable salt thereof, and at least another of said containers contains one or more agents selected from the group consisting of a chemotherapeutic agent and a radiosensitizer agent, or a pharmaceutically acceptable salt thereof, and a pharmaceutically acceptable carrier.

[54] In another preferred embodiment, the present invention provides a kit according to Embodiment 52, wherein the chemotherapeutic agent is selected from the group consisting of mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, and leutinizing hormone releasing factor.

[55] In another preferred embodiment, the present invention provides a kit according to Embodiment 52, wherein the chemotherapeutic agent is selected from the group consisting of mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, and lisuride.

[56] In another preferred embodiment, the present invention provides a kit according to Embodiment 52 wherein the chemotherapeutic agent is selected from the group consisting of oxymetholone, tamoxifen, progesterone, mepitiostane, epitiostanol, and formestane.

[57] In another preferred embodiment, the present invention provides a kit according to Embodiment 52 wherein the chemotherapeutic agent is selected from the group consisting of interferon-alpha, interferon-2 alpha, interferon-beta, interferon-gamma, colony stimulating factor-1, colony stimulating factor-2, denileukin diftitox, interleukin-2, and leutinizing hormone releasing factor.

[58] In another preferred embodiment, the present invention provides a kit according to Embodiment 52, wherein radiosensitizer agent is selected from the group consiting of 2-(3-nitro-1,2,4-triazol-1-yl)-N-(2-methoxyethyl)acetamide, N-(3-nitro-4-quinolinyl)-4-morpholinecarboxamidine, 3-amino-1,2,4-benzotriazine-1,4-dioxide, N-(2-hydroxyethyl)-2-nitroimidazole-1-acetamide, 1-(2-nitroimidazol-1-yl)-3-(1-piperidinyl)-2-propanol, and 1-(2-nitro-1-imidazolyl)-3-(1-aziridino)-2-propanol.

[59] In another preferred embodiment, the present invention provides a therapeutic metallopharmaceutical composition according to Embodiment 11, wherein the metallopharmaceutical is a therapeutic radiopharmaceutical, further comprising at least one agent selected from the group consisting of a chemotherapeutic agent and a radiosensitizer agent, or a pharmaceutically acceptable salt thereof.

[60] In another preferred embodiment, the present invention provides a therapeutic metallopharmaceutical composition according to Embodiment 59, wherein the chemotherapeutic agent is selected from the group consisting of mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, and leutinizing hormone releasing factor.

[61] In another preferred embodiment, the present invention provides a therapeutic metallopharmaceutical composition according to Embodiment 59, wherein radiosensitizer agent is selected from the group consiting of 2-(3-nitro-1,2,4-triazol-1-yl)-N-(2-methoxyethyl)acetamide, N-(3-nitro-4-quinolinyl)-4-morpholinecarboxamidine, 3-amino-1,2,4-benzotriazine-1,4-dioxide, N-(2-hydroxyethyl)-2-nitroimidazole-1-acetamide, 1-(2-nitroimidazol-1-yl)-3-(1-piperidinyl)-2-propanol, and 1-(2-nitro-1-imidazolyl)-3-(1-aziridino)-2-propanol.

[62] In another preferred embodiment, the present invention provides a method of treating cancer in a patient comprising: administering to a patient in need thereof a therapeutic radiopharmaceutical of Embodiment 19 or a pharmaceutically acceptable salt thereof, and at least one agent selected from the group consisting of a chemotherapeutic agent and a radiosensitizer agent, or a pharmaceutically acceptable salt thereof.

[63] In another preferred embodiment, the present invention provides a method of treating cancer according to Embodiment 62, wherein the administration is by injection or infusion.

[64] In another preferred embodiment, the present invention provides a method according to Embodiment 62 wherein administering the therapeutic radiopharmaceutical and agent is concurrent.

[65] In another preferred embodiment, the present invention provides a method according to Embodiment 62 wherein administering the therapeutic radiopharmaceutical and agent is sequential.

[66] In another preferred embodiment, the present invention provides a method according to Embodiment 62 wherein the cancer is selected from the group consisting of carcinomas of the lung, breast, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, and neuroblastomas.

[67] In another preferred embodiment, the present invention provides a method according to Embodiment 62 wherein the chemotherapeutic agent is selected from the group consisting of mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, and leutinizing hormone releasing factor.

[68] In another preferred embodiment, the present invention provides a method according to Embodiment 62 wherein the radiosensitizer agent is selected from the group consiting of 2-(3-nitro-1,2,4-triazol-1-yl)-N-(2-methoxyethyl)acetamide, N-(3-nitro-4-quinolinyl)-4-morpholinecarboxamidine, 3-amino-1,2,4-benzotriazine-1,4-dioxide, N-(2-hydroxyethyl)-2-nitroimidazole-1-acetamide, 1-(2-nitroimidazol-1-yl)-3-(1-piperidinyl)-2-propanol, and 1-(2-nitro-1-imidazolyl)-3-(1-aziridino)-2-propanol.

[69] In another preferred embodiment, the present invention provides a process for the preparation of diagnostic or therapeutic metallopharmaceutical composition, said process comprising generating a macrostructure from a plurality of molecular components wherein the plurality of components includes a targeting moiety and a chelator, wherein the targeting moiety is a peptide or peptidomimetic, which is bound to the chelator, and binds to a receptor that is upregulated during angiogenesis and the compound has 0–1 linking groups between the targeting moiety and chelator.

Another embodiment of the present invention is diagnostic kits for the preparation of radiopharmaceuticals useful as imaging agents for cancer or imaging agents for imaging formation of new blood vessels. Diagnostic kits of the present invention comprise one or more vials containing the sterile, non-pyrogenic, formulation comprised of a predetermined amount of a reagent of the present invention, and optionally other components such as one or two ancillary ligands, reducing agents, transfer ligands, buffers, lyophilization aids, stabilization aids, solubilization aids and bacteriostats. The inclusion of one or more optional components in the formulation will frequently improve the ease of synthesis of the radiopharmaceutical by the practicing end user, the ease of manufacturing the kit, the shelf-life of the kit, or the stability and shelf-life of the radiopharmaceutical. The inclusion of one or two ancillary ligands is required for diagnostic kits comprising reagent comprising a hydrazine or hydrazone bonding moiety. The one or more vials that contain all or part of the formulation can independently be in the form of a sterile solution or a lyophilized solid.

Another aspect of the present invention contemplates the combination of chemotherapeutics and angiogenesis-targeted therapeutic radiopharmaceuticals of the invention, which target the luminal side of the neovasculature of tumors, to provide a surprising, and enhanced degree of tumor suppression relative to each treatment modality alone without significant additive toxicity.

Another aspect of the present invention contemplates the compounds of the present invention (i.e. a compound comprising: a targeting moiety and a chelator, wherein the targeting moiety is bound to the chelator, is a peptide or peptidomimetic, and binds to a receptor that is upregulated during angiogenesis and the compound has 0–1 linking groups between the targeting moiety and chelator) which is administered in combination therapy, with one or more chemotherapeutic agent(s) selected from the group consisting of mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, and leutinizing hormone releasing factor.

This combination therapy may further, optionally, include a radiosensitizer agent, or a pharmaceutically acceptable salt thereof, to enhance the radiotherapeutic effect together with the chemotherapeutic agent, said radiosensitizer agent being selected from the group consisting of 2-(3-nitro-1,2,4-triazol-1-yl)-N-(2-methoxyethyl)acetamide, N-(3-nitro-4-quinolinyl)-4-morpholinecarboxamidine, 3-amino-1,2,4-benzotriazine-1,4-dioxide, N-(2-hydroxyethyl)-2-nitroimidazole-1-acetamide, 1-(2-nitroimidazol-1-yl)-3-(1 piperidinyl)-2-propanol, and 1-(2-nitro-1-imidazolyl)-3-(1-aziridino)-2-propanol. A thorough discussion of radiosensitizer agents is provided in the following: Rowinsky-E K, Oncology-Huntingt., 1999 October; 13 (10 Suppl 5): 61–70; Chen-A Y et al., Oncology-Huntingt. 1999 October; 13 (10 Suppl 5): 39–46; Choy-H, Oncology-Huntingt. 1999 October; 13 (10 Suppl 5): 23–38; and Herscher-L L et al, Oncology-Huntingt. 1999 October; 13 (10 Suppl 5): 11–22, which are incorporated herein by reference.

It is a further aspect of the invention to provide kits having a plurality of active ingredients (with or without carrier) which, together, may be effectively utilized for carrying out the novel combination therapies of the invention.

It is another aspect of the invention to provide a novel pharmaceutical composition which is effective, in and of itself, for utilization in a beneficial combination therapy because it includes compounds of the present invention, and a chemotherapeutic agent or a radiosensitizer agent, which may be utilized in accordance with the invention.

In another aspect, the present invention provides a method for treating cancer in a patient in need of such treatment, said method including the steps of administering a therapeutically effective amount of a compound of the present invention and administering a therapeutically effective amount of at least one agent selected from the group consisting of a chemotherapeutic agent and a radiosensitizer agent.

It is to be understood that this invention covers all appropriate combinations of the particular and preferred groupings and embodiments referred to herein.

DEFINITIONS

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention contain asymmetrically substituted carbon atoms, and may be isolated in optically active or racemic forms. It is well known in the art how to prepare optically active forms, such as by resolution of racemic forms or by synthesis from optically active starting materials. Two distinct isomers (cis and trans) of the peptide bond are known to occur; both can also be present in the compounds described herein, and all such stable isomers are contemplated in the present invention. The D and L-isomers of a particular amino acid are designated herein using the conventional 3-letter abbreviation of the amino acid, as indicated by the following examples: D-Leu, or L-Leu.

When any variable occurs more than one time in any substituent or in any formula, its definition on each occurrence is independent of its definition at every other occurrence. Thus, for example, if a group is shown to be substituted with 0–2 $R^{52}$, then said group may optionally be substituted with up to two $R^{52}$, and $R^{52}$ at each occurrence is selected independently from the defined list of possible $R^{52}$. Also, by way of example, for the group —N($R^{53}$)$_2$, each of the two $R^{53}$ substituents on N is independently selected from the defined list of possible $R^{53}$. Combinations of substituents and/or variables are permissible only if such combinations result in stable compounds. When a bond to a substituent is shown to cross the bond connecting two atoms in a ring, then such substituent may be bonded to any atom on the ring.

By "reagent" is meant a compound of this invention capable of direct transformation into a metallopharmaceutical of this invention. Reagents may be utilized directly for the preparation of the metallopharmaceuticals of this invention or may be a component in a kit of this invention.

The term "binding agent" means a metallopharmaceutical of this invention having affinity for and capable of binding to the vitronectin receptor. The binding agents of this invention preferably have Ki<1000 nM.

Metallopharmaceutical as used herein is intended to refer to a pharmaceutically acceptable compound containing a metal, wherein the compound is useful for imaging, magnetic resonance imaging, contrast imaging, or x-ray imaging. The metal is the cause of the imageable signal in diagnostic applications and the source of the cytotoxic radiation in radiotherapeutic applications. Radiopharmaceuticals are metallopharmaceuticals in which the metal is a radioisotope.

By "stable compound" or "stable structure" is meant herein a compound that is sufficiently robust to survive isolation to a useful degree of purity from a reaction mixture, and formulation into an efficacious pharmaceutical agent.

The term "substituted", as used herein, means that one or more hydrogens on the designated atom or group is replaced with a selection from the indicated group, provided that the designated atom's or group's normal valency is not exceeded, and that the substitution results in a stable compound. When a substituent is keto (i.e., =O), then 2 hydrogens on the atom are replaced.

The term "bond", as used herein, means either a single or double bond.

The term "salt", as used herein, is used as defined in the CRC Handbook of Chemistry and Physics, 65th Edition, CRC Press, Boca Raton, Fla., 1984, as any substance which yields ions, other than hydrogen or hydroxyl ions. As used herein, "pharmaceutically acceptable salts" refer to derivatives of the disclosed compounds modified by making acid or base salts. Examples of pharmaceutically acceptable salts include, but are not limited to, mineral or organic acid salts of basic residues such as amines; alkali or organic salts of acidic residues such as carboxylic acids; and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable prodrugs" as used herein means those prodrugs of the compounds useful according to the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group of the compounds of this invention. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Design of Prodrugs, H. Bundgaard, ed., Elsevier, 1985; Methods in Enzymology, K. Widder et al, Ed., Academic Press, 42, p. 309–396, 1985; A Textbook of Drug Design and Development, Krogsgaard-Larsen and H. Bundgaard, ed., Chapter 5; "Design and Applications of Prodrugs" p. 113–191, 1991; Advanced Drug Delivery Reviews, H. Bundgard, 8, p. 1–38, 1992; Journal of Pharmaceutical Sciences, 77, p. 285, 1988; Chem. Pharm. Bull., N. Nakeya et al, 32, p. 692, 1984; Pro-drugs as Novel Delivery Systems, T. Higuchi and V. Stella, Vol. 14 of the A.C.S. Symposium Series, and Bioreversible Carriers in Drug Design, Edward B. Roche, ed., American Pharmaceutical Association and Pergamon Press, 1987, which are incorporated herein by reference.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

As used herein, "alkyl" is intended to include both branched and straight-chain saturated aliphatic hydrocarbon groups having the specified number of carbon atoms. $C_{1-10}$ alkyl, is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl, is intended to include $C_3$, $C_4$, $C_5$, $C_6$, and $C_7$ cycloalkyl groups. Alkenyl" is intended to include hydrocarbon chains of either a straight or branched configuration and one or more unsaturated carbon—carbon bonds which may occur in any stable point along the chain, such as ethenyl and propenyl. $C_{2-10}$ alkenyl, is intended to include $C_2$, $C_3$, $C_4$, $C_5$, $C_6$, $C_7$, $C_8$, $C_9$, and $C_{10}$ alkenyl groups. "Alkynyl" is intended to include hydrocarbon chains of either a straight or branched configuration and one or more triple carbon—carbon bonds which may occur in any stable point along the chain, such as ethynyl and propynyl. $C_{2-10}$ alkynyl, is intended to include $C_2$, $C_3$, $C_4$, $C_5$, $C_6$, $C_7$, $C_8$, $C_9$, and $C_{10}$ alkynyl groups.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl.

As used herein, the term "alkaryl" means an aryl group bearing an alkyl group of 1, 2, 3, 4, 5, 6, 7, 8, 9, or 10 carbon atoms; the term "aralkyl" means an alkyl group of 1, 2, 3, 4, 5, 6, 7, 8, 9, or 10 carbon atoms bearing an aryl group; the term "arylalkaryl" means an aryl group bearing an alkyl group of 1–10 carbon atoms bearing an aryl group; and the term "heterocycloalkyl" means an alkyl group of 1, 2, 3, 4, 5, 6, 7, 8, 9, or 10 carbon atoms bearing a heterocycle.

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heterotams independently selected from the group consisting of N, NH, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benzotriazolyl, benzisoxazolyl, oxindolyl, benzoxazolinyl, and isatinoyl. Also included are fused ring and spiro compounds containing, for example, the above heterocycles.

A "polyalkylene glycol" is a polyethylene glycol, polypropylene glycol or polybutylene glycol having a molecular weight of less than about 5000, terminating in either a hydroxy or alkyl ether moiety.

A "carbohydrate" is a polyhydroxy aldehyde, ketone, alcohol or acid, or derivatives thereof, including polymers thereof having polymeric linkages of the acetal type.

A "cyclodextrin" is a cyclic oligosaccharide. Examples of cyclodextrins include, but are not limited to, α-cyclodextrin, hydroxyethyl-α-cyclodextrin, hydroxypropyl-α-cyclodextrin, β-cyclodextrin, hydroxypropyl-β-cyclodextrin, carboxymethyl-α-cyclodextrin, dihydroxypropyl-β-cyclodextrin, hydroxyethyl-β-cyclodextrin, 2,6 di-O-methyl-β-cyclodextrin, sulfated-β-cyclodextrin, γ-cyclodextrin, hydroxypropyl-γ-cyclodextrin, dihydroxypropyl-γ-cyclodextrin, hydroxyethyl-γ-cyclodextrin, and sulfated γ-cyclodextrin.

As used herein, the term "polycarboxyalkyl" means an alkyl group having between two and about 100 carbon atoms and a plurality of carboxyl substituents; and the term "polyazaalkyl" means a linear or branched alkyl group having between two and about 100 carbon atoms, interrupted by or substituted with a plurality of amine groups.

A "reducing agent" is a compound that reacts with a radionuclide, which is typically obtained as a relatively unreactive, high oxidation state compound, to lower its oxidation state by transferring electron(s) to the radionuclide, thereby making it more reactive. Reducing agents useful in the preparation of radiopharmaceuticals and in diagnostic kits useful for the preparation of said radiopharmaceuticals include but are not limited to stannous chloride, stannous fluoride, formamidine sulfinic acid, ascorbic acid, cysteine, phosphines, and cuprous or ferrous salts. Other reducing agents are described in Brodack et. al., PCT Application 94/22496, which is incorporated herein by reference.

A "transfer ligand" is a ligand that forms an intermediate complex with a metal ion that is stable enough to prevent unwanted side-reactions but labile enough to be converted to a metallopharmaceutical. The formation of the intermediate complex is kinetically favored while the formation of the metallopharmaceutical is thermodynamically favored. Transfer ligands useful in the preparation of metallopharmaceuticals and in diagnostic kits useful for the preparation of diagnostic radiopharmaceuticals include but are not limited to gluconate, glucoheptonate, mannitol, glucarate, N,N,N',N'-ethylenediaminetetraacetic acid, pyrophosphate and methylenediphosphonate. In general, transfer ligands are comprised of oxygen or nitrogen donor atoms.

The term "donor atom" refers to the atom directly attached to a metal by a chemical bond.

"Ancillary" or "co-ligands" are ligands that are incorporated into a radiopharmaceutical during its synthesis. They serve to complete the coordination sphere of the radionuclide together with the chelator or radionuclide bonding unit of the reagent. For radiopharmaceuticals comprised of a binary ligand system, the radionuclide coordination sphere is composed of one or more chelators or bonding units from one or more reagents and one or more ancillary or co-ligands, provided that there are a total of two types of ligands, chelators or bonding units. For example, a radiopharmaceutical comprised of one chelator or bonding unit from one reagent and two of the same ancillary or co-ligands and a radiopharmaceutical comprised of two chelators or bonding units from one or two reagents and one ancillary or co-ligand are both considered to be comprised of binary ligand systems. For radiopharmaceuticals comprised of a ternary ligand system, the radionuclide coordination sphere is composed of one or more chelators or bonding units from one or more reagents and one or more of two different types of ancillary or co-ligands, provided that there are a total of three types of ligands, chelators or bonding units. For example, a radiopharmaceutical comprised of one chelator or bonding unit from one reagent and two different ancillary or co-ligands is considered to be comprised of a ternary ligand system.

Ancillary or co-ligands useful in the preparation of radiopharmaceuticals and in diagnostic kits useful for the preparation of said radiopharmaceuticals are comprised of one or more oxygen, nitrogen, carbon, sulfur, phosphorus, arsenic, selenium, and tellurium donor atoms. A ligand can be a transfer ligand in the synthesis of a radiopharmaceutical and also serve as an ancillary or co-ligand in another radiopharmaceutical. Whether a ligand is termed a transfer or ancillary or co-ligand depends on whether the ligand remains in the radionuclide coordination sphere in the radiopharmaceutical, which is determined by the coordination chemistry of the radionuclide and the chelator or bonding unit of the reagent or reagents.

A "chelator" or "bonding unit" is the moiety or group on a reagent that binds to a metal ion through the formation of chemical bonds with one or more donor atoms.

The term "binding site" means the site in vivo or in vitro that binds a biologically active molecule.

A "diagnostic kit" or "kit" comprises a collection of components, termed the formulation, in one or more vials which are used by the practicing end user in a clinical or pharmacy setting to synthesize diagnostic radiopharmaceuticals. The kit provides all the requisite components to synthesize and use the diagnostic radiopharmaceutical except those that are commonly available to the practicing end user, such as water or saline for injection, a solution of the radionuclide, equipment for heating the kit during the synthesis of the radiopharmaceutical, if required, equipment necessary for administering the radiopharmaceutical to the patient such as syringes and shielding, and imaging equipment.

Therapeutic radiopharmaceuticals, X-ray contrast agent pharmaceuticals, ultrasound contrast agent pharmaceuticals and metallopharmaceuticals for magnetic resonance imaging contrast are provided to the end user in their final form in a formulation contained typically in one vial, as either a lyophilized solid or an aqueous solution. The end user reconstitutes the lyophilized with water or saline and withdraws the patient dose or just withdraws the dose from the aqueous solution formulation as provided.

A "lyophilization aid" is a component that has favorable physical properties for lyophilization, such as the glass transition temperature, and is added to the formulation to improve the physical properties of the combination of all the components of the formulation for lyophilization.

A "stabilization aid" is a component that is added to the metallopharmaceutical or to the diagnostic kit either to stabilize the metallopharmaceutical or to prolong the shelf-life of the kit before it must be used. Stabilization aids can be antioxidants, reducing agents or radical scavengers and can provide improved stability by reacting preferentially with species that degrade other components or the metallopharmaceutical.

A "solubilization aid" is a component that improves the solubility of one or more other components in the medium required for the formulation.

A "bacteriostat" is a component that inhibits the growth of bacteria in a formulation either during its storage before use of after a diagnostic kit is used to synthesize a radiopharmaceutical.

The term "amino acid" as used herein means an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Included within this term are modified and unusual amino acids, such as those disclosed in, for example, Roberts and Vellaccio (1983) *The Peptides,* 5: 342–429, the teaching of which is hereby incorporated by reference. Natural protein occurring amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Natural non-protein amino acids include, but are not limited to arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5'-triiodothyronine, and 3,3',5,5'-tetraiodothyronine. Modified or unusual amino acids which can be used to practice the invention include, but are not limited to, D-amino acids, hydroxylysine, 4-hydroxyproline, an N-Cbz-protected amino acid, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "peptide" as used herein means a linear compound that consists of two or more amino acids (as defined herein) that are linked by means of a peptide bond. A "peptide" as used in the presently claimed invention is intended to refer to a moiety with a molecular weight of less than 10,000 Daltons, preferable less than 5,000 Daltons, and more preferably less than 2,500 Daltons. The term "peptide" also includes compounds containing both peptide and non-peptide components, such as pseudopeptide or peptidomimetic residues or other non-amino acid components. Such a compound containing both peptide and non-peptide components may also be referred to as a "peptide analog".

A "pseudopeptide" or "peptidomimetic" is a compound which mimics the structure of an amino acid residue or a peptide, for example, by using linking groups other than amide linkages between the peptide mimetic and an amino acid residue (pseudopeptide bonds) and/or by using non-amino acid substituents and/or a modified amino acid residue. A "pseudopeptide residue" means that portion of an pseudopeptide or peptidomimetic that is present in a peptide.

The term "peptide bond" means a covalent amide linkage formed by loss of a molecule of water between the carboxyl group of one amino acid and the amino group of a second amino acid.

The term "pseudopeptide bonds" includes peptide bond isosteres which may be used in place of or as substitutes for the normal amide linkage. These substitute or amide "equivalent" linkages are formed from combinations of atoms not normally found in peptides or proteins which mimic the spatial requirements of the amide bond and which should stabilize the molecule to enzymatic degradation. The following abbreviations are used herein:

| | |
|---|---|
| Acm | acetamidomethyl |
| b-Ala, beta-Ala or bAla | 3-aminopropionic acid |
| ATA | 2-aminothiazole-5-acetic acid or 2-aminothiazole-5-acetyl group |
| Boc | t-butyloxycarbonyl |
| CBZ, Cbz or Z | Carbobenzyloxy |
| Cit | citrulline |
| Dap | 2,3-diaminopropionic acid |
| DCC | dicyclohexylcarbodiimide |
| DIEA | diisopropylethylamine |
| DMAP | 4-dimethylaminopyridine |
| EOE | ethoxyethyl |
| HBTU | 2-(1H-Benzotriazol-1-yl)-1,1,3,3-tetramethyluronium hexafluorophosphate |
| hynic | boc-hydrazinonicotinyl group or 2-[[[5-[carbonyl]-2-pyridinyl]hydrazono]methyl]-benzenesulfonic acid, |
| NMeArg or MeArg | a-N-methyl arginine |
| NMeAsp | a-N-methyl aspartic acid |
| NMM | N-methylmorpholine |
| OcHex | O-cyclohexyl |
| OBzl | O-benzyl |
| oSu | O-succinimidyl |
| TBTU | 2-(1H-Benzotriazol-1-yl)-1,1,3,3-tetramethyluronium tetrafluoroborate |
| THF | tetrahydrofuranyl |
| THP | tetrahydropyranyl |
| Tos | tosyl |
| Tr | trityl |

The following conventional three-letter amino acid abbreviations are used herein; the conventional one-letter amino acid abbreviations are NOT used herein:

| | |
|---|---|
| Ala | = alanine |
| Arg | = arginine |
| Asn | = asparagine |
| Asp | = aspartic acid |
| Cys | = cysteine |
| Gln | = glutamine |
| Glu | = glutamic acid |
| Gly | = glycine |
| His | = histidine |
| Ile | = isoleucine |
| Leu | = leucine |
| Lys | = lysine |
| Met | = methionine |
| Nle | = norleucine |
| Orn | = ornithine |
| Phe | = phenylalanine |
| Phg | = phenylglycine |
| Pro | = proline |
| Sar | = sarcosine |
| Ser | = serine |
| Thr | = threonine |
| Trp | = tryptophan |
| Tyr | = tyrosine |
| Val | = valine |

The pharmaceuticals of the present invention are comprised of a targeting moiety for a receptor that is expressed or upregulated in angiogenic tumor vasculature. For targeting the VEGF receptors, Flk-1/KDR, Flt-1, and neuropilin-1, the targeting moieties are comprised of peptides or peptidomimetics that bind with high affinity to the receptors. For example, peptides comprised of a 23 amino acid portion of the C-terminal domain of VEGF have been synthesized which competitively inhibit binding of VEGF to VEGFR (Soker, et. al., J. Biol. Chem., 1997, 272, 31582–8). Linear peptides of 11 to 23 amino acid residues that bind to the basic FGF receptor (bFGFR) are described by Cosic et. al., Mol. and Cell. Biochem., 1994, 130, 1–9. A preferred linear peptide antagonist of the bFGFR is the 16 amino acid peptide, Met-Trp-Tyr-Arg-Pro-Asp-Leu-Asp-Glu-Arg-Lys-Gln-Gln-Lys-Arg-Glu [SEQ. ID NO.: 67]. Gho et. al. (Cancer Research, 1997, 57, 3733–40) describe the identification of small peptides that bind with high affinity to the angiogenin receptor on the surface of endothelial cells. A preferred peptide is Ala-Gln-Leu-Ala-GlyGlu-Cys-Arg-Glu-Asn-Val-Cys-Met-Gly-Ile-Glu-Gly-Arg [SEQ. ID NO.: 68], in which the two Cys residues form an intramolecular disulfide bond. Yayon et. al. (Proc. Natl. Acad. Sci, USA, 1993, 90, 10643–7) describe other linear peptide antagonists of FGFR, identified from a random phage-displayed peptide library. Two linear octapeptides, Ala-Pro-Ser-Gly-His-Tyr-Lys-Gly [SEQ. ID NO.: 69] and Lys-Arg-Thr-Gly-Gln-Tyr-Lys-Leu [SEQ. ID NO.: 70] are preferred for inhibiting binding of bFGF to it receptor.

Targeting moieties for integrins expressed in tumor vasculature include peptides and peptidomimetics that bind to $\alpha_v\beta_3$, $\alpha_v\beta_5$, $\alpha_5\beta_1$, $\alpha_4\beta_1$, $\alpha_1\beta_1$, and $\alpha_2\beta_2$. Pierschbacher and Rouslahti (J. Biol. Chem., 1987, 262, 17294–8) describe peptides that bind selectively to $\alpha_5\beta_1$ and $\alpha_v\beta_3$. U.S. Pat. No. 5,536,814 describe peptides that bind with high affinity to the integrin $\alpha_5\beta_1$. Burgess and Lim (J. Med. Chem., 1996, 39, 4520–6) disclose the synthesis three peptides that bind with high affinity to $\alpha_v\beta_3$: cyclo[Arg-Gly-Asp-Arg-Gly-Asp] [SEQ. ID NO.: 71], cyclo[Arg-Gly-Asp-Arg-Gly-D-Asp] [SEQ. ID NO.: 72] and the linear peptide Arg-Gly-Asp-Arg-Gly-Asp [SEQ. ID NO.: 73]. U.S. Pat. No. 5,770,565 and U.S. Pat. No. 5,766,591 disclose peptides that bind with high affinity to $\alpha_v\beta_3$. U.S. Pat. No. 5,767,071 and U.S. Pat. No. 5,780,426, disclose cyclic peptides that have an exocyclic Arg amino acid that have high affinity for $\alpha_v\beta_3$. Srivatsa et. al., (Cardiovascular Res., 1997, 36, 408–28) describe the cyclic peptide antagonist for $\alpha_v\beta_3$, cyclo[Ala-Arg-Gly-Asp-Mamb] [SEQ. ID NO.: 74]. Tran et. al., (Bioorg. Med. Chem. Lett., 1997, 7, 997–1002) disclose the cyclic peptide cyclo[Arg-Gly-Asp-Val-Gly-Ser-BTD-Ser-Gly-Val-Ala] [SEQ. ID NO.: 75] that binds with high affinity to $\alpha_v\beta_3$. Arap et. al. (Science, 1998, 279, 377–80) describe cyclic peptides that bind to $\alpha_v\beta_3$ and $\alpha_v\beta_5$, Cys-Asp-Cys-Arg-Gly-Asp-Cys-Phe-Cys [SEQ. ID NO.: 76], and cyclo[Cys-Asn-Gly-Asp-Cys] [SEQ. ID NO.: 77]. Corbett et. al. (Biorg. Med. Chem. Lett., 1997, 7, 1371–6) describe a series of $\alpha_v\beta_3$ selective peptidomimetics. And Haubner et. al., (Angew. Chem. Int. Ed. Engl., 1997, 36, 1374–89) disclose peptides and peptidomimetic $\alpha_v\beta_3$ antagonists obtained from peptide libraries.

The targeting moieties of the present invention, preferably, have a binding affinity for the integrin $\alpha_v\beta_3$ of less than 1000 nM. More preferably, the targeting moieties of the present invention, preferably, have a binding affinity for the integrin $\alpha_v\beta_3$ of less than 100 nM. Even more preferably, the targeting moieties of the present invention, preferably, have a binding affinity for the integrin $\alpha_v\beta_3$ of less than 10 nM.

The ultrasound contrast agents of the present invention comprise a plurality of angiogenic tumor vasculature targeting moieties attached to or incorporated into a microbubble of a biocompatible gas, a liquid carrier, and a surfactant microsphere, further comprising an optional linking moiety, $L_n$, between the targeting moieties and the microbubble. In this context, the term liquid carrier means aqueous solution and the term surfactant means any amphiphilic material which produces a reduction in interfacial tension in a solution. A list of suitable surfactants for forming surfactant microspheres is disclosed in EP0727225A2, herein incorporated by reference. The term surfactant microsphere includes nanospheres, liposomes, vesicles and the like. The biocompatible gas can be air, or a fluorocarbon, such as a $C_3$–$C_5$ perfluoroalkane, for example, perflouropropane, perflourobutane, or perflouropentane, which provides the difference in echogenicity and thus the contrast in ultrasound imaging. The gas is encapsulated or contained in the microsphere to which is attached the biodirecting group, optionally via a linking group. The attachment can be covalent, ionic or by van der Waals forces. Specific examples of such contrast agents include lipid encapsulated perfluorocarbons with a plurality of tumor neovasculature receptor binding peptides or peptidomimetics.

$S_f$ as used herein is a surfactant which is either a lipid or a compound of the formula $A^1$-E-$A^2$, defined above. The surfactant is intended to form a vesicle (e.g., a microsphere) capable of containing an echogenic gas. The ultrasound contrast agent compositions of the present invention are intended to be capable upon agitation (e.g., shaking, stirring, etc . . . ) of encapsulating an echogenic gas in a vescicle in such a way as to allow for the resultant product to be useful as an ultrasound contrast agent.

"Vesicle" refers to a spherical entity which is characterized by the presence of an internal void. Preferred vesicles are formulated from lipids, including the various lipids described herein. In any given vesicle, the lipids may be in the form of a monolayer or bilayer, and the mono- or bilayer lipids may be used to form one of more mono- or bilayers. In the case of more than one mono- or bilayer, the mono- or bilayers are generally concentric. The lipid vesicles described herein include such entities commonly referred to as liposomes, micelles, bubbles, microbubbles, microspheres and the like. Thus, the lipids may be used to form a unilamellar vesicle (comprised of one monolayer or bilayer), an oligolamellar vesicle (comprised of about two or about three monolayers or bilayers) or a multilamellar vesicle (comprised of more than about three monolayers or bilayers). The internal void of the vesicles may be filled with a liquid, including, for example, an aqueous liquid, a gas, a gaseous precursor, and/or a solid or solute material, including, for example, a bioactive agent, as desired.

"Vesicular composition" refers to a composition which is formulate from lipids and which comprises vesicles.

"Vesicle formulation" refers to a composition which comprises vesicles and a bioactive agent.

Microsphere, as used herein, is preferably a sphere of less than or equal to 10 microns. Liposome, as used herein, may include a single lipid layer (a lipid monolayer), two lipid layers (a lipid bilayer) or more than two lipid layers (a lipid multilayer). "Lipsomes" refers to a generally spherical cluster or aggregate of amphipathic compounds, including lipid compounds, typically in the form of one or more concentric layers, for example, bilayers. They may also be referred to herein as lipid vesicles.

The term "bubbles", as used herein, refers to vesicles which are generally characterized by the presence of one or more membranes or walls surrounding an internal void that is filled with a gas or precursor thereto. Exemplary bubbles include, for example, liposomes, micelles and the like.

"Lipid" refers to a synthetic or naturally-occurring amphipathic compound which comprises a hydrophilic component and a hydrophobic component. Lipids include, for example, fatty acids, neutral fats, phosphatides, glycolipids, aliphatic alchols and waxes, terpenes and steroids.

"Lipid composition" refers to a composition which comprises a lipid compound. Exemplary lipid compositions include suspensions, emulsions and vesicular compositions.

"Lipid formulation" refers to a composition which comprises a lipid compound and a bioactive agent.

Examples of classes of suitable lipids and specific suitable lipids include: phosphatidylcholines, such as dioleoylphosphatidylcholine, dimyristoylphosphatidylcholine, dipalmitoylphosphatidylcholine (DPPC), and distearoylphosphatidylcholine; phosphatidylethanolamines, such as dipalmitoylphosphatidylethanolamine (DPPE), dioleoylphosphatidylethanolamine and N-succinyl-dioleoylphosphatidylethanolamine; phosphatidylserines; phosphatidylglycerols; sphingolipids; glycolipids, such as ganglioside GMI; glucolipids; sulfatides; glycosphingolipids; phosphatidic acids, such as dipalmatoylphosphatidic acid (DPPA); palmitic fatty acids; stearic fatty acids; arachidonic fatty acids; lauric fatty acids; myristic fatty acids; lauroleic fatty acids; physeteric fatty acids; myristoleic fatty acids; palmitoleic fatty acids; petroselinic fatty acids; oleic fatty acids; isolauric fatty acids; isomyristic fatty acids; isopalmitic fatty acids; isostearic fatty acids; cholesterol and cholesterol derivatives, such as cholesterol hemisuccinate, cholesterol sulfate, and cholesteryl-(4'-trimethylammonio)-butanoate; polyoxyethylene fatty acid esters; polyoxyethylene fatty acid alcohols; polyoxyethylene fatty acid alcohol ethers; polyoxyethylated sorbitan fatty acid esters; glycerol polyethylene glycol oxystearate; glycerol polyethylene glycol ricinoleate; ethoxylated soybean sterols; ethoxylated castor oil; polyoxyethylene-polyoxypropylene fatty acid polymers; polyoxyethylene fatty acid stearates; 12-(((7'-diethylaminocoumarin-3-yl)-carbonyl)-methylamino)-octadecanoic acid; N-[12-(((7'-diethylamino-coumarin-3-yl)-carbonyl)-methyl-amino)-octadecanoyl]-2-amino-palmitic acid; 1,2-dioleoyl-sn-glycerol; 1,2-dipalmitoyl-sn-3-succinylglycerol; 1,3-dipalmitoyl-2-succinyl-glycerol; and 1-hexadecyl-2-palmitoyl-glycerophosphoethanolamine and palmitoylhomocysteine; lauryltrimethylammonium bromide; cetyltrimethylammonium bromide; myristyltrimethylammonium bromide; alkyldimethylbenzylammonium chlorides, such as wherein alkyl is a $C_{12}$, $C_{14}$ or $C_{16}$ alkyl; benzyldimethyldodecylammonium bromide; benzyldimethyldodecylammonium chloride, benzyldimethylhexadecylammonium bromide; benzyldimethylhexadecylammonium chloride; benzyldimethyltetradecylammonium bromide; benzyldimethyltetradecylammonium chloride; cetyldimethylethylammonium bromide; cetyldimethylethylammonium chloride; cetylpyridinium bromide; cetylpyridinium chloride; N-[1,2,3-dioleoyloxy)-propyl]-N,N,N-trimethylammonium chloride (DOTMA); 1,2-dioleoyloxy-3-(trimethylammonio)propane (DOTAP); and 1,2-dioleoyl-c-(4'-trimethylammonio)-butanoyl-sn-glycerol (DOTB).

The echogenic gas may be one gas or mixture of gases, such as $CF_4$, $C_2F_6$, $C_3F_8$, cyclo-$C_4F_8$, $C_4F_{10}$, $C_5F_{12}$, cyclo-$C_5F_{10}$, cyclo-$C_4F_7$ (1-trifluoromethyl), propane (2-trifluoromethyl)-1,1,1,3,3,3 hexafluoro, and butane (2-trifluoromethyl)-1,1,1,3,3,3,4,4,4 nonafluoro. Also preferred are the the corresponding unsaturated versions of the above compounds, for example $C_2F_4$, $C_3F_6$, the isomers of $C_4F_8$. Also, mixtures of these gases, especially mixtures of perfluorocarbons with other perfluorocarbons and mixtures of perfluorocarbons with other inert gases, such as air, $N_2$, $O_2$, He, would be useful. Examples of these can be found in Quay, U.S. Pat. No. 5,595,723, the contents of which are herein incorporated by reference.

X-ray contrast agents of the present invention are comprised of one or more angiogenic tumor vasculature targeting moieties attached to one or more X-ray absorbing or "heavy" atoms of atomic number 20 or greater, further comprising an optional linking moiety, $L_n$, between the targeting moieties and the X-ray absorbing atoms. The frequently used heavy atom in X-ray contrast agents is iodine. Recently, X-ray contrast agents comprised of metal chelates (Wallace, R., U.S. Pat. No. 5,417,959) and polychelates comprised of a plurality of metal ions (Love, D., U.S. Pat. No. 5,679,810) have been disclosed. More recently, multinuclear cluster complexes have been disclosed as X-ray contrast agents (U.S. Pat. No. 5,804,161, PCT WO91/14460, and PCT WO 92/17215). Examples of X-ray agents include the non-radioactive or naturally occurring analogs of the above listed radionuclides (e.g., Re, Sm, Ho, Lu, Pm, Y, Bi, Pd, Gd, La, Au, Au, Yb, Dy, Cu, Rh, Ag, and Ir).

MRI contrast agents of the present invention are comprised of one or more angiogenic tumor vasculature targeting moieties attached to one or more paramagnetic metal ions, further comprising an optional linking moiety, $L_n$, between the targeting moieties and the paramagnetic metal ions. The paramagnetic metal ions are present in the form of metal complexes or metal oxide particles. U.S. Pat. Nos. 5,412,148, and 5,760,191, describe examples of chelators for paramagnetic metal ions for use in MRI contrast agents. U.S. Pat. No. 5,801,228, U.S. Pat. No. 5,567,411, and U.S. Pat. No. 5,281,704, describe examples of polychelants useful for complexing more than one paramagnetic metal ion for use in MRI contrast agents. U.S. Pat. No. 5,520,904, describes particulate compositions comprised of paramagnetic metal ions for use as MRI contrast agents.

Administration of a compound of the present invention in combination with such additional therapeutic agents, may afford an efficacy advantage over the compounds and agents alone, and may do so while permitting the use of lower doses of each. A lower dosage minimizes the potential of side effects, thereby providing an increased margin of safety. The combination of a compound of the present invention with such additional therapeutic agents is preferably a synergistic combination. Synergy, as described for example by Chou and Talalay, Adv. Enzyme Regul. 22:27–55 (1984), occurs when the therapeutic effect of the compound and agent when administered in combination is greater than the additive effect of the either the compound or agent when administered alone. In general, a synergistic effect is most clearly demonstrated at levels that are (therapeutically) sub-optimal for either the compound of the present invention, a chemotherapeutic agent or a radiosensitizer agent alone, but which are highly efficacious in combination. Synergy can be in terms of improved tumor response without substantial increases in toxicity over individual treatments alone, or some other beneficial effect of the combination compared with the individual components.

The compounds of the present invention, and a chemotherapeutic agent or a radiosensitizer agent, utilized in combination therapy may be administered simultaneously, in either separate or combined formulations, or at different times e.g., sequentially, such that a combined effect is achieved. The amounts and regime of administration will be adjusted by the practitioner, by preferably initially lowering their standard doses and then titrating the results obtained.

The invention also provides kits or single packages combining two or more active ingredients useful in treating cancer. A kit may provide (alone or in combination with a pharmaceutically acceptable diluent or carrier), the compound of the present invention and additionally at least one agent selected from the group consisting of a chemotherapeutic agent and a radiosensitizer agent (alone or in combination with diluent or carrier).

The pharmaceuticals of the present invention have the formulae, $(Q)_d—L_n—(C_h—X)$, $(Q)_d—L_n—(C_h—X^1)_{d'}$, $(Q)_d—L_n—(X^2)_{d''}$, and $(Q)_d—L_n—(X^3)$, wherein Q represents a peptide or peptidomimetic that binds to a receptor expressed in angiogenic tumor vasculature, d is 1–10, $L_n$ represents an optional linking group, $C_h$ represents a metal chelator or bonding moiety, X represents a radioisotope, $X^1$ represents paramagnetic metal ion, $X^2$ represents a paramagnetic metal ion or heavy atom containing insoluble solid particle, d" is 1–100, and $X^3$ represents a surfactant microsphere of an echogenic gas. Preferred pharmaceuticals of the present invention are comprised of targeting moieties, Q, that are peptides and peptidomimetics that bind to the vitronectin receptors $\alpha_v\beta_3$ and $\alpha_v\beta_5$. More preferred pharmaceuticals of the present invention are comprised of targeting moieties, Q, that are peptides and peptidomimetics that bind to $\alpha_v\beta_3$. Most preferred pharmaceuticals of the present invention are comprised of $\alpha_v\beta_3$ targeting moieties, Q, that are comprised of one to ten cyclic pentapeptides or peptidomimetics, independently attached to a therapeutic radioisotope or imageable moiety, further comprising an optional linking moiety, $L_n$, between the targeting moieties and the therapeutic radioisotopes or imageable moieties. The cyclic peptides are comprised of a tripeptide sequence that binds to the $\alpha_v\beta_3$ receptor and two amino acids either one of which can be attached to $L_n$, $C_h$, $X^2$, or $X^3$. The interaction of the tripeptide recognition sequences of the cyclic peptide or peptidomimetic portion of the pharmaceuticals with the $\alpha_v\beta_3$ receptor results in localization of the pharmaceuticals in angiogenic tumor vasculature, which express the $\alpha_v\beta_3$ receptor.

The pharmaceuticals of the present invention can be synthesized by several approaches. One approach involves the synthesis of the targeting peptide or peptidomimetic moiety, Q, and direct attachment of one or more moieties, Q, to one or more metal chelators or bonding moieties, $C_h$, or to a paramagnetic metal ion or heavy atom containing solid particle, or to an echogenic gas microbubble. Another approach involves the attachment of one or more moieties, Q, to the linking group, $L_n$, which is then attached to one or more metal chelators or bonding moieties, $C_h$, or to a paramagnetic metal ion or heavy atom containing solid particle, or to an echogenic gas microbubble. Another approach, useful in the synthesis of pharmaceuticals wherein d is 1, involves the synthesis of the moiety, Q—$L_n$, together, by incorporating an amino acid or amino acid mimetic residue bearing $L_n$ into the synthesis of the peptide or peptidomimetic. The resulting moiety, Q—$L_n$, is then attached to one or more metal chelators or bonding moieties, $C_h$, or to a paramagnetic metal ion or heavy atom containing solid particle, or to an echogenic gas microbubble. Another approach involves the synthesis of a peptide or peptidomimetic, Q, bearing a fragment of the linking group, $L_n$, one or more of which are then attached to the remainder of the linking group and then to one or more metal chelators or bonding moieties, $C_h$, or to a paramagnetic metal ion or heavy atom containing solid particle, or to an echogenic gas microbubble.

The peptides or peptidomimetics, Q, optionally bearing a linking group, $L_n$, or a fragment of the linking group, can be synthesized using standard synthetic methods known to those skilled in the art. Preferred methods include but are not limited to those methods described below.

Generally, peptides and peptidomimetics are elongated by deprotecting the alpha-amine of the C-terminal residue and coupling the next suitably protected amino acid through a peptide linkage using the methods described. This deprotection and coupling procedure is repeated until the desired sequence is obtained. This coupling can be performed with the constituent amino acids in a stepwise fashion, or condensation of fragments (two to several amino acids), or combination of both processes, or by solid phase peptide synthesis according to the method originally described by Merrifield, J. Am. Chem. Soc., 85, 2149–2154 (1963), the disclosure of which is hereby incorporated by reference.

The peptides and peptidomimetics may also be synthesized using automated synthesizing equipment. In addition to the foregoing, procedures for peptide and peptidomimetic synthesis are described in Stewart and Young, "Solid Phase Peptide Synthesis", 2nd ed, Pierce Chemical Co., Rockford, Ill. (1984); Gross, Meienhofer, Udenfriend, Eds., "The Peptides: Analysis, Synthesis, Biology, Vol. 1, 2, 3, 5, and 9, Academic Press, New York, (1980–1987); Bodanszky, "Peptide Chemistry: A Practical Textbook", Springer-Verlag, New York (1988); and Bodanszky et al. "The Practice of Peptide Synthesis" Springer-Verlag, New York (1984), the disclosures of which are hereby incorporated by reference.

The coupling between two amino acid derivatives, an amino acid and a peptide or peptidomimetic, two peptide or peptidomimetic fragments, or the cyclization of a peptide or peptidomimetic can be carried out using standard coupling procedures such as the azide method, mixed carbonic acid anhydride (isobutyl chloroformate) method, carbodiimide (dicyclohexylcarbodiimide, diisopropylcarbodiimide, or water-soluble carbodiimides) method, active ester (p-nitrophenyl ester, N-hydroxysuccinic imido ester) method, Woodward reagent K method, carbonyldiimidazole method, phosphorus reagents such as BOP-Cl, or oxidation-reduction method. Some of these methods (especially the carbodiimide) can be enhanced by the addition of 1-hydroxybenzotriazole. These coupling reactions may be performed in either solution (liquid phase) or solid phase.

The functional groups of the constituent amino acids or amino acid mimetics must be protected during the coupling reactions to avoid undesired bonds being formed. The protecting groups that can be used are listed in Greene, "Protective Groups in Organic Synthesis" John Wiley & Sons, New York (1981) and "The Peptides: Analysis, Synthesis, Biology, Vol. 3, Academic Press, New York (1981), the disclosure of which is hereby incorporated by reference.

The alpha-carboxyl group of the C-terminal residue is usually protected by an ester that can be cleaved to give the carboxylic acid. These protecting groups include: 1) alkyl esters such as methyl and t-butyl, 2) aryl esters such as benzyl and substituted benzyl, or 3) esters which can be cleaved by mild base treatment or mild reductive means such as trichloroethyl and phenacyl esters. In the solid phase case, the C-terminal amino acid is attached to an insoluble carrier (usually polystyrene). These insoluble carriers contain a group which will react with the carboxyl group to form a bond which is stable to the elongation conditions but readily cleaved later. Examples of which are: oxime resin (DeGrado and Kaiser (1980) *J. Org. Chem.* 45, 1295–1300) chloro or bromomethyl resin, hydroxymethyl resin, and aminomethyl resin. Many of these resins are commercially available with the desired C-terminal amino acid already incorporated.

The alpha-amino group of each amino acid must be protected. Any protecting group known in the art can be used. Examples of these are: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl. The preferred alpha-amino protecting group is either Boc or Fmoc. Many amino acid or amino acid mimetic derivatives suitably protected for peptide synthesis are commercially available.

The alpha-amino protecting group is cleaved prior to the coupling of the next amino acid. When the Boc group is used, the methods of choice are trifluoroacetic acid, neat or in dichloromethane, or HCl in dioxane. The resulting ammonium salt is then neutralized either prior to the coupling or in situ with basic solutions such as aqueous buffers, or tertiary amines in dichloromethane or dimethylformamide. When the Fmoc group is used, the reagents of choice are piperidine or substituted piperidines in dimethylformamide, but any secondary amine or aqueous basic solutions can be used. The deprotection is carried out at a temperature between 0° C. and room temperature.

Any of the amino acids or amino acid mimetics bearing side chain functionalities must be protected during the preparation of the peptide using any of the above-identified groups. Those skilled in the art will appreciate that the selection and use of appropriate protecting groups for these side chain functionalities will depend upon the amino acid or amino acid mimetic and presence of other protecting groups in the peptide or peptidomimetic. The selection of such a protecting group is important in that it must not be removed during the deprotection and coupling of the alpha-amino group.

For example, when Boc is chosen for the alpha-amine protection the following protecting groups are acceptable: p-toluenesulfonyl (tosyl) moieties and nitro for arginine; benzyloxycarbonyl, substituted benzyloxycarbonyls, tosyl or trifluoroacetyl for lysine; benzyl or alkyl esters such as cyclopentyl for glutamic and aspartic acids; benzyl ethers for serine and threonine; benzyl ethers, substituted benzyl ethers or 2-bromobenzyloxycarbonyl for tyrosine; p-methylbenzyl, p-methoxybenzyl, acetamidomethyl, benzyl, or t-butylsulfonyl for cysteine; and the indole of tryptophan can either be left unprotected or protected with a formyl group.

When Fmoc is chosen for the alpha-amine protection usually tert-butyl based protecting groups are acceptable. For instance, Boc can be used for lysine, tert-butyl ether for serine, threonine and tyrosine, and tert-butyl ester for glutamic and aspartic acids.

Once the elongation of the peptide or peptidomimetic, or the elongation and cyclization of a cyclic peptide or peptidomimetic is completed all of the protecting groups are removed. For the liquid phase synthesis the protecting groups are removed in whatever manner as dictated by the choice of protecting groups. These procedures are well known to those skilled in the art.

When a solid phase synthesis is used to synthesize a cyclic peptide or peptidomimetic, the peptide or peptidomimetic should be removed from the resin without simultaneously removing protecting groups from functional groups that might interfere with the cyclization process. Thus, if the peptide or peptidomimetic is to be cyclized in solution, the cleavage conditions need to be chosen such that a free a-carboxylate and a free a-amino group are generated without simultaneously removing other protecting groups. Alternatively, the peptide or peptidomimetic may be removed from the resin by hydrazinolysis, and then coupled by the azide method. Another very convenient method involves the synthesis of peptides or peptidomimetics on an oxime resin, followed by intramolecular nucleophilic displacement from the resin, which generates a cyclic peptide or peptidomimetic (Osapay, Profit, and Taylor (1990) *Tetrahedron Letters* 43, 6121–6124). When the oxime resin is employed, the Boc protection scheme is generally chosen. Then, the preferred method for removing side chain protecting groups generally involves treatment with anhydrous HF containing additives such as dimethyl sulfide, anisole, thioanisole, or p-cresol at 0° C. The cleavage of the peptide or peptidomimetic can also be accomplished by other acid reagents such as trifluoromethanesulfonic acid/trifluoroacetic acid mixtures.

Unusual amino acids used in this invention can be synthesized by standard methods familiar to those skilled in the art ("The Peptides: Analysis, Synthesis, Biology, Vol. 5, pp. 342–449, Academic Press, New York (1981)). N-Alkyl amino acids can be prepared using procedures described in previously (Cheung et al., (1977) *Can. J. Chem.* 55, 906; Freidinger et al., (1982) *J. Org. Chem.* 48, 77 (1982)), which are incorporated herein by reference.

Additional synthetic procedures that can be used by one of skill in the art to synthesize the peptides and peptidomimetics targeting moieties are described in PCT WO94/22910, the contents of which are herein incorporated by reference.

The attachment of linking groups, $L_n$, to the peptides and peptidomimetics, Q; chelators or bonding units, $C_h$, to the peptides and peptidomimetics, Q, or to the linking groups, $L_n$; and peptides and peptidomimetics bearing a fragment of the linking group to the remainder of the linking group, in combination forming the moiety, $(Q)_d$—$L_n$, and then to the moiety $C_h$; can all be performed by standard techniques. These include, but are not limited to, amidation, esterification, alkylation, and the formation of ureas or thioureas. Procedures for performing these attachments can be found in Brinkley, M., *Bioconjugate Chemistry* 1992, 3 (1), which is incorporated herein by reference.

A number of methods can be used to attach the peptides and peptidomimetics, Q, to paramagnetic metal ion or heavy atom containing solid particles, $X^2$, by one of skill in the art of the surface modification of solid particles. In general, the targeting moiety Q or the combination $(Q)_dL_n$ is attached to a coupling group that react with a constituent of the surface of the solid particle. The coupling groups can be any of a number of silanes which react with surface hydroxyl groups on the solid particle surface, as described in co-pending U.S.A.N 60/092,360, and can also include polyphosphonates, polycarboxylates, polyphosphates or mixtures thereof which couple with the surface of the solid particles, as described in U.S. Pat. No. 5,520,904.

A number of reaction schemes can be used to attach the peptides and peptidomimetics, Q, to the surfactant microsphere, $X^3$. These are illustrated in following reaction schemes where $S_f$ represents a surfactant moiety that forms the surfactant microsphere.

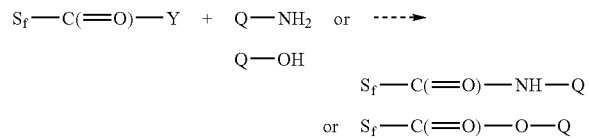

Y is a leaving group or active ester

Disulfide Coupling:

Sulfonamide Coupling:

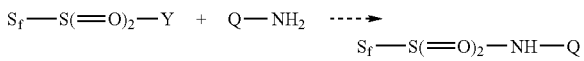

Reductive Amidation:

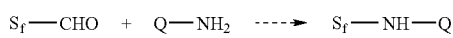

In these reaction schemes, the substituents $S_f$ and Q can be reversed as well.

The linking group $L_n$ can serve several roles. First it provides a spacing group between the metal chelator or bonding moiety, $C_h$, the paramagnetic metal ion or heavy atom containing solid particle, $X^2$, and the surfactant microsphere, $X^3$, and the one or more of the peptides or peptidomimetics, Q, so as to minimize the possibility that the moieties $C_h$—X, $C_h$—$X^1$, $X^2$, and $X^3$, will interfere with the interaction of the recognition sequences of Q with angiogenic tumor vasculature receptors. The necessity of incorporating a linking group in a reagent is dependent on the identity of Q, $C_h$—X, $C_h$—$X^1$, $X^2$, and $X^3$. If $C_h$—X, $C_h$—$X^1$, $X^2$, and $X^3$, cannot be attached to Q without substantially diminishing its affinity for the receptors, then a linking group is used. A linking group also provides a means of independently attaching multiple peptides and peptidomimetics, Q, to one group that is attached to $C_h$—X, $C_h$—$X^1$, $X^2$, or $X^3$.

The linking group also provides a means of incorporating a pharmacokinetic modifier into the pharmaceuticals of the present invention. The pharmacokinetic modifier serves to direct the biodistibution of the injected pharmaceutical other than by the interaction of the targeting moieties, Q, with the receptors expressed in the tumor neovasculature. A wide variety of functional groups can serve as pharmacokinetic modifiers, including, but not limited to, carbohydrates, polyalkylene glycols, peptides or other polyamino acids, and cyclodextrins. The modifiers can be used to enhance or decrease hydrophilicity and to enhance or decrease the rate of blood clearance. The modifiers can also be used to direct the route of elimination of the pharmaceuticals. Preferred pharmacokinetic modifiers are those that result in moderate to fast blood clearance and enhanced renal excretion.

The metal chelator or bonding moiety, $C_h$, is selected to form stable complexes with the metal ion chosen for the particular application. Chelators or bonding moieties for diagnostic radiopharmaceuticals are selected to form stable complexes with the radioisotopes that have imageable gamma ray or positron emissions, such as $^{99m}$Tc, $^{95}$Tc, $^{111}$In, $^{62}$Cu, $^{60}$Cu, $^{64}$Cu, $^{67}$Ga, $^{68}$Ga, $^{86}$Y.

Chelators for technetium, copper and gallium isotopes are selected from diaminedithiols, monoamine-monoamidedithiols, triamide-monothiols, monoamine-diamide-monothiols, diaminedioximes, and hydrazines. The chelators are generally tetradentate with donor atoms selected from nitrogen, oxygen and sulfur. Preferred reagents are comprised of chelators having amine nitrogen and thiol sulfur donor atoms and hydrazine bonding units. The thiol sulfur atoms and the hydrazines may bear a protecting group which can be displaced either prior to using the reagent to synthesize a radiopharmaceutical or preferably in situ during the synthesis of the radiopharmaceutical.

Exemplary thiol protecting groups include those listed in Greene and Wuts, "Protective Groups in Organic Synthesis" John Wiley & Sons, New York (1991), the disclosure of which is hereby incorporated by reference. Any thiol protecting group known in the art can be used. Examples of thiol protecting groups include, but are not limited to, the following: acetamidomethyl, benzamidomethyl, 1-ethoxyethyl, benzoyl, and triphenylmethyl.

Exemplary protecting groups for hydrazine bonding units are hydrazones which can be aldehyde or ketone hydrazones having substituents selected from hydrogen, alkyl, aryl and heterocycle. Particularly preferred hydrazones are described in co-pending U.S. Ser. No. 08/476,296 the disclosure of which is herein incorporated by reference in its entirety.

The hydrazine bonding unit when bound to a metal radionuclide is termed a hydrazido, or diazenido group and serves as the point of attachment of the radionuclide to the remainder of the radiopharmaceutical. A diazenido group can be either terminal (only one atom of the group is bound to the radionuclide) or chelating. In order to have a chelating diazenido group at least one other atom of the group must also be bound to the radionuclide. The atoms bound to the metal are termed donor atoms.

Chelators for $^{111}$In and $^{86}$Y are selected from cyclic and acyclic polyaminocarboxylates such as DTPA, DOTA, DO3A, 2-benzyl-DOTA, alpha-(2-phenethyl)1,4,7,10-tetraazazcyclododecane-1-acetic-4,7,10-tris(methylacetic) acid, 2-benzyl-cyclohexyldiethylenetriaminepentaacetic acid, 2-benzyl-6-methyl-DTPA, and 6,6"-bis[N,N,N",N"-tetra(carboxymethyl)aminomethyl]-4'-(3-amino-4-methoxyphenyl)-2,2':6',2"-terpyridine. Procedures for synthesizing these chelators that are not commercially available can be found in Brechbiel, M. and Gansow, O., *J. Chem. Soc. Perkin Trans.* 1992, 1, 1175; Brechbiel, M. and Gansow, O., *Bioconjugate Chem.* 1991, 2, 187; Deshpande, S., et. al., *J. Nucl. Med.* 1990, 31, 473; Kruper, J., U.S. Pat. No. 5,064,956, and Toner, J., U.S. Pat. No. 4,859,777, the disclosures of which are hereby incorporated by reference in their entirety.

The coordination sphere of metal ion includes all the ligands or groups bound to the metal. For a transition metal radionuclide to be stable it typically has a coordination number (number of donor atoms) comprised of an integer greater than or equal to 4 and less than or equal to 8; that is there are 4 to 8 atoms bound to the metal and it is said to have a complete coordination sphere. The requisite coordination number for a stable radionuclide complex is determined by the identity of the radionuclide, its oxidation state, and the type of donor atoms. If the chelator or bonding unit does not provide all of the atoms necessary to stabilize the metal radionuclide by completing its coordination sphere, the coordination sphere is completed by donor atoms from other ligands, termed ancillary or co-ligands, which can also be either terminal or chelating.

A large number of ligands can serve as ancillary or co-ligands, the choice of which is determined by a variety of considerations such as the ease of synthesis of the radiopharmaceutical, the chemical and physical properties of the ancillary ligand, the rate of formation, the yield, and the number of isomeric forms of the resulting radiopharmaceuticals, the ability to administer said ancillary or co-ligand to a patient without adverse physiological consequences to said patient, and the compatibility of the ligand in a lyophilized kit formulation. The charge and lipophilicity of the ancillary ligand will effect the charge and lipophilicity of the radiopharmaceuticals. For example, the use of 4,5-dihydroxy-1,3-benzene disulfonate results in radiopharmaceuticals with an additional two anionic groups because the sulfonate groups will be anionic under physiological conditions. The use of N-alkyl substituted 3,4-hydroxypyridinones results in radiopharmaceuticals with varying degrees of lipophilicity depending on the size of the alkyl substituents.

Preferred technetium radiopharmaceuticals of the present invention are comprised of a hydrazido or diazenido bonding unit and an ancillary ligand, $A_{L1}$, or a bonding unit and two types of ancillary $A_{L1}$ and $A_{L2}$, or a tetradentate chelator comprised of two nitrogen and two sulfur atoms. Ancillary ligands $A_{L1}$ are comprised of two or more hard donor atoms such as oxygen and amine nitrogen (sp$^3$ hybridized). The donor atoms occupy at least two of the sites in the coordination sphere of the radionuclide metal; the ancillary ligand $A_{L1}$ serves as one of the three ligands in the ternary ligand system. Examples of ancillary ligands $A_{L1}$ include but are not limited to dioxygen ligands and functionalized aminocarboxylates. A large number of such ligands are available from commercial sources.

Ancillary dioxygen ligands include ligands that coordinate to the metal ion through at least two oxygen donor atoms. Examples include but are not limited to: glucoheptonate, gluconate, 2-hydroxyisobutyrate, lactate, tartrate, mannitol, glucarate, maltol, Kojic acid, 2,2-bis(hydroxymethyl)propionic acid, 4,5-dihydroxy-1,3-benzene disulfonate, or substituted or unsubstituted 1,2 or 3,4 hydroxypyridinones. (The names for the ligands in these examples refer to either the protonated or non-protonated forms of the ligands.)

Functionalized aminocarboxylates include ligands that have a combination of amine nitrogen and oxygen donor atoms. Examples include but are not limited to: iminodiacetic acid, 2,3-diaminopropionic acid, nitrilotriacetic acid, N,N'-ethylenediamine diacetic acid, N,N,N'-ethylenediamine triacetic acid, hydroxyethylethylenediamine triacetic acid, and N,N'-ethylenediamine bis-hydroxyphenylglycine. (The names for the ligands in these examples refer to either the protonated or non-protonated forms of the ligands.)

A series of functionalized aminocarboxylates are disclosed by Bridger et. al. in U.S. Pat. No. 5,350,837, herein incorporated by reference, that result in improved rates of formation of technetium labeled hydrazino modified proteins. We have determined that certain of these aminocarboxylates result in improved yields of the radiopharmaceuticals of the present invention. The preferred ancillary ligands $A_{L1}$ functionalized aminocarboxylates that are derivatives of glycine; the most preferred is tricine (tris (hydroxymethyl)methylglycine).

The most preferred technetium radiopharmaceuticals of the present invention are comprised of a hydrazido or diazenido bonding unit and two types of ancillary designated $A_{L1}$ and $A_{L2}$, or a diaminedithiol chelator. The second type of ancillary ligands $A_{L2}$ are comprised of one or more soft donor atoms selected from the group: phosphine phosphorus, arsine arsenic, imine nitrogen (sp$^2$ hybridized), sulfur (sp$^2$ hybridized) and carbon (sp hybridized); atoms which have p-acid character. Ligands $A_{L2}$ can be monodentate, bidentate or tridentate, the denticity is defined by the number of donor atoms in the ligand. One of the two donor atoms in a bidentate ligand and one of the three donor atoms in a tridentate ligand must be a soft donor atom. We have disclosed in co-pending U.S. Ser. No. 08/415,908, and U.S. Ser. Nos. 60/013,360 and 08/646,886, the disclosures of which are herein incorporated by reference in their entirety, that radiopharmaceuticals comprised of one or more ancillary or co-ligands $A_{L2}$ are more stable compared to radiopharmaceuticals that are not comprised of one or more ancillary ligands, $A_{L2}$; that is, they have a minimal number of isomeric forms, the relative ratios of which do not change significantly with time, and that remain substantially intact upon dilution.

The ligands $A_{L2}$ that are comprised of phosphine or arsine donor atoms are trisubstituted phosphines, trisubstituted arsines, tetrasubstituted diphosphines and tetrasubstituted diarsines. The ligands $A_{L2}$ that are comprised of imine nitrogen are unsaturated or aromatic nitrogen-containing, 5 or 6-membered heterocycles. The ligands that are comprised of sulfur (sp$^2$ hybridized) donor atoms are thiocarbonyls, comprised of the moiety C=S. The ligands comprised of carbon (sp hybridized) donor atoms are isonitriles, comprised of the moiety CNR, where R is an organic radical. A large number of such ligands are available from commercial sources. Isonitriles can be synthesized as described in European Patent 0107734 and in U.S. Pat. No. 4,988,827, herein incorporated by reference.

Preferred ancillary ligands $A_{L2}$ are trisubstituted phosphines and unsaturated or aromatic 5 or 6 membered heterocycles. The most preferred ancillary ligands $A_{L2}$ are trisubstituted phosphines and unsaturated 5 membered heterocycles.

The ancillary ligands $A_{L2}$ may be substituted with alkyl, aryl, alkoxy, heterocycle, aralkyl, alkaryl and arylalkaryl groups and may or may not bear functional groups comprised of heteroatoms such as oxygen, nitrogen, phosphorus or sulfur. Examples of such functional groups include but are not limited to: hydroxyl, carboxyl, carboxamide, nitro, ether, ketone, amino, ammonium, sulfonate, sulfonamide, phosphonate, and phosphonamide. The functional groups may be chosen to alter the lipophilicity and water solubility of the ligands which may affect the biological properties of the radiopharmaceuticals, such as altering the distribution into non-target tissues, cells or fluids, and the mechanism and rate of elimination from the body.

Chelators or bonding moieties for therapeutic radiopharmaceuticals are selected to form stable complexes with the radioisotopes that have alpha particle, beta particle, Auger or Coster-Kronig electron emissions, such as $^{186}$Re, $^{188}$Re, $^{153}$Sm, $^{166}$Ho, $^{177}$Lu, $^{149}$Pm, $^{90}$Y, $^{212}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{67}$CU, $^{105}$Rh, $^{111}$Ag, and $^{192}$Ir. Chelators for rhenium, copper, palladium, platinum, iridium, rhodium, silver and gold isotopes are selected from diaminedithiols, monoamine-monoamidedithiols, triamide-monothiols, monoamine-diamide-monothiols, diaminedioximes, and hydrazines. Chelators for yttrium, bismuth, and the lanthanide isotopes are selected from cyclic and acyclic polyaminocarboxylates such as DTPA, DOTA, D03A, 2-benzyl-DOTA, alpha-(2-phenethyl) 1,4,7,10-tetraazacyclododecane-1-acetic-4,7,10-tris(methylacetic)acid, 2-benzyl-cyclohexyldiethylenetriaminepentaacetic acid, 2-benzyl-6-methyl-DTPA, and 6,6"-bis[N,N,N",N"-tetra(carboxymethyl)aminomethyl)-4'-(3-amino-4-methoxyphenyl)-2,2':6',2"-terpyridine.

Chelators for magnetic resonance imaging contrast agents are selected to form stable complexes with paramagnetic metal ions, such as Gd(III), Dy(III), Fe(III), and Mn(II), are selected from cyclic and acyclic polyaminocarboxylates such as DTPA, DOTA, D03A, 2-benzyl-DOTA, alpha-(2-phenethyl)1,4,7,10-tetraazacyclododecane-1-acetic-4,7,10-tris(methylacetic)acid, 2-benzyl-cyclohexyldiethylenetriaminepentaacetic acid, 2-benzyl-6-methyl-DTPA, and 6,6"-bis[N,N,N",N"-tetra(carboxymethyl)aminomethyl)-4'-(3-amino-4-methoxyphenyl)-2,2':6',2"-terpyridine.

The technetium and rhenium radiopharmaceuticals of the present invention comprised of a hydrazido or diazenido bonding unit can be easily prepared by admixing a salt of a radionuclide, a reagent of the present invention, an ancillary ligand $A_{L1}$, an ancillary ligand $A_{L2}$, and a reducing agent, in an aqueous solution at temperatures from 0 to 100° C. The technetium and rhenium radiopharmaceuticals of the present invention comprised of a tetradentate chelator having two nitrogen and two sulfur atoms can be easily prepared by admixing a salt of a radionuclide, a reagent of the present invention, and a reducing agent, in an aqueous solution at temperatures from 0 to 100° C.

When the bonding unit in the reagent of the present invention is present as a hydrazone group, then it must first be converted to a hydrazine, which may or may not be protonated, prior to complexation with the metal radionuclide. The conversion of the hydrazone group to the hydrazine can occur either prior to reaction with the radionuclide, in which case the radionuclide and the ancillary or co-ligand or ligands are combined not with the reagent but with a hydrolyzed form of the reagent bearing the chelator or bonding unit, or in the presence of the radionuclide in which case the reagent itself is combined with the radionuclide and the ancillary or co-ligand or ligands. In the latter case, the pH of the reaction mixture must be neutral or acidic.

Alternatively, the radiopharmaceuticals of the present invention comprised of a hydrazido or diazenido bonding unit can be prepared by first admixing a salt of a radionuclide, an ancillary ligand $A_{L1}$, and a reducing agent in an aqueous solution at temperatures from 0 to 100° C. to form an intermediate radionuclide complex with the ancillary ligand $A_{L1}$ then adding a reagent of the present invention and an ancillary ligand $A_{L2}$ and reacting further at temperatures from 0 to 100° C.

Alternatively, the radiopharmaceuticals of the present invention comprised of a hydrazido or diazenido bonding unit can be prepared by first admixing a salt of a radionuclide, an ancillary ligand $A_{L1}$, a reagent of the present invention, and a reducing agent in an aqueous solution at temperatures from 0 to 100° C. to form an intermediate radionuclide complex, and then adding an ancillary ligand $A_{L2}$ and reacting further at temperatures from 0 to 100° C.

The technetium and rhenium radonuclides are preferably in the chemical form of pertechnetate or perrhenate and a pharmaceutically acceptable cation. The pertechnetate salt form is preferably sodium pertechnetate such as obtained from commercial Tc-99m generators. The amount of pertechnetate used to prepare the radiopharmaceuticals of the present invention can range from 0.1 mCi to 1 Ci, or more preferably from 1 to 200 mCi.

The amount of the reagent of the present invention used to prepare the technetium and rhenium radiopharmaceuticals of the present invention can range from 0.01 µg to 10 mg, or more preferably from 0.5 µg to 200 µg. The amount used will be dictated by the amounts of the other reactants and the identity of the radiopharmaceuticals of the present invention to be prepared.

The amounts of the ancillary ligands $A_{L1}$ used can range from 0.1 mg to 1 g, or more preferably from 1 mg to 100 mg. The exact amount for a particular radiopharmaceutical is a function of identity of the radiopharmaceuticals of the present invention to be prepared, the procedure used and the amounts and identities of the other reactants. Too large an amount of $A_{L1}$ will result in the formation of by-products comprised of technetium labeled $A_{L1}$ without a biologically active molecule or by-products comprised of technetium labeled biologically active molecules with the ancillary ligand $A_{L1}$ but without the ancillary ligand $A_{L2}$. Too small an amount of $A_{L1}$ will result in other by-products such as technetium labeled biologically active molecules with the ancillary ligand $A_{L2}$ but without the ancillary ligand $A_{L1}$, or reduced hydrolyzed technetium, or technetium colloid.

The amounts of the ancillary ligands $A_{L2}$ used can range from 0.001 mg to 1 g, or more preferably from 0.01 mg to 10 mg. The exact amount for a particular radiopharmaceutical is a function of the identity of the radiopharmaceuticals of the present invention to be prepared, the procedure used and the amounts and identities of the other reactants. Too large an amount of $A_{L2}$ will result in the formation of by-products comprised of technetium labeled $A_{L2}$ without a biologically active molecule or by-products comprised of technetium labeled biologically active molecules with the ancillary ligand $A_{L2}$ but without the ancillary ligand $A_{L1}$. If the reagent bears one or more substituents that are comprised of a soft donor atom, as defined above, at least a ten-fold molar excess of the ancillary ligand $A_{L2}$ to the reagent of formula 2 is required to prevent the substituent from interfering with the coordination of the ancillary ligand $A_{L2}$ to the metal radionuclide.

Suitable reducing agents for the synthesis of the radiopharmaceuticals of the present invention include stannous salts, dithionite or bisulfite salts, borohydride salts, and formamidinesulfinic acid, wherein the salts are of any pharmaceutically acceptable form. The preferred reducing agent is a stannous salt. The amount of a reducing agent used can range from 0.001 mg to 10 mg, or more preferably from 0.005 mg to 1 mg.

The specific structure of a radiopharmaceutical of the present invention comprised of a hydrazido or diazenido bonding unit will depend on the identity of the reagent of the present invention used, the identity of any ancillary ligand $A_{L1}$, the identity of any ancillary ligand $A_{L2}$, and the identity of the radionuclide. Radiopharmaceuticals comprised of a hydrazido or diazenido bonding unit synthesized using concentrations of reagents of <100 μg/mL, will be comprised of one hydrazido or diazenido group. Those synthesized using >1 mg/mL concentrations will be comprised of two hydrazido or diazenido groups from two reagent molecules. For most applications, only a limited amount of the biologically active molecule can be injected and not result in undesired side-effects, such as chemical toxicity, interference with a biological process or an altered biodistribution of the radiopharmaceutical. Therefore, the radiopharmaceuticals which require higher concentrations of the reagents comprised in part of the biologically active molecule, will have to be diluted or purified after synthesis to avoid such side-effects.

The identities and amounts used of the ancillary ligands $A_{L1}$ and $A_{L2}$ will determine the values of the variables y and z. The values of y and z can independently be an integer from 1 to 2. In combination, the values of y and z will result in a technetium coordination sphere that is made up of at least five and no more than seven donor atoms. For monodentate ancillary ligands $A_{L2}$, z can be an integer from 1 to 2; for bidentate or tridentate ancillary ligands $A_{L2}$, z is 1. The preferred combination for monodentate ligands is y equal to 1 or 2 and z equal to 1. The preferred combination for bidentate or tridentate ligands is y equal to 1 and z equal to 1.

The indium, copper, gallium, silver, palladium, rhodium, gold, platinum, bismuth, yttrium and lanthanide radiopharmaceuticals of the present invention can be easily prepared by admixing a salt of a radionuclide and a reagent of the present invention, in an aqueous solution at temperatures from 0 to 100° C. These radionuclides are typically obtained as a dilute aqueous solution in a mineral acid, such as hydrochloric, nitric or sulfuric acid. The radionuclides are combined with from one to about one thousand equivalents of the reagents of the present invention dissolved in aqueous solution. A buffer is typically used to maintain the pH of the reaction mixture between 3 and 10.

The gadolinium, dysprosium, iron and manganese metallopharmaceuticals of the present invention can be easily prepared by admixing a salt of the paramagnetic metal ion and a reagent of the present invention, in an aqueous solution at temperatures from 0 to 100° C. These paramagnetic metal ions are typically obtained as a dilute aqueous solution in a mineral acid, such as hydrochloric, nitric or sulfuric acid. The paramagnetic metal ions are combined with from one to about one thousand equivalents of the reagents of the present invention dissolved in aqueous solution. A buffer is typically used to maintain the pH of the reaction mixture between 3 and 10.

The total time of preparation will vary depending on the identity of the metal ion, the identities and amounts of the reactants and the procedure used for the preparation. The preparations may be complete, resulting in >80% yield of the radiopharmaceutical, in 1 minute or may require more time. If higher purity metallopharmaceuticals are needed or desired, the products can be purified by any of a number of techniques well known to those skilled in the art such as liquid chromatography, solid phase extraction, solvent extraction, dialysis or ultrafiltration.

Buffers useful in the preparation of metallopharmaceuticals and in diagnostic kits useful for the preparation of said radiopharmaceuticals include but are not limited to phosphate, citrate, sulfosalicylate, and acetate. A more complete list can be found in the United States Pharmacopeia.

Lyophilization aids useful in the preparation of diagnostic kits useful for the preparation of radiopharmaceuticals include but are not limited to mannitol, lactose, sorbitol, dextran, Ficoll, and polyvinylpyrrolidine (PVP).

Stabilization aids useful in the preparation of metallopharmaceuticals and in diagnostic kits useful for the preparation of radiopharmaceuticals include but are not limited to ascorbic acid, cysteine, monothioglycerol, sodium bisulfite, sodium metabisulfite, gentisic acid, and inositol.

Solubilization aids useful in the preparation of metallopharmaceuticals and in diagnostic kits useful for the preparation of radiopharmaceuticals include but are not limited to ethanol, glycerin, polyethylene glycol, propylene glycol, polyoxyethylene sorbitan monooleate, sorbitan monoloeate, polysorbates, poly(oxyethylene)poly(oxypropylene)poly(oxyethylene) block copolymers (Pluronics) and lecithin. Preferred solubilizing aids are polyethylene glycol, and Pluronics.

Bacteriostats useful in the preparation of metallopharmaceuticals and in diagnostic kits useful for the preparation of radiopharmaceuticals include but are not limited to benzyl alcohol, benzalkonium chloride, chlorbutanol, and methyl, propyl or butyl paraben.

A component in a diagnostic kit can also serve more than one function. A reducing agent can also serve as a stabilization aid, a buffer can also serve as a transfer ligand, a lyophilization aid can also serve as a transfer, ancillary or co-ligand and so forth.

The diagnostic radiopharmaceuticals are administered by intravenous injection, usually in saline solution, at a dose of 1 to 100 mCi per 70 kg body weight, or preferably at a dose of 5 to 50 mCi. Imaging is performed using known procedures.

The therapeutic radiopharmaceuticals are administered by intravenous injection, usually in saline solution, at a dose of 0.1 to 100 mCi per 70 kg body weight, or preferably at a dose of 0.5 to 5 mCi per 70 kg body weight.

The magnetic resonance imaging contrast agents of the present invention may be used in a similar manner as other MRI agents as described in U.S. Pat. No. 5,155,215; U.S. Pat. No. 5,087,440; Margerstadt et al., Magn. Reson. Med., 1986, 3, 808; Runge et al., Radiology, 1988, 166, 835; and Bousquet et al., Radiology, 1988, 166, 693. Generally, sterile aqueous solutions of the contrast agents are administered to a patient intravenously in dosages ranging from 0.01 to 1.0 mmoles per kg body weight.

For use as X-ray contrast agents, the compositions of the present invention should generally have a heavy atom concentration of 1 mM to 5 M, preferably 0.1 M to 2 M. Dosages, administered by intravenous injection, will typically range from 0.5 mmol/kg to 1.5 mmol/kg, preferably 0.8 mmol/kg to 1.2 mmol/kg. Imaging is performed using known techniques, preferably X-ray computed tomography.

The ultrasound contrast agents of the present invention are administered by intravenous injection in an amount of 10 to 30 μL of the echogenic gas per kg body weight or by infusion at a rate of approximately 3 μL/kg/min. Imaging is performed using known techniques of sonography.

Other features of the invention will become apparent in the course of the following descriptions of exemplary embodiments which are given for illustration of the invention and are not intended to be limiting thereof.

EXAMPLES

Representative materials and methods that may be used in preparing the compounds of the invention are described further below.

Manual solid phase peptide synthesis was performed in 25 mL polypropylene filtration tubes purchased from BioRad Inc., or in 60 mL hour-glass reaction vessels purchased from Peptides International. Oxime resin (substitution level=0.96 mmol/g) was prepared according to published procedure (DeGrado and Kaiser, *J. Org. Chem.* 1980, 45, 1295), or was purchased from Novabiochem (substitution level=0.62 mmol/g). All chemicals and solvents (reagent grade) were used as supplied from the vendors cited without further purification. t-Butyloxycarbonyl (Boc) amino acids and other starting amino acids may be obtained commercially from Bachem Inc., Bachem Biosciences Inc. (Philadelphia, Pa.), Advanced ChemTech (Louisville, Ky.), Peninsula Laboratories (Belmont, Calif.), or Sigma (St. Louis, Mo.). 2-(1H-Benzotriazol-1-yl)-1,1,3,3-tetramethyluronium hexafluorophosphate (HBTU) and TBTU were purchased from Advanced ChemTech. N-methylmorpholine (NMM), m-cresol, D-2-aminobutyric acid (Abu), trimethylacetylchloride, diisopropylethylamine (DIEA), 1,2,4-triazole, stannous chloride dihydrate, and tris(3-sulfonatophenyl) phosphine trisodium salt (TPPTS) were purchased from Aldrich Chemical Company. Bis(3-sulfonatophenyl)phenylphosphine disodium salt (TPPDS) was prepared by the published procedure (Kuntz, E., U.S. Pat. No. 4,248,802). (3-Sulfonatophenyl)diphenylphosphine monosodium salt (TPPMS) was purchased from TCI America, Inc. Tricine was obtained from Research Organics, Inc. Technetium-99m-pertechnetate ($^{99m}TcO_4^-$) was obtained from a DuPont Pharma $^{99}Mo/^{99m}Tc$ Technelite® generator. In-111-chloride (Indichlor®) was obtained from Amersham Medi-Physics, Inc. Sm-153-chloride and Lutetium-177-chloride were obtained from the University of Missouri Research Reactor (MURR). Yttrium-90 chloride was obtained from the Pacific Northwest Research Laboratories. Dimethylformamide (DMF), ethyl acetate, chloroform ($CHCl_3$), methanol (MeOH), pyridine and hydrochloric acid (HCl) were obtained from Baker. Acetonitrile, dichloromethane (DCM), acetic acid (HOAc), trifluoroacetic acid (TFA), ethyl ether, triethylamine, acetone, and magnesium sulfate were commercially obtained. Absolute ethanol was obtained from Quantum Chemical Corporation.

General Procedure for Solid Phase Peptide Synthesis Using Boc-Chemistry on the Oxime Resin for the Preparation of Cyclic Peptides The appropriately protected cyclic peptides, described in the Examples, were prepared by manual solid phase peptide synthesis using Boc-teabag chemistry (Houghton, 1985) on a p-nitrobenzophenone oxime solid support (DeGrado, 1982, Scarr and Findeis, 1990). The 5.0 cm×5.0 cm teabags were made from 0.75 mm mesh polypropylene filters (Spectra Filters) and filled with 0.5 g (or 1 g) of the oxime resin. The coupling and deprotection steps were carried out in a polypropylene reactor using a table-top shaker for agitation. Synthesis of the protected pentapeptide-resin intermediate was achieved by first coupling Boc-Gly-OH to the oxime resin (substitution 0.69 mmol/g or 0.95 mmol/g). Attachment of Boc-Gly-OH onto the oxime resin was achieved by using five equivalents each of the amino acid, HBTU and diisopropylethylamine (DIPEA) in DMF. Coupling of the first amino acid generally occurred over 2–3 days. After thorough washing, substitution levels were determined using the picric acid assay (Stewart and Martin). Unreacted oxime groups on the resin were then capped with a solution of DIPEA and trimethylacetyl chloride in DMF. The boc-group was deprotected using 50% or 25% TFA in DCM (30 min). Coupling of the other protected boc-amino acids were performed in a similar manner by overnight shaking (1–2 days), and the coupling yields for each newly added amino acid was determined using the picric acid assay.

General Procedure for Solid Phase Peptide Synthesis Using Fmoc-Chemistry on the HMPB-BHA Resin for the Preparation of Cyclic Peptides The appropriately protected linear peptide precursors to the cyclic peptides, described in the Examples, were also prepared by automated solid phase peptide synthesis using Fmoc chemistry on an Advanced ChemTech Model 90 Synthesizer and using HMPB-BHA resin as the solid support. Synthesis of the protected pentapeptide-resin intermediates was achieved by coupling (for 3 h) the Fmoc-amino acids sequentially to the commercially available (Novabiochem) Fmoc-Gly-HMPB-BHA resin (usually 2 g, substitution 0.47 to 0.60 mmol/g) by using three to five equivalents each of the amino acid, HBTU, HOBt and diisopropylethylamine (DIPEA) in DMF. The Fmoc-group was deprotected using 20% piperidine in DMF (30 min). The peptides were cleaved from the HMPB-BHA resin using a solution of 1% TFA/DCM and collecting the peptide solutions in a solution of pyridine in methanol (1:10). The linear protected peptides were isolated by removing the solvents and reagents in vacuo and triturating the crude residue in diethyl ether.

The syntheses of several amino acids that are not commercially available are described in the following procedures.

Synthesis of Tfa-amino acids

Boc-HomoLys(Tfa)-OH and Boc-Cys(2-N-Tfa-aminoethyl)-OH are prepared via the reaction of Boc-HomoLys-OH and Boc-Cys(2-aminoethyl)-OH, respectively, with ethyl thioltrifluoroacetate in Aq. NaOH, and purified by recrystallization from ethanol.

Synthesis of Boc-Orn(d-N-Benzylcarbamoyl)

To a solution of Boc-Orn (1 mmol) in DMF (30 mL) is added benzylisocyanate (2.2 mmol), and diisopropylamine (3 mmol). The reaction mixture is then stirred overnight at room temperature. The volatiles are removed in vacuo and the crude material is purified by column chromatography to obtain the desired product.

Synthesis of Boc-Orn(d-N-1-Tos-2-Imidazolinyl)

A solution of Boc-Orn-OH (10 mmol), 1-tosyl-2-methylthio-2-imidazoline (12 mmol, (which in turn is prepared from the reaction of the commercially available 2-methylthio-2-imidazoline hydriodide and p-toluenesulfonic anhydride in methylene chloride (0° C. to RT) in the presence of triethylamine)), and diisopropylethylamine (12 mmol) is stirred at reflux, overnight. The volatiles are removed and the desired product isolated by chromatography.

Synthesis of Dap(b-(1-Tos-2-benzimidazolylacetyl))

To a solution of 1-Tos-2-benzimidazolylacetic acid (10 mmol, prepared using tosyl chloride and standard reported conditions) and N-methylmorpholine (10 mmol) in anhydrous DMF is added isobutyl chloroformate (10 mmol). After stirring at ice bath temperature for 5–10 min., Boc-Orn-OH (10 mmol) and N-methylmorpholine (20 mmol) in anhydrous DMF is added in one portion. The reaction mixture is stirred overnight at room temperature, the volatiles removed in vacuo, and the product is isolated by chromatography. (Alternatively, Boc-Orn-OMe is used and the product isolated is treated with aqueous LiOH to obtain the acid.)

The analytical HPLC methods utilized are described below:

| HPLC Method 1 | | | |
|---|---|---|---|
| Instrument: | HP1050 | | |
| Column: | Vydac C18 (4.6 × 250 mm) | | |
| Detector: | Diode array detector 220 nm/500 ref | | |
| Flow Rate: | 1.0 mL/min. | | |
| Column Temp: | 50° C. | | |
| Sample Size: | 15 uL | | |
| Mobile Phase: | A: 0.1% TFA in water | | |
| | B: 0.1% TFA in ACN/Water (9:1) | | |
| Gradient A: | Time (min) | % A | % B |
| | 0 | 80 | 20 |
| | 20 | 0 | 100 |
| | 30 | 0 | 100 |
| | 31 | 80 | 20 |
| Gradient B: | Time (min) | % A | % B |
| | 0 | 98 | 2 |
| | 16 | 63.2 | 36.8 |
| | 18 | 0 | 100 |
| | 28 | 0 | 100 |
| | 30 | 98 | 2 |

Example 1

Synthesis of cyclo{Arg-Gly-Asp-D-Tyr(N-[2-[carbonyl]-2-pyridinyl]hydrazono]methyl]-benzenesulfonic acid]-3-aminopropyl)-Val}
[SEQ. ID NO.: 1]

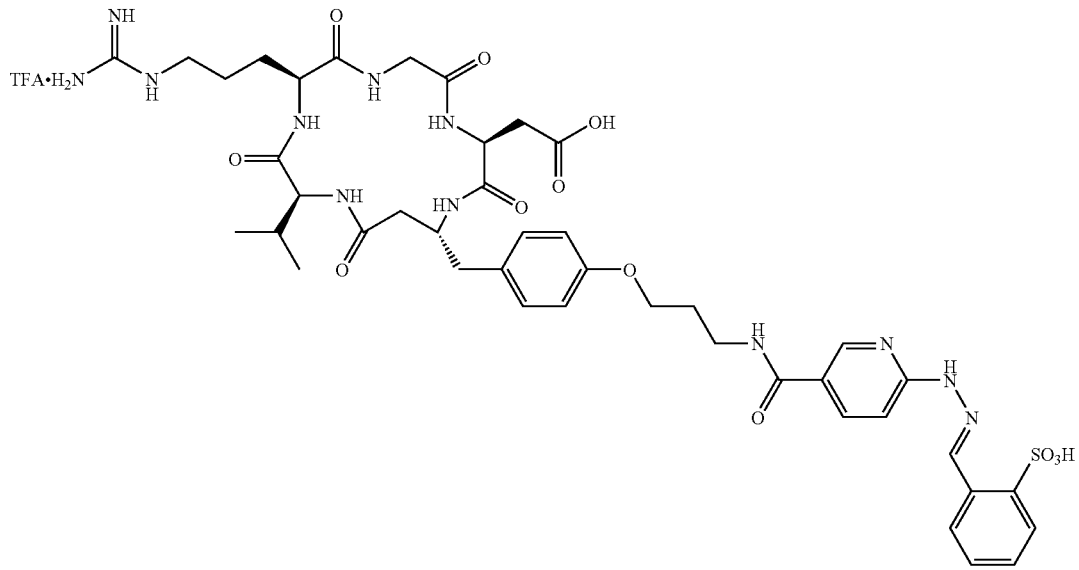

Part A. Preparation of cyclo{Arg(Tos)-Gly-Asp(OBzl)-D-Tyr(N-Cbz-3-aminopropyl)-Val} [SEQ. ID NO.: 78]

The N-terminus Boc-protecting group of the peptide sequence Boc-Asp(OBzl)-D-Tyr(N-Cbz-aminopropyl)-Val-Arg(Tos)-Gly[SEQ. ID NO.: 79]-Oxime resin was removed using standard deprotection (25% TFA in $CH_2Cl_2$). After eight washes with DCM, the resin was treated with 10% DIEA/DCM (2×10 min.). The resin was subsequently washed with DCM (×5) and dried under high vacuum. The resin (1.7474 g, 0.55 mmol/g) was then suspended in dimethylformamide (15 mL). Glacial acetic acid (55.0 μL, 0.961 mmol) was added, and the reaction mixture was heated at 50° C. for 72 h. The resin was filtered, and washed with DMF (2×10 mL). The filtrate was concentrated to an oil under high vacuum. The resulting oil was triturated with ethyl acetate. The solid thus obtained was filtered, washed with ethyl acetate, and dried under high vacuum to give 444.4 mg of the desired product. ESMS: Calcd. for $C_{51}H_{63}N_9O_{12}S$, 1025.43; Found, 1026.6 [M+H]+1. Analytical HPLC, Method 1A, $R_t$=14.366 min, Purity=75%.

Part B. Preparation of cyclo[Arg-Gly-Asp-D-Tyr(3-aminopropyl)-Val] [SEQ. ID NO.: 80] Trifluoroacetic Acid Salt.

| Preparative HPLC Method 1 | | | |
|---|---|---|---|
| Instrument: | Rainin Rabbit; Dynamax software | | |
| Column: | Vydac C-18 (21.2 mm × 25 cm) | | |
| Detector: | Knauer VWM | | |
| Flow Rate: | 15 ml/min | | |
| Column Temp: | RT | | |
| Mobile Phase: | A: 0.1% TFA in $H_2O$ | | |
| | B: 0.1% TFA in $ACN/H_2O$ (9:1) | | |
| Gradient: | Time (min) | % A | % B |
| | 0 | 98 | 2 |
| | 16 | 63.2 | 36.8 |
| | 18 | 0 | 100 |
| | 28 | 0 | 100 |
| | 30 | 98 | 2 |

Part C. Preparation of cyclo{Arg-Gly-Asp-D-Tyr(N-[2-[[[5-[carbonyl]-2-pyridinyl]hydrazono]methyl]-benzenesulfonic acid]-3-aminopropyl)-Val} [SEQ. ID NO.: 1]

Cyclo{Arg-Gly-Asp-D-Tyr(3-aminopropyl)-Val} [SEQ. ID NO.: 81] trifluoroacetic acid salt (0.020 g, 0.0228 mmol)

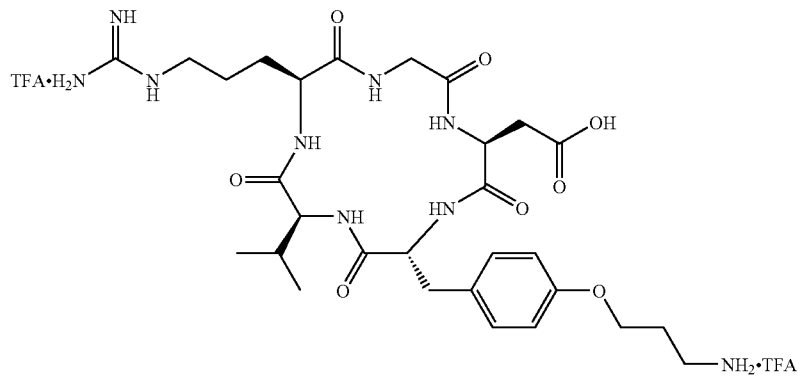

Cyclo {Arg(Tos)-Gly-Asp(OBzl)-D-Tyr(N-Cbz-3-aminopropyl)-Val} [SEQ. ID NO.: 78] (0.150 g, 0.146 mmol) was dissolved in trifluoroacetic acid (0.6 mL) and cooled to −10° C. Trifluoromethanesulfonic acid (0.5 mL) was added dropwise, maintaining the temperature at −10° C. Anisole (0.1 mL) was added and the reaction mixture was stirred at −10° C. for 3 h. Diethyl ether was added, the reaction mixture cooled to −35° C. and then stirred for 30 min. The reaction mixture was cooled further to −50° C. and stirred for 30 min. The crude product obtained was filtered, washed with diethyl ether, dried under high vacuum, and purified by preparative HPLC Method 1, to give 29.7 mg (23%) of the desired product as a lyophilized solid. ESMS: Calcd. for $C_{29}H_{45}N_9O_8$, 647.34; Found, 648.5 [M+H]+1. Analytical HPLC, Method 1B, $R_t$=10.432 min, Purity=91%.

was dissolved in DMF (1 mL). Triethylamine (9.5 μL, 0.0648 mmol) was added, and after 5 min of stirring 2-[[[5-[[(2,5-dioxo-1-pyrrolidinyl)oxy]carbonyl]-2-pyridinyl]hydrazono]methyl]-benzenesulfonic acid, monosodium salt (0.0121 g, 0.0274 mmol) was added. The reaction mixture was stirred for 7 days, and then concentrated to an oil under high vacuum. The oil was purified by preparative HPLC Method 1 to give 8.9 mg (37%) of the title product as a lyophilized solid (TFA salt). HRMS: Calcd. for $C_{42}H_{54}N_{12}O_{12}S+H$, 951.3783; Found, 951.3767. Analytical HPLC, Method 1B, $R_t$=14.317 min, Purity=95%.

Example 2

Synthesis of cyclo{Arg-Gly-Asp-D-Tyr((N-[2-[[[5-[carbonyl]-2-pyridinyl]hydrazono]methyl]-benzenesulfonic acid]-18-amino-14-aza-4,7,10-oxy-15-oxo-octadecoyl)-3-aminopropyl)-Val} [SEQ. ID NO.: 2]

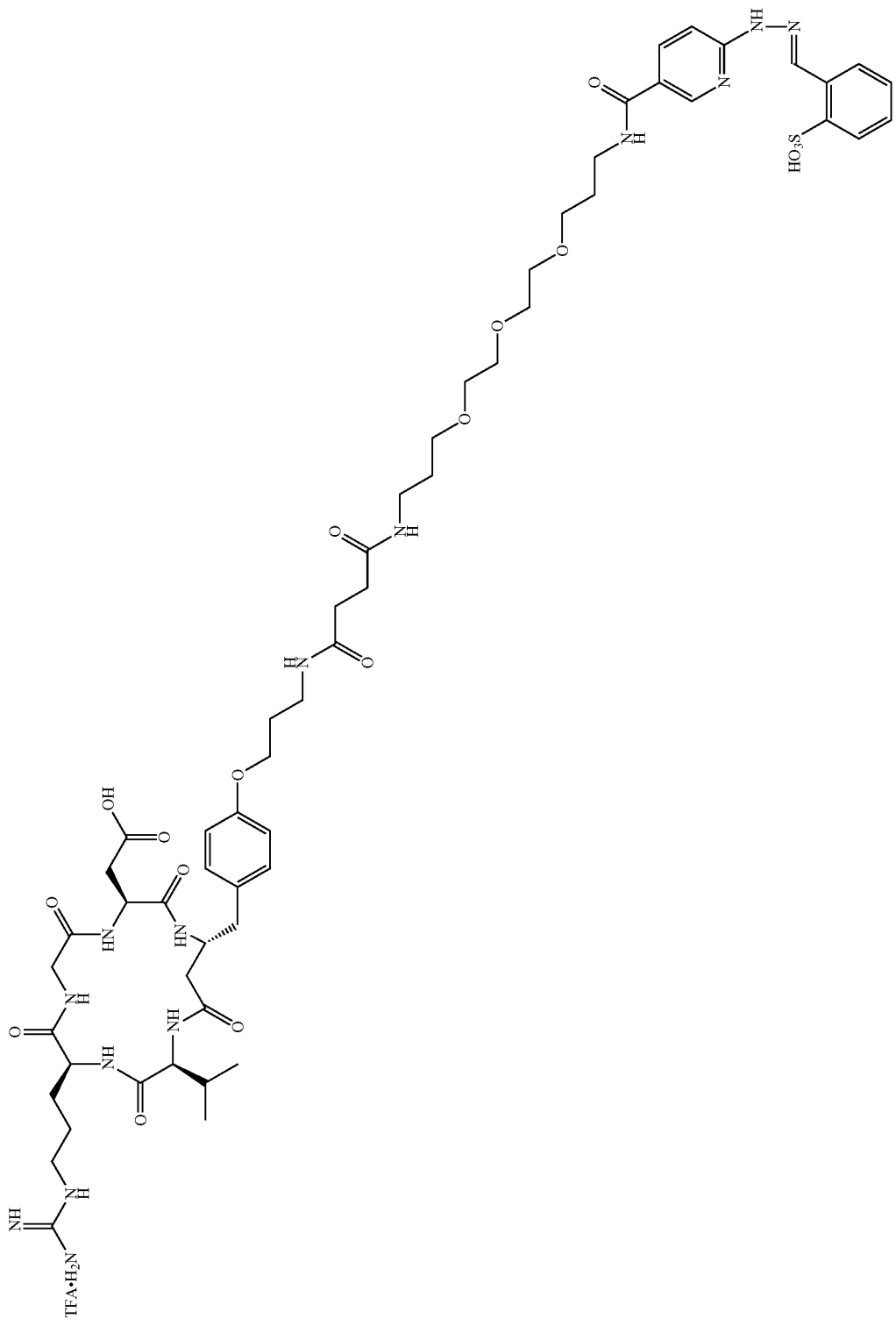

Part A. Preparation of 3-(N-(3-(2-(2-(3-((tert-butoxy)-carbonylamino)propoxy)ethoxy)ethoxy)propyl)carbamoyl)-propanoic acid N-(3-(2-(2-(3-Aminopropoxy)ethoxy)ethoxy)propyl) (tert-butoxy)formamide (1.5 g, 4.68 mmol) was added to DMF (15 mL). To this solution pyridine (15 mL), succinic anhydride (0.47 g, 4.68 mmol) were added, followed by dimethylaminopyridine (62 mL, 0.468 µmol). The reaction mixture was stirred overnight at 100° C. The mixture was concentrated under high vacuum and the residue was brought up in water, acidified to pH 2.5 with 1N HCl, and extracted with ethyl acetate (3×). The combined organic extracts were dried over MgSO$_4$ and filtered. The filtrate was concentrated in vacuo to provide 1.24 g of an oil product (63%). The desired product was used without further purification. $^1$H NMR (CDCl$_3$) 3.67–3.45 (m, 11H), 3.41–3.28 (m, 2H), 3.21–3.09 (m, 2H), 2.95–2.82 (m, 2H), 2.80–2.35 (m, 3H), 1.81–1.68 (m, 4H), 1.50–1.35 (s, 9H); ESMS: Calculated for C$_{19}$H$_{36}$N$_2$O$_8$, 420.2471 Found 419.3 [M−H]−1.

Part B. Preparation of 3-(N-(3-(2-(2-(3-((tert-butoxy)-carbonylamino)propoxy)ethoxy)ethoxy)propyl)carbamoyl) propanoic acid succinimide ester To a solution of 3-(N-(3-(2-(2-(3-((tert-butoxy)-carbonylamino)propoxy)ethoxy)ethoxy)propyl)carbamoyl)-propanoic acid (1.12 g, 2.66 mmol), N-hydroxysuccinimide (0.40 g, 3.46 mmol), and N,N-dimethylformamide (40 mL) was added 1-(3-dimethylaminopropyl)-3-ethylcarbodimide (0.67 g, 3.46 mmol). The reaction mixture was stirred at room temperature for 48 h. The mixture was concentrated under high vacuum and the residue was brought up in 0.1N HCl and extracted with ethyl acetate (3×). The combined organic extracts were washed with water (2×) then saturated sodium chloride, dried over MgSO$_4$, and filtered. The filtrate was cocnentrated in vacuo to give 1.0 g of the product as an oil (73%). The desired product was used without further purification. ESMS: Calculated for C$_{23}$H$_{39}$N$_3$O$_{10}$, 517.2635 Found 518.2 [M+H]+1.

Part C. Preparation of cyclo{Arg-Gly-Asp-D-Tyr(3-(N-(3-(2-(2-(3-((tert-butoxy)-carbonylamino)propoxy)ethoxy)-

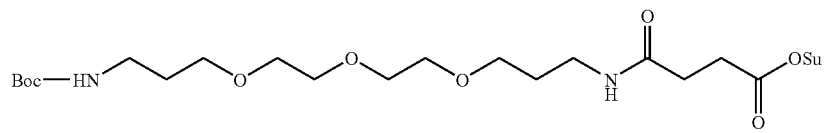

ethoxy)propyl) carbamoyl)-propanamido) propyl)-Val} [SEQ. ID NO.: 82]

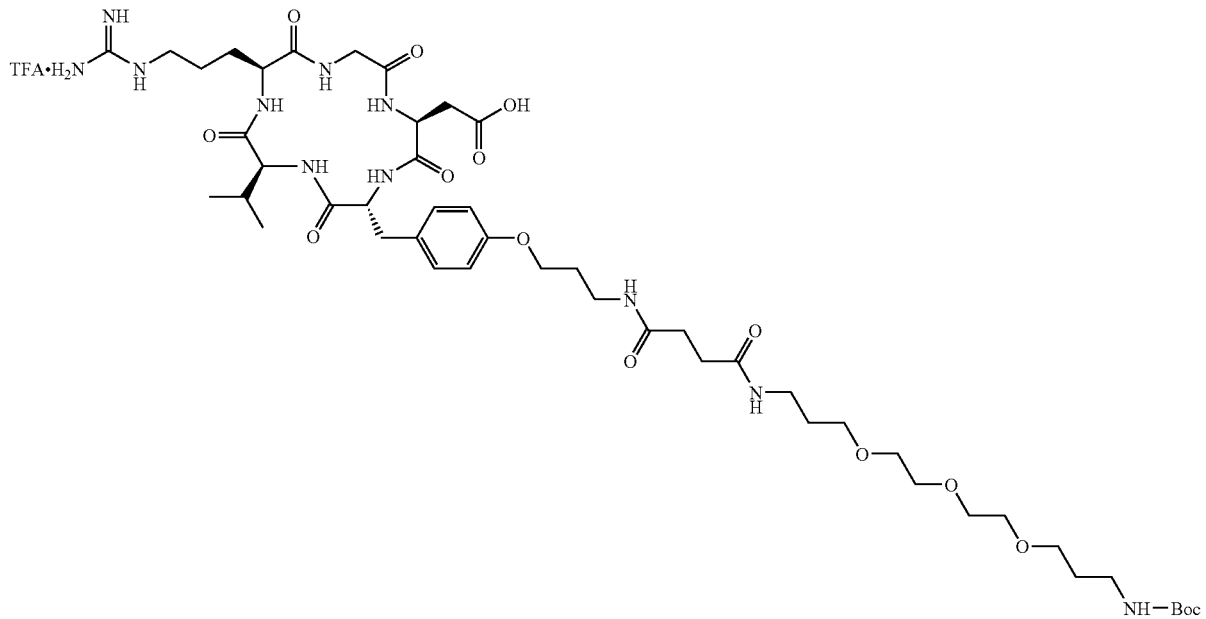

Cyclo{Arg-Gly-Asp-D-Tyr(3-aminopropyl)-Val} [SEQ. ID NO.: 80]. TFA salt (0.040 g, 0.0457 mmol) was dissolved in DMF (2 mL). Triethylamine (19.1 µL, 0.137 mmol) was added and after stirring for 5 minutes 3-(N-(3-(2-(2-(3-((tert-butoxy)-carbonylamino)propoxy)ethoxy)ethoxy)propyl) carbamoyl)propanoic acid succinimide ester (0.0284 g, 0.0548 mmol) was added. The reaction mixture was stirred under $N_2$ for 48 h and then concentrated to an oil under high vacuum. The oil was triturated with ethyl acetate, the product filtered, washed with ethyl acetate, and dried under high vacuum. The crude product was purified by Preparative HPLC Method 1 to give 7.4 mg (14%) of the desired product as a lyophilized solid. ESMS: Calcd. for $C_{48}H_{79}N_{11}O_{15}$, 1049.58; Found, 1050.5 [M+H]+1. Analytical HPLC, Method 1B, $R_t$=20.417 min, Purity=100%.

Part D. Preparation of cyclo{Arg-Gly-Asp-D-Tyr(3-(3-N-(3-(2-(3-(amino)propoxy)ethoxy)ethoxy)propyl)carbamoyl)-propanamido)propyl)-Val} [SEQ. ID NO.: 83]

Cyclo {Arg-Gly-Asp-D-Tyr(3-(3-(N-(3-(2-(2-(3-((tert-butoxy)-carbonylamino)propoxy)ethoxy)ethoxy)propyl)-carbamoyl)-propanamido)propyl)-Val} [SEQ. ID NO.: 82] (6.0 mg, 0.00515 mmol) was dissolved in methylene chloride (1 mL) and trifluoroacetic acid (1 mL) was added. The solution stirred for 2 h and then concentrated to an oil under high vacuum. The oil was triturated with diethyl ether, the product filtered, washed with diethyl ether, and dried under high vacuum to give 6.0 mg (98%) of the desired product. ESMS: Calcd. for $C_{43}H_{71}N_{11}O_{13}$, 949.52; Found, 950.6 [M+H]+1. Analytical HPLC, Method 1B, $R_t$=14.821 min, Purity=73%.

Part E. Preparation of cyclo{Arg-Gly-Asp-D-Tyr((N-2-[[[5-[carbonyl]-2-pyridinyl]hydrazono]methyl]-benzenesulfonic acid]-18-amino-14-aza-4,7,10-oxy-15-oxo-octadecoyl)-3-aminopropyl)-Val} [SEQ. ID NO.: 2]

Cyclo{Arg-Gly-Asp-D-Tyr(3-(3-(N-(3-(2-(2-(3-(amino) propoxy)ethoxy)ethoxy)propyl)carbamoyl)-propanamido) propyl)-Val} [SEQ. ID NO.: 83] (5.0 mg, 0.00424 mmol) was dissolved in dimethylformamide (1 mL). Triethylamine (1.8 µL, 0.0127 mmol) was added, and after stirring for 5 min 2-[[[5-[[(2,5-dioxo-1-pyrrolidinyl)oxy]-carbonyl]-2-pyridinyl]hydrazono]methyl]-benzenesulfonic acid, monosodium salt (2.2 mg, 0.00509 mmol) was added. The reaction mixture was stirred for 24 h and then concentrated to an oil under high vacuum. The oil was purified by preparative HPLC Method 1 to give 2.2 mg (38%) of the desired product as a lyophilized solid (TFA salt). ESMS: Calcd. for $C_{56}H_{80}N_{14}O_{17}S$, 1252.6; Found, 1253.7 (M+H$^+$). Analytical HPLC, Method 1B, $R_t$=17.328 min, Purity=100%.

Example 3

Synthesis of [2-[[[5-[carbonyl]-2-pyridinyl]hydrazono]methyl]-benzenesulfonic acid]-Glu(cyclo{D-Tyr(3-aminopropyl)-Val-Arg-Gly-Asp})-cyclo{D-Tyr(3-aminopropyl)-Val-Arg-Gly-Asp}
[SEQ. ID NO.: 3]

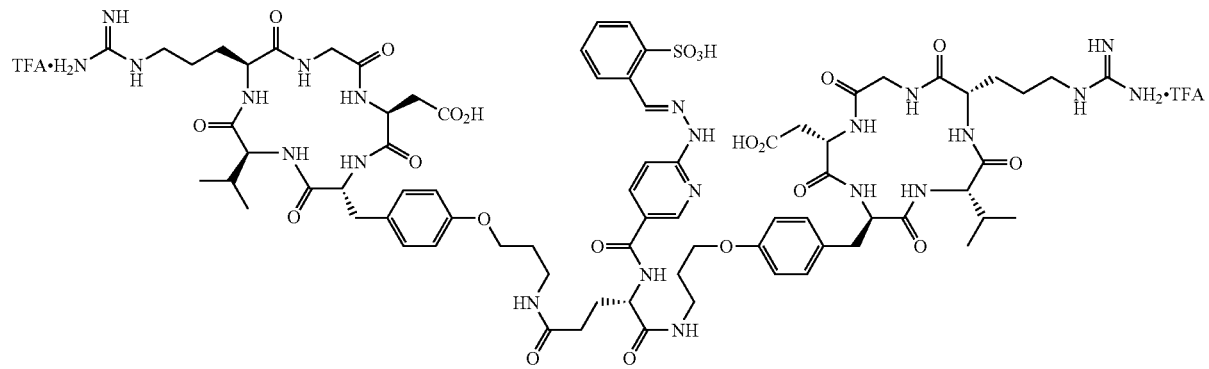

Part A. Preparation of Boc-Glu(cyclo{D-Tyr(3-aminopropyl)-Val-Arg-Gly-Asp})-cyclo{D-Tyr(3-aminopropyl)-Val-Arg-Gly-Asp} [SEQ. ID NO.: 84]

Cyclo{D-Tyr(3-aminopropyl)-Val-Arg-Gly-Asp} [SEQ. ID NO.: 85] (0.040 g, 0.0457 mmol) was dissolved in dimethylformamide (2 mL). Triethylamine (19.1 µL, 0.137 mmol) was added and the reaction mixture was stirred for 5 minutes. Boc-Glu(OSu)-OSu (0.0101 g, 0.0229 mmol) was added and the reaction mixture was stirred under $N_2$ for 18 h. The reaction mixture was then concentrated to an oil under high vacuum. The oil was triturated with ethyl acetate. The product was filtered, washed with ethyl acetate, and dried under high vacuum to give 38.0 mg (55%) of the desired product. ESMS: Calcd. for $C_{68}H_{103}N_{19}O_{20}$, 1505.76; Found, 1504.9 [M−H]−1. Analytical HPLC, Method 1B, $R_t$=19.797 min, Purity=73%.

Part B. Preparation of Glu(cyclo{D-Tyr(3-aminopropyl)-Val-Arg-Gly-Asp})-cyclo{D-Tyr(3-aminopropyl)-Val-Arg-Gly-Asp} [SEQ. ID NO.: 86]. TFA salt

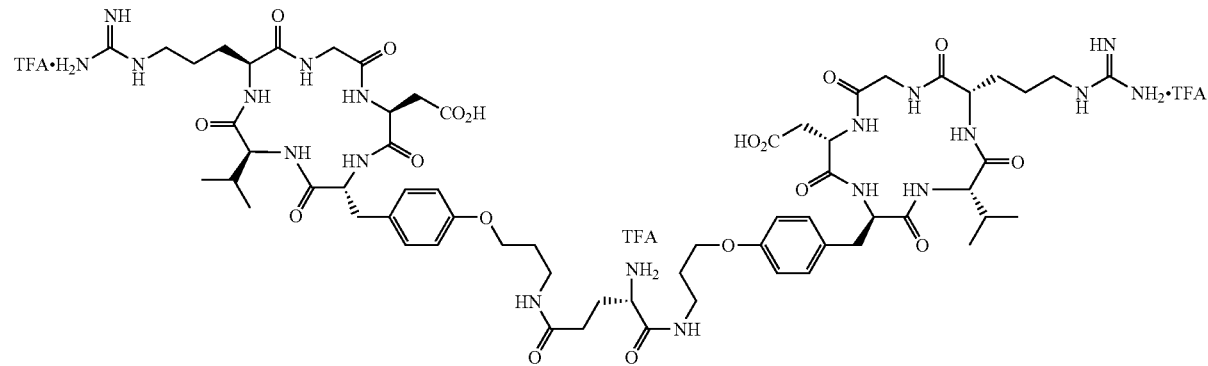

Boc-Glu(cyclo{D-Tyr(3-aminopropyl)-Val-Arg-Gly-Asp})-cyclo{D-Tyr(3-aminopropyl)-Val-Arg-Gly-Asp} [SEQ. ID NO.: 87] (0.035 g, 0.0232 mmol) was dissolved in methylene chloride (1 mL). Trifluoroacetic acid (1 mL) was added, and the reaction mixture was stirred for 2 h, concentrated to an oil under high vacuum and triturated with ether. The product obtained was filtered, washed with diethyl ether, and dried under high vacuum to give 30.7 mg (76%) of the desired product. ESMS: Calcd. for $C_{63}H_{95}N_{19}O_{18}$, 1405.71; Found, 1404.7 [M–H]–1. Analytical HPLC, Method 1B, $R_t$=15.907 min, Purity=77%.

Part C. Preparation of [2-[[[5-[carbonyl]-2-pyridinyl]hydrazono]methyl]-benzenesulfonic acid]-Glu(cyclo{D-Tyr(3-aminopropyl)-Val-Arg-Gly-Asp})-cyclo{D-Tyr(3-aminopropyl)-Val-Arg-Gly-Asp} [SEQ. ID NO.: 3]

To a solution of Glu(cyclo{D-Tyr(3-aminopropyl)-Val-Arg-Gly-Asp})-cyclo{D-Tyr(3-aminopropyl)-Val-Arg-Gly-Asp} [SEQ. ID NO.: 88] (0.025 g, 0.0143 mmol) in dimethylformamide (2 mL) was added triethylamine (6.0 µL, 0.0429 mmol) and the reaction mixture was stirred for 5 min. 2-[[[5-[[(2,5-Dioxo-1-pyrrolidinyl)oxy]carbonyl]-2-pyridinyl]hydrazono]methyl]-benzenesulfonic acid, monosodium salt (0.0076 g, 0.0172 mmol) was added, and the reaction mixture was stirred for 5 days, then concentrated to an oil under high vacuum. The oil was purified by Preparative HPLC Method 1 to give 12.0 mg (43%) of the desired product as a lyophilized solid. ESMS: Calcd. for $C_{76}H_{104}N_{22}O_{22}S$, 1708.7; Found, 1710.1 (M+H$^+$). Analytical HPLC, Method 1B, $R_t$=17.218 min, Purity=94%.

Example 4

Synthesis of cyclo(Arg-Gly-Asp-D-Tyr-Lys([2-[[[5-[carbonyl]-2-pyridinyl]hydrazono]methyl]-benzenesulfonic acid])} [SEQ. ID NO.: 4]

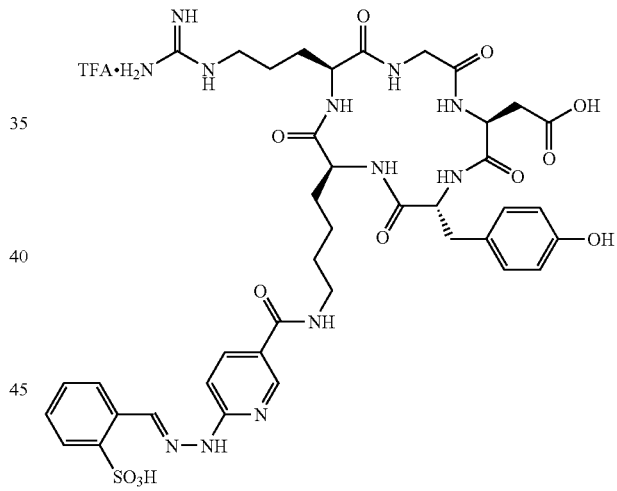

Part A. Preparation of cyclo{Arg(Tos)-Gly-Asp(OBzl)-D-Tyr(Bzl)-Lys(Cbz)} [SEQ. ID NO.: 89]

The N-terminus Boc-protecting group of the peptide sequence Boc-Asp(OBzl)-D-Tyr(Bzl)-Lys(Z)-Arg(Tos)-Gly [SEQ. ID NO.: 90]-oxime resin was removed using standard deprotection (25% TFA in CH$_2$Cl$_2$). After eight washes with DCM, the resin was treated with 10% DIEA/DCM (2×10 min.). The resin was subsequently washed with DCM (×5) and dried under high vacuum. The resin (1.8711 g, 0.44 mmol/g) was then suspended in DMF (15 mL). Glacial acetic acid (47.1 µL, 0.823 mmol) was added, and the reaction was heated at 60° C. for 72 h. The resin was filtered, and washed with DMF (2×10 mL). The filtrate was concentrated to an oil under high vacuum. The resulting oil was triturated with ethyl acetate. The solid thus obtained was filtered, washed with ethyl acetate, and dried under high vacuum to give 653.7 mg of the desired product. ESMS: Calcd. for $C_{56}H_{65}N_9O_{12}S$, 1087.45; Found, 1088.7 [M+H]+1. Analytical HPLC, Method 1A, $R_t$=17.559 min, Purity=82%.

Part B. Preparation of cyclo{Arg-Gly-Asp-D-Tyr-Lys} [SEQ. ID NO.: 91]

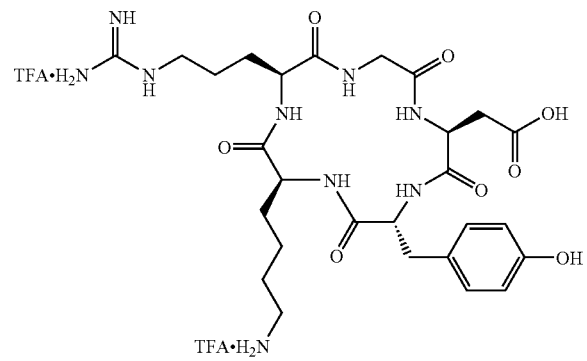

Cyclo{Arg(Tos)-Gly-Asp(OBzl)-D-Tyr(Bzl)-Lys(Cbz)} [SEQ. ID NO.: 89] (0.200 g, 0.184 mmol) was dissolved in trifluoroacetic acid (0.6 mL) and cooled to −10° C. Trifluoromethanesulfonic acid (0.5 mL) was added dropwise, maintaining the temperature at −10° C. Anisole (0.1 mL) was added and the reaction mixture was stirred at −10° C. for 3 h. Diethyl ether was added, the reaction was cooled to −50° C., and stirred for 1 h. The crude product was filtered, washed with diethyl ether, and dried under high vacuum. The crude product was purified by Preparative HPLC Method 1, to give 15.2 mg (10%) of the desired product as a lyophilized solid. HRMS: Calcd. for $C_{27}H_{41}N_9O_8$+H, 620.3156; Found, 620.3145. Analytical HPLC, Method 1B, $R_t$=8.179 min, Purity=100%.

Part C. Preparation of cyclo{Arg-Gly-Asp-D-Tyr-Lys([2-[[[5-[carbonyl]-2-pyridinyl]hydrazono]methyl]-benzenesulfonic acid])} [SEQ. ID NO.: 4]

Cyclo{Arg-Gly-Asp-D-Tyr-Lys} [SEQ. ID NO.: 91] TFA salt (0.010 g, 0.0118 mmol) was dissolved in DMF (1 mL). Triethylamine (5.0 μL, 0.0354 mmol) was added, and after stirring for 5 min 2-[[[5-[[(2,5-Dioxo-1-pyrrolidinyl)oxy]carbonyl]-2-pyridinyl]hydrazono]-methyl]-benzenesulfonic acid, monosodium salt (0.0062 g, 0.0142 mmol) was added. The reaction mixture was stirred for 20 h and then concentrated to an oil under high vacuum. The oil was purified by Preparative HPLC Method 1 to give 6.2 mg (46%) of the desired product as a lyophilized solid. HRMS: Calcd. for $C_{40}H_{50}N_{12}O_{12}S$+H, 923.3470; Found, 923.3486. Analytical HPLC, Method 1B, $R_t$=11.954 min, Purity=100%.

Example 5

Synthesis of cyclo{Arg-Gly-Asp-D-Phe-Lys([2-[[[5-[carbonyl]-2-pyridinyl]hydrazono]methyl]-benzenesulfonic acid])} [SEQ. ID NO.: 5]

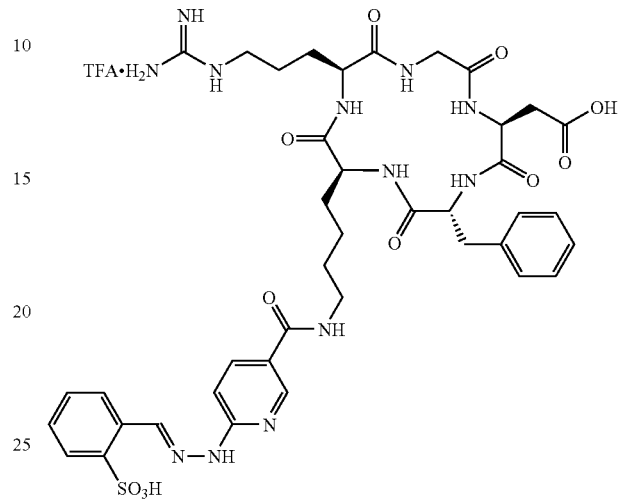

Part A. Preparation of cyclo{Arg(Tos)-Gly-Asp(OBzl)-D-Lys(Cbz)} [SEQ. ID NO.: 92]

The N-terminus Boc-protecting group of the peptide sequence Boc-Asp(OBzl)-D-Phe-Lys(Z)-Arg(Tos)-Gly [SEQ. ID NO.: 93]-Oxime resin was removed using standard deprotection (25% TFA in $CH_2Cl_2$). After eight washes with DCM, the resin was treated with 10% DIEA/DCM (2×10 min.). The resin was subsequently washed with DCM (×5) and dried under high vacuum. The resin (1.7053 g, 0.44 mmol/g) was then suspended in dimethylformamide (15 mL). Glacial acetic acid (43.0 μL, 0.750 mmol) was added, and the reaction was heated to 60° C. for 72 h. The resin was filtered, and washed with DMF (2×10 mL). The filtrate was concentrated to an oil under high vacuum. The resulting oil was triturated with ethyl acetate. The solid thus obtained was filtered, washed with ethyl acetate, and dried under high vacuum to give 510.3 mg of the desired product. ESMS: Calcd. for $C_{49}H_{59}N_9O_{11}S$, 981.40; Found, 982.6 [M+H]+1. Analytical HPLC, Method 1A, $R_t$=15.574 min, Purity=89%.

Part B. Preparation of cyclo{Arg-Gly-Asp-D-Phe-Lys} [SEQ. ID NO.: 94]

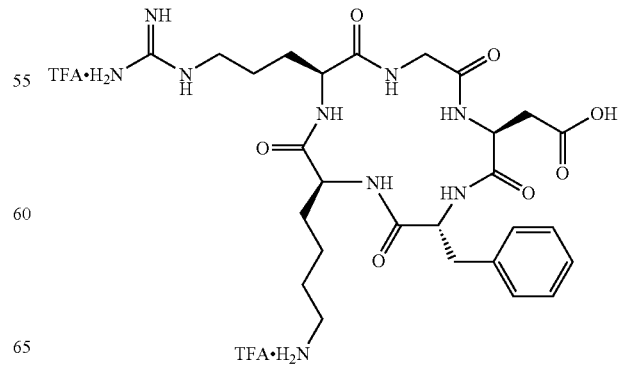

Cyclo{Arg(Tos)-Gly-Asp(OBzl)-D-Phe-Lys(Cbz)} [SEQ. ID NO.: 92] (0.200 g, 0.204 mmol) was dissolved in trifluoracetic acid (0.6 mL) and cooled to −10° C. Trifluoromethanesulfonic acid (0.5 mL) was added dropwise, maintaining the temperature at −10° C. Anisole (0.1 mL) was added and the reaction was stirred at −10° C. for 3 h. Diethyl ether was added, the reaction was cooled to −50° C., and stirred for 1 h. The crude product was filtered, washed with diethyl ether, dried under high vacuum and purified by Preparative HPLC Method 1, to give 121.1 mg (71%) of the desired product as a lyophilized solid. HRMS: Calcd. for $C_{27}H_{41}N_9O_7+H$, 604.3207; Found, 604.3206. Analytical HPLC, Method 1B, $R_t$=11.197 min, Purity=100%.

Part C. Preparation of cyclo{Arg-Gly-Asp-D-Phe-Lys([2-[[[5-[carbonyl]-2-pyridinyl]hydrazono]methyl]-benzenesulfonic acid])} [SEQ. ID NO.: 5]

Cyclo{Arg-Gly-Asp-D-Phe-Lys} [SEQ. ID NO.: 94] TFA salt (0.040 g, 0.0481 mmol) was dissolved in DMF (2 mL). Triethylamine (20.1 μL, 0.144 mmol) was added, and after 5 min of stirring 2-[[[5-[[(2,5-dioxo-1-pyrrolidinyl)oxy]carbonyl]-2-pyridinyl]hydrazono]-methyl]-benzenesulfonic acid, monosodium salt (0.0254 g, 0.0577 mmol) was added. The reaction mixture was stirred for 20 h and then concentrated to an oil under high vacuum. The oil was purified by Preparative HPLC Method 1 to give 38.2 mg (78%) of the desired product as a lyophilized solid. HRMS: Calcd. for $C_{40}H_{50}N_{12}O_{11}S+H$, 907.3521; Found, 907.3534. Analytical HPLC, Method 1B, $R_t$=14.122 min, Purity=91%.

Example 6

Synthesis of [2-[[[5-[carbonyl]-2-pyridinyl]hydrazono]methyl]-benzenesulfonic acid]-Glu(cyclo{Lys-Arg-Gly-Asp-D-Phe})-cyclo{Lys-Arg-Asp-D-Phe} [SEQ. ID NO.: 6]

Part A. Preparation of Boc-Glu(OSu)-OSu

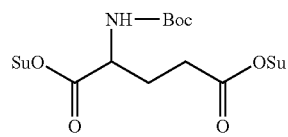

To a solution of Boc-Glu-OH (8.0 g, 32.25 mmol), N-hydroxysuccinimide (8.94 g, 77.64 mmol), and DMF (120 m]L) was added 1-(3-dimethylaminopropyl)-3-ethylcarbodimide (14.88 g, 77.64 mmol). The reaction mixture was stirred at room temperature for 48 h. The mixture was concentrated under high vacuum and the residue was brought up in 0.1 N HCl and extracted with ethyl acetate (3×). The combined organic extracts were washed with water, saturated sodium bicarbonate and then saturated sodium chloride, dried over MgSO₄, and filtered. The filtrate was concentrated in vacuo and purified via reverse-phase HPLC (Vydac C18 column, 18 to 90% acetonitrile gradient containing 0.1% TFA, $R_t$=9.413 min) to afford 8.5 g (60%) of the desired product as a white powder. $^1$H NMR (CDCl₃): 2.98–2.70 (m, 11H), 2.65–2.25 (m, 2H), 1.55–1.40 (s, 9H); ESMS: Calculated for $C_{18}H_{23}N_3O_{10}$, 441.1383 Found 459.2 [M+NH₄]+1.

Part B. Preparation of Boc-Gly(cyclo{Lys-Arg-Gly-Asp-D-Phe})-cyclo{Lys-Arg-Gly-Asp-D-Phe} [SEQ. ID NO.: 95]

To a solution of cyclo(Lys-Arg-Gly-Asp-D-Phe) [SEQ. ID NO.: 96] (0.050 g, 0.0601 mmol) in dimethylformamide (2 mL) was added triethylamine (25.1 μL, 0.183 mmol). After stirring for 5 minutes Boc-Glu(OSu)-OSu (0.0133 g, 0.0301 mmol) was added. The reaction mixture was stirred under N₂ for 20 h, then concentrated to an oil under high vacuum and triturated with ethyl acetate. The product thus obtained was filtered, washed with ethyl acetate, and dried under high vacuum to give 43.7 mg (44%) of the desired product. ESMS: Calcd. for $C_{64}H_{95}N_{19}O_{18}$, 1417.71; Found, 1418.8 [M+H]+1. Analytical HPLC, Method 1B, $R_t$=19.524 min, Purity=73%.

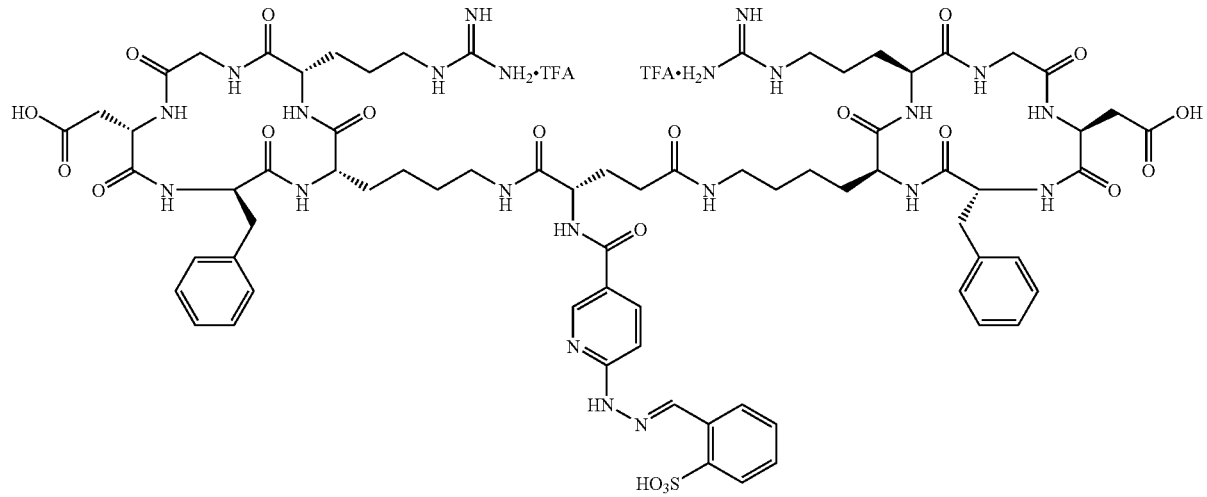

Part C. Preparation of Glu(cyclo{Lys-Arg-Gly-Asp-D-Phe})-cyclo{Lys-Arg-Gly-Asp-D-Phe} [SEQ. ID NO.: 97] TFA salt

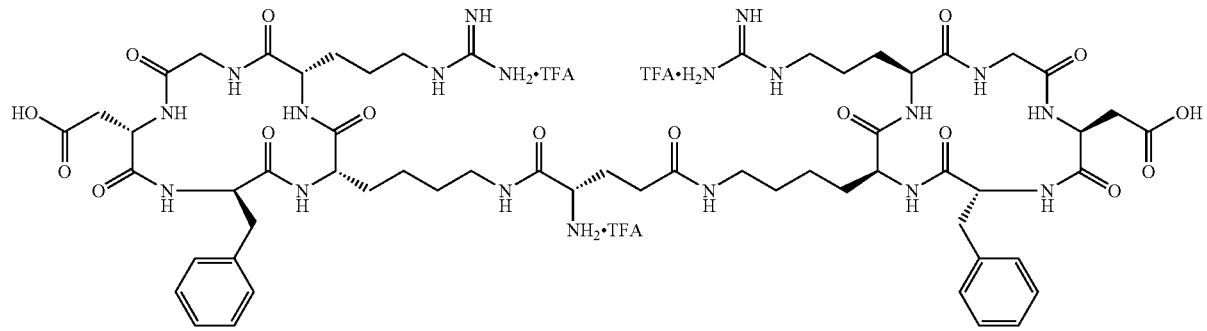

To a solution of Boc-Glu(cyclo{Lys-Arg-Gly-Asp-D-Phe})-cyclo{Lys-Arg-Gly-Asp-D-Phe} [SEQ. ID NO.: 95] (0.040 g, 0.0243 mmol) in methylene chloride (1 mL) was added trifluoroacetic acid (1 mL). The reaction mixture was stirred for 2 h, concentrated to an oil under high vacuum and triturated with diethyl ether. The product was filtered, washed with diethyl ether, and dried under high vacuum to give 39.9 mg (100%) of the desired product. ESMS: Calcd. for $C_{59}H_{87}N_{19}O_{16}$, 1317.66; Found, 1318.9 [M+H]+1. Analytical HPLC, Method 1B, $R_t$=15.410 min, Purity=73%.

Part D. Preparation of [2-[[[5-[carbonyl]-2-pyridinyl]-hydrazono]methyl]-benzenesulfonic acid]-Gly(cyclo{Lys-Arg-Asp-D-Phe})-cyclo{Lys-Arg-Gly-Asp-D-Phe} [SEQ. ID NO.: 6]

To a solution of Glu(cyclo{Lys-Arg-Gly-Asp-D-Phe})-cyclo{Lys-Arg-Gly-Asp-D-Phe} [SEQ. ID NO.: 97] (0.030 g, 0.0183 mmol) in dimethylformamide (3 mL) was added triethylamine (7.6 µL, 0.0549 mmol) and the reaction mixture was stirred for 5 min. 2-[[[5-[[(2,5-Dioxo-1-pyrrolidinyl)oxy]carbonyl]-2-pyridinyl]-hydrazono]methyl]-benzenesulfonic acid, monosodium salt (0.0096 g, 0.0220 mmol) was added, and the reaction mixture was stirred for 18 h, then concentrated to an oil under high vacuum. The oil was purified by Preparative HPLC Method 1 to give 11.0 mg (32%) of the desired product as a lyophilized solid. ESMS: Calcd. for $C_{72}H_{96}N_{22}O_{20}S$, 1620.7; Found, 1620.1 (M−H⁺). Analytical HPLC, Method 1B, $R_t$=16.753 min, Purity=91%.

Example 7

Synthesis of [2-[[[5-[carbonyl]-2-pyridinyl]hydrazono]methyl]-benzenesulfonic acid]-Phe-Glu(cyclo{Lys-Arg-Gly-Asp-D-Phe})-cyclo{Lys-Arg-Gly-Asp-D-Phe} [SEQ. ID NO.: 7]

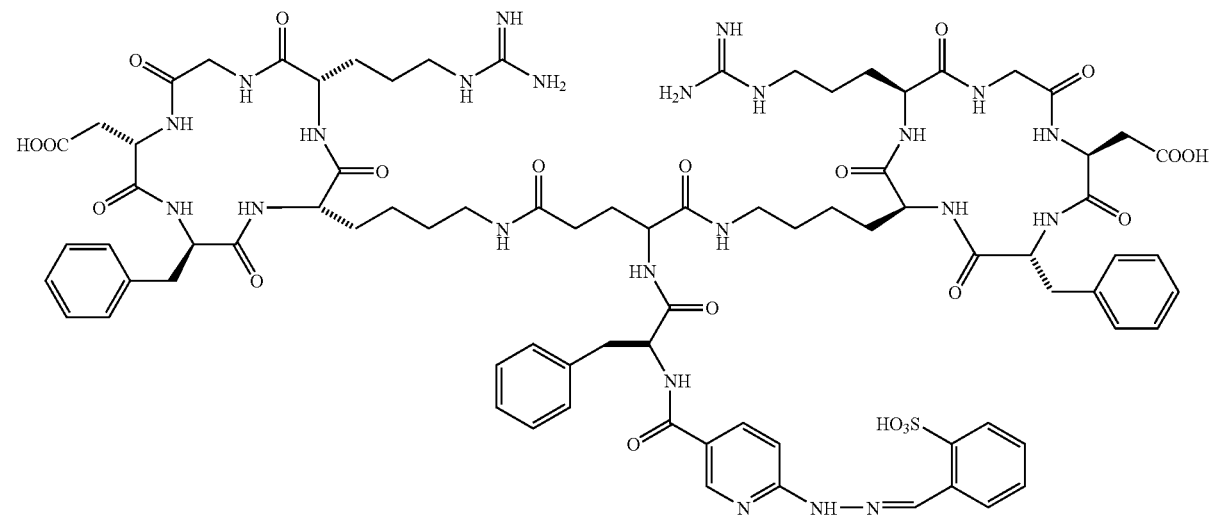

Part A. Preparation of Phe-Glu(cyclo{Lys-Arg-Gly-Asp-D-Phe})-cyclo{Lys-Arg-Gly-Asp-D-Phe} [SEQ. ID NO.: 98]

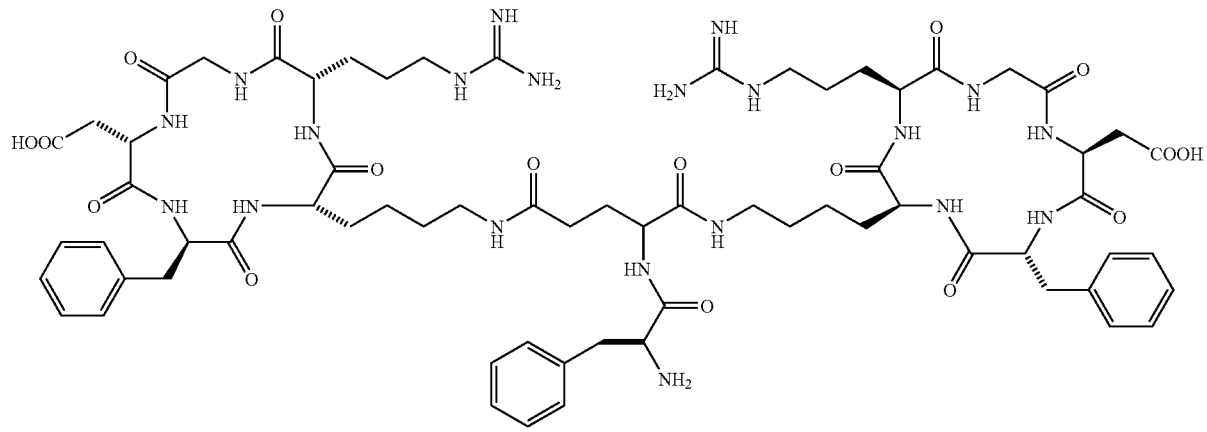

A solution of Glu(cyclo{Lys-Arg-Gly-Asp-D-Phe})-cyclo{Lys-Arg-Gly-Asp-D-Phe} [SEQ. ID NO.: 97] (23.4 mg, 0.014 mmol) and triethylamine (7.8 μL, 0.56 mmol) in DMF (2 mL) was stirred for 5 min. To this was added Boc-Phe-OSu (5.1 mg, 0.014 mmol) and the reaction mixture was stirred overnight at room temperature under nitrogen. DMF was removed in vacuo, and the resulting residue was dissolved in TFA (1.5 mL) and methylene chloride (1.5 mL). The solution was stirred for 2 h and concentrated in vacuo to provide 31 mg of the desired product as the TFA salt. ESMS: Calcd. for $C_{68}H_{96}N_{20}O_{17}$, 1464.7; Found, 1465.6 (M+H)+1. Analytical HPLC, Method 1B, $R_t$=15.48 min, Purity=95%.

Part B. Preparation of [2-[[[5-[carbonyl]-2-pyridinyl]hydrazono]methyl]-benzenesulfonic acid]-Phe-Glu(cyclo{Lys-Arg-Gly-Asp-D-Phe})-cyclo{Lys-Arg-Gly-Asp-D-Phe} [SEQ. ID NO.: 7]

To a solution of Phe-Glu(cyclo{Lys-Arg-Gly-Asp-D-Phe})-cyclo{Lys-Arg-Gly-Asp-D-Phe} [SEQ. ID NO.: 98] (0.030 g, 0.016 mmol) in dimethylformamide (2 mL) was added triethylamine (9 μL, 0.064 mmol) and the reaction mixture was stirred for 5 min. 2-[[[5-[[(2,5-Dioxo-1-pyrrolidinyl)oxy]carbonyl]-2-pyridinyl]-hydrazono]methyl]-benzenesulfonic acid, monosodium salt (0.0099 g, 0.0220 mmol) was added, and the reaction mixture was stirred for 18 h, then concentrated under high vacuum. The residue was purified by preparative RP-HPLC Method 1 to give 7 mg (22%) of the desired product as a lyophilized solid (TFA salt). ESMS: Calcd. for $C_{81}H_{105}N_{23}O_{21}S$, 1767.8; Found, 1768.8 (M−H+). Analytical HPLC, Method 1B, $R_t$=17.68 min, Purity=99%.

Example 8

Synthesis of cyclo{Arg-Gly-Asp-D-Nal-Lys([2-[[[5-[carbonyl]-2-pyridinyl]hydrazono]methyl]-benzenesulfonic acid])} [SEQ. ID NO.: 8]

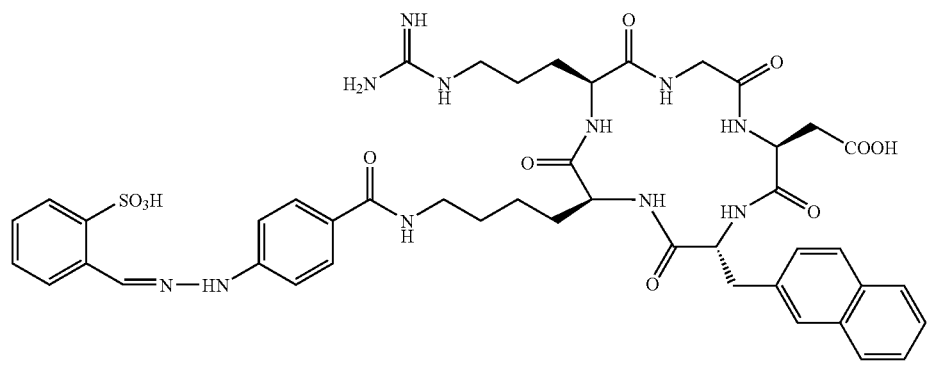

Part A. Preparation of cyclo{Arg(Mtr)-Gly-Asp(OtBu)-D-NaI-Lys(Boc)} [SEQ. ID NO.: 99]

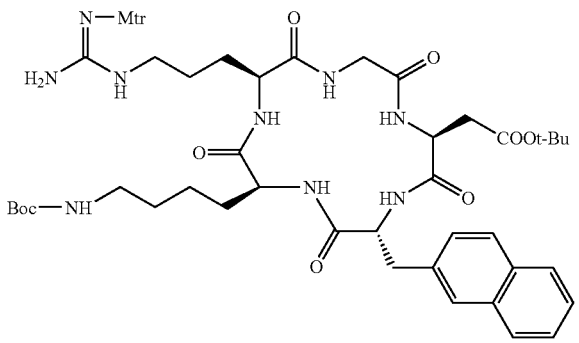

The peptide Asp(OtBu)-D-NaI-Lys(Boc)-Arg(Mtr)-Gly [SEQ. ID NO.: 100] was obtained by automated solid phase peptide synthesis using Fmoc chemistry. A 100 mL round bottom flask was charged with HBTU (349 mg, 0.92 mmol) and DMF (10 mL). The solution was stirred at 60° C. for 5 min. To this a solution of Asp(OtBu)-D-NaI-Lys(Boc)Arg(Mtr)-Gly [SEQ. ID NO.: 100] (0.684 g) and Hunig's base (0.34 mL, 1.97 mmol.) in DMF (10 mL) was added and the solution stirred at 60° C. for 4 h under nitrogen. The solvent was then removed in vacuo and the residue was triturated with ethyl acetate. The solids were filtered and washed with ethyl acetate (3×5 mL) and dried in vacuo to give the desired product (520 mg, 86%). ESMS: Calcd. for $C_{50}H_{71}N_9O_{12}S$, 1021.5; Found, 1022.5 [M+H]+1. Analytical HPLC, Method 1A, $R_t$=15.91 min (purity 99%).

Part B. Preparation of cyclo{Arg-Gly-Asp-D-NaI-Lys} [SEQ. ID NO.: 101] bis TFA salt

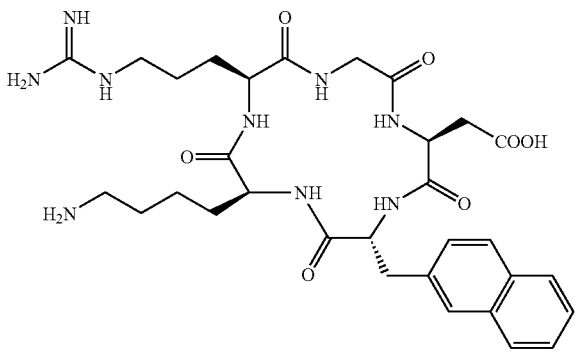

A solution of cyclo{Arg(Mtr)-Gly-Asp(OtBu)-D-NaI-Lys(Boc)} [SEQ. ID NO.: 99] (500 mg, 0.49 mmol), TFA (7 mL), triisopropylsilane (0.25 mL) and water (0.25 mL) was stirred at room temperature under nitrogen for 18 h. The solvents were removed in vacuo (over 3 h) and the residue triturated with diethyl ether to give the desired product as the TFA salt (426 mg, 98%). ESMS: Calcd. for $C_{31}H_{43}N_9O_7$, 653.3; Found, 654.3 [M+H]+1. Analytical HPLC, Method 1B, $R_t$=13.30 min, Purity=97%.

Part C. Preparation of cyclo{Arg-Gly-Asp-D-NaI-Lys([2-[[[5-[carbonyl]-2-pyridinyl]hydrazono]methyl]-benzenesulfonic acid])} [SEQ. ID NO.: 8]

Cyclo{Arg-Gly-Asp-D-NaI-Lys} [SEQ. ID NO.: 101] TFA salt (0.056 g, 0.064 mmol) was dissolved in DMF (2 mL). Triethylamine (27 µL, 0.19 mmol) was added, and after 5 min of stirring 2-[[[5-[[(2,5-dioxo-1-pyrrolidinyl)oxy]carbonyl]-2-pyridinyl]-hydrazono]-methyl]-benzenesulfonic acid, monosodium salt (0.039 g, 0.089 mmol) was added. The reaction mixture was stirred overnight, under nitrogen, and then concentrated to an oil under high vacuum. The oil was purified by Preparative HPLC Method 1 to give 49.3 mg (72%) of the desired product as a lyophilized solid (TFA salt). ESMS: Calcd. for $C_{44}H_{52}N_{12}O_{11}S$, 956.4; Found, 957.5 [M+H]+1. Analytical HPLC, Method 1B, $R_t$=16.19 min, Purity=99%.

Example 9

Synthesis of [2-[[[5-[carbonyl]-2-pyridinyl]-hydrazono]methyl]-benzenesulfonic acid]-Glu(cyclo{Lys-Arg-Gly-Asp-D-NaI})-cyclo{Lys-Arg-Gly-Asp-D-NaI} [SEQ. ID NO.: 9]

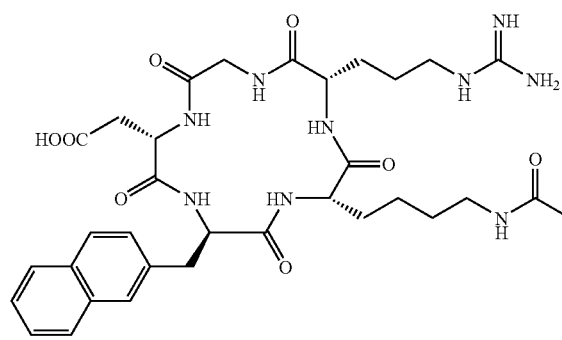

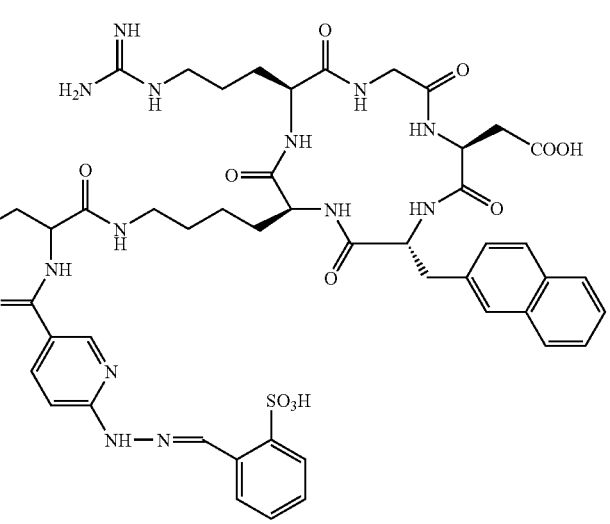

Part A. Preparation of Boc-Glu(cyclo{Lys-Arg-Gly-Asp-D-Nal})-cyclo{Lys-Arg-Gly-Asp-D-Nal} [SEQ. ID NO.: 102]

To a solution of cyclo{Lys-Arg-Gly-Asp-D-Nal} [SEQ. ID NO.: 103] (0.052 g, 0.059 mmol) in dimethylformamide (2 mL) was added triethylamine (25 µL). After stirring for 5 minutes Boc-Glu(OSu)-OSu (0.013 g, 0.029 mmol) was added. The reaction mixture was stirred under $N_2$ for 20 h, then concentrated to an oil under high vacuum and triturated with ethyl acetate. The product thus obtained was filtered, washed with ethyl acetate, and dried under high vacuum to give 35.2 mg of the desired product in crude form. ESMS: Calcd. for $C_{72}H_{99}N_{19}O_{18}$, 1517.7; Found, 760.1 [M+2H]+2. Analytical HPLC, Method 1B, $R_t$=21.07 min (65%).

Part B. Preparation of Glu(cyclo{Lys-Arg-Gly-Asp-D-Nal})-cyclo{Lys-Arg-Gly-Asp-D-Nal} [SEQ. ID NO.: 104]

Part C. Preparation of [2-[[[5-[carbonyl]-2-pyridinyl]hydrazono]methyl]-benzenesulfonic acid]-Glu(cyclo{Lys-Arg-Gly-Asp-D-Nal})-cyclo{Lys-Arg-Gly-Asp-D-Nal} [SEQ. ID NO.: 9]

To a solution of Glu(cyclo{Lys-Arg-Gly-Asp-D-Nal})-cyclo{Lys-Arg-Gly-Asp-D-Nal} [SEQ. ID NO.: 104] (34.9 mg) in dimethylformamide (2 mL) was added triethylamine (10 µL, 0.074 mmol) and the reaction mixture was stirred for 5 min. 2-[[[5[[(2,5-Dioxo-1-pyrrolidinyl)oxy]carbonyl]-2-pyridinyl]-hydrazono]methyl]-benzenesulfonic acid, monosodium salt (15.2 mg, 0.0344 mmol) was added, and the reaction mixture was stirred for 18 h, then concentrated to an oil under high vacuum. The oil was purified by preparative RP-HPLC Method 1 to give 3 mg of the desired product

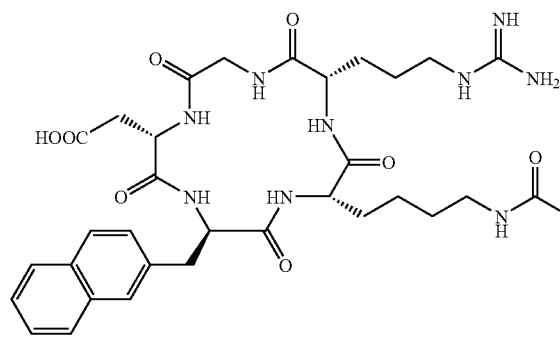
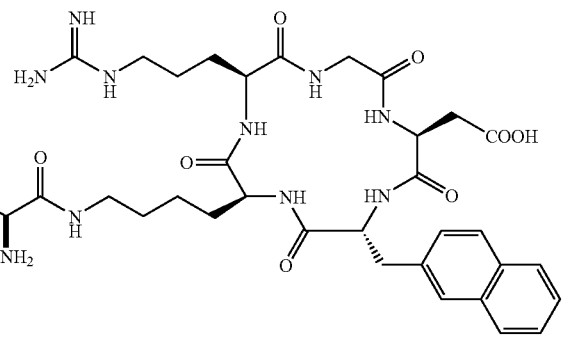

30

To a solution of the crude Boc-Glu(cyclo{Lys-Arg-Gly-Asp-D-Nal})-cyclo{Lys-Arg-Gly-Asp-D-Nal} [SEQ. ID NO.: 102] (35.2 mg) in methylene chloride (1.5 mL) was added trifluoroacetic acid (1.5 mL). The reaction mixture was stirred for 2 h, concentrated to an oil under high vacuum and triturated with diethyl ether. The product was filtered, washed with diethyl ether, and dried under high vacuum to give 34.9 mg of the crude desired product (TFA salt). ESMS: Calcd. for $C_{67}H_{91}N_{19}O_{16}$, 1417.69; Found, 1418.7 [M+H]+1. Analytical HPLC, Method 1B, $R_t$=19.1 min, Purity=62%.

(TFA salt). ESMS: Calcd. for $C_{80}H_{100}N_{22}O_{20}S$, 1720.7; Found, 1722.6 (M+H)+1. Analytical HPLC, Method 1B, $R_t$=19.78 min, Purity=92%.

Example 10

Synthisis of cyclo{Arg-Gly-Asp-Lys([2-[[[5-[carbonyl]-2-pyridinyl]hydrazono]methyl]-benzenesulfonic acid])-D-Val} [SEQ. ID NO.: 10]

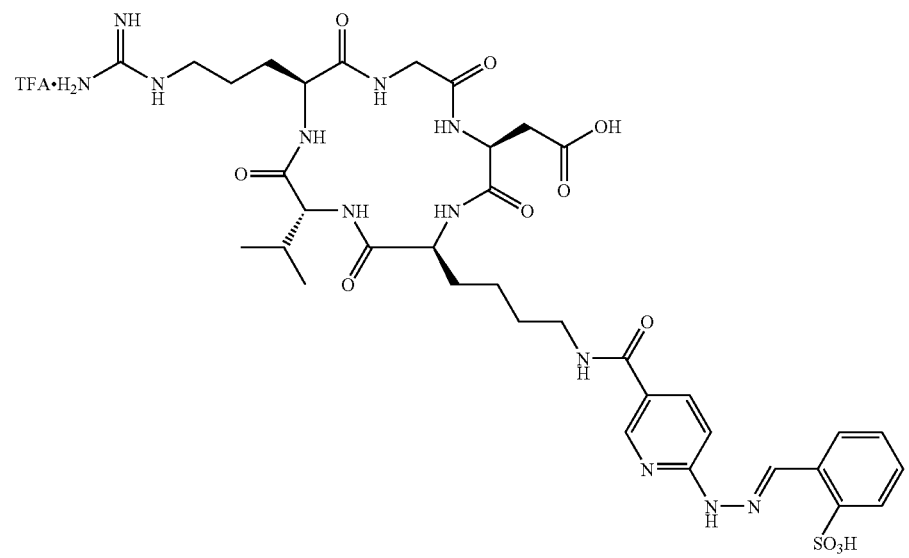

Part A. Preparation of cyclo{Arg(Tos)-Gly-Asp(OBzl)-Lys(Cbz)-D-Val} [SEQ. ID NO.: 105]

The N-terminus Boc-protecting group of the peptide sequence Boc-Asp(OBzl)Lys(Z)-D-Val-Arg(Tos)-Gly [SEQ. ID NO.: 106]-Oxime resin was removed using standard deprotection (25% TFA in $CH_2Cl_2$). After eight washes with DCM, the resin was treated with 10% DIEA/DCM (2×10 min.). The resin was subsequently washed with DCM (×5) and dried under high vacuum. The resin (1.3229 g, 0.44 mmol/g) was then suspended in dimethylformamide (10 mL). Glacial acetic acid (33.3 µL, 0.582 mmol) was added, and the reaction was heated at 65° C. for 72 h. The resin was filtered, and washed with DMF (2×10 mL). The filtrate was concentrated to an oil under high vacuum. The resulting oil was triturated with ethyl acetate. The solid thus obtained was filtered, washed with ethyl acetate, dried under high vacuum, then purified by Preparative HPLC Method 2 to give 93.0 mg of the desired product as a lyophilized solid. ESMS: Calcd. for $C_{45}H_{59}N_9O_{11}S$, 933.41; Found, 934.5 [M+H]+1. Analytical HPLC, Method 1A, $R_t$=14.078 min, Purity=85%.

| Preparative HPLC Method 2 | | | |
|---|---|---|---|
| Instrument: | Rainin Rabbit; Dynamax software | | |
| Column: | Vydac C-18 (21.2 mm × 25 cm) | | |
| Detector: | Knauer VWM | | |
| Flow Rate: | 15 ml/min | | |
| Column Temp: | RT | | |
| Mobile Phase: | A: 0.1% TFA in $H_2O$ | | |
| | B: 0.1% TFA in ACN/$H_2O$ (9:1) | | |
| Gradient: | Time (min) | % A | % B |
| | 0 | 80 | 20 |
| | 20 | 0 | 100 |
| | 30 | 0 | 100 |
| | 31 | 80 | 20 |

Part B. Preparation of cyclo{Arg-Gly-Asp-Lys-D-Val} [SEQ. ID NO.: 107]

Cyclo{Arg(Tos)-Gly-Asp(OBzl)-Lys(Cbz)-D-Val} [SEQ. ID NO.: 105] (0.080 g, 0.0856 mmol) was dissolved in trifluoroacetic acid (0.6 mL) and cooled to −10° C. Trifluoromethanesulfonic acid (0.5 mL) was added dropwise, maintaining the temperature at −10° C. Anisole (0.1 mL) was added and the reaction mixture was stirred at −10° C. for 3 h. Diethyl ether was added, the reaction mixture cooled to −50° C. and stirred for 30 mins. The crude product obtained was filtered, washed with ether, dried under high vacuum and purified by Preparative HPLC Method 1, to give 44.2 mg (66%) of the desired product as a lyophilized solid. ESMS: Calcd. for $C_{23}H_{41}N_9O_7$, 555.31; Found, 556.3 [M+H]+1. Analytical HPLC, Method 1B, $R_t$=8.959 min, Purity=92%.

Part C. Preparation of cyclo{Arg-Gly-Asp-Lys([2-[[[5-[carbonyl]-2-pyridinyl]hydrazono]methyl]-benzenesulfonic acid])-D-Val} [SEQ. ID NO.: 10]

To a solution of cyclo{Arg-Gly-Asp-Lys-D-Val} [SEQ. ID NO.: 107] (0.036 g, 0.0459 mmol) in dimethylformamide (3 mL) was added triethylamine (19.2 µL, 0.0138 mmol) and stirred for 5 min. Methyl sulfoxide was added (0.7 mL) followed by 2-[[[5[[(2,5-dioxo-1-pyrrolidinyl)oxy]carbonyl]-2-pyridinyl]-hydrazono]methyl]-benzenesulfonic acid, monosodium salt (0.0243 g, 0.0551 mmol) and the reaction mixture stirred for 20 h. The reaction mixture was concentrated to an oil under high vacuum and purified by Preparative HPLC Method 1 to give 13.9 mg (31%) of the desired product as a lyophilized solid. HRMS: Calcd. for $C_{36}H_{50}N_{12}O_{11}S$+H, 859.3443; Found, 859.3503. Analytical HPLC, Method 1B, $R_t$=13.479 min, Purity=92%.

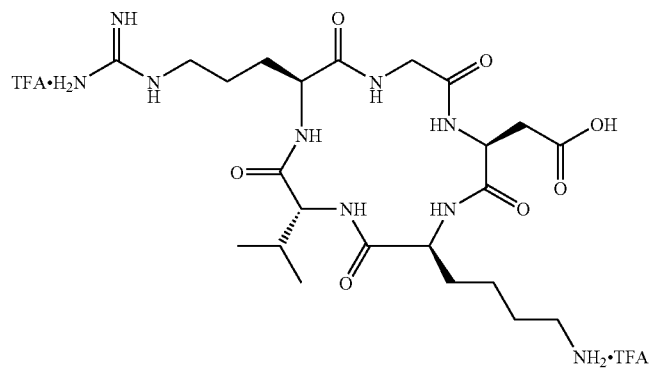

Example 11

Synthesis of [2-[[[5-[carbonyl]-2-pyridinyl]hydrazono]methyl]-benzenesulfonic acid]-Glu(cyclo{Lys-D-Val-Arg-Gly-Asp})-cyclo{Lys-D-Val-Arg-Gly-Asp} [SEQ. ID NO.: 11]

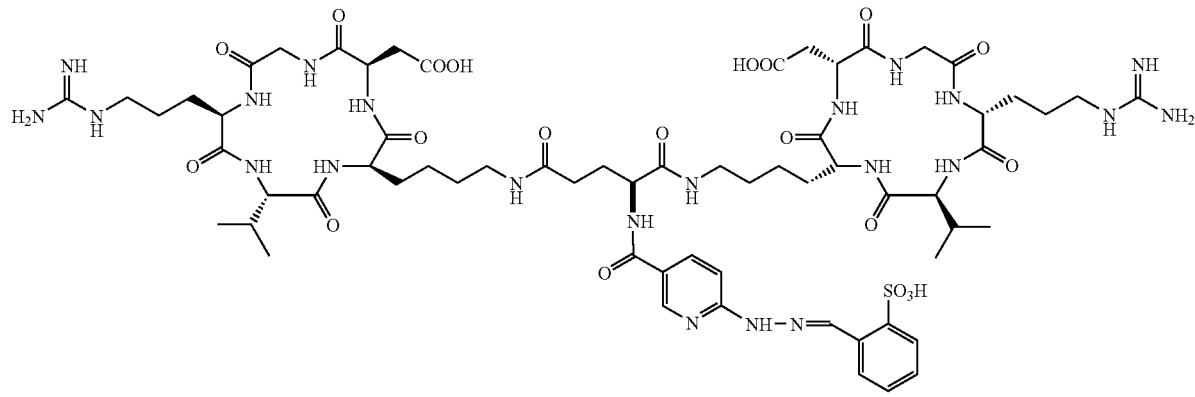

Part A. Preparation of Boc-Glu(cyclo{Lys-D-Val-Arg-Gly-Asp})-cyclo{Lys-D-Val-Arg-Gly-Asp} [SEQ. ID NO.: 108]

To a solution of cyclo{Lys-D-Val-Arg-Gly-Asp} [SEQ. ID NO.: 109] (0.400 g, 0.51 mmol) in dimethylformamide (7 mL) was added triethylamine (0.21 mL, 1.53 mmol). After stirring for 5 minutes Boc-Glu(OSu)-OSu (115 mg, 0.26 mmol) was added. The reaction mixture was stirred under $N_2$ for 20 h, then concentrated to an oil. The product thus obtained was partially purified by preparative RP-HPLC to give 124 mg of product. ESMS: Calcd. for $C_{56}H_{95}N_{19}O_{18}$, 1321.71; Found, 1322.6 [M+H]+1.

Part B. Preparation of Glu(cyclo{Lys-D-Val-Arg-Gly-Asp}-cyclo{Lys-D-Val-Arg-Gly-Asp} [SEQ. ID NO.: 110]

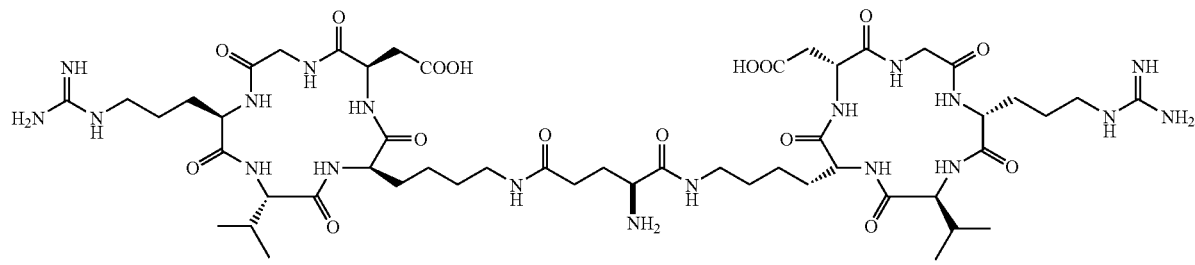

To a solution of the impure Boc-Glu(cyclo{Lys-D-Val-Arg-Gly-Asp})-cyclo{Lys-D-Val-Arg-Gly-Asp} [SEQ. ID NO.: 111] (0.124 g) in methylene chloride (5 mL) was added trifluoroacetic acid (5 mL). The reaction mixture was stirred for 2 h, concentrated to an oil under high vacuum and triturated with diethyl ether. The product was filtered, washed with diethyl ether, and dried under high vacuum to give 16.2 mg of the desired product after RP-HPLC (TFA salt). ESMS: Calcd. for $C_{51}H_{87}N_{19}O_{16}$, 1221.66; Found, 1222.6 [M+H]+1. Analytical HPLC, Method 1B, $R_t$=11.43 min, Purity=93%.

Part C. Preparation of [2-[[[5-[carbonyl]-2-pyridinyl]hydrazono]methyl]-benzenesulfonic acid]-Glu(cyclo{Lys-D-Val-Arg-Gly-Asp})-cyclo{Lys-D-Val-Arg-Gly-Asp} [SEQ. ID NO.: 11]

To a solution of Glu(cyclo{Lys-D-Val-Arg-Gly-Asp})-cyclo{Lys-D-Val-Arg-Gly-Asp} [SEQ. ID NO.: 110] (0.016 g, 0.01 mmol) in dimethylformamide (2 mL) was added triethylamine (4.2 µL) and the reaction mixture was stirred for 5 min. 2-[[[5-[[(2,5-Dioxo-1-pyrrolidinyl)oxy]carbonyl]-2-pyridinyl]-hydrazono]methyl]-benzenesulfonic acid, monosodium salt (0.0063 g, 0.014 mmol) was added, and the reaction mixture was stirred for 18 h, then concentrated to an oil under high vacuum. The residue was purified by preparative RP-HPLC Method 1 to give the desired product (TFA salt). ESMS: Calcd. for $C_{64}H_{96}N_{22}O_{20}S$, 1524.7; Found, 1525.7 (M+H)+1. Analytical HPLC, Method 1B, $R_t$=13.20 min, Purity=99%.

Example 12

Synthesis of {cyclo(Arg-D-Val-D-Tyr(N-(N-[2-[[[5-[carbonyl]-2-pyridinyl]hydrazono]methyl]-benzene-sulfonic acid]-3-aminopropyl)-D-Asp-Gly} [SEQ. ID NO.: 12]

acid (67 mL, 1.16 mmol) was added and the reaction mixture was heated to 55° C. for 72 h. The resin was filtered and washed with DMF (3×10 mL). The filtrate was concentrated under high vacuum to give an oil. The resulting oil was triturated with ethyl acetate. The solid obtained was purified by reverse-phase HPLC (Vydac C18 column, 18 to 90% acetonitrile gradient containing 0.1% TFA, $R_t$=15.243 min) to afford 101 mg of a white powdered product (30%). ESMS: Calculated for $C_{44}H_{57}N_9O_{12}S$, 935.3847 Found 936.5 [M+H]+1.

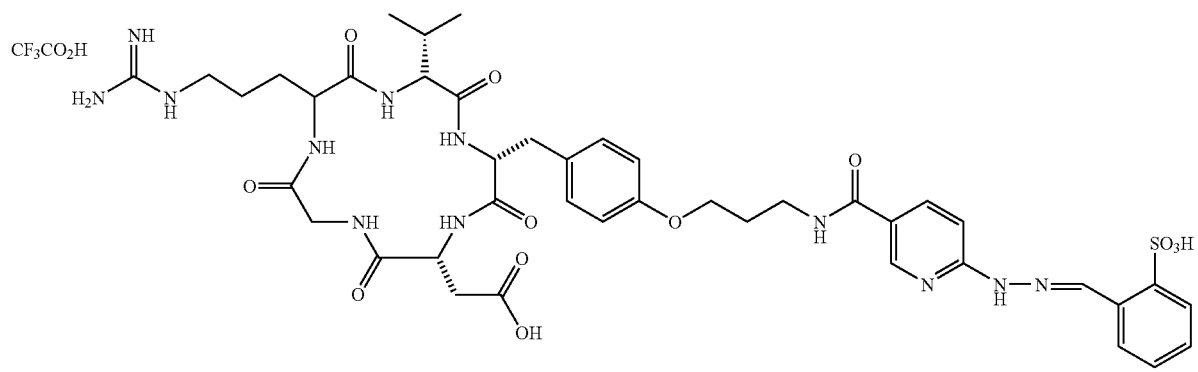

Part B. Preparation of cyclo{Arg-D-Val-D-Tyr(3-aminopropyl)-D-Asp-Gly} [SEQ. ID NO.: 114]

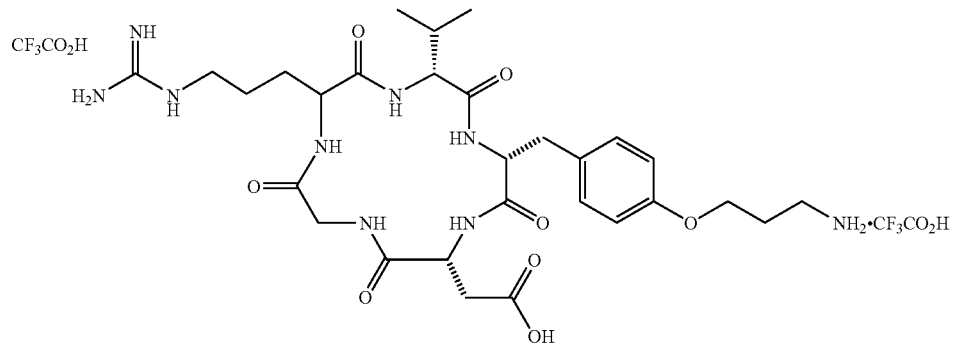

Part A. Preparation of cyclo{Arg(Tos)-D-Val-D-Tyr(N-Cbz-3-aminopropyl)-D-Asp(OBzl)-Gly} [SEQ. ID NO.: 112]

The N-terminus Boc-protecting group of the peptide sequence Boc-Arg(Tos)-D-Val-D-Tyr(N-Cbz-aminopropyl)-D-Asp(OBzl)-Gly [SEQ. ID NO.: 113]-Oxime resin was removed using standard deprotection (50% TFA in $CH_2Cl_2$). After washing with DCM (8×), the resin was neutralized with 10% DIEA/DCM (2×10 min). The resin was washed with DCM (5×) and dried under high vacuum overnight. The resin (1.08 g, 0.36 mmol/g) was then suspended in N,N-dimethylformamide (12 mL). Glacial acetic The protected cyclic peptide cyclo{Arg(Tos)-D-Val-D-Tyr(N-Cbz-3-aminopropyl)-D-Asp(OBzl)-Gly} [SEQ. ID NO.: 112] (90 mg, 0.0961 mmol) was dissolved in trifluoroacetic acid (0.95 μL) and cooled to −10° C. in a dry ice/acetone bath. To this solution was added trifluoromethanesulfonic acid (0.1.16 mmol), followed by anisole (190 mL). The reaction mixture was stirred at −16° C. for 3 h. The dry ice/acetone bath was then cooled to −35° C. and cold ether (40 mL) was added to the solution. The mixture was stirred for 30 min at −35° C., then cooled to −50° C. and stirred for another 30 min. The crude product was filtered, redissolved in water/acetonitrile (1/1), lyophilized, and purified by reverse-phase HPLC (Vydac C18 Column, 1.8 to 90% acetonitrile gradient containing 0.1% TFA, $R_f$=13.383 min) to generate 17 mg of the title product (27%). ESMS: Calculated for $C_{29}H_{45}N_9O_8$, 647.3391 Found 648.2 [M+H]+1.

Part C. Preparation of {cyclo(Arg-D-Val-D-Tyr(N-2-[[[5-[carbonyl]-2-pyridinyl]hydrazono]methyl]-benzenesulfonic acid]-3-aminopropyl)-D-Asp-Gly} [SEQ. ID NO.: 12]

A solution of cyclo{Arg-D-Val-D-Tyr(3-aminopropyl)-D-Asp-Gly} [SEQ. ID NO.: 114] (14 mg, 0.0216 mmol) in N,N-dimethylformamide (2 mL) was added triethylamine (15 mL, 0.108 mmol) and stirred at room temperature for 10 min. 2-[[[5-[[(2,5-Dioxo-1-pyrrolidinyl)oxy]carbonyl-2-pyridinyl]-hydrazono]methyl-benzenesulfonic acid, monosodium salt (11 mg, 0.0260 mmol) was added, and the mixture was stirred for 18 h. The mixture was concentrated under high vacumm and the residue was purified by reverse-phase HPLC (Vydac C18 Column, 1.8 to 90% acetonitrile gradient containing 0.1% TFA, $R_f$=16.264 min) to afford 10 mg of a white powdered product (49%). ESMS: Calculated for $C_{42}H_{54}N_{12}O_{12}S$, 950.3705 Found 951.3 [M+H]+1.

Example 13

Synthsis of cyclo{D-Lys([2-[[[5-[carbonyl]-2-pyridinyl]hydrazono]methyl]-benzenesulfonic acid])-D-Phe-D-Asp-Gly-Arg} [SEQ. ID NO.: 13]

trated to an oil under high vacuum. The resulting oil was triturated with ethyl acetate. The solid thus obtained was filtered, washed with ethyl acetate, and dried under high vacuum to give the desired product which was then purified by preparative RP-HPLC (yield=252 mg). ESMS: Calcd. for $C_{49}H_{59}N_9O_{11}S$, 981.40; Found, 982.3 [M+H]+1. Analytical HPLC, Method 1A, $R_f$=14.577 min.

Part B. Preparation of cyclo{D-Lys-D-Phe-D-Asp-Gly-Arg} [SEQ. ID NO.: 117] TFA salt

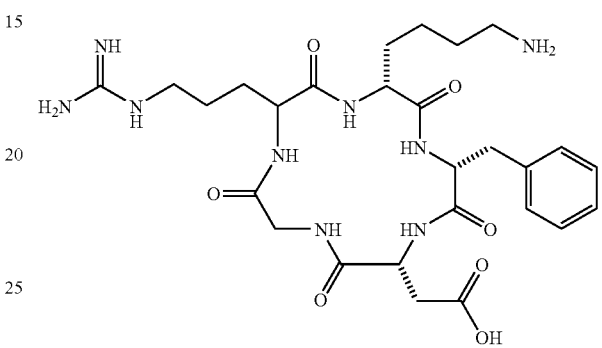

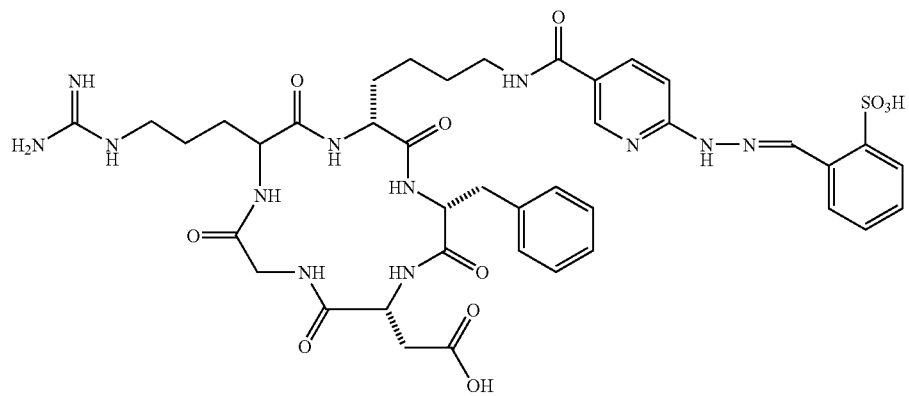

Part A. Preparation of cyclo{D-Lys(Cbz)-D-Phe-D-Asp(OBzl)-Gly-Arg(Tos)} [SEQ. ID NO.: 115]

The N-terminus Boc-protecting group of the peptide sequence Boc-Arg(Tos)-D-Lys(Cbz)-D-Phe-D-Asp(OBzl)-Gly [SEQ. ID NO.: 116]-Oxime resin was removed using standard deprotection (25% TFA in $CH_2Cl_2$). After eight washes with DCM, the resin was treated with 10% DIEA/DCM (2×10 min.). The resin was subsequently washed with DCM (×5) and dried under high vacuum. The resin (1.93 g, 0.44 mmol/g) was then suspended in dimethylformamide (15 mL). Glacial acetic acid (77 μL) was added, and the reaction was heated to 60° C. for 72 h. The resin was filtered, and washed with DMF (2×10 mL). The filtrate was concen- Cyclo{D-Lys(Cbz)-D-Phe-D-Asp(OBzl)-Gly-Arg(Tos)} [SEQ. ID NO.: 115] (0.152 g, 0.155 mmol) was dissolved in trifluoracetic acid (1.55 mL) and cooled to −16° C. Trifluoromethanesulfonic acid (1.86 mL) was added dropwise, maintaining the temperature at −16° C. Anisole (0.31 mL) was added and the reaction was stirred at −16° C. for 3 h. Diethyl ether was added, the reaction was cooled to −35° C., and stirred for 20 min. The crude product was filtered, washed with diethyl ether, dried under high vacuum and purified by Preparative HPLC Method 1, to give 69 mg (~53%) of the desired product as a lyophilized solid (TFA salt). ESMS: Calcd. for $C_{27}H_{41}N_9O_7$+H, 604.3207; Found, 604.4. Analytical HPLC, Method 1B, $R_t$=10.35 min, Purity=93%.

Part C: Preparation of cyclo{D-Lys([2-[[[5-[carbonyl]-2-pyridinyl]hydrazono]methyl]-benzenesulfonic acid])-D-Phe-D-Asp-Gly-Arg} [SEQ. ID NO.: 13] TFA salt Cyclo{D-Lys-D-Phe-D-Asp-Gly-Arg}[SEQ. ID NO.: 117] TFA salt (0.056 g, 0.0673 mmol) was dissolved in DMF (2 mL). Triethylamine (28 µL, 0.202 mmol) was added, and after 5 min of stirring 2-[[[5-[[(2,5-dioxo-1-pyrrolidinyl)oxy]carbonyl]-2-pyridinyl]hydrazono]-methyl]-benzenesulfonic acid, monosodium salt (0.029 g, 0.0673 mmol) was added. The reaction mixture was stirred for 70 h and then concentrated to an oil under high vacuum. The oil was purified by preparative HPLC Method 1 to give 14 mg (78%) of the desired product as a lyophilized solid (TFA salt). ESMS: Calcd. for $C_{40}H_{50}N_{12}O_{11}S$+H, 907.3521; Found, 907.3. Analytical HPLC, Method 1B, $R_t$=14.17 min, Purity=99%.

Example 14

Synthesis of [2-[[[5-[carbonyl]-2-pyridinyl]hydrazono]methyl]-benzenesulfonic acid]-Glu(cyclo{D-Lys-D-Phe-D-Asp-Gly-Arg})-cyclo{D-Lys-D-Phe-D-Asp-Gly-Arg})-cyclo{D-Lys-D-Phe-D-Asp-Gly-Arg} [SEQ. ID NO.: 14]

Part A. Preparation of Boc-Glu(cyclo{D-Lys-D-Phe-D-Asp-Gly-Arg})-cyclo{D-Lys-D-Phe-D-Asp-Gly-Arg} [SEQ. ID NO.: 118]

To a solution of cyclo(D-Lys-D-Phe-D-Asp-Gly-Arg) [SEQ. ID NO.: 117] (0.190 g, 0.228 mmol) in dimethylformamide (5 mL) was added triethylamine (95 µL, 0.684 mmol). After stirring for 5 minutes Boc-Glu(OSu)-OSu (0.050 g, 0.114 mmol) was added. The reaction mixture was stirred under $N_2$ for 20 h, then concentrated to an oil under high vacuum and triturated with ethyl acetate. The product thus obtained was filtered, washed with ethyl acetate, and dried under high vacuum to give 172 mg of the desired product in crude form. ESMS: Calcd. for $C_{64}H_{95}N_{19}O_{18}$, 1417.71; Found, 1418.7 [M+H]+1. Analytical HPLC, Method 1B, $R_t$=16.8 min.

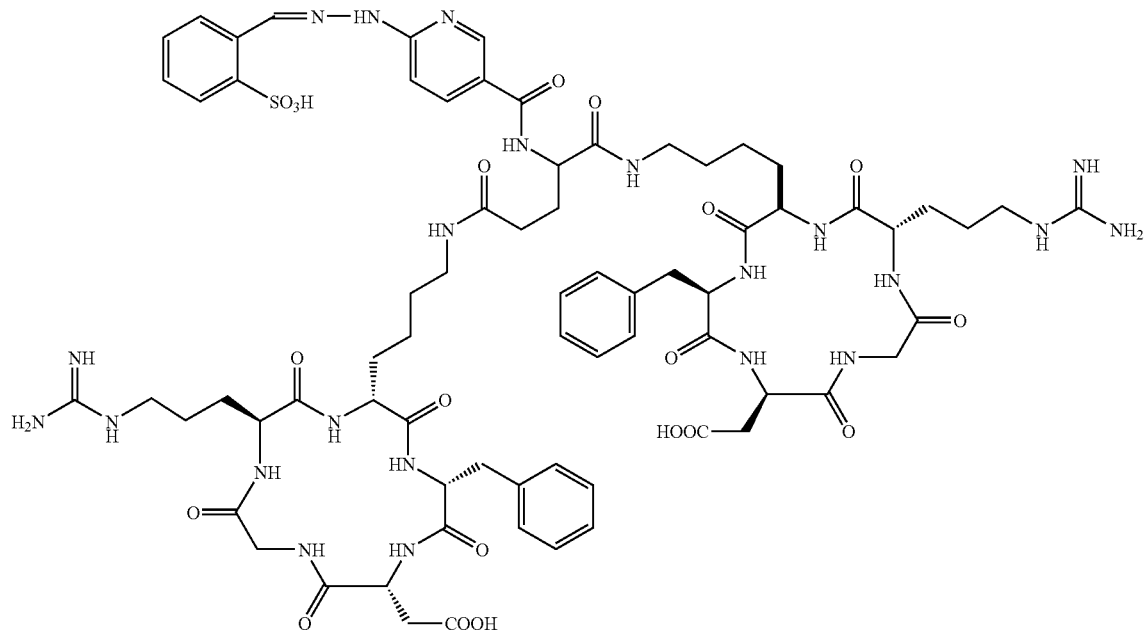

Part B. Preparation of Glu(cyclo{D-Lys-D-Phe-D-Asp-Gly-Arg})-cyclo{D-Lys-D-Phe-D-Asp-Gly-Arg} [SEQ. ID NO.: 119]

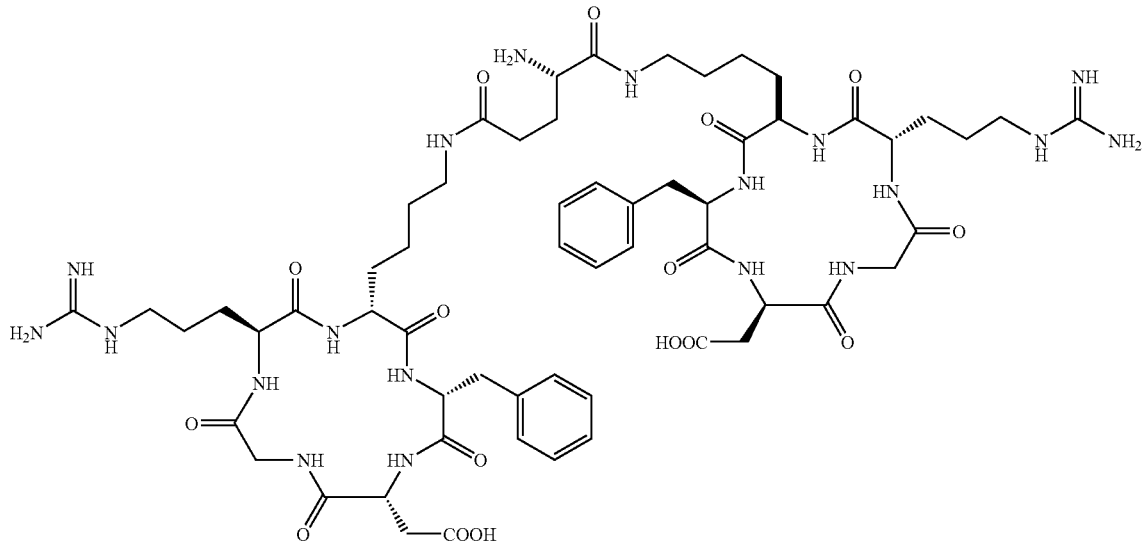

To a solution of the crude Boc-Glu(cyclo{D-Lys-D-Phe-D-Asp-Gly-Arg})-cyclo{D-Lys-D-Phe-D-Asp-Gly-Arg} [SEQ. ID NO.: 118] (0.172 g) in methylene chloride (4.5 mL) was added trifluoroacetic acid (4.5 mL). The reaction mixture was stirred for 2 h, concentrated to an oil under high vacuum and triturated with diethyl ether. The product was filtered, washed with diethyl ether, and dried under high vacuum to give 38 mg of the desired product after RP-HPLC as a lyophilized solid (TFA salt). ESMS: Calcd. for $C_{59}H_{87}N_{19}O_{16}$, 1317.66; Found, 1318.9 [M+H]+1. Analytical HPLC, Method 1B, $R_t$=13.06 min, Purity=93%.

Part C. Preparation of [2-[[[5-[carbonyl]-2-pyridinyl]hydrazono]methyl]-benzenesulfonic acid]-Glu(cyclo{D-Lys-D-Phe-D-Asp-Gly-Arg})-cyclo{D-Lys-D-Phe-D-Asp-Gly-Arg} [SEQ. ID NO.: 14]

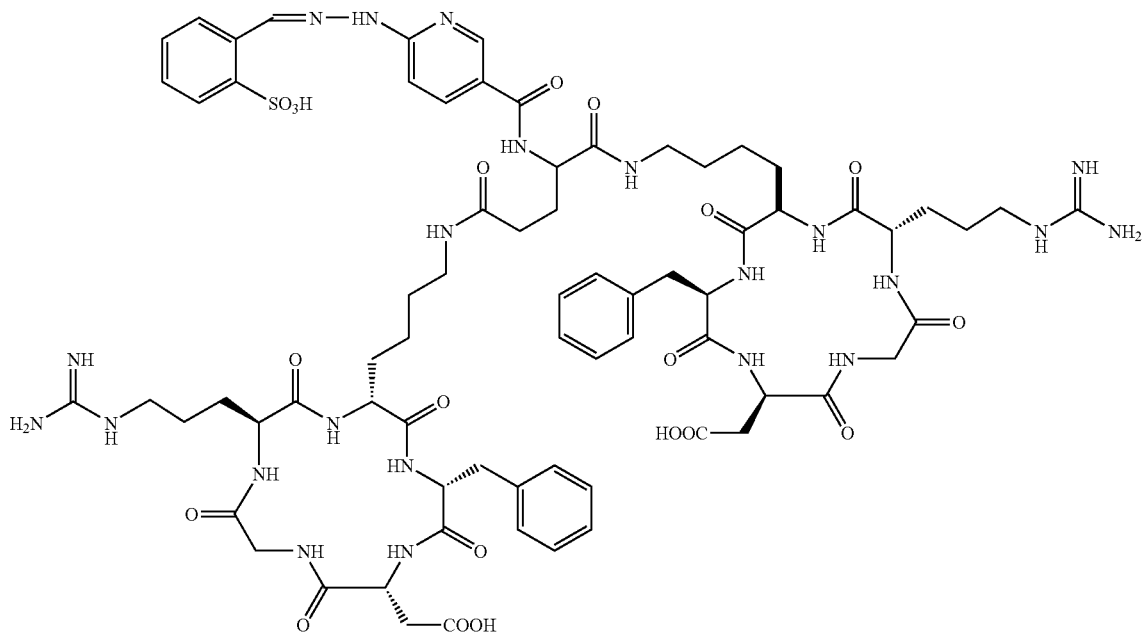

To a solution of Glu(cyclo{D-Lys-D-Phe-D-Asp-Gly-Arg})-cyclo{D-Lys-D-Phe-D-Asp-Gly-Arg} [SEQ. ID NO.: 119] (0.025 g, 0.015 mmol) in dimethylformamide (2 mL) was added triethylamine (6.3 μL, 0.045 mmol) and the reaction mixture was stirred for 5 min. 2-[[[5-[[(2,5-Dioxo-1-pyrrolidinyl)oxy]carbonyl]-2-pyridinyl]hydrazono]methyl]-benzenesulfonic acid, monosodium salt (0.0092 g, 0.0210 mmol) was added, and the reaction mixture was stirred for 18 h, then concentrated to an oil under high vacuum. The oil was purified by Preparative HPLC Method 1 to give 12.5 mg of the desired product as a lyophilized solid (TFA salt). ESMS: Calcd. for $C_{72}H_{96}N_{22}O_{20}S$, 1620.7; Found, 1622.5 (M+H)+1. Analytical HPLC, Method 1B, $R_t$=14.62 min, Purity=96%.

Example 15

Synthesis of cyclo{D-Phe-D-Lys([2-[[[5-[carbonyl]-2-pyridinyl]hydrazono]methyl]-benzenesulfonic acid])-D-Asp-Gly-Arg} [SEQ. ID NO.: 15]

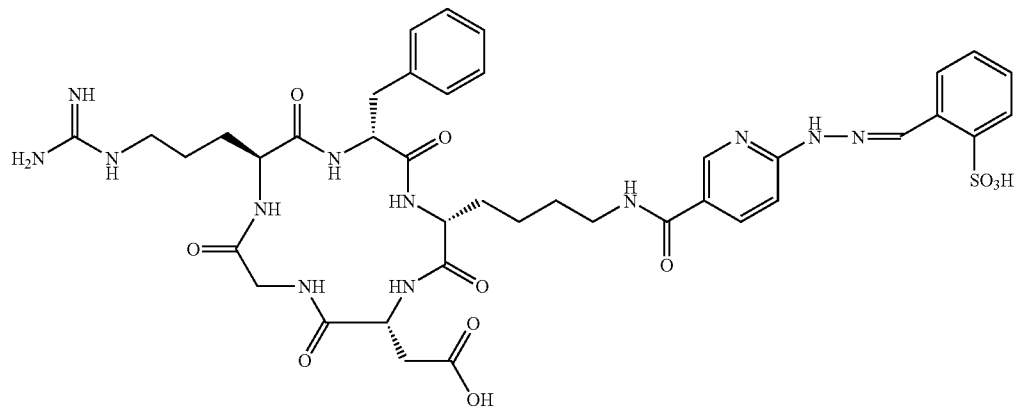

Part A. Preparation of cyclo{D-Phe-D-Lys(Cbz)-D-Asp(OBzl)-Gly-Arg(Tos)} [SEQ. ID NO.: 120]

The N-terminus Boc-protecting group of the peptide sequence Boc-Arg(Tos)-D-Phe-D-Lys(Cbz)-D-Asp(OBzl)-Gly [SEQ. ID NO.: 121]-Oxime resin was removed using standard deprotection (25% TFA in $CH_2Cl_2$). After eight washes with DCM, the resin was treated with 10% DIEA/DCM (2×10 min.). The resin was subsequently washed with DCM (×5) and dried under high vacuum. The resin (1.5 g, 0.44 mmol/g) was then suspended in dimethylformamide (12 mL). Glacial acetic acid (61 μL) was added, and the reaction was heated to 60° C. for 72 h. The resin was filtered, and washed with DMF (2×10 mL). The filtrate was concentrated to an oil under high vacuum. The resulting oil was triturated with ethyl acetate. The solid thus obtained was filtered, washed with ethyl acetate, and dried under high vacuum to give the desired product (yield=370 mg). ESMS: Calcd. for $C_{49}H_{59}N_9O_{11}S$, 981.40; Found, 982.4 [M+H]+1. Analytical HPLC, Method 1A, $R_t$=14.32 min (purity 60%).

Part B. Preparation of cyclo{D-Phe-D-Lys-D-Asp-Gly-Arg} [SEQ. ID NO.: 122] bis TFA Salt

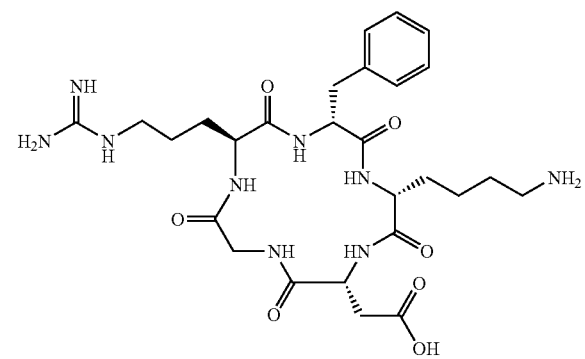

The crude cyclo{D-Phe-D-Lys(Cbz)-D-Asp(OBzl)-Gly-Arg(Tos)} [SEQ. ID NO.: 120] (0.146 g) was dissolved in trifluoracetic acid (1.5 mL) and cooled to −16° C. Trifluoromethanesulfonic acid (1.8 mL) was added dropwise, maintaining the temperature at −16° C. Anisole (0.3 mL) was added and the reaction was stirred at −16° C. for 3 h. Diethyl ether was added, the reaction was cooled to −35° C., and stirred for 20 min. The crude product was filtered, washed with diethyl ether, dried under high vacuum and purified by Preparative HPLC Method 1, to give 100 mg of the desired product as a lyophilized solid (TFA salt). ESMS: Calcd. for $C_{27}H_{41}N_9O_7+H$, 604.3; Found, 604.3. Analytical HPLC, Method 1B, $R_t$=10.25 min, Purity=90%.

Part C. Preparation of cyclo{D-Phe-D-Lys([2-[[[5-[carbonyl]-2-pyridinyl]hydrazono]methyl]-benzenesulfonic acid])-D-Asp-Gly-Arg} [SEQ. ID NO.: 15]

Cyclo{D-Phe-D-Lys-D-Asp-Gly-Arg} [SEQ. ID NO.: 122] TFA salt (0.090 g, 0.108 mmol) was dissolved in DMF (2 mL). Triethylamine (45 μL, 0.324 mmol) was added, and after 5 min of stirring 2-[[[5-[[(2,5-dioxo-1-pyrrolidinyl) oxy]carbonyl]-2-pyridinyl]hydrazono]-methyl]-benzenesulfonic acid, monosodium salt (0.048 g, 0.108 mmol) was added. The reaction mixture was stirred for 70 h and then concentrated to an oil under high vacuum. The oil was purified by Preparative HPLC Method 1 to give 10 mg of the desired product as a lyophilized solid (TFA salt). ESMS: Calcd. for $C_{40}H_{50}N_{12}O_{11}S+H$, 907.4; Found, 907.3. Analytical HPLC, Method 1B, $R_t$=13.47 min, Purity=89%.

Example 16

Synthesis of cyclo{N-Me-Arg-Gly-Asp-ATA-D-Lys ([2-[[[5-[carbonyl]-2-pyridinyl]hydrazono]methyl]-benzenesulfonic acid])} [SEQ. ID NO.: 16]

Part B. Preparation of cycl{N-Me-Arg-Gly-Asp-ATA-D-Lys} [SEQ. ID NO.: 125]

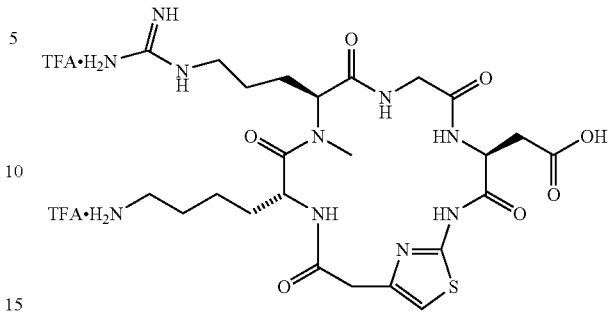

Cyclo{N-Me-Arg(Tos)-Gly-Asp(OBzl)-ATA-D-Lys (Cbz)} [SEQ. ID NO.: 123] (36 mg, 0.0364 mmol) was dissolved in trifluoroacetic acid (0.364 mL) and cooled to −10° C. in a dry ice/acetone bath. To this solution was added trifluoromethanesulfonic acid (0.437 mmol), followed by anisole (70 mL). The reaction mixture was stirred at −10° C. for 3 h. The dry ice/acetone bath was then cooled to −35° C. and cold ether (40 mL) was added to the solution. The mixture was stirred for 30 min at −35° C., then cooled further to −50° C. and stirred for another 30 min. The crude product was filtered, redissolved in water/acetonitrile (1/1),

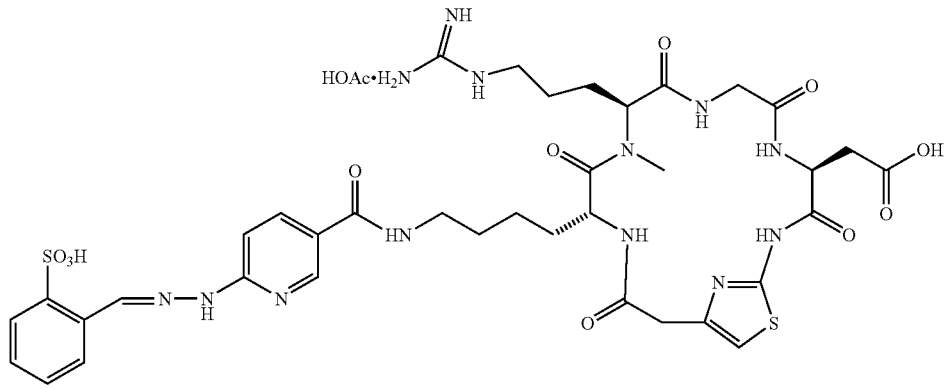

Part A. Preparation of cyclo{N-Me-Arg(Tos)-Gly-Asp (OBzl)-ATA-D-Lys(Cbz)} [SEQ. ID NO.: 123]

The N-terminus Boc-protecting group of the peptide sequence Boc-Asp(OBzl)ATA-D-Lys(Z)-N-Me-Arg(Tos)-Gly [SEQ. ID NO.: 124]-Oxime resin was removed using standard deprotection (50% TFA in $CH_2Cl_2$). After washing with DCM (8×), the resin was treated with 10% DIEA/DCM (2×10 min). The resin was washed with DCM (5×) and dried under high vacuum overnight. The resin (1.24 g, 0.39 mmol/g) was then suspended in DMF (12 mL). Glacial acetic acid (67 mL, 1.16 mmol) was added and the reaction mixture was heated at 50° C. for 72 h. The resin was filtered and washed with DMF (3×10 mL). The filtrate was concentrated under high vacuum to give an oil. The resulting oil was triturated with ethyl acetate. The solid obtained was purified by reverse-phase HPLC (Vydac C18 column, 18 to 90% acetonitrile gradient containing 0.1% TFA, $R_t$=14.129 min) to afford 42 mg (9%) of the desired product as a lyophilized solid. ESMS: Calculated for $C_{46}H_{56}N_{10}O_{11}S_2$, 988.3571 Found 989.4 [M+H]+1.

and lyophilized to generate 35 mg of the title product (100%). ESMS: Calculated for $C_{24}H_{38}N_{10}O_7S$, 610.2646 Found 611.4 [M+H]+1.

Part C. Preparation of cyclo{N-Me-Arg-Gly-Asp-ATA-D-Lys([2-[[[5-[carbonyl]-2-pyridinyl]hydrazono]methyl]-benzenesulfonic acid])} [SEQ. ID NO.: 16]

To a solution of cyclo{N-Me-Arg-Gly-Asp-ATA-D-Lys} [SEQ. ID NO.: 125] (31 mg, 0.051 mmol) in DMF (2 mL) was added triethylamine (28 mL, 0.204 mmol) and the reaction mixture stirred at room temperature for 10 min. 2-[[[5-[[(2,5-Dioxo-1-pyrrolidinyl)-oxy]carbonyl-2-pyridinyl]hydrazono]methyl-benzenesulfonic acid, monosodium salt (27 mg, 0.0612 mmol) was added, the mixture stirred for 18 h and then concentrated under high vacumm. The residue obtained was purified by reverse-phase HPLC (Shandon HS-BDS column, 3 to 10% acetonitrile, $R_t$=13.735 min) to afford 4 mg (8.8%) of the desired product as a lyophilized solid. ESMS: Calculated for $C_{37}H_{47}N_{13}O_{11}S_2$, 913.2959 Found 914.5 [M+H]+1.

Example 17

Synthesis of cyclo{Cit-Gly-Asp-D-Phe-Lys([22-[[[5-[carbonyl]-2-pyridinyl]hydrazono]methyl]-benzenesulfonic acid])} [SEQ. ID NO.: 17]

Part C. Preparation of cyclo{Cit-Gly-Asp-D-Phe-Lys([2-[[[5-[carbonyl]-2-pyridinyl]hydrazono]methyl]-benzenesulfonic acid])} [SEQ. ID NO.: 17]

Cyclo{Cit-Gly-Asp-D-Phe-Lys} [SEQ. ID NO.: 128] TFA salt (0.044 g) was dissolved in DMF (2 mL). Triethylamine (22 µL, 0.156 mmol) was added, and after 5 min of

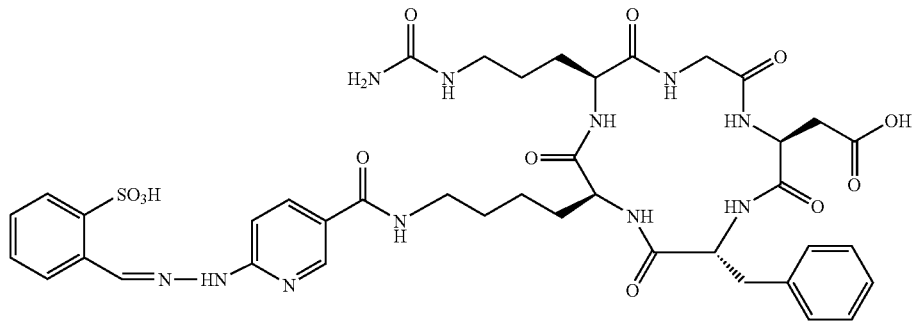

Part A. Preparation of cyclo{Cit-Gly-Asp(OtBu)-D-Phe-Lys(Boc)} [SEQ. ID NO.: 126]

The peptide Asp(OtBu)-D-Phe-Lys(Boc)-Cit-Gly [SEQ. ID NO.: 127] was obtained by automated solid phase peptide synthesis using Fmoc chemistry (see general procedure). A 100 mL round bottom flask was charged with HBTU (271 mg, 0.71 mmol) and DMF (10 mL). The solution was stirred at 60° C. for 5 min. To this a solution of Asp(OtBu)-D-Phe-Lys(Boc)-Cit-Gly (0.456 g) and Hunig's base (0.27 mL, 1.53 mmol.) in DMF (10 µL) was added and the solution stirred at 60° C. for 4 h under nitrogen. The solvent was then removed in vacuo and the residue was triturated with ethyl acetate. The solids were filtered and washed with ethyl acetate (3×6 mL) and dried in vacuo to give the desired product (305 mg, 78%). ESMS: Calcd. for $C_{36}H_{56}N_8O_{10}$, 760.4; Found, 761.4 [M+H]+1. Analytical HPLC, Method 1A, $R_t$=11.8 min (purity 99%).

Part B. Preparation of cyclo{Cit-Gly-Asp(OtBu)-D-Phe-Lys(Boc)} [SEQ. ID NO.: 126]

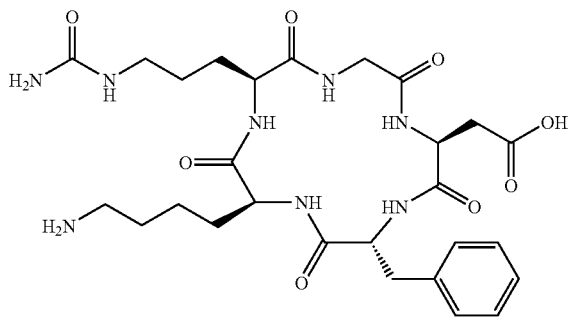

A solution of cyclo{Cit-Gly-Asp(OtBu)-D-Phe-Lys(Boc)} (287 mg, 0.38 mmol), TFA (6 mL), triisopropylsilane (0.25 mL) and water (0.25 mL) was stirred at room temperature under nitrogen for 4 h. The solvents were removed in vacuo (over 3 h) and the residue triturated with diethyl ether, filtered and washed with ether to give the desired product (315 mg) (TFA salt). ESMS: Calcd. for $C_{27}H_{40}N_8O_8$, 604.3; Found, 605.4 [M+H]+1. Analytical HPLC, Method 1B, $R_t$=9.6 min, Purity=97%.

stirring 2-[[[5-[[(2,5-dioxo-1-pyrrolidinyl)oxy]carbonyl]-2-pyridinyl]hydrazono]-methyl]-benzenesulfonic acid, monosodium salt (0.032 g, 0.073 mmol) was added. The reaction mixture was stirred overnight, under nitrogen, and then concentrated under high vacuum. The residue was purified by preparative RP-HPLC Method 1 to give 37 mg (70%) of the desired product as a lyophilized solid (TFA salt). ESMS: Calcd. for $C_{40}H_{49}N_{11}O_{12}S$, 907.3; Found, 908.4 [M+H]+1. Analytical HPLC, Method 1B, $R_t$=14.15 min, Purity=99%.

Example 18A

Synthesis of tris(t-butyl)-1,4,7,10-tetraazacyclododecane-1,4,7,10-tetraacetic acid

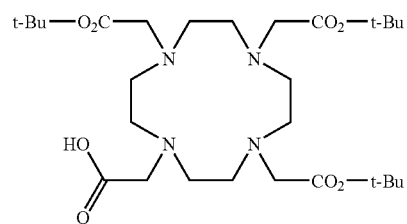

Part A. Preparation of Phenylmethyl 2-(1,4,7,10-Tetraaza-4,7,10-tris(((tert-butyl)oxycarbonyl)methyl)cyclododecyl)acetate

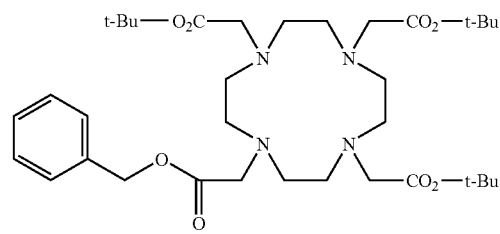

A solution of tert-butyl (1,4,7,10-tetraaza-4,7-bis(((tert-butyl)oxycarbonyl)methyl)cyclododecyl)acetate (0.922 g, 1.79 mmol), TEA (1.8 mL) and benzyl bromoacetate (0.86 mL, 5.37 mmol) in anhydrous DMF (24 mL) was stirred at ambient temperatures under a nitrogen atmosphere for 24 h. The DMF was removed under vacuum and the resulting oil was dissolved in EtOAc (300 mL). This solution was washed consecutively with water (2×50 mL) and saturated NaCl (50 mL), dried (MgSO₄), and concentrated to give the title compound as an amorphous solid (1.26 g). MS: m/e 663.5 [M+H].

Part B. Preparation of 2-(1,4,7,10-tetraaza-4,7,10-tris(((tert-butyl)oxycarbonyl)methyl)cyclododecyl)acetic acid The product from Part A, above (165 mg, 0.25 mmol) was hydrogenolyzed over 10% Pd on carbon (50 mg) in EtOH (15 mL) at 60 psi for 24 h. The catalyst was removed by filtration through filter aid and washed with EtOH. The filtrates were concentrated to give the title compound as an amorphous solid (134 mg, 94%). MS: m/e 573.5 [M+H].

Example 18

Synthesis of 2-(1,4,7,10-tetraaza-4,7,10-tris(carboxymethyl)-1-cyclododecyl)acetyl-Glu(cyclo{Lys-Arg-Gly-Asp-D-Phe})-cyclo{Lys-Arg-Gly-Asp-D-Phe} [SEQ. ID NO.: 18]

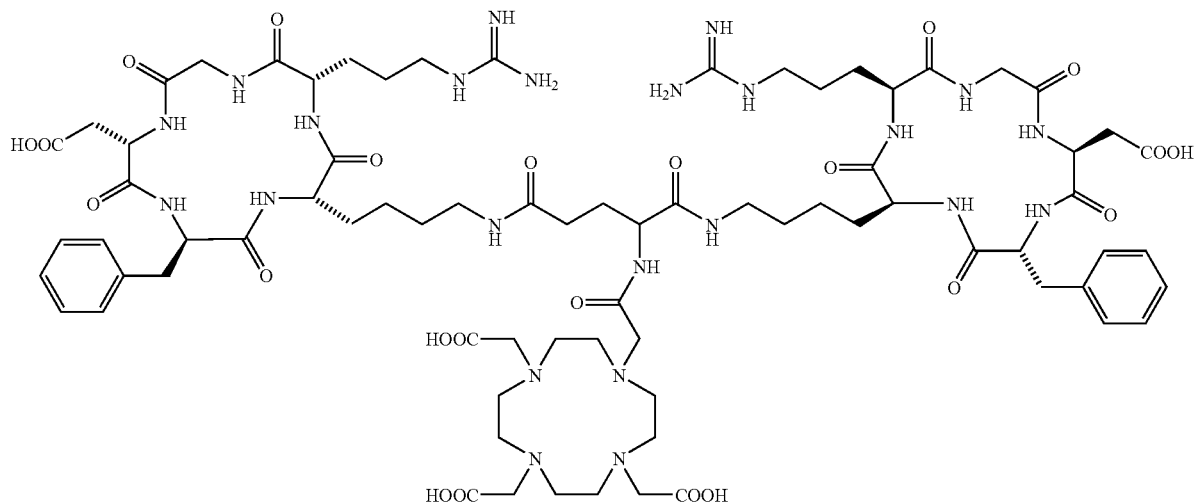

Part A. Preparation of 2-(1,4,7,10-tetraaza-4,7,10-tris(t-butoxycarbonylmethyl)-1-cyclododecyl)acetyl-Glu (cyclo{Lys-Arg-Gly-Asp-D-Phe})-cyclo{Lys-Arg-Gly-Asp-D-Phe} [SEQ. ID NO.: 129]

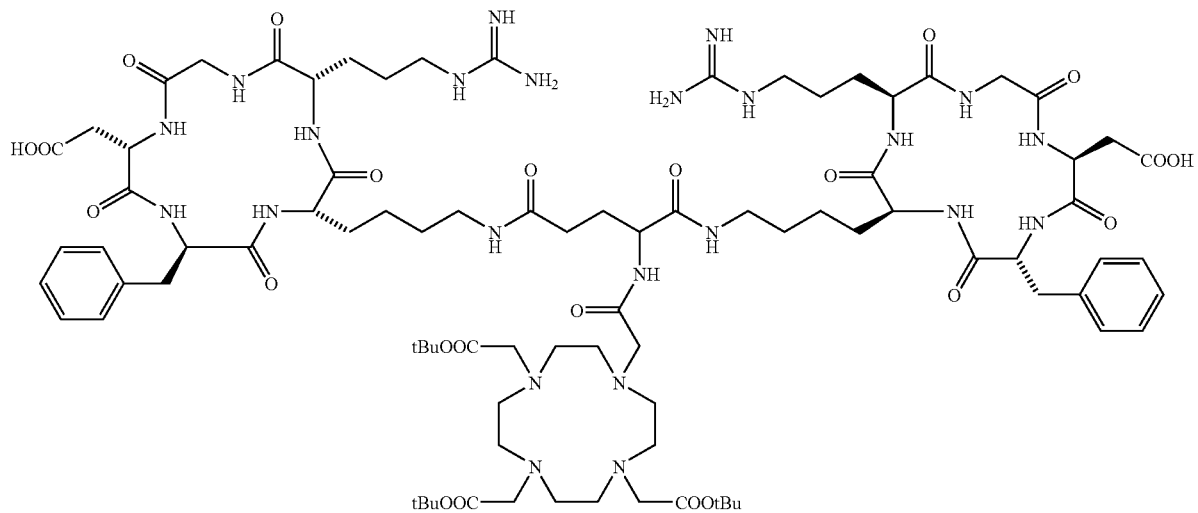

To a solution of tris(t-butyl)-1,4,7,10-tetra-azacyclododecane-1,4,7,10-tetraacetic acid (28 mg, 0.049 mmol) and Hunig's base (14 μL) in DMF (2 mL) was added HBTU (17 mg, 0.0456 mmol) and the mixture stirred for 5 min. To this was added a solution of Glu(cyclo{Lys-Arg-Gly-Asp-D-Phe})-cyclo{Lys-Arg-Gly-Asp-D-Phe} [SEQ. ID NO.: 130] (54.1 mg, 0.0326 mmol) in DMF (1 mL) and the reaction mixture allowed to stir under nitrogen at room temperature for 4 h. The solvent was removed in vacuo and the residue purified by preparative RP-HPLC to give the product as a lyophilized solid (18.3 mg) (TFA salt). ESMS: Calcd. for $C_{87}H_{137}N_{23}O_{23}$, 1872.0; Found, 937.2 [M+2H]+2. Analytical HPLC, Method 1B, $R_t$=19.98 min, Purity=99%.

Part B. Preparation of 2-(1,4,7,10-tetraaza-4,7,10-tris(carboxymethyl)-1-cyclododecyl)acetyl-Glu(cyclo{Lys-Arg-Gly-Asp-D-Phe})-cyclo{Lys-Arg-Gly-Asp-D-Phe} [SEQ. ID NO.: 18]

A solution of 2-(1,4,7,10-tetraaza-4,7,10-tris(t-butoxycarbonylmethyl)-1-cyclododecyl)acetyl-Glu(cyclo {Lys-Arg-Gly-Asp-D-Phe})-cyclo{Lys-Arg-Gly-Asp-D-Phe} [SEQ. ID NO.: 129] (18.3 mg, 8.71 mmol) in TFA (3 mL) was stirred at room temperature under nitrogen for 5 h. The solution was concentrated in vacuo and the residue was purified by preparative RP-HPLC to give 8 mg (45%) of the desired product as the lyophilized solid (TFA salt). ESMS: Calcd. for $C_{75}H_{113}N_{23}O_{23}$, 1703.8; Found, 853.0 [M+2H]+2. Analytical HPLC, Method 1B, $R_t$=13.13 min, Purity=99%.

Example 19

Synthesis of cyclo{Arg-Gly-Asp-D-Phe-Lys(DTPA)} [SEQ. ID NO.: 19]

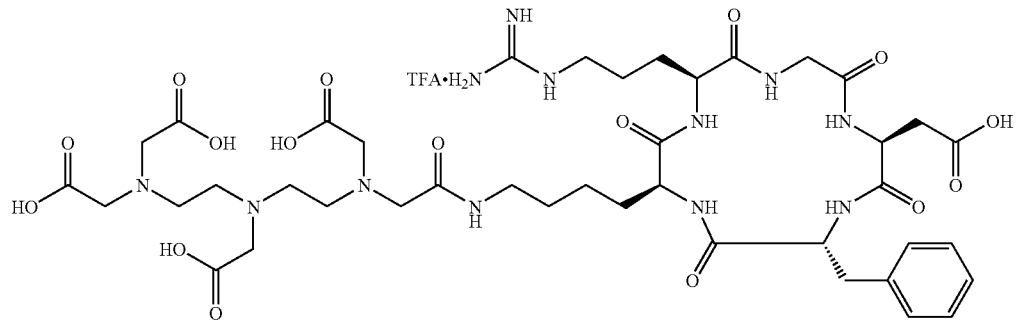

To a solution of cyclo{Arg-Gly-Asp-D-Phe-Lys} [SEQ. ID NO.: 131] (0.050 g, 0.0601 mmol) in DMF (2 mL) was added triethylamine (41.9 μL, 0.301 mmol). This solution was added dropwise over 4 h to a solution of diethylenetriaminepentaacetic dianhydride (0.1074 g, 0.301 mmol) in DMF (2 mL) and methyl sulfoxide (2 mL). The reaction mixture was then stirred for 16 h, concentrated to an oil under high vacuum and purified by Preparative HPLC Method 1 to give 29.9 mg (46%) of the desired product as a lyophilized solid. ESMS: Calcd. for $C_{41}H_{62}N_{12}O_{16}$, 978.4; Found, 977.5 (M–H+). Analytical HPLC, Method 1B, $R_t$=11.916 min. Purity=100%.

Example 20

Synthesis of cyclo{Arg-Gly-Asp-D-Phe-Lys}$_2$ (DTPA) [SEQ. ID NO.: 20]

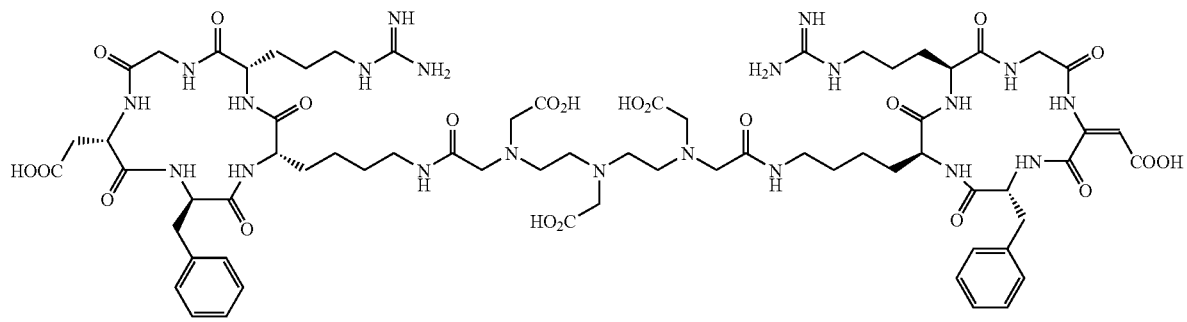

The oil obtained in Example 9 upon purification by Preparative HPLC Method 1, also gave 21.5 mg (21%) of the title product as a lyophilized solid. ESMS: Calcd. for $C_{68}H_{101}N_{21}O_{22}$, 1563.7; Found, 1562.8 (M–H$^+$). Analytical HPLC, Method 1B, $R_t$=15.135 min, Purity=93%.

Example 21

Synthesis of Cyclo{Arg-Gly-Asp-D-Tyr(N-DTPA-3-aminopropyl)-Val} [SEQ. ID NO.: 21]

To a solution of cyclo{Arg-Gly-Asp-D-Tyr(3-aminopropyl)-Val} [SEQ. ID NO.: 132] (0.050 g, 0.0571 mmol) in dimethylformamide (2 mL) was added triethylamine (39.8 µL, 0.286 mmol). This solution was added dropwise over 5 h to a solution of diethylenetriamine-pentaacetic dianhydride (0.1020 g, 0.286 mmol) in methyl sulfoxide (2 mL). The reaction mixture was stirred for an additional 18 h, then concentrated to an oil under high vacuum and purified by Preparative HPLC Method 1 to give 41.9 mg (65%) of the desired product as a lyophilized solid. ESMS: Calcd. for $C_{43}H_{66}N_{12}O_{17}$, 1022.5; Found, 1021.4 (M–H$^+$). Analytical HPLC, Method 1B, $R_t$=15.690 min, Purity=96%.

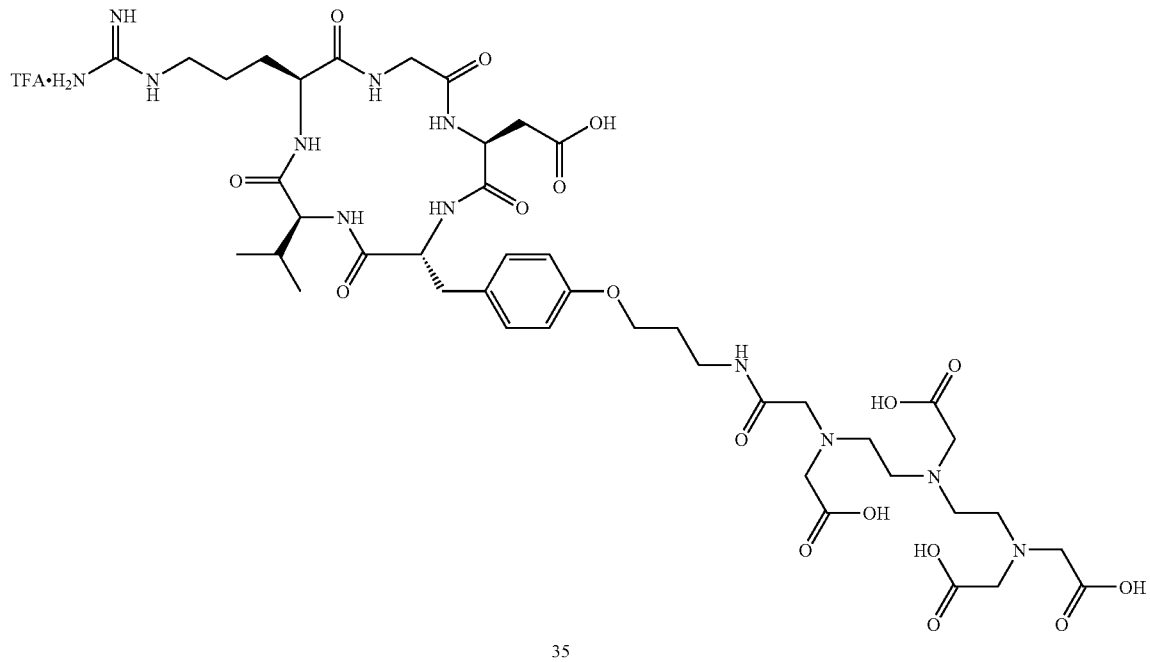

Example 22

Synthesis of cyclo{Orn(d-N-2-Imidazolinyl)-Gly-Asp-D-Tyr(N-[2-[[[5-[carbonyl]-2-pyridinyl]hydrazono]methyl]-benzenesulfonic acid]-3-aminopropyl)-Val} [SEQ. ID NO.: 22]

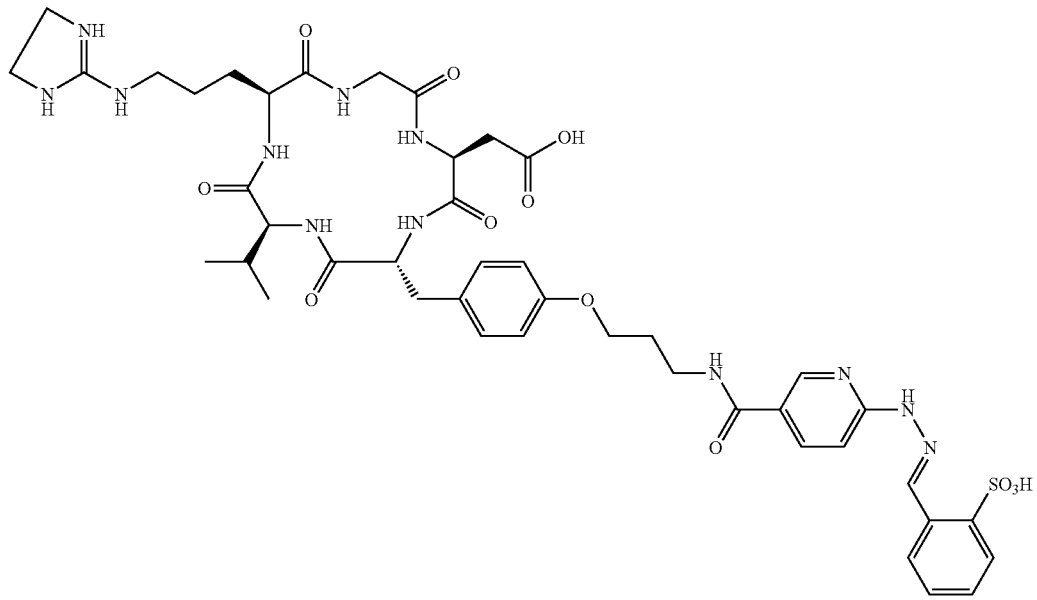

Part A. Preparation of cyclo{Orn(d-N-1-Tos-2-Imidazolinyl)-Gly-Asp(OBzl)-D-Tyr(N-Cbz-3-aminopropyl)-Val} [SEQ. ID NO.: 133]

The N-terminus Boc-protecting group of the peptide sequence Boc-Asp(OBzl)-D-Tyr(N-Cbz-aminopropyl)-Val-Orn(d-N-1-Tos-2-Imidazolinyl)-Gly [SEQ. ID NO.: 134]-Oxime resin is removed using standard deprotection (25% TFA in CH$_2$Cl$_2$). After eight washes with DCM, the resin is treated with 10% DIEA/DCM (2×10 min.). The resin is subsequently washed with DCM (×5) and dried under high vacuum. The resin (1.75 g, 0.55 mmol/g) is then suspended in dimethylformamide (15 mL). Glacial acetic acid (55.0 μL, 0.961 mmol) is added, and the reaction mixture is heated at 50° C. for 72 h. The resin is filtered, and washed with DMF (2×10 mL). The filtrate is concentrated to an oil under high vacuum. The resulting oil is triturated with ethyl acetate. The solid is filtered, washed with ethyl acetate, and is dried under high vacuum to obtain the desired product.

Part B. Preparation of cyclo{Orn(d-N-2-Imidazolinyl)-Gly-Asp-D-Tyr(3-aminopropyl)-Val} [SEQ. ID NO.: 135]. Trifluoroacetic acid salt.

Cyclo {Orn(d-N-1-Tos-2-Imidazolinyl)-Gly-Asp(OBzl)-D-Tyr(N-Cbz-3-aminopropyl)-Val} [SEQ. ID NO.: 133] (0.146 mmol) is dissolved in trifluoroacetic acid (0.6 mL) and cooled to −10° C. Trifluoromethanesulfonic acid (0.5 mL) is added dropwise, maintaining the temperature at −10° C. Anisole (0.1 mL) is added and the reaction mixture is stirred at −10° C. for 3 h. Diethyl ether is added, the reaction mixture cooled to −35° C. and then stirred for 30 min. The reaction mixture is cooled further to −50° C. and stirred for 30 min. The crude product is filtered, washed with diethyl ether, dried under high vacuum, and is purified by preparative HPLC to obtain the desired product.

Part C. Preparation of cyclo{Orn(d-N-2-Imidazolinyl)-Gly-Asp-D-Tyr(3-aminopropyl)-Val} [SEQ. ID NO.: 135] trifluoroacetic acid salt (0.0228 mmol) is dissolved in DMF (1 mL).

Cyclo{Orn(d-N-2-Imidazolinyl)-Gly-Asp-D-Tyr(3-aminopropyl)-Val} [SEQ. ID NO.: 135] trifluoroacetic acid salt (0.0228 mmol) is dissolved in DMF (1 mL). Triethylamine (0.0648 mmol) is added, and after 5 min of stirring 2-[[[5-[[(2,5-dioxo-1-pyrrolidinyl)oxy]carbonyl]-2-pyridinyl]hydrazono]methyl]-benzenesulfonic acid, monosodium salt (0.0274 mmol) is added. The reaction mixture is stirred for 1–2 days, and then concentrated to an oil under high vacuum. The oil is purified by preparative HPLC to obtain the desired product.

Example 23

Synthesis of cyclo{Lys-Gly-Asp-D-Tyr(N-[2-[[[5-[carbonyl]-2-pyridinyl]hydrazono]methyl]-benzenesulfonic acid]-3-aminopropyl)-Val} [SEQ. ID NO.: 23]

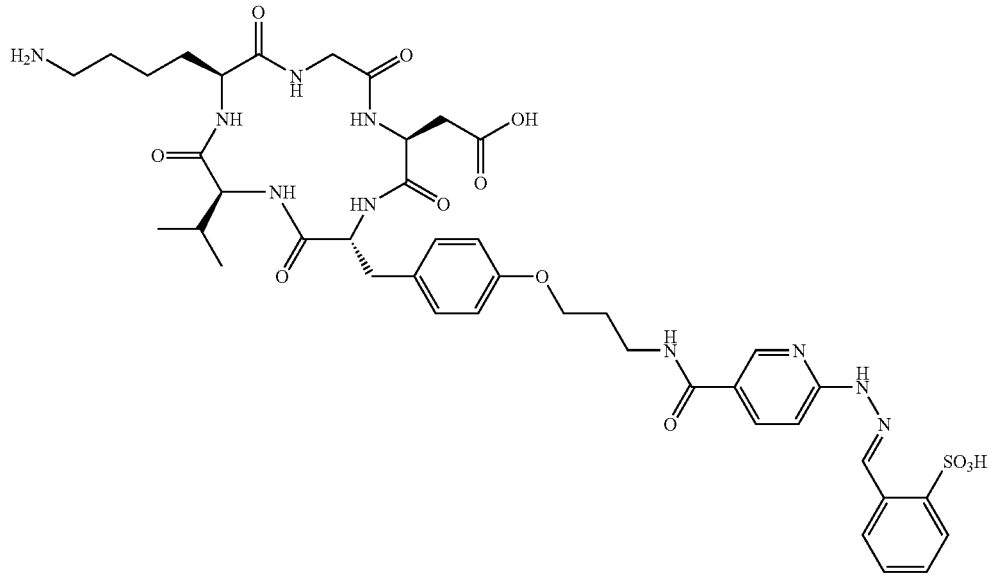

Part A. Preparation of cyclo{Lys(Tfa)-Gly-Asp(OBzl)-D-Tyr(N-Cbz-3-aminopropyl)-Val} [SEQ. ID NO.: 136]

The N-terminus Boc-protecting group of the peptide sequence Boc-Asp(OBzl)-D-Tyr(N-Cbz-aminopropyl)-Val-Lys(Tfa)-Gly [SEQ. ID NO.: 137]-Oxime resin is removed using standard deprotection (25% TFA in CH$_2$Cl$_2$). After eight washes with DCM, the resin is treated with 10% DIEA/DCM (2×10 min.). The resin is subsequently washed with DCM (×5) and dried under high vacuum. The resin (1.75 g, 0.55 mmol/g) is then suspended in dimethylformamide (15 mL). Glacial acetic acid (55.0 μL, 0.961 mmol) is added, and the reaction mixture is heated at 50° C. for 72 h. The resin is filtered, and washed with DMF (2×10 mL). The filtrate is concentrated to an oil under high vacuum. The resulting oil is triturated with ethyl acetate. The solid thus obtained is filtered, washed with ethyl acetate, and is dried under high vacuum to obtain the desired product.

Part B. Preparation of cyclo{Lys(Tfa)-Gly-Asp-D-Tyr(3-aminopropyl)-Val} [SEQ. ID NO.: 138] Trifluoroacetic acid salt.

Cyclo {Lys(Tfa)-Gly-Asp(OBzl)-D-Tyr(N-Cbz-3-aminopropyl)-Val} [SEQ. ID NO.: 136] (0.146 mmol) is dissolved in trifluoroacetic acid (0.6 mL) and cooled to −10° C. Trifluoromethanesulfonic acid (0.5 mL) is added dropwise, maintaining the temperature at −10° C. Anisole (0.1 mL) is added and the reaction mixture is stirred at −10° C. for 3 h. Diethyl ether is added, the reaction mixture cooled to −35° C. and then stirred for 30 min. The reaction mixture is cooled further to −50° C. and stirred for 30 min. The crude product obtained is filtered, washed with diethyl ether, dried under high vacuum, and is purified by preparative HPLC to obtain the desired product.

Part C. Preparation of cyclo{Lys-Gly-Asp-D-Tyr(N-[2-[[[5-[carbonyl]-2-pyridinyl]hydrazono]methyl]-benzenesulfonic acid]-3-aminopropyl)-Val} [SEQ. ID NO.: 23]

Cyclo{Lys(Tfa)-Gly-Asp-D-Tyr(3-aminopropyl)-Val} [SEQ. ID NO.: 138] trifluoroacetic acid salt (0.0228 mmol) is dissolved in DMF (1 mL). Triethylamine (0.0648 mmol) is added, and after 5 min of stirring 2-[[[5-[[(2,5-dioxo-1-pyrrolidinyl)oxy]carbonyl]-2-pyridinyl]hydrazono]methyl]-benzenesulfonic acid, monosodium salt (0.0274 mmol) is added. The reaction mixture is stirred for 1–2 days, and then concentrated to an oil under high vacuum. The oil is treated with 20% piperidine in DMF, and the crude material is purified by preparative HPLC to obtain the desired product.

Example 24

Synthesis of cyclo{Cys(2-aminoethyl)-Gly-Asp-D-Tyr(N-[2-[[[5-[carbonyl]-2-pyridinyl]hydrazono]methyl]-benzenesulfonic acid]-3-aminopropyl)-Val} [SEQ. ID NO.: 24]

in dimethylformamide (15 mL). Glacial acetic acid (55.0 μL, 0.961 mmol) is added, and the reaction mixture is heated at 50° C. for 72 h. The resin is filtered, and washed with DMF (2×10 mL). The filtrate is concentrated to an oil under high vacuum. The resulting oil is triturated with ethyl acetate. The solid thus obtained is filtered, washed with ethyl acetate, and dried under high vacuum to obtain the desired product.

Part B. Preparation of cyclo{Cys(2-N-Tfa-aminoethyl)-Gly-Asp-D-Tyr(3-aminopropyl)-Val} [SEQ. ID NO.: 141]. Trifluoroacetic acid salt.

Cyclo {Cys(2-N-Tfa-aminoethyl)-Gly-Asp(OBzl)-D-Tyr(N-Cbz-3-aminopropyl)Val} [SEQ. ID NO.: 139] (0.146 mmol) is dissolved in trifluoroacetic acid (0.6 mL) and cooled to −10° C. Trifluoromethanesulfonic acid (0.5 mL) is added dropwise, maintaining the temperature at −10° C. Anisole (0.1 mL) is added and the reaction mixture is stirred at −10° C. for 3 h. Diethyl ether is added, the reaction mixture cooled to −35° C. and then stirred for 30 min. The reaction mixture is cooled further to −50° C. and stirred for 30 min. The crude product obtained is filtered, washed with diethyl ether, dried under high vacuum, and is purified by preparative HPLC to obtain the desired product.

Part C. Preparation of cyclo{Cys(2-aminoethyl)-Gly-Asp-D-Tyr(N-[2-[[[5-[carbonyl]-2-pyridinyl]hydrazono]methyl]-benzenesulfonic acid]-3-aminopropyl)-Val} [SEQ. ID NO.: 24]

Cyclo{Cys(2-N-Tfa-aminoethyl)-Gly-Asp-D-Tyr(3-aminopropyl)-Val} [SEQ. ID NO.: 141] trifluoroacetic acid salt

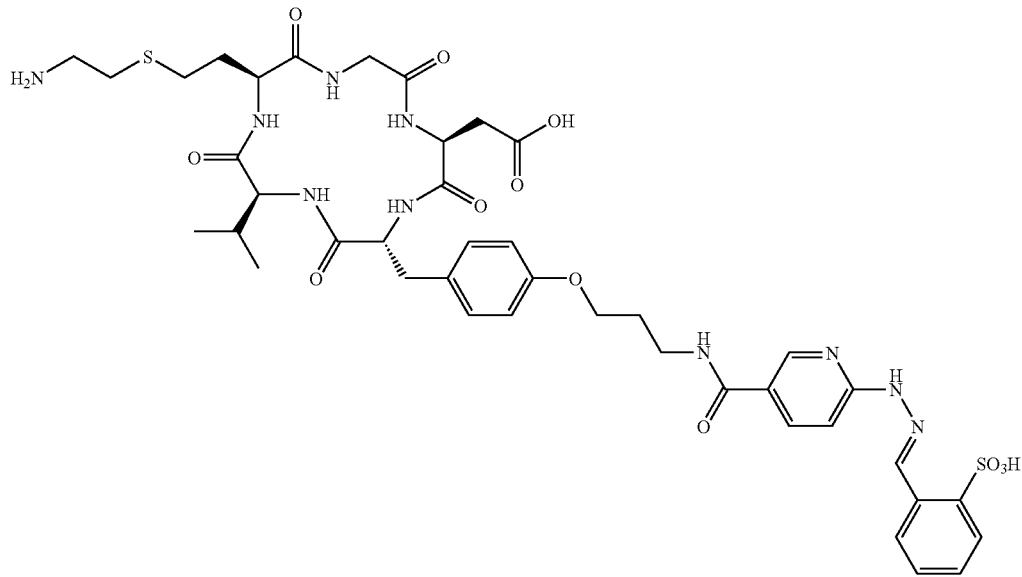

Part A. Preparation of cyclo{Cys(2-N-Tfa-aminoethyl)-Gly-Asp(OBzl)-D-Tyr(N-Cbz-3-aminopropyl)-Val} [SEQ. ID NO.: 139]

The N-terminus Boc-protecting group of the peptide sequence Boc-Asp(OBzl)-D-Tyr(N-Cbz-aminopropyl)-Val-Cys(2-N-Tfa-aminoethyl)-Gly [SEQ. ID NO.: 140]-Oxime resin is removed using standard deprotection (25% TFA in CH$_2$Cl$_2$). After eight washes with DCM, the resin is treated with 10% DIEA/DCM (2×10 min.). The resin is subsequently washed with DCM (×5) and dried under high vacuum. The resin (1.75 g, 0.55 mmol/g) is then suspended (0.0228 mmol) is dissolved in DMF (1 mL). Triethylamine (9.5 μL, 0.0648 mmol) is added, and after 5 min of stirring 2-[[[5-[[(2,5-dioxo-1-pyrrolidinyl)oxy]carbonyl]-2-pyridinyl]hydrazono]methyl]-benzenesulfonic acid, monosodium salt (0.0121 g, 0.0274 mmol) is added. The reaction mixture is stirred for 1–2 days, and then concentrated to an oil under high vacuum. The oil is treated with 20% piperidine in DMF, and the crude material is purified by preparative HPLC to obtain the desired product.

Example 25

Synthesis of cyclo{HomoLys-Gly-Asp-D-Tyr(N-[2-[[[5-[carbonyl]-2-pyridinyl]hydrazono]methyl]-benzenesulfonic acid]-3-aminopropyl)-Val} [SEQ. ID NO.: 25]

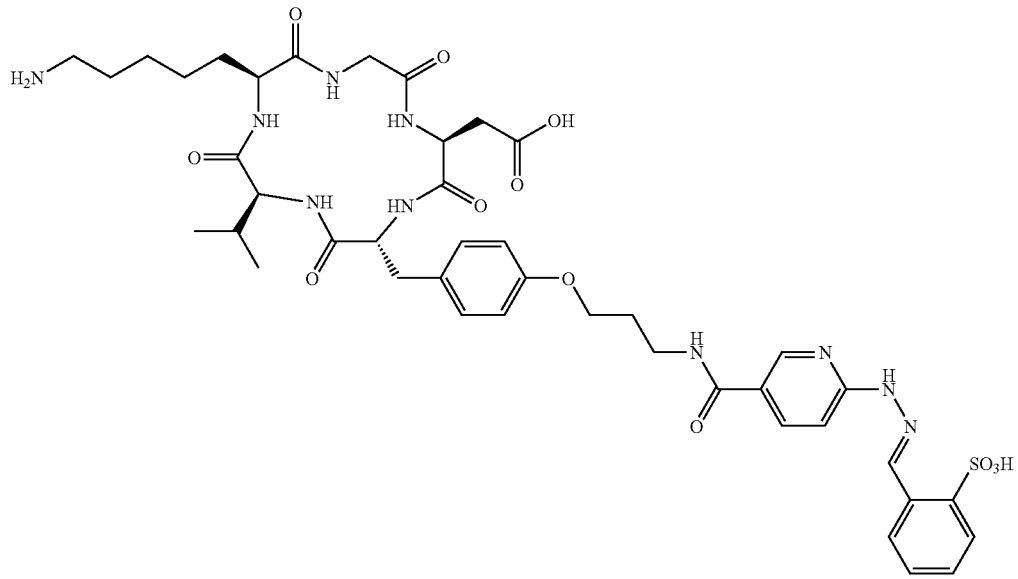

Part A. Preparation of cyclo{HomoLys(Tfa)-Gly-Asp(OBzl)-D-Tyr(N-Cbz-3-aminopropyl)-Val} [SEQ. ID NO.: 142]

The N-terminus Boc-protecting group of the peptide sequence Boc-Asp(OBzl)-D-Tyr(N-Cbz-aminopropyl)-Val-HomoLys(Tfa)-Gly [SEQ. ID NO.: 143]-Oxime resin is removed using standard deprotection (25% TFA in CH₂Cl₂). After eight washes with DCM, the resin is treated with 10% DIEA/DCM (2×10 min.). The resin is subsequently washed with DCM (×5) and dried under high vacuum. The resin (1.75 g, 0.55 mmol/g) is then suspended in dimethylformamide (15 mL). Glacial acetic acid (55.0 μL, 0.961 mmol) is added, and the reaction mixture is heated at 50° C. for 72 h. The resin is filtered, and washed with DMF (2×10 mL). The filtrate is concentrated to an oil under high vacuum. The resulting oil is triturated with ethyl acetate. The solid thus obtained is filtered, washed with ethyl acetate, and dried under high vacuum to obtain the desired product.

Part B. Preparation of cyclo{HomoLys(Tfa)-Gly-Asp-D-Tyr(3-aminopropyl)-Val} [SEQ. ID NO.: 144], Trifluoroacetic acid salt.

Cyclo {HomoLys(Tfa)-Gly-Asp(OBzl)-D-Tyr(N-Cbz-3-aminopropyl)-Val} [SEQ. ID NO.: 145] (0.146 mmol) is dissolved in trifluoroacetic acid (0.6 mL) and cooled to −10° C. Trifluoromethanesulfonic acid (0.5 mL) is added dropwise, maintaining the temperature at −10° C. Anisole (0.1 mL) is added and the reaction mixture is stirred at −10° C. for 3 h. Diethyl ether is added, the reaction mixture cooled to −35° C. and then stirred for 30 min. The reaction mixture is cooled further to −50° C. and stirred for 30 min. The crude product obtained is filtered, washed with diethyl ether, dried under high vacuum, and is purified by preparative HPLC to obtain the desired product.

Part C. Preparation of cyclo{HomoLys-Gly-Asp-D-Tyr(N-[2-[[[5-[carbonyl]-2-pyridinyl]hydrazono]methyl]-benzenesulfonic acid]-3-aminopropyl)-Val} [SEQ. ID NO.: 25]

Cyclo{HomoLys(Tfa)-Gly-Asp-D-Tyr(3-aminopropyl)-Val} [SEQ. ID NO.: 144] trifluoroacetic acid salt (0.0228 mmol) is dissolved in DMF (1 mL). Triethylamine (9.5 μL, 0.0648 mmol) is added, and after 5 min of stirring 2-[[[5-[[(2,5-dioxo-1-pyrrolidinyl)oxy]carbonyl]-2-pyridinyl]hydrazono]methyl]-benzenesulfonic acid, monosodium salt (0.0121 g, 0.0274 mmol) is added. The reaction mixture is stirred for 1–2 days, and then concentrated to an oil under high vacuum. The oil is treated with 20% piperidine in DMF, and the crude material is purified by preparative HPLC to obtain the desired product.

Example 26

Synthesis of cyclo{Orn(d-N-Benzylcarbamoyl)-Gly-Asp-D-Tyr(N-[2-[[[5-[carbonyl]-2-pyridinyl]hydrazono]methyl]-benzenesulfonic acid]-3-aminopropyl)-Val} [SEQ. ID NO.: 26]

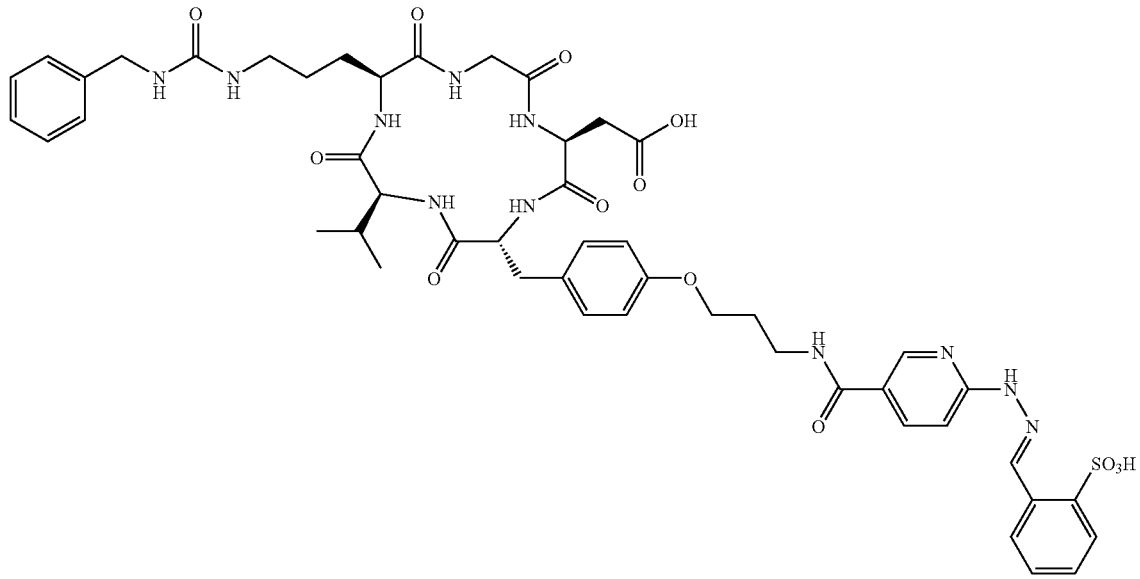

Part A. Preparation of cyclo{Orn(d-N-Benzylcarbamoyl)-Gly-Asp(OBzl)-D-Tyr(N-Cbz-3-aminopropyl)-Val} [SEQ. ID NO.: 146]

The N-terminus Boc-protecting group of the peptide sequence Boc-Asp(OBzl)-D-Tyr(N-Cbz-aminopropyl)-Val-Orn(d-N-Benzylcarbamoyl)-Gly [SEQ. ID NO.: 147]-Oxime resin is removed using standard deprotection (25% TFA in CH$_2$Cl$_2$). After eight washes with DCM, the resin is treated with 10% DIEA/DCM (2×10 min.). The resin is subsequently washed with DCM (×5) and dried under high vacuum. The resin (1.75 g, 0.55 mmol/g) is then suspended in dimethylformamide (15 mL). Glacial acetic acid (55.0 μL, 0.961 mmol) is added, and the reaction mixture is heated at 50° C. for 72 h. The resin is filtered, and washed with DMF (2×10 mL). The filtrate is concentrated to an oil under high vacuum. The resulting oil is triturated with ethyl acetate. The solid thus obtained is filtered, washed with ethyl acetate, and dried under high vacuum to obtain the desired product.

Part B. Preparation of cyclo{Orn(d-N-Benzylcarbamoyl)-Gly-Asp-D-Tyr(3-aminopropyl)-Val} [SEQ. ID NO.: 148]. Trifluoroacetic acid salt Cyclo {Orn(d-N-Benzylcarbamoyl)-Gly-Asp(OBzl)-D-Tyr(N-Cbz-3-aminopropyl)Val} [SEQ. ID NO.: 146] (0.146 mmol) is dissolved in trifluoroacetic acid (0.6 mL) and cooled to −10° C. Trifluoromethanesulfonic acid (0.5 mL) is added dropwise, maintaining the temperature at −10° C. Anisole (0.1 mL) is added and the reaction mixture is stirred at −10° C. for 3 h. Diethyl ether is added, the reaction mixture cooled to −35° C. and then stirred for 30 min. The reaction mixture is cooled further to −50° C. and stirred for 30 min. The crude product obtained is filtered, washed with diethyl ether, dried under high vacuum, and is purified by preparative HPLC to obtain the desired product.

Part C. Preparation of cyclo{Orn(d-N-Benzylcarbamoyl)-Gly-Asp-D-Tyr(N-[2-[[[5-[carbonyl]-2-pyridinyl]hydrazono]methyl]-benzenesulfonic acid]-3-aminopropyl)-Val} [SEQ. ID NO.: 26]

Cyclo {Orn(d-N-Benzylcarbamoyl)-Gly-Asp-D-Tyr(3-aminopropyl)-Val} [SEQ. ID NO.: 148] trifluoroacetic acid salt (0.0228 mmol) is dissolved in DMF (1 mL). Triethylamine (9.5 μL, 0.0648 mmol) is added, and after 5 min of stirring 2-[[[5-[[(2,5-dioxo-1-pyrrolidinyl)oxy]carbonyl]-2-pyridinyl]hydrazono]methyl]-benzenesulfonic acid, monosodium salt (0.0121 g, 0.0274 mmol) is added. The reaction mixture is stirred for 1–2 days, and then concentrated to an oil under high vacuum. The oil is purified by preparative HPLC to obtain the desired product.

Example 27

Synthesis of cyclo{Dap(b-(2-benzimidazolylacetyl))-Gly-Asp-D-Tyr(N-[2-[[[5-[carbonyl]-2-pyridinyl]hydrazono]methyl]-benzenesulfonic acid]-3aminopropyl)-Val} [SEQ. ID NO.: 27]

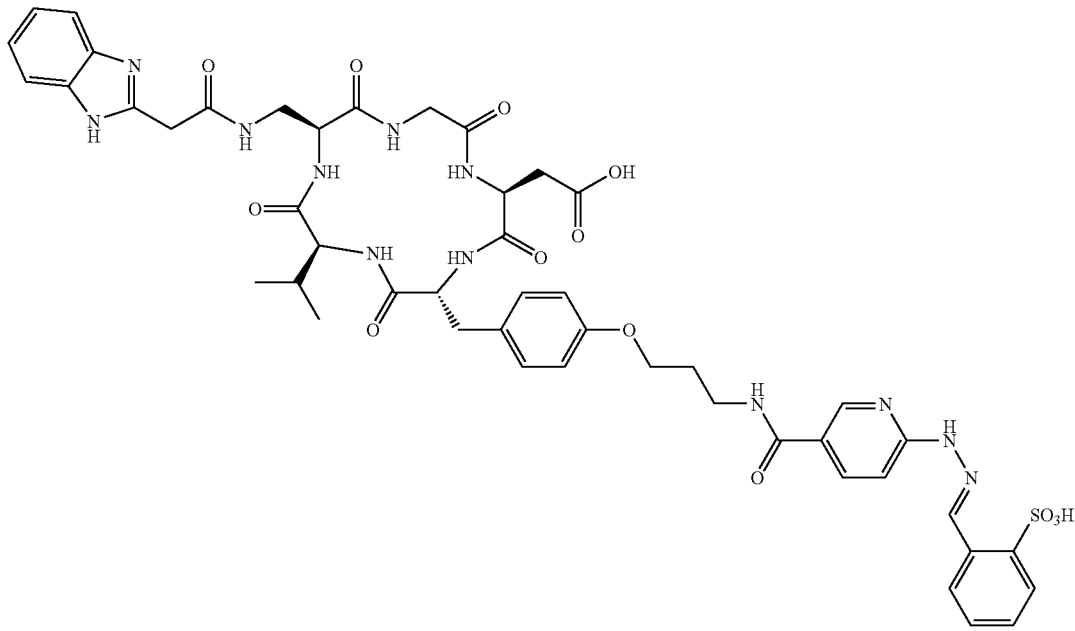

Part A. Preparation of cyclo{Dap(b-(1-Tos-2-benzimidazolylaacetyl))-Gly-Asp(OBzl)-D-Tyr(N-Cbz-3-aminopropyl)-Val} [SEQ. ID NO.: 149]

The N-terminus Boc-protecting group of the peptide sequence Boc-Asp(OBzl)-D-Tyr(N-Cbz-aminopropyl)-Val-Dap(b-(1-Tos-2-benzimidazolylacetyl))-Gly [SEQ. ID NO.: 150]-Oxime resin is removed using standard deprotection (25% TFA in $CH_2Cl_2$). After eight washes with DCM, the resin is treated with 10% DIEA/DCM (2×10 min.). The resin is subsequently washed with DCM (×5) and dried under high vacuum. The resin (1.75 g, 0.55 mmol/g) is then suspended in dimethylformamide (15 mL). Glacial acetic acid (55.0 µL, 0.961 mmol) is added, and the reaction mixture is heated at 50° C. for 72 h. The resin is filtered, and washed with DMF (2×10 mL). The filtrate is concentrated to an oil under high vacuum. The resulting oil is triturated with ethyl acetate. The solid thus obtained is filtered, washed with ethyl acetate, and dried under high vacuum to obtain the desired product.

Part B. Preparation of cyclo{Dap(b-(2-benzimidazolylacetyl))-Gly-Asp-D-Tyr(3-aminopropyl)-Val} [SEQ. ID NO.: 151]. Trifluoroacetic acid salt Cyclo{Dap(b-(1-Tos-2-benzimidazolylacetyl))-Gly-Asp(OBzl)-D-Tyr(N-Cbz-3-aminopropyl)-Val} [SEQ. ID NO.: 149] (0.146 mmol) is dissolved in trifluoroacetic acid (0.6 mL) and cooled to −10° C. Trifluoromethanesulfonic acid (0.5 mL) is added dropwise, maintaining the temperature at −10° C. Anisole (0.1 m]L) is added and the reaction mixture is stirred at −10° C. for 3 h. Diethyl ether is added, the reaction mixture cooled to −35° C. and then stirred for 30 min. The reaction mixture is cooled further to −50° C. and stirred for 30 min. The crude product obtained is filtered, washed with diethyl ether, dried under high vacuum, and purified by preparative HPLC to obtain the desired product.

Part C. Preparation of cyclo{Dap(b-(2-benzimidazolylacetyl))-Gly-Asp-D-Tyr(N-[2-[[[5-[carbonyl]-2-pyridinyl]hydrazono]methyl]-benzenesulfonic acid]-3-aminopropyl)-Val} [SEQ. ID NO.: 27]

Cyclo {Dap(b-(2-benzimidazolylacetyl))-Gly-Asp-D-Tyr (3-aminopropyl)-Val} [SEQ. ID NO.: 151] trifluoroacetic acid salt (0.0228 mmol) is dissolved in DMF (1 mL). Triethylamine (9.5 µL, 0.0648 mmol) is added, and after 5 min of stirring 2-[[[5-[[(2,5-dioxo-1-pyrrolidinyl)oxy]carbonyl]-2-pyridinyl]hydrazono] methyl]-benzenesulfonic acid, monosodium salt (0.0121 g, 0.0274 mmol) is added. The reaction mixture is stirred for 1–2 days, and then concentrated to an oil under high vacuum. The oil is purified by the method described below to obtain the desired product.

Example 28

Synthesis of cyclo{Orn(d-N-2-Imidazolinyl)-Gly-Asp-D-Phe-Lys(N-[2-[[[5-[carbonyl]-2-pyridinyl]hydrazono]methyl]-benzenesulfonic acid])}
[SEQ. ID NO.: 28]

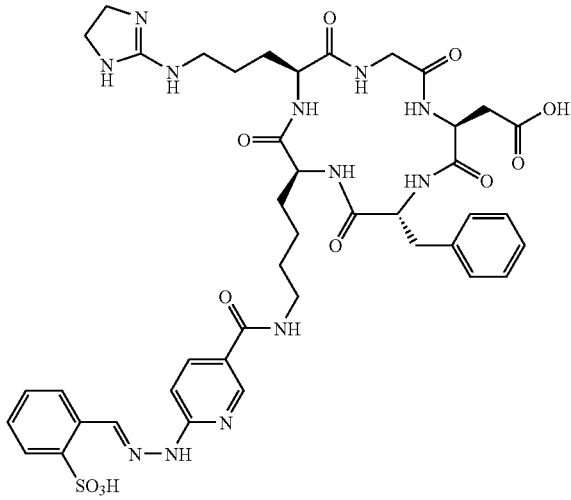

Part A. Preparation of cyclo{Orn(d-N-1-Tos-2-Imidazolinyl)-Gly-Asp(OBzl)-D-Phe-Lys(Cbz)} [SEQ. ID NO.: 152]

The N-terminus Boc-protecting group of the peptide sequence Boc-Asp(OBzl)-D-Phe-Lys(Z)-Orn(d-N-1-Tos-2-Imidazolinyl)-Gly [SEQ. ID NO.: 153]-Oxime resin is removed using standard deprotection (25% TFA in $CH_2Cl_2$). After eight washes with DCM, the resin is treated with 10% DIEA/DCM (2×10 min.). The resin is subsequently washed with DCM (×5) and dried under high vacuum. The resin (1.75 g, 0.55 mmol/g) is then suspended in dimethylformamide (15 mL). Glacial acetic acid (55.0 µL, 0.961 mmol) is added, and the reaction mixture is heated at 50° C. for 72 h. The resin is filtered, and washed with DMF (2×10 mL). The filtrate is concentrated to an oil under high vacuum. The resulting oil is triturated with ethyl acetate. The solid thus obtained is filtered, washed with ethyl acetate, and dried under high vacuum to obtain the desired product.

Part B. Preparation of cyclo{Orn(d-N-2-Imidazolinyl)-Gly-Asp-D-Phe-Lys} [SEQ. ID NO.: 154]

Cyclo{Orn(d-N-1-Tos-2-Imidazolinyl)-Gly-Asp(OBzl)-D-Phe-Lys(Cbz)} [SEQ. ID NO.: 152] (0.204 mmol) is dissolved in trifluoroacetic acid (0.6 mL) and cooled to −10° C. Trifluoromethanesulfonic acid (0.5 mL) is added dropwise, maintaining the temperature at −10° C. Anisole (0.1 mL) is added and the reaction is stirred at −10° C. for 3 h. Diethyl ether is added, the reaction is cooled to −50° C., and stirred for 1 h. The crude product is filtered, washed with diethyl ether, dried under high vacuum and purified by preparative HPLC to obtain the desires product.

Part C. Preparation of cyclo{Orn(d-N-2-Imidazolinyl)-Gly-Asp-D-Phe-Lys(N-[2-[[[5-[carbonyl]-2-pyridinyl]hydrazono]methyl]-benzenesulfonic acid])} [SEQ. ID NO.: 28]

Cyclo{Orn(d-N-2-Imidazolinyl)-Gly-Asp-D-Phe-Lys} [SEQ. ID NO.: 154] TFA salt (0.0481 mmol) is dissolved in DMF (2 mL). Triethylamine (20.1 µL, 0.144 mmol) is added, and after 5 min of stirring 2-[[[5-[[(2,5-dioxo-1-pyrrolidinyl)oxy]carbonyl]-2-pyridinyl]hydrazono]-methyl]-benzenesulfonic acid, monosodium salt (0.0254 g, 0.0577 mmol) is added. The reaction mixture is stirred for 20 h and then concentrated to an oil under high vacuum. The oil is purified by preparative HPLC to obtain the desired product.

Example 29

Synthesis of cyclo{Orn(d-N-Benzylcarbamoyl)-Gly-Asp-D-Phe-Lys(N-[2-[[[5-[carbonyl]-2-pyridinyl]hydrazono]methyl]-benzenesulfonic acid])}
[SEQ. ID NO.: 29]

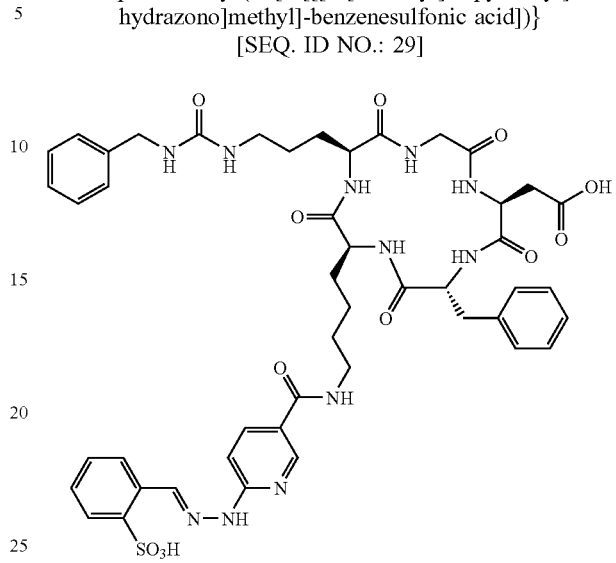

Part A. Preparation of cyclo[Orn(d-N-Benzylcarbamoyl)-Gly-Asp(OBzl)-D-Phe-Lys(Cbz)} [SEQ. ID NO.: 155]

The N-terminus Boc-protecting group of the peptide sequence Boc-Asp(OBzl)-D-Phe-Lys(Z)-Orn(d-N-Benzylcarbamoyl)-Gly [SEQ. ID NO.: 156]-Oxime resin is removed using standard deprotection (25% TFA in $CH_2Cl_2$). After eight washes with DCM, the resin is treated with 10% DIEA/DCM (2×10 min.). The resin is subsequently washed with DCM (×5) and dried under high vacuum. The resin (1.75 g, 0.55 mmol/g) is then suspended in dimethylformamide (15 mL). Glacial acetic acid (55.0 µL, 0.961 mmol) is added, and the reaction mixture is heated at 50° C. for 72 h. The resin is filtered, and washed with DMF (2×10 mL). The filtrate is concentrated to an oil under high vacuum. The resulting oil is triturated with ethyl acetate. The solid thus obtained is filtered, washed with ethyl acetate, and dried under high vacuum to obtain the desired product.

Part B. Preparation of cyclo[Orn(d-N-Benzylcarbamoyl)-Gly-Asp-D-Phe-Lys} [SEQ. ID NO.: 157]

Cyclo {Orn(d-N-Benzylcarbamoyl)-Gly-Asp(OBzl)-D-Phe-Lys(Cbz)} [SEQ. ID NO.: 155] (0.204 mmol) is dissolved in trifluoroacetic acid (0.6 mL) and cooled to −10° C. Trifluoromethanesulfonic acid (0.5 mL) is added dropwise, maintaining the temperature at −10° C. Anisole (0.1 mL) is added and the reaction is stirred at −10° C. for 3 h. Diethyl ether is added, the reaction is cooled to −50° C., and stirred for 1 h. The crude product is filtered, washed with diethyl ether, dried under high vacuum and purified by preparative HPLC to obtain the desires product.

Part C. Preparation of cyclo{Orn(d-N-Benzylcarbamoyl)-Gly-Asp-D-Phe-Lys(N-[2-[[[5-[carbonyl]-2-pyridinyl]hydrazono]methyl]-benzenesulfonic acid])} [SEQ. ID NO.: 29]

Cyclo{Orn(d-N-Benzylcarbamoyl)-Gly-Asp-D-Phe-Lys} [SEQ. ID NO.: 157] TFA salt (0.0481 mmol) is dissolved in DMF (2 mL). Triethylamine (20.1 µL, 0.144 mmol) is added, and after 5 min of stirring 2-[[[5-[[(2,5-dioxo-1-pyrrolidinyl)oxy]carbonyl]-2-pyridinyl]hydrazono]-methyl]-benzenesulfonic acid, monosodium salt (0.0254 g, 0.0577 mmol) is added. The reaction mixture is stirred for 20 h and then concentrated to an oil under high vacuum. The oil is purified by preparative HPLC to obtain the desired product.

Example 30

Synthesis of cyclo{Lys-D-Val-D-Tyr(N-[2-[[[5-[carbonyl]-2-pyridinyl]hydrazono]methyl]-benzenesulfonic acid]-3-aminopropyl)-D-Asp-Gly} [SEQ. ID NO.: 30]

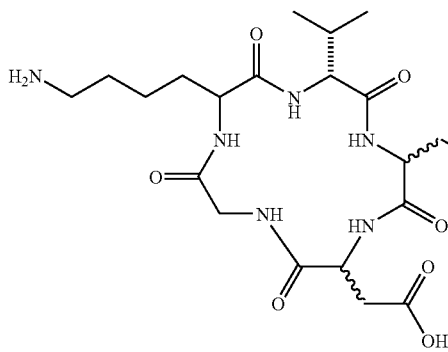

Part A. Preparation of cyclo{Lys(Tfa)-D-Val-D-Tyr(N-Cbz-3-aminopropyl)-D-Asp(OBzl)-Gly} [SEQ. ID NO.: 158]

The N-terminus Boc-protecting group of the peptide sequence Boc-Lys(Tfa)-D-Val-D-Tyr(N-Cbz-aminopropyl)-D-Asp(OBzl)-Gly [SEQ. ID NO.: 159]-Oxime resin is removed using standard deprotection (50% TFA in $CH_2Cl_2$). After washing with DCM (8×), the resin is neutralized with 10% DIEA/DCM (2×10 min). The resin is washed with DCM (5×) and dried under high vacuum overnight. The resin (1.0 g, about 0.36 mmol/g) is then suspended in N,N-dimethylformamide (12 mL). Glacial acetic acid (67 mL, 1.16 mmol) is added and the reaction mixture is heated to 55° C. for 72 h. The resin is filtered and washed with DMF (3×10 mL). The filtrate is concentrated under high vacuum to give an oil. The resulting oil is triturated with ethyl acetate. The desired product is purified by reverse-phase HPLC.

Part B. Preparation of cyclo{Lys-D-Val-D-Tyr(3-aminopropyl)-D-Asp-Gly} [SEQ. ID NO.: 160], Trifuoroacetic acid salt The protected cyclic peptide cyclo{Lys(Tfa)-D-Val-D-Tyr(N-Cbz-3-aminopropyl)-D-Asp(OBzl)-Gly} [SEQ. ID NO.: 158] (0.10 mmol) is dissolved in trifluoroacetic acid (0.95 mL) and cooled to −10° C. in a dry ice/acetone bath. To this solution is added trifluoromethanesulfonic acid (0.12 mmol), followed by anisole (190 mL). The reaction mixture is stirred at −16° C. for 3 h. The dry ice/acetone bath is then cooled to −35° C. and cold ether (40 mL) is added to the solution. The mixture is stirred for 30 min at −35° C., then cooled to −50° C. and stirred for another 30 min. The crude product is filtered, redissolved in water/acetonitrile (1/1), lyophilized, and purified by reverse-phase HPLC to give the desired product.

Part C. Preparation of cyclo{Lys-D-Val-D-Tyr(N-[2-[[[5-[carbonyl]-2-pyridinyl]hydrazono]methyl]-benzenesulfonic acid]-3-aminopropyl)-D-Asp-Gly} [SEQ. ID NO.: 30]

A solution of cyclo{Lys(Tfa)-D-Val-D-Tyr(3-aminopropyl)-D-Asp-Gly} [SEQ. ID NO.: 160] (0.0216 mmol) in N,N-dimethylformamide (2 mL) is added triethylamine (15 mL, 0.108 mmol) and stirred at room temperature for 10 min. 2-[[[5-[[(2,5-Dioxo-1-pyrrolidinyl)oxy]carbonyl-2-pyridinyl]-hydrazono]methyl-benzenesulfonic acid, monosodium salt (0.0260 mmol) is added, and the mixture is stirred for 18 h. The mixture is concentrated under high vacumm, the oil is treated with 20% piperidine in DMF, and is again concntrated in vacuo. The residue is purified by reverse-phase HPLC to give the desired product.

Example 31

Synthesis of cyclo{Orn(d-N-Benzylcarbamoyl)-D-Val-D-Tyr(N-[2-[[[5-[carbonyl]-2-pyridinyl]hydrazono]methyl]-benzenesulfonic acid]-3-aminopropyl)-D-Asp-Gly} [SEQ. ID NO.: 31]

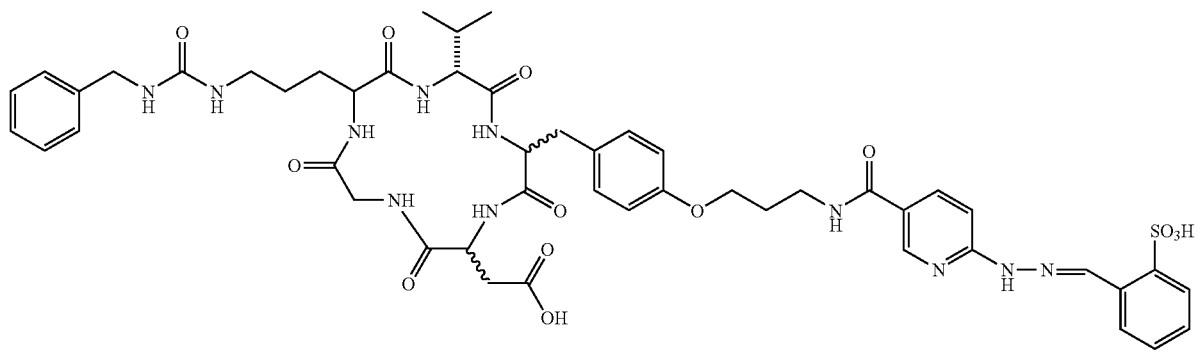

Part A. Preparation of cyclo{Orn(d-N-Benzylcarbamoyl)-D-Val-D-Tyr(N-Cbz-3-aminopropyl)-D-Asp(OBzl)-Gly} [SEQ. ID NO.: 161]

The N-terminus Boc-protecting group of the peptide sequence Boc-Orn(d-N-Benzylcarbamoyl)-D-Val-D-Tyr(N-Cbz-aminopropyl)-D-Asp(OBzl)-Gly [SEQ. ID NO.: 162]-Oxime resin is removed using standard deprotection (50% TFA in CH$_2$Cl$_2$). After washing with DCM (8×), the resin is neutralized with 10% DIEA/DCM (2×10 min). The resin is washed with DCM (5×) and dried under high vacuum overnight. The resin (1.0 g, about 0.36 mmol/g) is then suspended in N,N-dimethylformamide (12 mL). Glacial acetic acid (67 mL, 1.16 mmol) is added and the reaction mixture is heated to 55° C. for 72 h. The resin is filtered and washed with DMF (3×10 mL). The filtrate is concentrated under high vacuum to give an oil. The resulting oil is triturated with ethyl acetate. The desired product is purified by reverse-phase HPLC.

Part B. Preparation of cyclo{Orn(d-N-Benzylcarbamoyl)-D-Val-D-Tyr(3-aminopropyl)-D-Asp-Gly} [SEQ. ID NO.: 163], Trifuoroacetic acid salt The protected cyclic peptide cyclo{Orn(d-N-Benzylcarbamoyl)-D-Val-D-Tyr(N-Cbz-3-aminopropyl)-D-Asp (OBzl)-Gly} [SEQ. ID NO.: 161] (0.10 mmol) is dissolved in trifluoroacetic acid (0.95 mL) and cooled to −10° C. in a dry ice/acetone bath. To this solution is added trifluoromethanesulfonic acid (0.12 mmol), followed by anisole (190 mL). The reaction mixture is stirred at −16° C. for 3 h. The dry ice/acetone bath is then cooled to −35° C. and cold ether (40 mL) is added to the solution. The mixture is stirred for 30 min at −35° C., then cooled to −50° C. and stirred for another 30 min. The crude product is filtered, redissolved in water/acetonitrile (1/1), lyophilized, and purified by reverse-phase HPLC to give the desired product.

Part C. Preparation of cyclo{Orn(d-N-Benzylcarbamoyl)-D-Val-D-Tyr(N-2-[[[5-[carbonyl]-2-pyridinyl]hydrazono]methyl]-benzenesulfonic acid]-3-aminopropyl)-D-Asp-Gly} [SEQ. ID NO.: 42]

A solution of cyclo{Orn(d-N-Benzylcarbamoyl)-D-Val-D-Tyr(3-aminopropyl)-D-Asp-Gly} [SEQ. ID NO.: 163] (0.0216 mmol) in N,N-dimethylformamide (2 mL) is added triethylamine (15 mL, 0.108 mmol) and stirred at room temperature for 10 min. 2-[[[5[[(2,5-Dioxo-1-pyrrolidinyl)oxy]carbonyl-2-pyridinyl]-hydrazono]methyl-benzenesulfonic acid, monosodium salt (0.0260 mmol) is added, and the mixture is stirred for 18 h. The mixture is concentrated under high vacumm and the residue is purified by reverse-phase HPLC to give the desired product.

Example 32

Synthesis of cyclo{Orn(d-N-2-Imidazolinyl-D-Val-D-Tyr(N-[2-[[[5-[carbonyl]-2-pyridinyl]hydrazono] methyl]-benzenesulfonic acid]-3-aminopropyl)-D-Asp-Gly} [SEQ. ID NO.: 32]

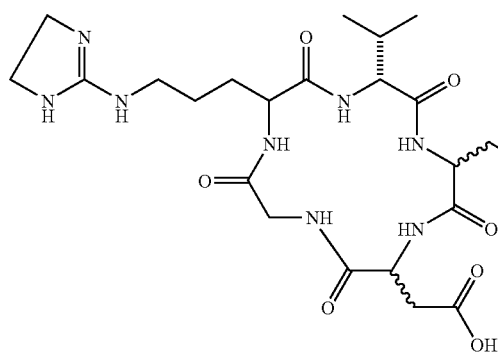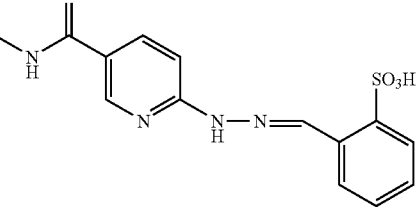

Part A. Preparation of cyclo{Orn(d-N-1-Tos-2-Imidazolinyl)-D-Val-D-Tyr(N-Cbz-3-aminopropyl)-D-Asp(OBzl)-Gly} [SEQ. ID NO.: 164]

The N-terminus Boc-protecting group of the peptide sequence Boc-Orn(d-N-1-Tos-2-Imidazolinyl)-D-Val-D-Tyr(N-Cbz-aminopropyl)-D-Asp(OBzl)-Gly [SEQ. ID NO.: 165]-Oxime resin is removed using standard deprotection (50% TFA in CH$_2$Cl$_2$). After washing with DCM (8×), the resin is neutralized with 10% DIEA/DCM (2×10 min). The resin is washed with DCM (5×) and dried under high vacuum overnight. The resin (1.0 g, about 0.36 mmol/g) is then suspended in N,N-dimethylformamide (12 mL). Glacial acetic acid (67 mL, 1.16 mmol) is added and the reaction mixture is heated to 55° C. for 72 h. The resin is filtered and washed with DMF (3×10 mL). The filtrate is concentrated under high vacuum to give an oil. The resulting oil is triturated with ethyl acetate. The desired product is purified by reverse-phase HPLC.

Part B. Preparation of cyclo{Orn(d-N-2-Imidazolinyl)-D-Val-D-Tyr(3-aminopropyl)-D-Asp-Gly} [SEQ. ID NO.: 166], Trifuoroacetic acid salt The protected cyclic peptide cyclo{Orn(d-N-1-Tos-2-Imidazolinyl)-D-Val-D-Tyr(N-Cbz-3-aminopropyl)-D-Asp (OBzl)-Gly} [SEQ. ID NO.: 164] (0.10 mmol) is dissolved in trifluoroacetic acid (0.95 mL) and cooled to −10° C. in a dry ice/acetone bath. To this solution is added trifluoromethanesulfonic acid (0.12 mmol), followed by anisole (190 mL). The reaction mixture is stirred at −16° C. for 3 h. The dry ice/acetone bath is then cooled to −35° C. and cold ether (40 mL) is added to the solution. The mixture is stirred for 30 min at −35° C., then cooled to −50° C. and stirred for another 30 min. The crude product is filtered, redissolved in water/acetonitrile (1/1), lyophilized, and purified by reverse-phase HPLC to give the desired product.

Part C. Preparation of cyclo{Orn(d-N-2-Imidazolinyl)-D-Val-D-Tyr(N-[2-[[[5-[carbonyl]-2-pyridinyl]hydrazono]methyl]-benzenesulfonic acid]-3-aminopropyl)-D-Asp-Gly} [SEQ. ID NO.: 32]

A solution of cyclo{Orn(d-N-2-Imidazolinyl)-D-Val-D-Tyr(3-aminopropyl)-D-Asp-Gly} [SEQ. ID NO.: 166] (0.0216 mmol) in N,N-dimethylformamide (2 mL) is added triethylamine (15 mL, 0.108 mmol) and stirred at room temperature for 10 min. 2-[[[5-[[(2,5-Dioxo-1-pyrrolidinyl)oxy]carbonyl-2-pyridinyl]-hydrazono]methyl-benzene-sulfonic acid, monosodium salt (0.0260 mmol) is added, and the mixture is stirred for 18 h. The mixture is concentrated under high vacuum and the residue is purified by reverse-phase HPLC to give the desired product.

RADIOPHARMACEUTICAL EXAMPLES

The following procedures (A, B) describe the synthesis of radiopharmaceuticals of the present invention of the formula $^{99m}$Tc(VnA)(tricine)(phosphine), in which (VnA) represents the vitronectin receptor antagonist compound bonded to the Tc through a diazenido (—N=N—) or hydrazido (=N—NH—) moiety. The diazenido or hydrazido moiety results from the reaction of the hydrazinonicotinamido group, present either as the free hydrazine or protected as a hydrazone, with the Tc-99m. The other two ligands in the Tc coordination sphere are tricine and a phosphine.

Procedure A

Synthesis of Tc-99m Vitronectin Receptor Antagonist Complexes of the Formula $^{99m}$Tc(VnA)(tricine)(phosphine) Using Stannous Reducing Agent 10–30 μg (0.2–0.4 μL) of a reagent of the present invention dissolved in saline or 50% aqueous ethanol, 40 mg (0.4 mL) of tricine in water, 1–7 mg (0.10–0.30 mL) of phosphine dissolved in water or ethanol, 25 μg (25 μL) SnCl$_2$.2H$_2$O dissolved in 0.1 M HCl, 0–0.25 mL ethanol and 50–150 mCi $^{99m}$TcO$_4^-$ in saline were combined in a 10 cc vial. The kit was heated in a 100° C. water bath for 10–20 minutes, then a 50 μL sample analyzed by HPLC Method 3. If necessary, the complex was purified by performing a 300–400 μL injection on the HPLC and collecting the fraction into a shielded flask. The collected fraction was evaporated to dryness, redissolved in saline containing 0–5 vol % Tween 80, and then re-analyzed using HPLC Method 3.

Procedure B

Synthesis of Tc-99m Vitronectin Receptor Antagonist Complexes of the Formula $^{99m}$Tc(VnA)(tricine)(TPPTS) Without Using Stannous Reducing Agent To a lyophilized vial containing 4.84 mg TPPTS, 6.3 mg tricine, 40 mg mannitol and 0.25 mmol succinate buffer, pH 4.8, was added 0.2–0.4 mL (20–40 μg) of a reagent of the present invention dissolved in saline or 50% aqueous ethanol, 50–100 mCi $^{99m}$TcO$_4^-$ in saline, and additional saline to give a total volume of 1.3–1.5 mL. The kit is heated in an 100° C. water bath for 10–15 minutes, and a sample was then analyzed by HPLC Method 3. If necessary, the complex was purified by performing a 300–400 μL injection on the HPLC and collecting the fraction into a shielded flask. The collected fraction was evaporated to dryness, redissolved in saline containing 0–5 vol % Tween 80, and then re-analyzed using HPLC Method 3.

TABLE 1

Analytical and Yield Data for $^{99m}$Tc(VnA) (tricine) (Phosphine) Complexes

| Complex Ex. No. | Reagent Ex. No. | Phosphine | % Yield | RT (min) |
|---|---|---|---|---|
| 33 | 1 | TPPTS | 88 | 8.2 |
| 34 | 2 | TPPTS | 96 | 19.5 |
| 35 | 3 | TPPTS | 91 | 33.7 |
| 36 | 4 | TPPTS | 92 | 21.8 |
| 37 | 5 | TPPTS | 65 | 25.1 |
| 38 | 6 | TPPTS | 91 | 41.7 |
| 39 | 7 | TPPTS | 89 | 20.4 |
| 40 | 8 | TPPTS | 93 | 16.4 |
| 41 | 9 | TPPTS | 90 | 13.4 |
| 42 | 10 | TPPTS | 93 | 12.9 |
| 43 | 12 | TPPMS | 94 | 23.5 |
| 44 | 12 | TPPDS | 93 | 18.1 |
| 45 | 12 | TPPTS | 93 | 13.6 |
| 46 | 13 | TPPTS | 93 | 11.2 |
| 47 | 14 | TPPTS | 79 | 11.0 |
| 48 | 15 | TPPTS | 94 | 11.2 |
| 49 | 16 | TPPTS | 81 | 9.2 |
| 50 | 17 | TPPTS | 97 | 10.4 |

The following example describes the synthesis of radiopharmaceuticals of the present invention of the formula $^{99m}$Tc(VnA)(tricine)(L) (L=Imine-Nitrogen Containing Heterocycle), in which (VnA) represents the vitronectin receptor antagonist compound bonded to the Tc through a diazenido (—N=N—) or hydrazido (=N—NH—) moiety. The other two ligands in the Tc coordination sphere are tricine and an imine-nitrogen containing heterocycle.

Example 51

Synthesis of Tc-99m Vitronectin Receptor Antagonist Complex $^{99m}$Tc(VnA)(tricine)(1,2,4-triazole)

30 μg of the Reagent of Example 1 (0.30 mL 50/50 EtOH/H$_2$O), 40 mg tricine (0.25 mL/H$_2$O), 8 mg 1,2,4-triazole (0.25 mL/H$_2$O), 25 μg SnCl$_2$ (25 μL/0.1 N HCl), 0.50 mL water and 0.20 mL 50±5 mCi $^{99m}$TcO$_4^-$ were combined in a shielded 10 cc vial and heated at 100° C. for 10 minutes. 50 μL of the kit contents were analyzed by HPLC using Method listed below. The product eluted at a retention time of 8.33 min and had a radiochemical purity of 88.1%.

Reagents of the present invention comprised of either a DOTA (Example 18), DTPA monoamide (Examples 19 and 20) or DTPA bisamide chelator (Example 21) readily form complexes with metal ions of elements 31, 39, 49, and 58–71. The following examples demonstrate the synthesis of complexes with $^{153}$Sm, $^{177}$Lu, and $^{90}$Y, beta particle emitting isotopes used in radiopharmaceutical therapy, and $^{111}$In, a gamma emitting isotope used in radiopharmaceutical imaging agents. In both types of complexes, the metal ion is bound to the DOTA, DTPA monoamide or DTPA bisamide chelator moiety of the reagents.

Examples 52 and 53

Synthesis of Y-90 and Lu-177 DOTA-Containing Vitronectin Antagonist Complexes To a clean sealed 10 mL vial was added 0.5 mL of the reagent of Example 18 (200 µg/mL in 0.25 M ammonium acetate buffer, pH 7.0), followed by 0.05–0.1 mL of gentisic acid (sodium salt, 10 mg/mL in 0.25 M ammonium acetate buffer, pH 7.0) solution, 0.3 mL of 0.25 M ammonium acetate buffer (pH 7.0), and 0.05 mL of $^{177}$LuCl$_3$ solution or $^{90}$YCl$_3$ solution (100–200 mCi/mL) in 0.05 N HCl. The resulting mixture was heated at 100° C. for 35 min. After cooling to room temperature, a sample of the resulting solution was analyzed by radio-HPLC and ITLC. The complex of Example 53 was analyzed by mass spectroscopy (Found [M+H$^+$]=1877.6, Calcd. 1875.8 for $C_{75}H_{110}N_{23}O_{23}Lu$) which confirmed identity.

Example 54

Synthesis of a $^{111}$In DOTA-Containing Vitronectin Antagonist Complex

To a lead shielded 300 µL autosampler vial was added 50 µL of gentisic acid (10 mg/mL in 0.1 M ammonium acetate buffer, pH 6.75) solution, followed by 100 µL of the reagent of Example 18 (200 µg/mL in 0.2 M ammonium acetate buffer, pH 5.0), and 50 µL of $^{111}$InCl$_3$ solution (10 mCi/mL) in 0.04 N HCl. The pH of the reaction mixture was about 4.0. The solution was heated at 100° C. for 25 min. A sample of the resulting solution was analyzed by radio-HPLC and ITLC.

Table 1A: Analytical and Yield Data for Y-90, In-111, and Lu-177 Complexes of DOTA-Conjugated Vitronectin Receptor Antagonists.

TABLE 1A

Analytical and Yield Data for
Y-90, In-111, and Lu-177 Complexes of
DOTA-Conjugated Vitronectin Receptor Antagonists.

| Complex Ex. No. | Reagent Ex. No. | Isotope | % Yield | HPLC Ret. Time (min) |
|---|---|---|---|---|
| 52 | 18 | Y-90 | 96 | 16.5 |
| 53 | 18 | Lu-177 | 96 | 16.5 |
| 54 | 18 | In-111 | 95 | 16.5 |

Examples 55 and 56

Synthesis of In-111 DTPA-monoamide or DTPA-bisamide Containing Vitronectin Antagonist Complexes 0.2 mL of $^{111}$InCl$_3$ (1.7 mCi) in 0.1 N HCl, 0.2 mL of 1.0 M ammonium acetate buffer (pH 6.9) and 0.1 ml of the reagent of the present invention dissolved in water were combined in a 10 cc glass vial and allowed to react at room temperature for 30 min. The reaction mixture was analyzed by HPLC Method 3.

Table 2. Analytical and Yield Data for $^{111}$In Complexes

TABLE 2

Analytical and Yield Data for $^{111}$In Complexes

| Complex Ex. No. | Reagent Ex. No. | % Yield | HPLC Ret. Time (min) |
|---|---|---|---|
| 55 | 19 | 86 | 11.1 |
| 56 | 20 | 96 | 18.8 |

Examples 57–59

Synthesis of Sm-153 Vitronectin Antagonist Complexes 0.25 mL of a $^{153}$SmCl$_3$ stock solution (54 mCi/µmol Sm, 40 mCi/mL) in 0.1 N HCl was combined with the reagent of the present invention (50-fold molar excess) dissolved in 1 N ammonium acetate buffer in a 10 cc glass vial. The reaction was allowed to proceed at room temperature for ~30 min and was then analyzed by ITLC and HPLC (Method 3). If necessary, the complex was purified by performing a 300–400 µL injection on the HPLC and collecting the fraction into a shielded flask. The collected fraction was evaporated to dryness, redissolved in saline, and then re-analyzed using HPLC Method 3.

Table 3. Analytical and Yield Data for $^{153}$Sm Complexes

TABLE 3

Analytical and Yield Data for $^{153}$Sm Complexes

| Complex Ex. No. | Reagent Ex. No. | % Yield | HPLC Ret. Time (min) |
|---|---|---|---|
| 57 | 19 | 91 | 11.7 |
| 58 | 20 | 84 | 13.1 |
| 59 | 21 | 96 | 16.9 |

The non-radioactive (naturally occurring) samarium analog of the Radiopharmaceutical of Example 59 was prepared by combining 3.3. mg (2.9 µmol) of the Reagent of Example 21 dissolved in 2 mL of 1 M ammonium acetate buffer, pH 7, and 0.29 mL of 0.01 M solution of SmCl$_3$ in 0.1 N HCl. The reaction was allowed to proceed for ~5 h at room temperature and then the product was isolated by HPLC Method 3. The volatiles were removed by lyophilization. The identity of the complex was confirmed by mass spectroscopy. (API-ESMS:Found [M+2H$^+$=1172.4, Calcd. 1172.9 for $C_{43}H_{64}N_{12}O_{17}Sm$] A stock solution of the complex was made in water and its concentration determined by ICP analysis for use in determining the binding affinity of the complex for the vitronectin receptor $\alpha_v\beta_3$.

The structures of representative In-111 (Example 56), Y-90 (Example 52) and Sm-153 (Example 59) radiopharmaceuticals of the present invention are shown below.

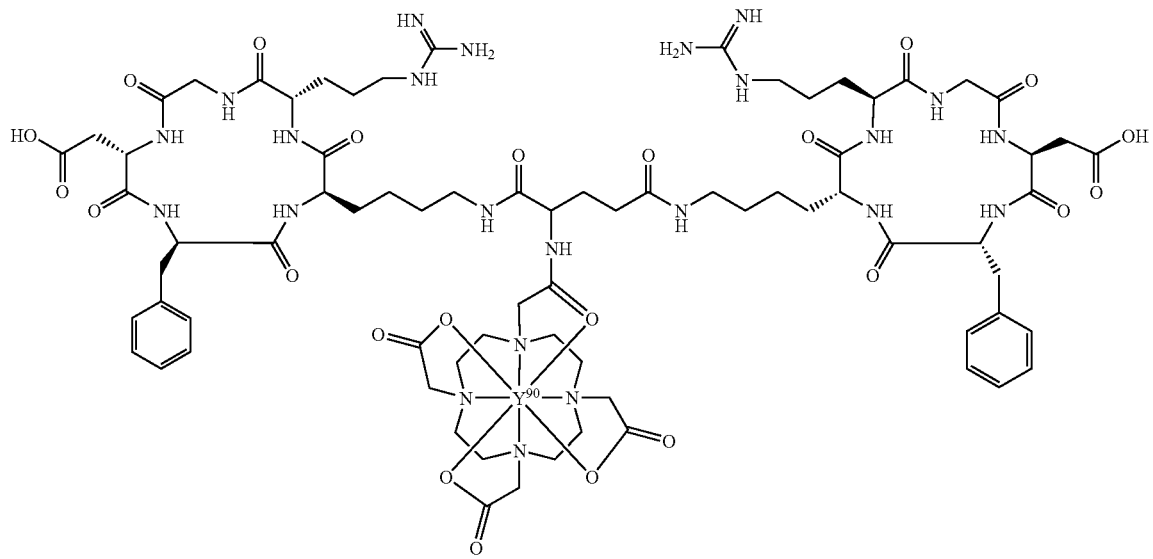

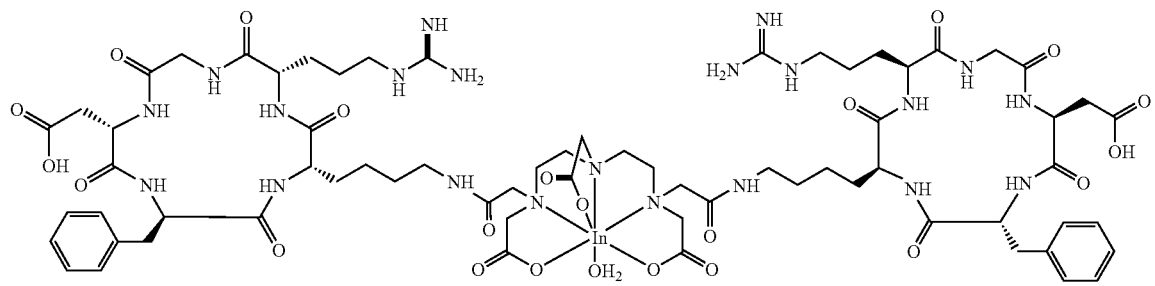

Examples 60–62

Example 63

Synthesis of Lu-177 Vitronectin Antagonist Complexes $5 \times 10^{-9}$ mol of a reagent of the present invention was dissolved in 1.0 mL of 0.1 N acetate buffer, pH 6.8. $1 \times 10^{-9}$ mol of Lu-177 (40 µl, 3 mCi) dissolved in 0.1 N HCl was added and the reaction allowed to proceed at room temperature for 30–45 min. The reaction mixtures were analyzed by HPLC Method 3.

Table 4. Analytical and Yield Data for $^{177}$Lu Complexes

TABLE 4

Analytical and Yield Data for $^{177}$Lu Complexes

| Complex Ex. No. | Reagent Ex. No. | % Yield | HPLC Ret. Time (min) |
|---|---|---|---|
| 60 | 19 | 98 | 11.0 |
| 61 | 20 | 98 | 15.6 |
| 62 | 21 | 98 | 11.7 |

The gadolinium complex of the reagent of Example 21 was prepared according to the following procedure. 3–3.5 mg of the reagent was dissolved in 2 mL 1 M ammonium acetate buffer at pH 7.0, and one equivalent Gd(NO$_3$)$_3$ solution (0.02 M in water) was added to it. The reaction mixture was allowed to stay at room temperature for 3–5 hours and the product was isolated by HPLC Method 4. The fraction containing the complex was lyophilized and dissolved in 1 mL H$_2$O resulting in a solution approximately 2 mM in Gd as determined by ICP analysis. The identity of the complex was confirmed by mass spectroscopy. (API-ESMS: Found [M+2H$^+$]=1176.9, Calcd. 1176.2 for C$_{43}$H$_{64}$N$_{12}$O$_{17}$Gd].

The following examples describe the synthesis of ultrasound contrast agents of the present invention comprised of targeting moieties for tumor neovasculature that are $\alpha_v\beta_3$ receptor antagonists.

Example 64

Part A. Synthesis of 1(1,2Dipalmitoyl-sn-glycero-3-phosphoethanolamino)-12-(cyclo(Arg-Gly-Asp-D-Phe-Lys)-dodecane-1,12-dione [SEQ. ID NO.: 64]

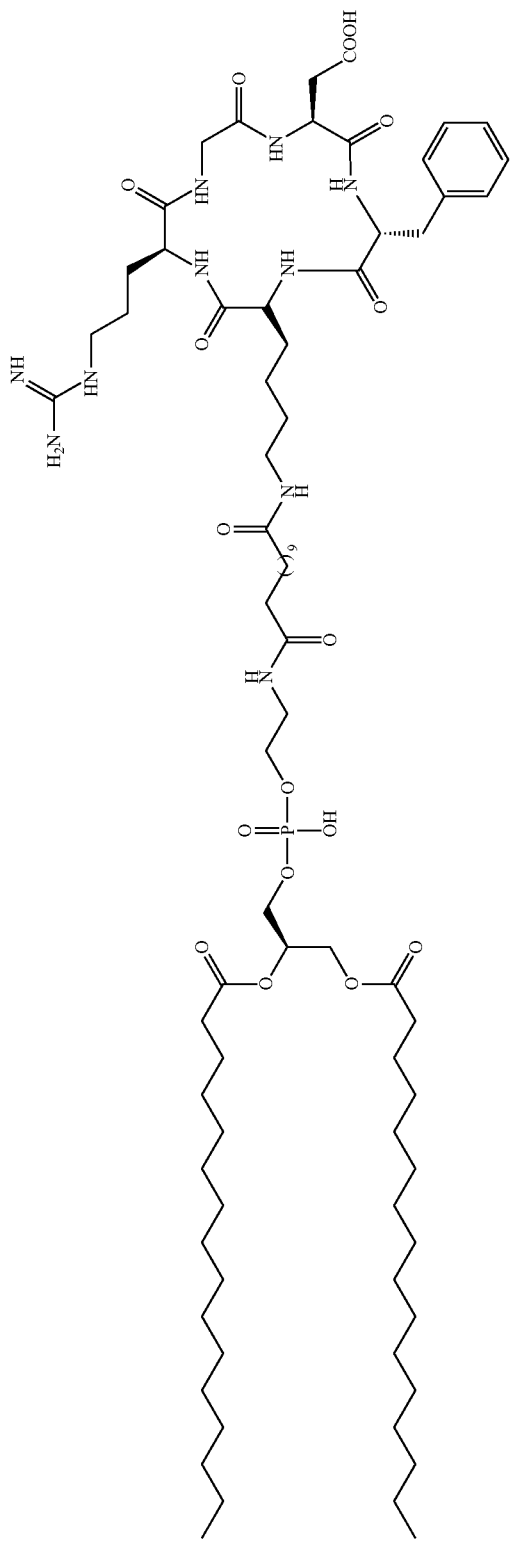

A solution of disuccinimidyl dodecane-1,12-dioate (0.424 g, 1 mmol), 1,2-dipalmitoyl-sn-glycero-3-phosphoethanolamine (1.489 g, 1 mmol) and cyclo(Arg-Gly-Asp-D-Phe-Lys) TFA salt (0.831 g, 1 mmol) in 25 ml chloroform is stirred for 5 min. Sodium carbonate (1 mmol) and sodium sulfate (1 mmol) are added and the solution is stirred at room temperature under nitrogen for 18 h. DMF is removed in vacuo and the crude product is purified to obtain the title compound.

Part B. Preparation of Contrast Agent Composition

The Synthesis of 1-(1,2-Dipalmitoyl-sn-glycero-3-phosphoethanolamino)-12-(cyclo(Arg-Gly-Asp-D-Phe-Lys)-dodecane-1,12-dione [SEQ. ID NO.: 64] is admixed with three other lipids, 1,2-dipalmitoyl-sn-glycero-3-phosphotidic acid, 1,2-dipalmitoyl-sn-glycero-3-phosphatidylcholine, and N-(methoxypolyethylene glycol 5000 carbamoyl)-1,2-dipalmitoyl-sn-glycero-3-phosphatidylethanolamine in relative amounts of 1 wt. %:6 wt. %:54 wt. %:41 wt. %. An aqueous solution of this lipid admixture (1 mg/mL), sodium chloride (7 mg/mL), glycerin (0.1 mL/mL), propylene glycol (0.1 mL/mL), at pH 6–7 is then prepared in a 2 cc glass vial. The air in the vial is evacuated and replaced with perfluoropropane and the vial is sealed. The ultrasound contrast agent composition is completed by agitating the sealed vial in a dental amalgamator for 30–45 sec. to form a milky white solution.

Example 65

Part A. Preparation of (ω-amino-PEG$_{3400}$-α-carbonyl)-cyclo(Arg-Gly-D-Phe-Lys) [SEQ. ID NO.: 65]

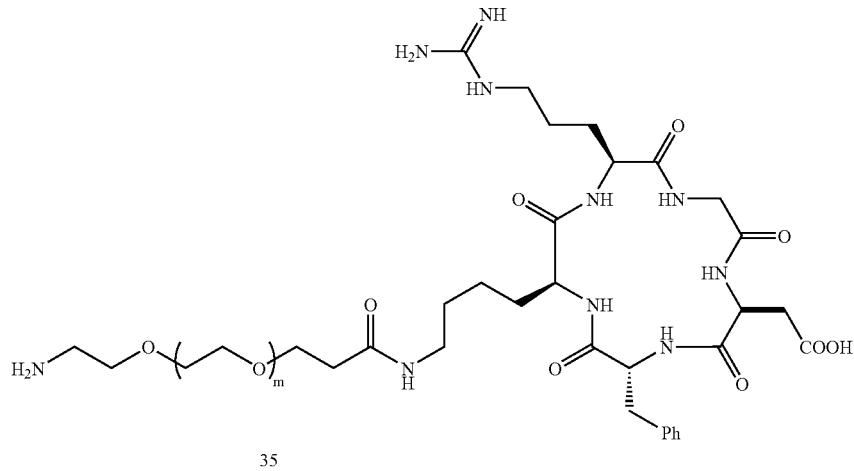

To a solution of N-Boc-ω-amino-PEG$_{3400}$-α-carboxylate sucinimidyl ester (1 mmol) and cyclo(Arg-Gly-Asp-D-Phe-Lys) [SEQ. ID NO.: 97] (1 mmol) in DMF (25 mL) is added triethylamine (3 mmol). The reaction mixture is stirred under nitrogen at room temperature overnight and the solvent is removed in vacuo. The crude product is dissolved in 50% trifluoroacetic acid/dichloromethane and is stirred for 4 h. The volatiles are removed and the title compound is isolated as the TFA salt via trituration in diethyl ether.

Part B. Preparation of 1-(1,2-Dipalmitoyl-sn-glycero-3-phosphoethanolamino)-12-((ω-amino-PEG$_{3400}$-α-carbonyl)-cyclo(Arg-Gly-Asp-D-Phe-Lys))-Dodecane-1,12-Dione [SEQ. ID NO.: 65]

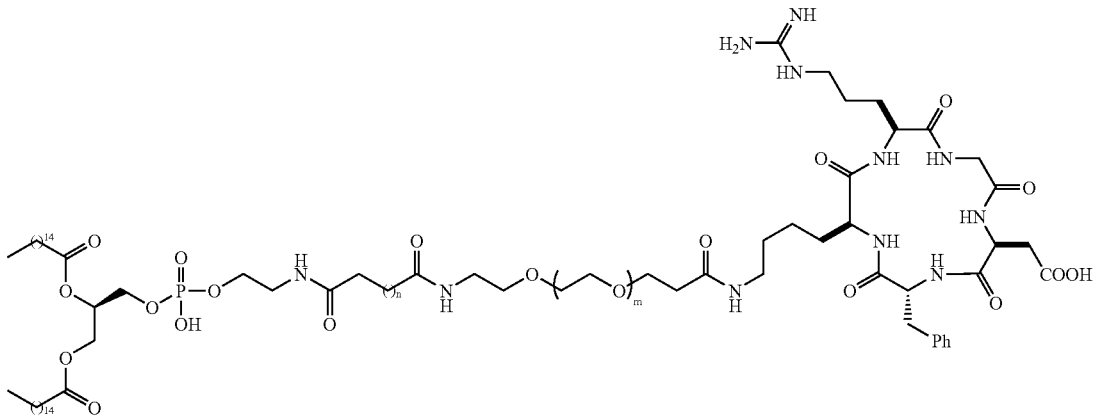

A solution of disuccinimidyl dodecanoate (1 mmol), 1,2-dipalmitoyl-sn-glycero-3-phosphoethanolamine-(1 mmol) and (ω-amino-PEG$_{3400}$-α-carbonyl)-cyclo(Arg-Gly-Asp-D-Phe-Lys) [SEQ. ID NO.: 167] TFA salt (1 mmol) in 25 ml chloroform is stirred for 5 min. Sodium carbonate (1 mmol) and sodium sulfate (1 mmol) are added and the solution is stirred at room temperature under nitrogen for 18 h. DMF is removed in vacuo and the crude product is purified to obtain the title compound.

Part C. Preparation of Contrast Agent Composition

The 1-(1,2-Dipalmitoyl-sn-glycero-3-phosphoethanolamino)-12-((ω-amino-PEG$_{3400}$-α-carbonyl)-cyclo(Arg-Gly-Asp-D-Phe-Lys))-Dodecane-1,12-Dione [SEQ. ID NO.: 65] is admixed with three other lipids, 1,2-dipalmitoyl-sn-glycero-3-phosphotidic acid, 1,2-dipalmitoyl-sn-glycero-3-phosphatidylcholine, and N-(methoxypolyethylene glycol 5000 carbamoyl)-1,2-dipalmitoyl-sn-glycero-3-phosphatidylethanolamine in relative amounts of 1 wt. %:6 wt. %:54 wt. %:41 wt. %. An aqueous solution of this lipid admixture (1 mg/mL), sodium chloride (7 mg/mL), glycerin (0.1 mL/mL), propylene glycol (0.1 mL), at pH 6–7 is then prepared in a 2 cc glass vial. The air in the vial is evacuated and replaced with perfluoropropane and the vial is sealed. The ultrasound contrast agent composition is completed by agitating the sealed vial in a dental amalgamator for 30–45 sec. to form a milky white solution.

Example 66

Part A. Preparation of Synthesis of (ω-amino-PEG$_{3400}$-α-carbonyl)-Glu-(cyclo(Arg-Gly-Asp-D-Phe-Lys))$_2$ [SEQ. ID NO.: 168]

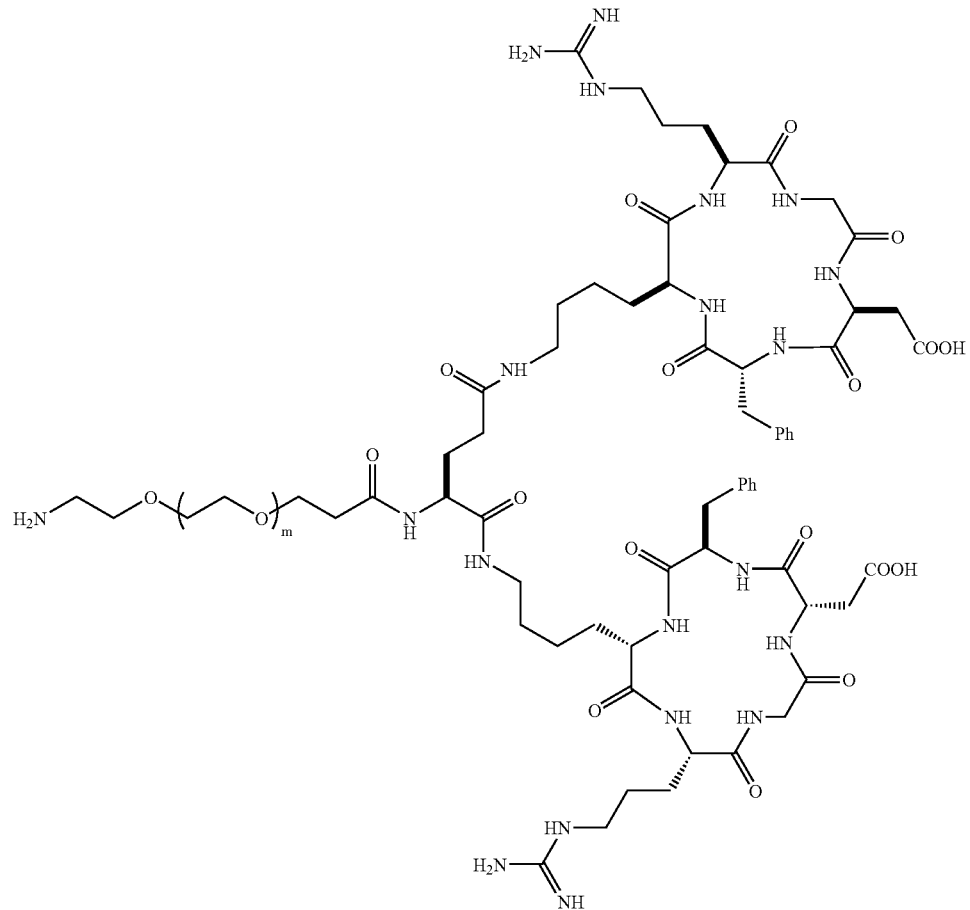

To a solution of N-Boc-ω-amino-PEG$_{3400}$-α-carboxylate sucinimidyl ester (1 mmol) and Glu-(cyclo(Arg-Gly-Asp-D-Phe-Lys))$_2$ [SEQ. ID NO.: 169] (1 mmol) in DMF (25 mL) is added triethylamine (3 mmol). The reaction mixture is stirred under nitrogen at room temperature overnight and the solvent is removed in vacuo. The crude product is dissolved in 50% trifluoroacetic acid/dichloromethane and is stirred for 4 h. The volatiles are removed and the title compound is isolated as the TFA salt via trituration in diethyl ether.

Part B. Preparation of 1-(1,2-Dipalmitoyl-sn-glycero-3-phosphoethanolamino)-12-((ω-amino-PEG$_{3400}$-α-carbonyl)-Glu-(cyclo(Arg-Gly-Asp-D-Phe-Lys))$_2$)-Dodecane-1,12-Dione [SEQ. ID NO.: 66]

Column Temperature: ambient
Flow: 1.0 mL/min
Solvent A: 10 mM sodium phosphate buffer pH 6
Solvent B: 100% Acetonitrile

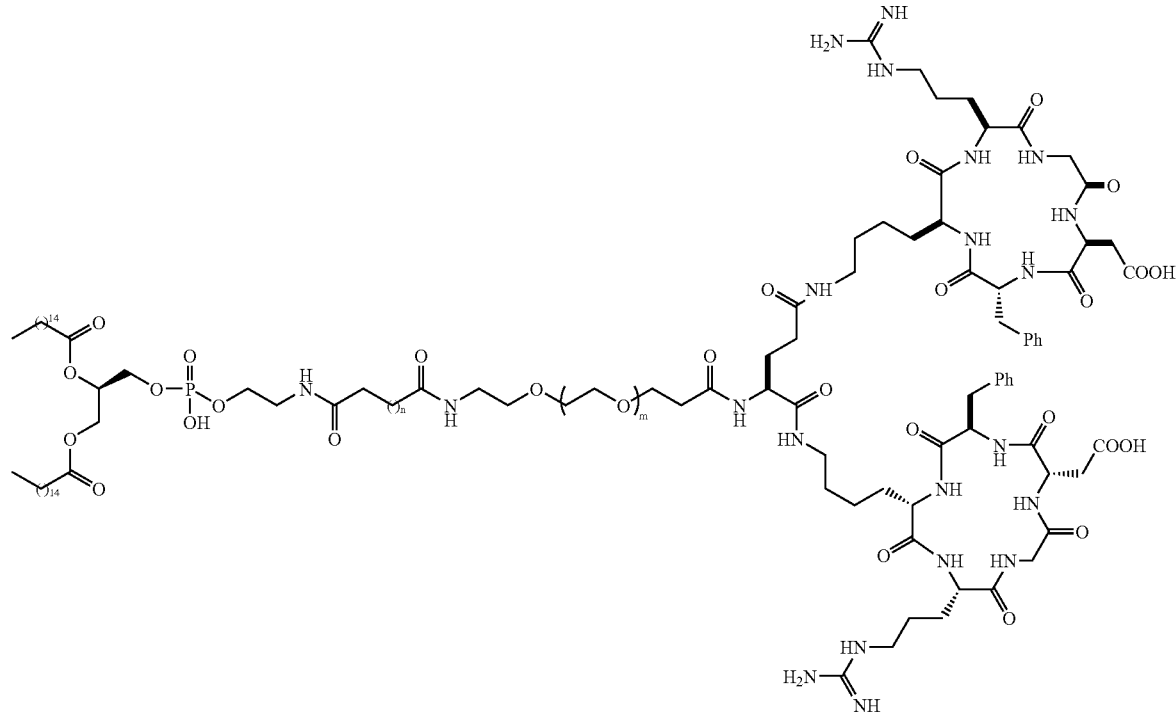

A solution of disuccinimidyl dodecanoate (1 mmol), 1,2-dipalmitoyl-sn-glycero-3-phosphoethanolamine (1 mmol) and (ω-amino-PEG$_{3400}$-α-carbonyl)-Glu-(cyclo(Arg-Gly-Asp-D-Phe-Lys))$_2$ [SEQ. ID NO.: 168] TFA salt (1 mmol) in 25 ml chloroform is stirred for 5 min. Sodium carbonate (1 mmol) and sodium sulfate (1 mmol) are added and the solution is stirred at room temperature under nitrogen for 18 h. DMF is removed in vacuo and the crude product is purified to obtain the title compound.

Part C. Preparation of Contrast Agent Composition

The 1-(1,2-Dipalmitoyl-sn-glycero-3-phosphoethanolamino)-12-((ω-amino-PEG$_{3400}$-α-carbonyl)-Glu-(cyclo(Arg-Gly-Asp-D-Phe-Lys))$_2$)-Dodecane-1,12-Dione [SEQ. ID NO.: 66] is admixed with three other lipids, 1,2-dipalmitoyl-sn-glycero-3-phosphotidic acid, 1,2-dipalmitoyl-sn-glycero-3-phosphatidylcholine, and N(methoxypolyethylene glycol 5000 carbamoyl)-1,2-dipalmitoyl-sn-glycero-3-phosphatidylethanolamine in relative amounts of 1 wt. %:6 wt. %:54 wt. %:41 wt. %. An aqueous solution of this lipid admixture (1 mg/mL), sodium chloride (7 mg/mL), glycerin (0.1 mL/mL), propylene glycol (0.1 mL), at pH 6–7 is then prepared in a 2 cc glass vial. The air in the vial is evacuated and replaced with perfluoropropane and the vial is sealed. The ultrasound contrast agent composition is completed by agitating the sealed vial in a dental amalgamator for 30–45 sec. to form a milky white solution.

Analytical Methods

HPLC Method 3

Column: Zorbax C18, 25 cm×4.6 mm or Vydac C18, 25 cm×4.6 mm

Detector: sodium iodide (NaI) radiometric probe or beta detector

| Gradient A (Exs. 33, 51) | | | | | | |
|---|---|---|---|---|---|---|
| t (min) | 0 | 20 | 30 | 31 | 40 | |
| % B | 0 | 75 | 75 | 0 | 0 | |
| Gradient B (Exs. 39, 40, 43, 44, 45, 46, 48, 50) | | | | | | |
| t (min) | 0 | 20 | 30 | 31 | 35 | 36 | 40 |
| % B | 0 | 25 | 25 | 75 | 75 | 0 | 0 |
| Gradient C (Examples 34, 35, 36, 37, 38, 42): | | | | | | |
| t (min) | 0 | 40 | 41 | 46 | 47 | 55 | |
| % B | 0 | 35 | 75 | 75 | 0 | 0 | |
| Gradient D (Ex. 49) | | | | | | |
| t (min) | 0 | 20 | 30 | 31 | 40 | |
| % B | 0 | 25 | 25 | 0 | 0 | |
| Gradient E (Exs. 55, 56): | | | | | | |
| t (min) | 0 | 20 | 21 | 30 | 31 | 40 |
| % B | 0 | 20 | 50 | 50 | 0 | 0 |
| Gradient F (Exs. 57, 58): | | | | | | |
| t (min) | 0 | 15 | 16 | 25 | 26 | 35 |
| % B | 0 | 20 | 75 | 75 | 0 | 0 |
| Gradient G (Ex. 59): | | | | | | |
| t (min) | 0 | 20 | 21 | 30 | 31 | 40 |
| % B | 0 | 20 | 75 | 75 | 0 | 0 |
| Gradient H (Exs. 60, 61, 62): | | | | | | |
| t (min) | 0 | 15 | 16 | 21 | 22 | 40 |
| % B | 0 | 20 | 50 | 50 | 0 | 0 |

-continued

| Gradient I (Exs. 52, 53, 54) | | | | | | |
|---|---|---|---|---|---|---|
| t (min) | 0 | 20 | 21 | 30 | 31 | 40 |
| % Solvent B | 5 | 20 | 60 | 60 | 5 | 5 |
| Gradient J (Ex. 41) | | | | | | |
| t (min) | 0 | 20 | 30 | 31 | 40 | |
| % Solvent B | 0 | 50 | 50 | 0 | 0 | |
| Gradient K (Ex. 47) | | | | | | |
| t (min) | 0 | 20 | 21 | 30 | 31 | 40 |
| % Solvent B | 10 | 20 | 60 | 60 | 10 | 10 |

HPLC Method 4
Column: Zorbax C18, 25 cm × 4.6 mm
Flow: 1.0 mL/min
Solvent A: 10 mM ammonium acetate
Solvent B: 100% methanol
Gradient:

| t (mm) | 0 | 23 | 26 | 27 |
|---|---|---|---|---|
| % B | 8 | 100 | 100 | 8 |

UV Detection

ITLC Method
  Gelman ITLC-SG strips (2 cm×7.5 cm)
  Solvent System: 1:1 acetone:saline
  Detection using a Bioscan System 200.

UTILITY

The pharmaceuticals of the present invention are useful for imaging angiogenic tumor vasculature in a patient or for treating cancer in a patient. The radiopharmaceuticals of the present invention comprised of a gamma emitting isotope are useful for imaging of pathological processes involving angiogenic neovasculature, including cancer, diabetic retinopathy, macular degeneration, restenosis of blood vessels after angioplasty, and wound healing. Diagnostic utilities also include imaging of unstable coronary syndromes (e.g., unstable coronary plaque). The radiopharmaceuticals of the present invention comprised of a beta, alpha or Auger electron emitting isotope are useful for treatment of pathological processes involving angiogenic neovasculature, by delivering a cytotoxic dose of radiation to the locus of the angiogenic neovasculature. The treatment of cancer is affected by the systemic administration of the radiopharmaceuticals resulting in a cytotoxic radiation dose to tumors.

The compounds of the present invention comprised of one or more paramagnetic metal ions selected from gadolinium, dysprosium, iron, and manganese, are useful as contrast agents for magnetic resonance imaging (MRI) of pathological processes involving angiogenic neovasculature.

The compounds of the present invention comprised of one or more heavy atoms with atmic number of 20 or greater are useful as X-ray contrast agents for X-ray imaging of pathological processes involving angiogenic neovasculature.

The compounds of the present invention comprised of an echogenic gas containing surfactant microsphere are useful as ultrasound contrast agents for sonography of pathological processes involving angiogenic neovasculature.

Representative compounds of the present invention were tested in the following in vitro and in vivo assays and models and were found to be active.

Immobilized Human Placental $\alpha_v\beta_3$ Receptor Assay

The assay conditions were developed and validated using [I-125]vitronectin. Assay validation included Scatchard format analysis (n=3) where receptor number (Bmax) and Kd (affinity) were determined. Assay format is such that compounds are preliminarily screened at 10 and 100 nM final concentrations prior to IC50 determination. Three standards (vitronectin, anti-$\alpha_v\beta_3$ antibody, LM609, and anti-$\alpha_v\beta_5$, P1F6) and five reference peptides have been evaluated for IC50 determination. Briefly, the method involves immobilizing previously isolated receptors in 96 well plates and incubating overnight. The receptors were isolated from normal, fresh, non-infectious (HIV, hepatitis B and C, syphilis, and HTLV free) human placenta. The tissue was lysed and tissue debris removed via centrifugation. The lysate was filtered. The receptors were isolated by affinity chromatography using the immobilized anti-$\alpha_v\beta_3$ antibody. The plates are then washed 3× with wash buffer. Blocking buffer is added and plates incubated for 120 minutes at room temperature. During this time, compounds to be tested and [I-125]vitronectin are premixed in a reservoir plate. Blocking buffer is removed and compound mixture pipetted. Competition is carried out for 60 minutes at room temperature. Unbound material is then removed and wells are separated and counted via gamma scintillation.

Other Receptor Binding Assays

Whole cell assays for the determination of the binding affinity of pharmaceuticals of the present invention for the VEGF receptors, Flk-1/KDR and Flt-1, are described in Ortega, et. al., Amer. J. Pathol., 1997, 151, 1215–1224, and Dougher, et. al., Growth Factors, 1997, 14, 257–268. An in vitro assay for determining the affinity of pharmaceuticals of the present invention for the bFGF receptor is described in Yayon, et. al., Proc. Natl. Acad. Sci USA, 1993, 90, 10643–10647. Gho et. al., Cancer Research, 1997, 57, 3733–40, describe assays for angiogenin receptor binding peptides. Senger, et. al., Proc. Natl. Acad. Sci USA, 1997, 94, 13612–13617 describe assays for antagonists of the integrins a1B1 and a2B1. U.S. Pat. No. 5,536,814 describes assays for compounds that bind to the integrin a5B1.

Oncomouse® Imaging

The study involves the use of the c-Neu Oncomouse® and FVB mice simultaneously as controls. The mice are anesthetized with sodium pentobarbital and injected with approximately 0.5 mCi of radiopharmaceutical. Prior to injection, the tumor locations on each Oncomouse® are recorded and tumor size measured using calipers. The animals are positioned on the camera head so as to image the anterior or posterior of the animals. 5 Minute dynamic images are acquired serially over 2 hours using a 256×256 matrix and a zoom of 2×. Upon completion of the study, the images are evaluated by circumscribing the tumor as the target region of interest (ROI) and a background site in the neck area below the carotid salivary glands.

This model can also be used to assess the effectiveness of the radiopharmaceuticals of the present invention comprised of a beta, alpha or Auger electron emitting isotope. The radiopharmaceuticals are administered in appropriate amounts and the uptake in the tumors can be quantified either non-invasively by imaging for those isotopes with a coincident imageable gamma emission, or by excision of the tumors and counting the amount of radioactivity present by standard techniques. The therapeutic effect of the radiopharmaceuticals can be assessed by monitoring the rate of growth of the tumors in control mice versus those in the mice administered the radiopharmaceuticals of the present invention.

This model can also be used to assess the compounds of the present invention comprised of paramagnetic metals as MRI contrast agents. After administration of the appropriate amount of the paramagnetic compounds, the whole animal can be placed in a commercially available magnetic resonance imager to image the tumors. The effectiveness of the contrast agents can be readily seen by comparison to the images obtain from animals that are not administered a contrast agent.

This model can also be used to assess the compounds of the present invention comprised of heavy atoms as X-ray contrast agents. After administration of the appropriate amount of the X-ray absorbing compounds, the whole animal can be placed in a commercially available X-ray imager to image the tumors. The effectiveness of the contrast agents can be readily seen by comparison to the images obtain from animals that are not administered a contrast agent.

This model can also be used to assess the compounds of the present invention comprised of an echogenic gas containing surfactant microsphere as ultrasound contrast agents. After administration of the appropriate amount of the echogenic compounds, the tumors in the animal can be imaging using an ultrasound probe held proximate to the tumors. The effectiveness of the contrast agents can be readily seen by comparison to the images obtain from animals that are not administered a contrast agent.

Rabbit Matrigel Model

This model was adapted from a matrigel model intended for the study of angiogenesis in mice. Matrigel (Becton & Dickinson, USA) is a basement membrane rich in laminin, collagen IV, entactin, HSPG and other growth factors. When combined with growth factors such as bFGF [500 ng/ml] or VEGF [2 μg/ml] and injected subcutaneously into the mid-abdominal region of the mice, it solidifies into a gel and stimulates angiogenesis at the site of injection within 4–8 days. In the rabbit model, New Zealand White rabbits (2.5–3.0 kg) are injected with 2.0 ml of matrigel, plus 1 μg bFGF and 4 μg VEGF. The radiopharmaceutical is then injected 7 days later and the images obtained.

This model can also be used to assess the effectiveness of the radiopharmaceuticals of the present invention comprised of a beta, alpha or Auger electron emitting isotope. The radiopharmaceuticals are administered in appropriate amounts and the uptake at the angiogenic sites can be quantified either non-invasively by imaging for those isotopes with a coincident imageable gamma emission, or by excision of the angiogenic sites and counting the amount of radioactivity present by standard techniques. The therapeutic effect of the radiopharmaceuticals can be assessed by monitoring the rate of growth of the angiogenic sites in control rabbits versus those in the rabbits administered the radiopharmaceuticals of the present invention.

This model can also be used to assess the compounds of the present invention comprised of paramagnetic metals as MRI contrast agents. After administration of the appropriate amount of the paramagnetic compounds, the whole animal can be placed in a commercially available magnetic resonance imager to image the angiogenic sites. The effectiveness of the contrast agents can be readily seen by comparison to the images obtain from animals that are not administered a contrast agent.

This model can also be used to assess the compounds of the present invention comprised of heavy atoms as X-ray contrast agents. After administration of the appropriate amount of the X-ray absorbing compounds, the whole animal can be placed in a commercially available X-ray imager to image the angiogenic sites. The effectiveness of the contrast agents can be readily seen by comparison to the images obtain from animals that are not administered a contrast agent.

This model can also be used to assess the compounds of the present invention comprised of an echogenic gas containing surfactant microsphere as ultrasound contrast agents. After administration of the appropriate amount of the echogenic compounds, the angiogenic sites in the animal can be imaging using an ultrasound probe held proximate to the tumors. The effectiveness of the contrast agents can be readily seen by comparison to the images obtain from animals that are not administered a contrast agent.

Canine Spontaneous Tumor Model

Adult dogs with spontaneous mammary tumors were sedated with xylazine (20 mg/kg)/atropine (1 ml/kg). Upon sedation the animals were intubated using ketamine (5 mg/kg)/diazepam (0.25 mg/kg) for full anethesia. Chemical restraint was continued with ketamine (3 mg/kg)/xylazine (6 mg/kg) titrating as necessary. If required the animals were ventilated with room air via an endotrachael tube (12 strokes/min, 25 ml/kg) during the study. Peripheral veins were catheterized using 20 G I.V. catheters, one to serve as an infusion port for compound while the other for exfusion of blood samples. Heart rate and EKG were monitored using a cardiotachometer (Biotech, Grass Quincy, Mass.) triggered from a lead II electrocardiogram generated by limb leads. Blood samples are generally taken at ~10 minutes (control), end of infusion, (1 minute), 15 min, 30 min, 60 min, 90 min, and 120 min for whole blood cell number and counting. Radiopharmaceutical dose was 300 μCi/kg administered as an i.v. bolus with saline flush. Parameters were monitored continuously on a polygraph recorder (Model 7E Grass) at a paper speed of 10 mm/min or 10 mm/sec.

Imaging of the laterals were for 2 hours with a 256×256 matrix, no zoom, 5 minute dynamic images. A known source is placed in the image field (20–90 μCi) to evaluate region of interest (ROI) uptake. Images were also acquired 24 hours post injection to determine retention of the compound in the tumor. The uptake is determined by taking the fraction of the total counts in an inscribed area for ROI/source and multiplying the known μCi. The result is μCi for the ROI.

This model can also be used to assess the effectiveness of the radiopharmaceuticals of the present invention comprised of a beta, alpha or Auger electron emitting isotope. The radiopharmaceuticals are administered in appropriate amounts and the uptake in the tumors can be quantified either non-invasively by imaging for those isotopes with a coincident imageable gamma emission, or by excision of the tumors and counting the amount of radioactivity present by standard techniques. The therapeutic effect of the radiopharmaceuticals can be assessed by monitoring the size of the tumors over time.

This model can also be used to assess the compounds of the present invention comprised of paramagnetic metals as MRI contrast agents. After administration of the appropriate amount of the paramagnetic compounds, the whole animal can be placed in a commercially available magnetic resonance imager to image the tumors. The effectiveness of the contrast agents can be readily seen by comparison to the images obtain from animals that are not administered a contrast agent.

This model can also be used to assess the compounds of the present invention comprised of heavy atoms as X-ray contrast agents. After administration of the appropriate amount of the X-ray absorbing compounds, the whole animal can be placed in a commercially available X-ray imager to image the tumors. The effectiveness of the contrast agents can be readily seen by comparison to the images obtain from animals that are not administered a contrast agent.

This model can also be used to assess the compounds of the present invention comprised of an echogenic gas containing surfactant microsphere as ultrasound contrast agents. After administration of the appropriate amount of the echogenic compounds, the tumors in the animal can be imaging using an ultrasound probe held proximate to the tumors. The effectiveness of the contrast agents can be readily seen by comparison to the images obtain from animals that are not administered a contrast agent.

Obviously, numerous modifications and variations of the present invention are possible in light of the above teachings. It is therefore to be understood that within the scope of the appended claims, the invention may be practiced otherwise that as specifically described herein.

What is claimed is:

1. A kit for treating cancer, comprising a peptide or peptidomimetic targeting moiety that binds to $\alpha_5\beta_1$ receptor, and a chelator, wherein the targeting moiety is bound to the chelator and the compound has 0–1 linking groups between the targeting moiety and chelator, or a pharmaceutically acceptable salt thereof, and a chemotherapeutic agent or a pharmaceutically acceptable salt thereof, and a pharmaceutically acceptable carrier.

2. A kit according to claim 1 wherein said kit comprises a plurality of separate containers, at least one of said containers containing a chemotherapeutic agent or a pharmaceutically acceptable salt thereof.

3. A kit according to claim 1, wherein the chemotherapeutic agent is selected from the group consisting of mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, and leutinizing hormone releasing factor.

4. A kit according to claim 1, wherein the chemotherapeutic agent is selected from the group consisting of mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, and lisuride.

5. A kit according to claim 1 wherein the chemotherapeutic agent is selected from the group consisting of oxymetholone, tamoxifen, progesterone, mepitiostane, epitiostanol, and formestane.

6. A kit according to claim 1 wherein the chemotherapeutic agent is selected from the group consisting of interferon-alpha, interferon-2 alpha, interferon-beta, interferon-gamma, colony stimulating factor-1, colony stimulating factor-2, denileukin diftitox, interleukin-2, and leutinizing hormone releasing factor.

7. A method of treating cancer in a patient, comprising:
   administering a radiopharmaceutical comprising:
   (i) a metal;
   (ii) a chemotherapeutic agent or a pharmaceutically acceptable salt thereof;
   (iii) a peptide or peptidomimetic targeting moiety that binds to $\alpha_5\beta_1$ receptor, and a chelator, wherein the targeting moiety is bound to the chelator and the compound has 0–1 linking groups between the targeting moiety and chelator, or a pharmaceutically acceptable salt thereof; and
   (iv) a pharmaceutically acceptable carrier, to a patient.

8. A method according to claim 7 wherein the cancer is selected from the group consisting of carcinomas of the lung, breast, ovary, stomach, pancreas, larynx, esophagus, testes, liver, parotid, biliary tract, colon, rectum, cervix, uterus, endometrium, kidney, bladder, prostate, and thyroid, squamous cell carcinomas, adenocarcinomas, small cell carcinomas, melanomas, gliomas, and neuroblastomas.

9. A method according to claim 7 wherein the chemotherapeutic agent is selected from the group consisting of mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, and leutinizing hormone releasing factor.

10. A composition comprising:
(i) a metal;
(ii) a chemotherapeutic agent or a pharmaceutically acceptable salt thereof;
(iii) a peptide or peptidomimetic targeting moiety that binds to $\alpha_5\beta_1$ receptor, and a chelator, wherein the targeting moiety is bound to the chelator and the compound has 0–1 linking groups between the targeting moiety and chelator, or a pharmaceutically acceptable salt thereof; and
(iv) a pharmaceutically acceptable carrier.

11. A composition according to claim 10, wherein the targeting moiety, linking group, and chelator are of the formula:

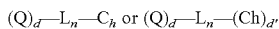

wherein, Q is a peptide independently selected from the group:

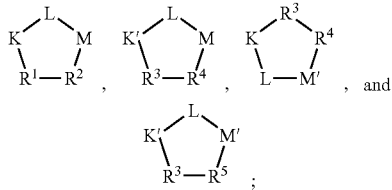

K is an L-amino acid independently selected at each occurrence from the group: arginine, citrulline, N-methylarginine, lysine, homolysine, 2-aminoethylcysteine, δ-N-2-imidazolinylornithine, δ-N-benzylcarbamoylornithine, and β-2-benzimidazolylacetyl-1,2-diaminopropionic acid;

K' is a D-amino acid independently selected at each occurrence from the group: arginine, citrulline, N-methylarginine, lysine, homolysine, 2-aminoethylcysteine, δ-N-2-imidazolinylornithine, δ-N-benzylcarbamoylornithine, and β-2-benzimidazolylacetyl-1,2-diaminopropionic acid;

L is independently selected at each occurrence from the group: glycine, L-alanine, and D-alanine;

M is L-aspartic acid;

M' is D-aspartic acid;

$R^1$ is an amino acid substituted with 0–1 bonds to $L_n$, independently selected at each occurrence from the group: glycine, L-valine, D-valine, alanine, leucine, isoleucine, norleucine, 2-aminobutyric acid, 2-aminohexanoic acid, tyrosine, phenylalanine, thienylalanine, phenylglycine, cyclohexylalanine, homophenylalanine, 1-naphthylalanine, lysine, serine, ornithine, 1,2-diaminobutyric acid, 1,2-diaminopropionic acid, cysteine, penicillamine, and methionine;

$R^2$ is an amino acid, substituted with 0–1 bonds to $L_n$, independently selected at each occurrence from the group: glycine, valine, alanine, leucine, isoleucine, norleucine, 2-aminobutyric acid, 2-aminohexanoic acid, tyrosine, L-phenylalanine, D-phenylalanine, thienylalanine, phenylglycine, biphenylglycine, cyclohexylalanine, homophenylalanine, L-1-naphthylalanine, D-1-naphthylalanine, lysine, serine, ornithine, 1,2-diaminobutyric acid, 1,2-diaminopropionic acid, cysteine, penicillamine, methionine, and 2-aminothiazole-4-acetic acid;

$R^3$ is an amino acid, substituted with 0–1 bonds to $L_n$, independently selected at each occurrence from the group: glycine, D-valine, D-alanine, D-leucine, D-isoleucine, D-norleucine, D-2-aminobutyric acid, D-2-aminohexanoic acid, D-tyrosine, D-phenylalanine, D-thienylalanine, D-phenylglycine, D-cyclohexylalanine, D-homophenylalanine, D-1-naphthylalanine, D-lysine, D-serine, D-ornithine, D-1,2-diaminobutyric acid, D-1,2-diaminopropionic acid, D-cysteine, D-penicillamine, and D-methionine;

$R^4$ is an amino acid, substituted with 0–1 bonds to $L_n$, independently selected at each occurrence from the group: glycine, D-valine, D-alanine, D-leucine, D-isoleucine, D-norleucine, D-2-aminobutyric acid, D-2-aminohexanoic acid, D-tyrosine, D-phenylalanine, D-thienylalanine, D-phenylglycine, D-cyclohexylalanine, D-homophenylalanine, D-1-naphthylalanine, D-lysine, D-serine, D-ornithine, D-1,2-diaminobutyric acid, D-1,2-diaminopropionic acid, D-cysteine, D-penicillamine, D-methionine, and 2-aminothiazole-4-acetic acid;

$R^5$ is an amino acid, substituted with 0–1 bonds to $L_n$, independently selected at each occurrence from the group: glycine, L-valine, L-alanine, L-leucine, L-isoleucine, L-norleucine, L-2-aminobutyric acid, L-2-aminohexanoic acid, L-tyrosine, L-phenylalanine, L-thienylalanine, L-phenylglycine, L-cyclohexylalanine, L-homophenylalanine, L-1-naphthylalanine, L-lysine, L-serine, L-ornithine, L-1,2-diaminobutyric acid, L-1,2-diaminopropionic acid, L-cysteine, L-penicillamine, L-methionine, and 2-aminothiazole-4-acetic acid;

provided that one of $R^1$, $R^2$, $R^3$, $R^4$, and $R^5$ in each Q is substituted with a bond to $L_n$, further provided that when $R^2$ is 2-aminothiazole-4-acetic acid, K is N-methylarginine, further provided that when $R^4$ is 2-aminothiazole-4-acetic acid, K and K' are N-methylarginine, and still further provided that when $R^5$ is 2-aminothiazole-4-acetic acid, K' is N-methylarginine;

d is selected from 1, 2, 3, 4, 5, 6, 7, 8, 9, and 10;

$L_n$ is a linking group having the formula:

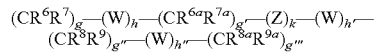

provided that $g+h+g'+k+h'+g''+h''+g'''$ is other than 0;

W is independently selected at each occurrence from the group: O, S, NH, NHC(=O), C(=O)NH, C(=O), C(=O)O, OC(=O), NHC(=S)NH, NHC(=O)NH, $SO_2$, $(OCH_2CH_2)_s$, $(CH_2CH_2O)_{s'}$, $(OCH_2CH_2CH_2)_{s''}$, $(CH_2CH_2CH_2O)_t$, and $(aa)_{t'}$;

aa is independently at each occurrence an amino acid;

Z is selected from the group: aryl substituted with 0–3 $R^{10}$, $C_{3-10}$ cycloalkyl substituted with 0–3 $R^{10}$, and a 5–10 membered heterocyclic ring system containing 1–4 heteroatoms independently selected from N, S, and O and substituted with 0–3 $R^{10}$;

$R^6$, $R^{6a}$, $R^7$, $R^{7a}$, $R^8$, $R^{8a}$, $R^9$ and $R^{9a}$ are independently selected at each occurrence from the group: H, =O, COOH, $SO_3H$, $PO_3H$, $C_1$–$C_5$ alkyl substituted with 0–3 $R^{10}$, aryl substituted with 0–3 $R^{10}$, benzyl substituted with 0–3 $R^{10}$, and $C_1$–$C_5$ alkoxy substituted with 0–3 $R^{10}$, NHC(=O)$R^{11}$, C(=O)NH$R^{11}$, NHC(=O)NH$R^{11}$, NH$R^{11}$, $R^{11}$, and a bond to $C_h$;

$R^{10}$ is independently selected at each occurrence from the group: a bond to $C_h$, COOR$^{11}$, OH, NHR$^{11}$, $SO_3H$, $PO_3H$, aryl substituted with 0–3 $R^{11}$, $C_{1-5}$ alkyl substituted with 0–1 $R^{12}$, $C_{1-5}$ alkoxy substituted with 0–1 $R^{12}$, and a 5–10 membered heterocyclic ring system containing 1–4 heteroatoms independently selected from N, S, and O and substituted with 0–3 $R^{11}$;

$R^{11}$ is independently selected at each occurrence from the group: H, aryl substituted with 0–1 $R^{12}$, a 5–10 membered heterocyclic ring system containing 1–4 heteroatoms independently selected from N, S, and O and substituted with 0–1 $R^{12}$, $C_{3-10}$ cycloalkyl substituted with 0–1 $R^{12}$, polyalkylene glycol substituted with 0–1 $R^{12}$, carbohydrate substituted with 0–1 $R^{12}$, cyclodextrin substituted with 0–1 $R^{12}$, amino acid substituted with 0–1 $R^{12}$, polycarboxyalkyl substituted with 0–1 $R^{12}$, polyazaalkyl substituted with 0–1 $R^{12}$, peptide substituted with 0–1 $R^{12}$, wherein the peptide is comprised of 2–10 amino acids, and a bond to $C_h$;

$R^{12}$ is a bond to $C_h$;

k is selected from 0, 1, and 2;

h is selected from 0, 1, and 2;

h' is selected from 0, 1, 2, 3, 4, and 5;

h" is selected from 0, 1, 2, 3, 4, and 5;

g is selected from 0, 1, 2, 3, 4, 5, 6, 7, 8, 9, and 10;

g' is selected from 0, 1, 2, 3, 4, 5, 6, 7, 8, 9, and 10;

g" is selected from 0, 1, 2, 3, 4, 5, 6, 7, 8, 9, and 10;

g''' is selected from 0, 1, 2, 3, 4, 5, 6, 7, 8, 9, and 10;

s is selected from 0, 1, 2, 3, 4, 5, 6, 7, 8, 9, and 10;

s' is selected from 0, 1, 2, 3, 4, 5, 6, 7, 8, 9, and 10;

s" is selected from 0, 1, 2, 3, 4, 5, 6, 7, 8, 9, and 10;

t is selected from 0, 1, 2, 3, 4, 5, 6, 7, 8, 9, and 10;

t' is selected from 0, 1, 2, 3, 4, 5, 6, 7, 8, 9, and 10;

$C_h$ is a metal bonding unit having a formula selected from the group:

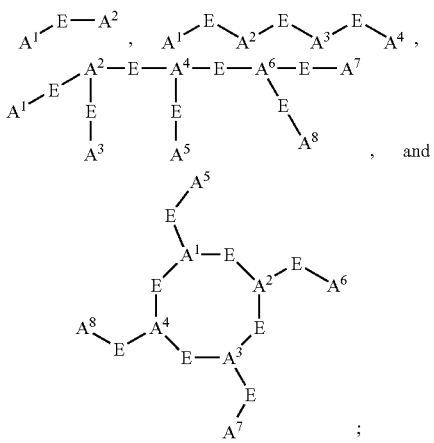

$A^1$, $A^2$, $A^3$, $A^4$, $A^5$, $A^6$, $A^7$, and $A^8$ are independently selected at each occurrence from the group N, $NR^{13}$, $NR^{13}R^{14}$, S, SH, S(Pg), O, OH, $PR^{13}$, $PR^{13}R^{14}$, $P(O)R^{15}R^{16}$, and a bond to $L_n$;

E is a bond, CH, or a spacer group independently selected at each occurrence from the group: $C_1$–$C_{10}$ alkyl substituted with 0–3 $R^{17}$, aryl substituted with 0–3 $R^{17}$, $C_{3-10}$ cycloalkyl substituted with 0–3 $R^{17}$, heterocyclo-$C_{1-10}$ alkyl substituted with 0–3 $R^{17}$, wherein the heterocyclo group is a 5–10 membered heterocyclic ring system containing 1–4 heteroatoms independently selected from N, S, and O, $C_{6-10}$ aryl-$C_{1-10}$ alkyl substituted with 0–3 $R^{17}$, $C_{1-10}$ alkyl-$C_{6-10}$ aryl-substituted with 0–3 $R^{17}$, and a 5–10 membered heterocyclic ring system containing 1–4 heteroatoms independently selected from N, S, and O and substituted with 0–3 $R^{17}$;

$R^{13}$, and $R^{14}$ are each independently selected from the group: a bond to $L_n$, hydrogen, $C_1$–$C_{10}$ alkyl substituted with 0–3 $R^{17}$, aryl substituted with 0–3 $R^{17}$, $C_{1-10}$ cycloalkyl substituted with 0–3 $R^{17}$, heterocyclo-$C_{1-10}$ alkyl substituted with 0–3 $R^{17}$, wherein the heterocyclo group is a 5–10 membered heterocyclic ring system containing 1–4 heteroatoms independently selected from N, S, and O, $C_{6-10}$ aryl-$C_{1-10}$ alkyl substituted with 0–3 $R^{17}$, $C_{1-10}$ alkyl-$C_{6-10}$ aryl-substituted with 0–3 $R^{17}$, a 5–10 membered heterocyclic ring system containing 1–4 heteroatoms independently selected from N, S, and O and substituted with 0–3 $R^{17}$, and an electron, provided that when one of $R^{13}$ or $R^{14}$ is an electron, then the other is also an electron;

alternatively, $R^{13}$ and $R^{14}$ combine to form $=C(R^{20})(R^{21})$;

$R^{15}$ and $R^{16}$ are each independently selected from the group: a bond to $L_n$, —OH, $C_1$–$C_{10}$ alkyl substituted with 0–3 $R^{17}$, $C_1$–$C_{10}$ alkyl substituted with 0–3 $R^{17}$, aryl substituted with 0–3 $R^{17}$, $C_{3-0}$ cycloalkyl substituted with 0–3 $R^{17}$, heterocyclo-$C_1$–$C_{10}$ substituted with 0–3 $R^{17}$, wherein the heterocyclo group is a 5–10 membered heterocyclic ring system containing 1–4 heteroatoms independently selected from N, S, and O, $C_{6-10}$ aryl-$C_{1-10}$ alkyl substituted with 0–3 $R^{17}$, $C_{1-10}$ alkyl-$C_{6-10}$ aryl-substituted with 0–3 $R^{17}$, and a 5–10 membered heterocyclic ring system containing 1–4 heteroatoms independently selected from N, S, and O and substituted with 0–3 $R^{17}$;

$R^{17}$ is independently selected at each occurrence from the group: a bond to $L_n$, =O, F, Cl, Br, I, —$CF_3$, —CN, —$CO_2R^{18}$, —C(=O)$R^{18}$, —C(=O)N($R^{18}$)$_2$, —CHO, —$CH_2OR^{18}$, —OC(=O)$R^{18}$, —OC(=O)$OR^{18a}$, —$OR^{18}$, —OC(=O)N($R^{18}$)$_2$, —$NR^{19}$C(=O)$R^{18}$, —$NR^{19}$C(=O)$OR^{18a}$, —$NR^{19}$C(=O)N($R^{18}$)$_2$, —$NR^{19}SO_2$N($R^{18}$)$_2$, —$NR^{19}SO_2R^{18a}$, —$SO_3H$, —$SO_2R^{18a}$, —$SR^{18}$, S(=O)$R^{18a}$, —$SO_2$N($R^{18}$)$_2$, —N($R^{18}$)$_2$, —NHC(=S)$NHR^{18}$, =$NOR^{18}$, $NO_2$, —C(=O)$NHOR^{18}$, —C(=O)$NHNR^{18}R^{18a}$, —$OCH_2CO_2H$, 2-(1-morpholino)ethoxy, $C_1$–$C_5$ alkyl, $C_2$–$C_4$ alkenyl, $C_3$–$C_6$ cycloalkyl, $C_3$–$C_6$ cycloalkylmethyl, $C_2$–$C_6$ alkoxyalkyl, aryl substituted with 0–2 $R^{18}$, and a 5–10 membered heterocyclic ring system containing 1–4 heteroatoms independently selected from N, S, and O;

$R^{18}$, $R^{18a}$ and $R^{19}$ are independently selected at each occurrence from the group: a bond to $L_n$, H, $C_1$–$C_6$ alkyl, phenyl, benzyl, $C_1$–$C_6$ alkoxy, halide, nitro, cyano, and trifluoromethyl;

Pg is a thiol protecting group;

$R^{20}$ and $R^{21}$ are independently selected from the group: H, $C_1$–$C_{10}$ alkyl, —CN, —$CO_2R^{25}$, —C(=O)$R^{25}$, —C(=O)N($R^{25}$)$_2$, $C_2$–$C_{10}$ 1-alkene substituted with 0–3 $R^{23}$, $C_2$–$C_{10}$ 1-alkyne substituted with 0–3 $R^{23}$, aryl substituted with 0–3 $R^{23}$, unsaturated 5–10 membered heterocyclic ring system containing 1–4 heteroatoms independently selected from N, S, and O and substituted with 0–3 $R^{23}$, and unsaturated $C_{3-10}$ carbocycle substituted with 0–3 $R^{23}$;

alternatively, $R^{20}$ and $R^{21}$, taken together with the divalent carbon radical to which they are attached form:

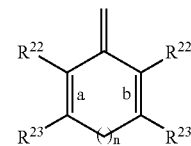

$R^{22}$ and $R^{23}$ are independently selected from the group: H, $R^{24}$, $C_1$–$C_{10}$ alkyl substituted with 0–3 $R^{24}$, $C_2$–$C_{10}$ alkenyl substituted with 0–3 $R^{24}$, $C_2$–$C_{10}$ alkynyl substituted with 0–3 $R^{24}$, aryl substituted with 0–3 $R^{24}$, a 5–10 membered heterocyclic ring system containing 1–4 heteroatoms independently selected from N, S, and O and substituted with 0–3 $R^{24}$, and $C_{3-10}$ carbocycle substituted with 0–3 $R^{24}$;

alternatively, $R^{22}$, $R^{23}$ taken together form a fused aromatic or a 5–10 membered heterocyclic ring system containing 1–4 heteroatoms independently selected from N, S, and O;

a and b indicate the positions of optional double bonds and n is 0 or 1;

$R^{24}$ is independently selected at each occurrence from the group: =O, F, Cl, Br, I, —CF$_3$, —CN, —CO$_2$R$^{25}$, —C(=O)R$^{25}$, —C(=O)N(R$^{25}$)$_2$, —N(R$^{25}$)$_3$', —CH$_2$OR$^{25}$, —OC(=O)R$^{25}$, —OC(=O)OR$^{25a}$, —OR$^{25}$, —OC(=O)N(R$^{25}$)$_2$, —NR$^{26}$C(=O)R$^{25}$, —NR$^{26}$C(=O)OR$^{25a}$, —NR$^{26}$C(=O)N(R$^{25}$)$_2$, —NR$^{26}$SO$_2$N(R$^{25}$)$_2$, —NR$^{26}$SO$_2$R$^{25a}$, —SO$_3$H, —SO$_2$R$^{25a}$, —SR$^{25}$, —S(=O)R$^{25a}$, —SO$_2$N(R$^{25}$)$_2$, —N(R$^{25}$)$_2$, =NOR$^{25}$, —C(=O)NHOR$^{25}$, —OCH$_2$CO$_2$H, and 2-(1-morpholino)ethoxy; and, $R^{25}$, $R^{25a}$, and $R^{26}$ are each independently selected at each occurrence from the group: hydrogen and $C_1$–$C_6$ alkyl;

and a pharmaceutically acceptable salt thereof.

12. A composition according to claim 11 wherein:

L is glycine;

$R^1$ is an amino acid, optionally substituted with a bond to $L_n$, independently selected at each occurrence from the group: L-valine, D-valine, alanine, leucine, isoleucine, norleucine, 2-aminobutyric acid, tyrosine, phenylalanine, phenylglycine, cyclohexylalanine, homophenylalanine, lysine, ornithine, 1,2-diaminobutyric acid, and 1,2-diaminopropionic acid;

$R^2$ is an amino acid, optionally substituted with a bond to $L_n$, independently selected at each occurrence from the group: valine, alanine, leucine, isoleucine, norleucine, 2-aminobutyric acid, tyrosine, L-phenylalanine, D-phenylalanine, thienylalanine, phenylglycine, biphenylglycine, cyclohexylalanine, homophenylalanine, L-1-naphthylalanine, D-1-naphthylalanine, lysine, ornithine, 1,2-diaminobutyric acid, 1,2-diaminopropionic acid, and 2-aminothiazole-4-acetic acid;

$R^3$ is an amino acid, optionally substituted with a bond to $L_n$, independently selected at each occurrence from the group: D-valine, D-alanine, D-leucine, D-isoleucine, D-norleucine, D-2-aminobutyric acid, D-tyrosine, D-phenylalanine, D-phenylglycine, D-cyclohexylalanine, D-homophenylalanine, D-lysine, D-serine, D-ornithine, D-1,2-diaminobutyric acid, and D-1,2-diaminopropionic acid;

$R^4$ is an amino acid, optionally substituted with a bond to $L_n$, independently selected at each occurrence from the group: D-valine, D-alanine, D-leucine, D-isoleucine, D-norleucine, D-2-aminobutyric acid, D-tyrosine, D-phenylalanine, D-thienylalanine, D-phenylglycine, D-cyclohexylalanine, D-homophenylalanine, D-1-naphthylalanine, D-lysine, D-ornithine, D-1,2-diaminobutyric acid, D-1,2-diaminopropionic acid, and 2-aminothiazole-4-acetic acid;

$R^5$ is an amino acid, optionally substituted with a bond to $L_n$, independently selected at each occurrence from the group: L-valine, L-alanine, L-leucine, L-isoleucine, L-norleucine, L-2-aminobutyric acid, L-tyrosine, L-phenylalanine, L-thienylalanine, L-phenylglycine, L-cyclohexylalanine, L-homophenylalanine, L-1-naphthylalanine, L-lysine, L-ornithine, L-1,2-diaminobutyric acid, L-1,2-diaminopropionic acid, and 2-aminothiazole-4-acetic acid;

d is selected from 1, 2, and 3;

W is independently selected at each occurrence from the group: O, NH, NHC(=O), C(=O)NH, C(=O), C(=O)O, OC(=O), NHC(=S)NH, NHC(=O)NH, SO$_2$, (OCH$_2$CH$_2$)$_s$, (CH$_2$CH$_2$O)$_{s'}$, (OCH$_2$CH$_2$)$_{s''}$, and (CH$_2$CH$_2$CH$_2$O)$_t$;

Z is selected from the group: aryl substituted with 0–1 $R^{10}$, $C_{3-10}$ cycloalkyl substituted with 0–1 $R^{10}$, and a 5–10 membered heterocyclic ring system containing 1–4 heteroatoms independently selected from N, S, and O and substituted with 0–1 $R^{10}$;

$R^6$, $R^{6a}$, $R^7$, $R^{7a}$, $R^8$, $R^{8a}$, $R^9$, and $R^{9a}$ are independently selected at each occurrence from the group: H, =O, COOH, SO$_3$H, $C_1$–$C_5$ alkyl substituted with 0–1 $R^{10}$, aryl substituted with 0–1 $R^{10}$, benzyl substituted with 0–1 $R^{10}$, and $C_1$–$C_5$ alkoxy substituted with 0–1 $R^{10}$, NHC(=O)R$^{11}$, C(=O)NHR$^{11}$, NHC(=O)NHR$^{11}$, NHR$^{11}$, R$^{11}$, and a bond to $C_h$;

$R^{10}$ is independently selected at each occurrence from the group: COOR$^{11}$, OH, NHR$^{11}$, SO$_3$H, aryl substituted with 0–1 $R^{11}$, a 5–10 membered heterocyclic ring system containing 1–4 heteroatoms independently selected from N, S, and O and substituted with 0–1 $R^{11}$, $C_1$–$C_5$ alkyl substituted with 0–1 $R^{12}$, $C_1$–$C_5$ alkoxy substituted with 0–1 $R^{12}$, and a bond to $C_h$;

$R^{11}$ is independently selected at each occurrence from the group: H, aryl substituted with 0–1 $R^{12}$, a 5–10 membered heterocyclic ring system containing 1–4 heteroatoms independently selected from N, S, and O and substituted with 0–1 $R^{12}$, polyalkylene glycol substituted with 0–1 $R^{12}$, carbohydrate substituted with 0–1 $R^{12}$, cyclodextrin substituted with 0–1 $R^{12}$, amino acid substituted with 0–1 $R^{12}$, and a bond to $C_h$;

k is 0 or 1;

h is 0 or 1;

h' is 0 or 1;

s is selected from 0, 1, 2, 3, 4, and 5;

s' is selected from 0, 1, 2, 3, 4, and 5;

s" is selected from 0, 1, 2, 3, 4, and 5;

t is selected from 0, 1, 2, 3, 4, and 5;

$A^1$, $A^2$, $A^3$, $A^4$, $A^5$, $A^6$, $A^7$, and $A^8$ are independently selected at each occurrence from the group: NR$^{13}$, NR$^{13}$R$^{14}$, S, SH, S(Pg), OH, and a bond to $L_n$;

E is a bond, CH, or a spacer group independently selected at each occurrence from the group: $C_1$–$C_{10}$ alkyl substituted with 0–3 $R^{17}$, aryl substituted with 0–3 $R^{17}$, $C_{3-10}$ cycloalkyl substituted with 0–3 $R^{17}$, and a 5–10 membered heterocyclic ring system containing 1–4 heteroatoms independently selected from N, S, and O and substituted with 0–3 $R^{17}$;

$R^{13}$, and $R^{14}$ are each independently selected from the group: a bond to $L_n$, hydrogen, $C_1$–$C_{10}$ alkyl substituted with 0–3 $R^{17}$, aryl substituted with 0–3 $R^{17}$, a 5–10 membered heterocyclic ring system containing 1–4 heteroatoms independently selected from N, S, and O and substituted with 0–3 $R^{17}$, and an electron, provided that when one of $R^{13}$ or $R^{14}$ is an electron, then the other is also an electron;

alternatively, $R^{13}$ and $R^{14}$ combine to form =C(R$^{20}$)(R$^{21}$);

$R^{17}$ is independently selected at each occurrence from the group: a bond to $L_n$, =O, F, Cl, Br, I, —CF$_3$, —CN, —CO$_2$R$^{18}$, —C(=O)R$^{18}$, —C(=O)N(R$^{18}$)$_2$, —CH$_2$OR$^{18}$, —OC(=O)R$^{18}$, —OC(=O)OR$^{18a}$, —OR$^{18}$, —OC(=O)N(R$^{18}$)$_2$, —NR$^{19}$C(=O)R$^{18}$, —NR$^{19}$C(=O)OR$^{18a}$, —NR$^{19}$C(=O)N(R$^{18}$)$_2$, —NR$^{19}$SO$_2$N(R$^{18}$)$_2$, —NR$^{19}$SO$_2$R$^{18a}$, —SO$_3$H, —SO$_2$R$^{18a}$, —S(=O)R$^{18a}$, —SO$_2$N(R$^{18}$)$_2$, —N(R$^{18}$)$_2$, —NHC(=S)NHR$^{18}$, =NOR$^{18}$, —C(=O)NHNR$^{18}$R$^{18a}$, —OCH$_2$CO$_2$H, and 2-(1-morpholino)ethoxy;

R$^{18}$, R$^{18a}$, and R$^{19}$ are independently selected at each occurrence from the group: a bond to L$_n$, H, and C$_1$–C$_6$ alkyl;

R$^{20}$ and R$^{21}$ are independently selected from the group: H, C$_1$–C$_5$ alkyl, —CO$_2$R$^{25}$, C$_2$–C$_5$ 1-alkene substituted with 0–3 R$^{23}$, C$_2$–C$_5$ 1-alkyne substituted with 0–3 R$^{23}$, aryl substituted with 0–3 R$^{23}$, and unsaturated 5–10 membered heterocyclic ring system containing 1–4 heteroatoms independently selected from N, S, and O and substituted with 0–3 R$^{23}$;

alternatively, R$^{20}$ and R$^{21}$, taken together with the divalent carbon radical to which they are attached form:

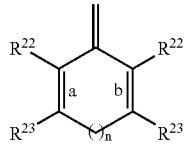

R$^{22}$ and R$^{23}$ are independently selected from the group: H, and R$^{24}$;

alternatively, R$^{22}$, R$^{23}$ taken together form a fused aromatic or a 5–10 membered heterocyclic ring system containing 1–4 heteroatoms independently selected from N, S, and O;

R$^{24}$ is independently selected at each occurrence from the group: —CO$_2$R$^{25}$, —C(=O)N(R$^{25}$)$_2$, —CH$_2$OR$^{25}$, —OC(=O)R$^{25}$, —OR$^{25}$, —SO$_3$H, —N(R$^{25}$)$_2$, and —OCH$_2$CO$_2$H; and, R$^{25}$ is independently selected at each occurrence from the group: H and C$_1$–C$_3$ alkyl.

13. A composition according to claim 12 wherein:

Q is a peptide selected from the group:

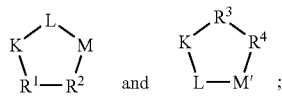

R$^1$ is L-valine, D-valine, D-lysine optionally substituted on the ε amino group with a bond to L$_n$ or L-lysine optionally substituted on the ε amino group with a bond to L$_n$;

R$^2$ is L-phenylalanine, D-phenylalanine, D-1-naphthylalanine, 2-aminothiazole-4-acetic acid, L-lysine optionally substituted on the ε amino group with a bond to L$_n$ or tyrosine, the tyrosine optionally substituted on the hydroxy group with a bond to L$_n$;

R$^3$ is D-valine, D-phenylalanine, or L-lysine optionally substituted on the ε amino group with a bond to L$_n$;

R$^4$ is D-phenylalanine, D-tyrosine substituted on the hydroxy group with a bond to L$_n$, or L-lysine optionally substituted on the ε amino group with a bond to L$_n$;

provided that one of R$^1$ and R$^2$ in each Q is substituted with a bond to L$_n$, and further provided that when R$^2$ is 2-aminothiazole-4-acetic acid, K is N-methylarginine;

d is 1 or 2;

W is independently selected at each occurrence from the group: NHC(=O), C(=O)NH, C(=O), (CH$_2$CH$_2$O)$_{s'}$, and (CH$_2$CH$_2$CH$_2$O)$_t$;

R$^6$, R$^{6a}$, R$^7$, R$^{7a}$, R$^8$, R$^{8a}$, R$^9$, and R$^{9a}$ are independently selected at each occurrence from the group: H, NHC(=O)R$^{11}$, and a bond to C$_h$;

k is 0;
h" is selected from 0, 1, 2, and 3;
g is selected from 0, 1, 2, 3, 4, and 5;
g' is selected from 0, 1, 2, 3, 4, and 5;
g" is selected from 0, 1, 2, 3, 4, and 5;
g''' is selected from 0, 1, 2, 3, 4, and 5;
s' is 1 or 2;
t is 1 or 2;

C$_h$ is
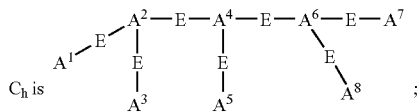

A$^1$ is selected from the group: OH, and a bond to L$_n$;
A$^2$, A$^4$, and A$^6$ are each N;
A$^3$, A$^5$, and A$^8$ are each OH;
A$^7$ is a bond to L$_n$ or NH-bond to L$_n$;
E is a C$_2$ alkyl substituted with 0–1 R$^{17}$;
R$^{17}$ is =O;
alternatively, C$_h$ is

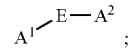

A$^1$ is NH$_2$ or N=C(R$^{20}$)(R$^{21}$);
E is a bond;
A$^2$ is NHR$^{13}$;
R$^{13}$ is a heterocycle substituted with R$^{17}$, the heterocycle being selected from pyridine and pyrimidine;
R$^{17}$ is selected from a bond to L$_n$, C(=O)NHR$^{18}$, and C(=O)R$^{18}$;
R$^{18}$ is a bond to L$_n$;
R$^{24}$ is selected from the group: —CO$_2$R$^{25}$, —OR$^{25}$, —SO$_3$H, and —N(R$^{25}$)$_2$;
R$^{25}$ is independently selected at each occurrence from the group: hydrogen and methyl;
alternatively, C$_h$ is

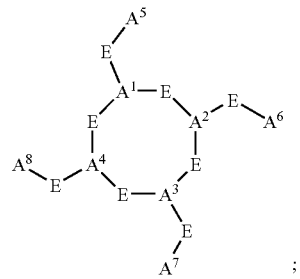

A$^1$, A$^2$, A$^3$, and A$^4$ are each N;
A$^5$, A$^6$, and A$^8$ are each OH;
A$^7$ is a bond to L$_n$;
E is a C$_2$ alkyl substituted with 0–1 R$^{17}$; and,
R$^{17}$ is =O.

14. A composition according to claim 10, wherein the metal is selected from the group: $^{99m}$Tc, $^{95}$Tc, $^{111}$In, $^{62}$Cu, $^{64}$Cu, $^{67}$Ga, and $^{68}$Ga.

15. A composition according to claim 14, further comprising a first ancillary ligand and a second ancillary ligand capable of stabilizing the composition.

16. A composition according to claim 14 comprising a compound selected from the group:
- $^{99m}$Tc(tricine)(TPPTS)(cyclo(Arg-Gly-Asp-D-Tyr(N-[[5-[carbonyl]-2-pyridinyl]diazenido]-3-aminopropyl)-Val)) [SEQ. ID NO.: 33];
- $^{99m}$Tc(tricine)(TPPMS)(cyclo(Arg-D-Val-D-Tyr(N-[[5-[carbonyl]-2-pyridinyl]diazenido]-3-aminopropyl)-D-Asp-Gly)) [SEQ. ID NO.: 34];
- $^{99m}$Tc(tricine)(TPPDS)(cyclo(Arg-D-Val-D-Tyr(N-[[5-[carbonyl]-2-pyridinyl]diazenido]-3-aminopropyl)-D-Asp-Gly)) [SEQ. ID NO.: 35];
- $^{99m}$Tc(tricine)(TPPTS)(cyclo(Arg-D-Val-D-Tyr(N-[[5-[carbonyl]-2-pyridinyl]diazenido]-3-aminopropyl)-D-Asp-Gly)) [SEQ. ID NO.: 36];
- $^{99m}$Tc(tricine)(TPPTS)(cyclo(Arg-Gly-Asp-D-Phe-Lys(N-[[5-[carbonyl]-2-pyridinyl]diazenido]))) [SEQ. ID NO.: 37];
- $^{99m}$Tc(tricine)(TPPTS)(cyclo(Arg-Gly-Asp-D-Tyr-Lys(N-[[5-carbonyl]-2-pyridinyl]diazenido]))) [SEQ. ID NO.: 38];
- $^{99m}$Tc(tricine)(TPPTS)([2-[[[5-[carbonyl]-2-pyridinyl]hydrazono]methyl]-benzenesulfonic acid]-Phe-Gly(cyclo{Lys-Arg-Gly-Asp-D-Phe})-cyclo{Lys-Arg-Gly-Asp-D-Phe}) [SEQ. ID NO.: 39];
- $^{99m}$Tc(tricine)(TPPTS)(cyclo{Arg-Gly-Asp-D-Nal-Lys([2-[[[5-[carbonyl]-2-pyridinyl]hydrazono]methyl]-benzenesulfonic acid])}) [SEQ. ID NO.: 40];
- $^{99m}$Tc(tricine)(TPPTS)([2-[[[5-[carbonyl]-2-pyridinyl]-hydrazono]methyl]-benzenesulfonic acid]-Glu(cyclo{Lys-Arg-Gly-Asp-D-Nal})-cyclo{Lys-Arg-Gly-Asp-D-Nal}) [SEQ. ID NO.: 41];
- $^{99m}$Tc(tricine)(TPPTS)(cyclo(Arg-Gly-Asp-D-Tyr((N-[[5-[carbonyl]-2-pyridinyl]diazenido]-18-amino-14-aza-4,7,10-oxy-15-octadecoyl)-3-aminopropyl)-Val)) [SEQ. ID NO.: 42];
- $^{99m}$Tc(tricine)(TPPTS)(N-[[5-[carbonyl]-2-pyridinyl]diazenido]-Glu(O-cyclo(Lys-Arg-Gly-Asp-D-Phe))-O-cyclo(Lys-Arg-Gly-Asp-D-Phe)) [SEQ. ID NO.: 43];
- $^{99m}$Tc(tricine)(TPPTS)(N-[[5-[carbonyl]-2-pyridinyl]diazenido]-Glu(O-cyclo(D-Tyr(3-aminopropyl)-Val-Arg-Gly-Asp))-O-cyclo(D-Tyr(3-aminopropyl)-Val-Arg-Gly-Asp)) [SEQ. ID NO.: 44];
- $^{99m}$Tc(tricine)(TPPTS)(cyclo(Arg-Gly-Asp-Lys(N-[[5-[carbonyl]-2-pyridinyl]diazenido])-D-Val)) [SEQ. ID NO.: 45];
- $^{99m}$Tc(tricine)(TPPTS)(cyclo{D-Lys([2-[[[5-[carbonyl]-2-pyridinyl]hydrazono]methyl]-benzenesulfonic acid])-D-Phe-D-Asp-Gly-Arg}) [SEQ. ID NO.: 46];
- $^{99m}$Tc(tricine)(TPPTS)([2-[[[5-[carbonyl]-2-pyridinyl]hydrazono]methyl]-benzenesulfonic acid]-Glu(cyclo{D-Lys-D-Phe-D-Asp-Gly-Arg})-cyclo{D-Lys-D-Phe-D-Asp-Gly-Arg}) [SEQ. ID NO.: 47];
- $^{99m}$Tc(tricine)(TPPTS)(cyclo{D-Phe-D-Lys([2[[[5-[carbonyl]-2-pyridinyl]hydrazono]methyl]-benzenesulfonic acid])-D-Asp-Gly-Arg}) [SEQ. ID NO.: 48];
- $^{99m}$Tc(tricine)(TPPTS)(cyclo(N-Me-Arg-Gly-Asp-ATA-D-Lys(N-[[5-[carbonyl]-2-pyridinyl]diazenido]))) [SEQ. ID NO.: 49];
- $^{99m}$Tc(tricine)(TPPTS)(cyclo{Cit-Gly-Asp-D-Phe-Lys([2-[[[5-[carbonyl]-2-pyridinyl]hydrazono]methyl]-benzenesulfonic acid])}) [SEQ. ID NO.: 50];
- $^{99m}$Tc(tricine)(1,2,4-triazole)(cyclo(Arg-Gly-Asp-D-Tyr(N-[[5-[carbonyl]-2-pyridinyl]diazenido]-3-aminopropyl)-Val)) [SEQ. ID NO.: 51];
- (DOTA-$^{111}$In)-Gly(cyclo{Lys-Arg-Gly-Asp-D-Phe})-cyclo{Lys-Arg-Gly-Asp-D-Phe} [SEQ. ID NO.: 52];
- cyclo(Arg-Gly-Asp-D-Phe-Lys(DTPA-$^{111}$In)) [SEQ. ID NO.: 53]; and
- cyclo(Arg-Gly-Asp-D-Phe-Lys)$_2$(DTPA-$^{11}$In) [SEQ. ID NO.: 54].

17. A composition according to claim 10, wherein the metal is selected from the group: $^{33}$P, $^{125}$I, $^{186}$Re, $^{188}$Re, $^{153}$Sm, $^{166}$Ho, $^{177}$Lu, $^{149}$Pm, $^{90}$Y, $^{212}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{67}$Cu, $^{105}$Rh, $^{111}$Ag, and $^{192}$Ir.

18. A composition according to claim 17 comprising a compound selected from the group:
- cyclo(Arg-Gly-Asp-D-Phe-Lys(DTPA-$^{153}$Sm)) [SEQ. ID NO.: 55];
- cyclo(Arg-Gly-Asp-D-Phe-Lys)$_2$(DTPA-$^{153}$Sm) [SEQ. ID NO.: 56];
- cyclo(Arg-Gly-Asp-D-Tyr(N-DTPA($^{153}$Sm)-3-aminopropyl)-Val [SEQ. ID NO.: 57];
- cyclo(Arg-Gly-Asp-D-Phe-Lys(DTPA-$^{177}$Lu)) [SEQ. ID NO.: 58];
- (DOTA-$^{177}$Lu)-Glu(cyclo{Lys-Arg-Gly-Asp-D-Phe})-cyclo{Lys-Arg-Gly-Asp-D-Phe} [SEQ. ID NO.: 59];
- cyclo(Arg-Gly-Asp-D-Phe-Lys)$_2$(DTPA-$^{177}$Lu) [SEQ. ID NO.: 60];
- yclo(Arg-Gly-Asp-D-Tyr(N-DTPA($^{177}$Lu)-3-aminopropyl) [SEQ. ID NO.: 61]; and
- (DOTA-$^{90}$Y)-Glu(cyclo{Lys-Arg-Gly-Asp-D-Phe})-cyclo{Lys-Arg-Gly-Asp-D-Phe} [SEQ. ID NO.: 62].

19. A composition according to claim 10, wherein the metal is selected from the group: Gd(III), Dy(III), Fe(III), and Mn(II).

20. A composition according to claim 19 wherein the compound is:
- cyclo(Arg-Gly-Asp-D-Tyr(N-DTPA(Gd(III))-3-aminopropyl)-Val) [SEQ ID NO.: 63].

21. A composition according to claim 10, wherein the metal is selected from the group: Re, Sm, Ho, Lu, Pm, Y, Bi, Pd, Gd, La, Au, Au, Yb, Dy, Cu, Rh, Ag, and Ir.

22. A composition according to claim 10, further comprising a therapeutic isotope selected from the group: $^{35}$S, $^{32}$P, $^{125}$I, $^{131}$I, and $^{211}$At.

* * * * *

SEQUENCE LISTING

```
<160> NUMBER OF SEQ ID NOS: 169

<210> SEQ ID NO 1
<211> LENGTH: 5
<212> TYPE: PRT
<213> ORGANISM: Artificial Sequence
<220> FEATURE:
<223> OTHER INFORMATION: Synthethic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: (N-[2-[[[5-carbonyl]-2-
      pyridinyl]hydrazono]methyl]-benezenesulfonic acid]-3-aminopropyl)
<220> FEATURE:
<221> NAME/KEY: MISC_FEATURE
<222> LOCATION: (4)..(4)
<223> OTHER INFORMATION: D amino acid

<400> SEQUENCE: 1

Arg Gly Asp Tyr Val
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: (N-[2-[[[5-carbonyl]-2-
    pyridinyl]hydrazono]methyl]-benzenesulfonic acid-18-amino-14-aza-
    4,7,10-oxy-15-oxo-octadecoyl)-3-aminoprophy)
<220> FEATURE:
<221> NAME/KEY: MISC_FEATURE
<222> LOCATION: (4)..(4)
<223> OTHER INFORMATION: D amino acid

<400> SEQUENCE: 2

Arg Gly Asp Tyr Val
1               5

<210> SEQ ID NO 3
<211> LENGTH: 11
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MISC_FEATURE
<222> LOCATION: (1)..(1)
<223> OTHER INFORMATION: [2-[5-[carbonyl]-2-
      pyridinyl]hydrazono]methyl-benzenesulfonic acid]
<220> FEATURE:
<221> NAME/KEY: MISC_FEATURE
<222> LOCATION: (2)..(2)
<223> OTHER INFORMATION: (3-aminopropyl)
<220> FEATURE:
<221> NAME/KEY: MISC_FEATURE
<222> LOCATION: (2)..(2)
<223> OTHER INFORMATION: D amino acid
<220> FEATURE:
<221> NAME/KEY: MISC_FEATURE
<222> LOCATION: (2)..(6)
<223> OTHER INFORMATION: cyclic amino acid
<220> FEATURE:
<221> NAME/KEY: MISC_FEATURE
<222> LOCATION: (7)..(7)
<223> OTHER INFORMATION: (3-aminopropyl)
<220> FEATURE:
<221> NAME/KEY: MISC_FEATURE
<222> LOCATION: (7)..(7)
<223> OTHER INFORMATION: D amino acid

<400> SEQUENCE: 3

Glu Tyr Val Arg Gly Asp Tyr Val Arg Gly Asp
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (5)..(5)
<223> OTHER INFORMATION: ([2-[[[5-carbonyl]-2-
      pyridinyl]hydrazono]methyl]-benezenesulfonic acid)

<400> SEQUENCE: 4

Arg Gly Asp Tyr Lys
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (5)..(5)
<223> OTHER INFORMATION: (N-[2-[[[5-carbonyl]-2-
      pyridinyl]hydrazono]methyl]-benezenesulfonic acid)
<220> FEATURE:
<221> NAME/KEY: MISC_FEATURE
```

```
<222> LOCATION: (5)..(5)
<223> OTHER INFORMATION: ([2-[[[5-carbonyl]-2-
      pyridinyl]hydrazono]methyl]-benezenesulfonic acid)

<400> SEQUENCE: 5

Arg Gly Asp Phe Lys
1               5

<210> SEQ ID NO 6
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: ([2-[[[5-carbonyl]-2-
      pyridinyl]hydrazono]methyl]-benezenesulfonic acid)
<220> FEATURE:
<221> NAME/KEY: MISC_FEATURE
<222> LOCATION: (2)..(6)
<223> OTHER INFORMATION: cyclic amino acid
<220> FEATURE:
<221> NAME/KEY: MISC_FEATURE
<222> LOCATION: (6)..(6)
<223> OTHER INFORMATION: D amino acid
<220> FEATURE:
<221> NAME/KEY: MISC_FEATURE
<222> LOCATION: (7)..(11)
<223> OTHER INFORMATION: cyclic amino acid
<220> FEATURE:
<221> NAME/KEY: MISC_FEATURE
<222> LOCATION: (11)..(11)
<223> OTHER INFORMATION: D amino acid

<400> SEQUENCE: 6

Glu Lys Arg Gly Asp Phe Lys Arg Gly Asp Phe
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: [2-[[[5-[carbonyl]-2-
      pyridinyl]hydrazono]methyl]-benzenesulfonic acid]
<220> FEATURE:
<221> NAME/KEY: MISC_FEATURE
<222> LOCATION: (3)..(7)
<223> OTHER INFORMATION: cyclic amino acid
<220> FEATURE:
<221> NAME/KEY: MISC_FEATURE
<222> LOCATION: (7)..(7)
<223> OTHER INFORMATION: D amino acid
<220> FEATURE:
<221> NAME/KEY: MISC_FEATURE
<222> LOCATION: (8)..(12)
<223> OTHER INFORMATION: cyclic amino acid
<220> FEATURE:
<221> NAME/KEY: MISC_FEATURE
<222> LOCATION: (12)..(12)
<223> OTHER INFORMATION: D amino acid

<400> SEQUENCE: 7

Phe Glu Lys Arg Gly Asp Phe Lys Arg Gly Asp Phe
1               5                   10

<210> SEQ ID NO 8
```

```
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa = naphthyl alanine
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (5)..(5)
<223> OTHER INFORMATION: ([2-[[[5-[carbonyl]-2-
      pyridinyl]hydrazono]methyl]-benezenesulfonic acid])

<400> SEQUENCE: 8

Arg Gly Asp Xaa Lys
1               5

<210> SEQ ID NO 9
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: [2-[[[5-[carbonyl]-2-pyridinyl]-
      hydrazono]methyl]-benzenesulfonic acid]
<220> FEATURE:
<221> NAME/KEY: MISC_FEATURE
<222> LOCATION: (2)..(6)
<223> OTHER INFORMATION: cyclic amino acid
<220> FEATURE:
<221> NAME/KEY: MISC_FEATURE
<222> LOCATION: (6)..(6)
<223> OTHER INFORMATION: Xaa = naphthyl alanine
<220> FEATURE:
<221> NAME/KEY: MISC_FEATURE
<222> LOCATION: (6)..(6)
<223> OTHER INFORMATION: D amino acid
<220> FEATURE:
<221> NAME/KEY: MISC_FEATURE
<222> LOCATION: (7)..(11)
<223> OTHER INFORMATION: cyclic amino acid
<220> FEATURE:
<221> NAME/KEY: MISC_FEATURE
<222> LOCATION: (11)..(11)
<223> OTHER INFORMATION: Xaa = naphthyl alanine
<220> FEATURE:
<221> NAME/KEY: MISC_FEATURE
<222> LOCATION: (11)..(11)
<223> OTHER INFORMATION: D amino acid

<400> SEQUENCE: 9

Glu Lys Arg Gly Asp Xaa Lys Arg Gly Asp Xaa
1               5                   10

<210> SEQ ID NO 10
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
```

```
<222> LOCATION: (4)..(4)
<223> OTHER INFORMATION: [2-[[[5-[carbonyl]-2-
      pyridinyl]hydrazono]methyl]-benzenesulfonic acid]
<220> FEATURE:
<221> NAME/KEY: MISC_FEATURE
<222> LOCATION: (5)..(5)
<223> OTHER INFORMATION: D amino acid

<400> SEQUENCE: 10

Arg Gly Asp Lys Val
1               5

<210> SEQ ID NO 11
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: [2-[[[5-[carbonyl]-2-
      pyridinyl]hydrazono]methyl]-benzenesulfonic acid]
<220> FEATURE:
<221> NAME/KEY: MISC_FEATURE
<222> LOCATION: (2)..(6)
<223> OTHER INFORMATION: cyclic amino acid
<220> FEATURE:
<221> NAME/KEY: MISC_FEATURE
<222> LOCATION: (3)..(3)
<223> OTHER INFORMATION: D amino acid
<220> FEATURE:
<221> NAME/KEY: MISC_FEATURE
<222> LOCATION: (7)..(11)
<223> OTHER INFORMATION: cyclic amino acid
<220> FEATURE:
<221> NAME/KEY: MISC_FEATURE
<222> LOCATION: (8)..(8)
<223> OTHER INFORMATION: D amino acid

<400> SEQUENCE: 11

Glu Lys Val Arg Gly Asp Lys Val Arg Gly Asp
1               5                   10

<210> SEQ ID NO 12
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (2)..(4)
<223> OTHER INFORMATION: D amino acid
<220> FEATURE:
<221> NAME/KEY: MISC_FEATURE
<222> LOCATION: (3)..(3)
<223> OTHER INFORMATION: (N-[2-[[[5-[carbonyl]-2-
      pyridinyl]hydrazono]methyl]-benzenesulfonic acid]-3-aminopropyl)

<400> SEQUENCE: 12

Arg Val Tyr Asp Gly
1               5

<210> SEQ ID NO 13
<211> LENGTH: 5
<212> TYPE: PRT
<213> ORGANISM: Artificial Sequence
<220> FEATURE:
```

```
-continued
<223> OTHER INFORMATION: Synthetic Construct
<220> FEATURE:
<221> NAME/KEY: MISC_FEATURE
<222> LOCATION: (1)..(1)
<223> OTHER INFORMATION: [2-[[[5-[carbonyl]-2-
      pyridinyl]hydrazono]methyl]-benzenesulfonic acid]
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(3)
<223> OTHER INFORMATION: D amino acid

<400> SEQUENCE: 13

Lys Phe Asp Gly Arg
1               5

<210> SEQ ID NO 14
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: [2-[[[5-[carbonyl]-2-
      pyridinyl]hydrazono]methyl]-benzenesulfonic acid]
<220> FEATURE:
<221> NAME/KEY: MISC_FEATURE
<222> LOCATION: (2)..(6)
<223> OTHER INFORMATION: cyclic amino acid
<220> FEATURE:
<221> NAME/KEY: MISC_FEATURE
<222> LOCATION: (2)..(4)
<223> OTHER INFORMATION: D amino acid
<220> FEATURE:
<221> NAME/KEY: MISC_FEATURE
<222> LOCATION: (7)..(11)
<223> OTHER INFORMATION: cyclic amino acid
<220> FEATURE:
<221> NAME/KEY: MISC_FEATURE
<222> LOCATION: (7)..(9)
<223> OTHER INFORMATION: D amino acid

<400> SEQUENCE: 14

Glu Lys Phe Asp Gly Arg Lys Phe Asp Gly Arg
1               5                   10

<210> SEQ ID NO 15
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(3)
<223> OTHER INFORMATION: D amino acid
<220> FEATURE:
<221> NAME/KEY: MISC_FEATURE
<222> LOCATION: (2)..(2)
<223> OTHER INFORMATION: [2-[[[5-[carbonyl]-2-
      pyridinyl]hydrazono]methyl]-benzenesulfonic acid]

<400> SEQUENCE: 15

Phe Lys Asp Gly Arg
1               5
```

```
<210> SEQ ID NO 16
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: a-N-methyl
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: Xaa = 2-aminothiazole-5-acetic acid or 2-
      aminothiazole-5-acetyl group
<220> FEATURE:
<221> NAME/KEY: MISC_FEATURE
<222> LOCATION: (5)..(5)
<223> OTHER INFORMATION: ([2-[[[5-[carbonyl]-2-
      pyridinyl]hydrazono]methyl]-benzenesulfonic acid])
<220> FEATURE:
<221> NAME/KEY: MISC_FEATURE
<222> LOCATION: (5)..(5)
<223> OTHER INFORMATION: D amino acid

<400> SEQUENCE: 16

Arg Gly Asp Xaa Lys
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = citrulline
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (5)..(5)
<223> OTHER INFORMATION: ([2-[[[5-[carbonyl]-2-
      pyridinyl]hydrazono]methyl]-benzenesulfonic acid])

<400> SEQUENCE: 17

Xaa Gly Asp Phe Lys
1               5

<210> SEQ ID NO 18
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 2-(1,4,7,10-tetraaza-4,7,10-
      tris(carboxymethyl)-1-cyclododecyl)acetyl
<220> FEATURE:
```

```
<221> NAME/KEY: MISC_FEATURE
<222> LOCATION: (2)..(6)
<223> OTHER INFORMATION: cyclic amino acid
<220> FEATURE:
<221> NAME/KEY: MISC_FEATURE
<222> LOCATION: (6)..(6)
<223> OTHER INFORMATION: D amino acid
<220> FEATURE:
<221> NAME/KEY: MISC_FEATURE
<222> LOCATION: (7)..(11)
<223> OTHER INFORMATION: cyclic amino acid
<220> FEATURE:
<221> NAME/KEY: MISC_FEATURE
<222> LOCATION: (11)..(11)
<223> OTHER INFORMATION: D amino acid

<400> SEQUENCE: 18

Glu Lys Arg Gly Asp Phe Lys Arg Gly Asp Phe
1               5                   10

<210> SEQ ID NO 19
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (5)..(5)
<223> OTHER INFORMATION: (DTPA)

<400> SEQUENCE: 19

Arg Gly Asp Phe Lys
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (5)..(5)
<223> OTHER INFORMATION: 2 (DTPA)

<400> SEQUENCE: 20

Arg Gly Asp Phe Lys
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: (N-DTPA-3-aminopropyl)
<220> FEATURE:
<221> NAME/KEY: MISC_FEATURE
<222> LOCATION: (4)..(4)
<223> OTHER INFORMATION: D amino acid

<400> SEQUENCE: 21

Arg Gly Asp Tyr Val
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: (d-N-2-Imadazolinyl)
<220> FEATURE:
<221> NAME/KEY: MISC_FEATURE
<222> LOCATION: (1)..(1)
<223> OTHER INFORMATION: Xaa = ornithine
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: (N-[2-[[[5-[carbonyl]-2-
     pyridinyl]hydrazono]methyl]-benzenesulfonic acid]-3-aminoprophyl)
<220> FEATURE:
<221> NAME/KEY: MISC_FEATURE
<222> LOCATION: (4)..(4)
<223> OTHER INFORMATION: D amino acid

<400> SEQUENCE: 22

Xaa Gly Asp Tyr Val
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(5)
<223> OTHER INFORMATION: (N-[2-[[[5-[carbonyl]-2-
     pyridinyl]hydrazono]methyl]-benzenesulfonic acid]-3-aminoprophyl)
<220> FEATURE:
<221> NAME/KEY: MISC_FEATURE
<222> LOCATION: (4)..(4)
<223> OTHER INFORMATION: D amino acid

<400> SEQUENCE: 23

Lys Gly Asp Tyr Val
1               5

<210> SEQ ID NO 24
```

```
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: (2-aminoethyl)
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (4)..(4)
<223> OTHER INFORMATION: (N-[2-[[[5-[carbonyl]-2-
      pyridinyl]hydrazono]methyl]-benzenesulfonic acid]-3-aminopropyl)

<400> SEQUENCE: 24

Cys Gly Asp Tyr Val
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
<223> OTHER INFORMATION: Homo
<220> FEATURE:
<221> NAME/KEY: MISC_FEATURE
<222> LOCATION: (4)..(4)
<223> OTHER INFORMATION: (N-[2-[[[5-[carbonyl]-2-
      pyridinyl]hydrazono]methyl]-benzenesulfonic acid]-3-aminopropyl)
<220> FEATURE:
<221> NAME/KEY: MISC_FEATURE
<222> LOCATION: (4)..(4)
<223> OTHER INFORMATION: D amino acid

<400> SEQUENCE: 25

Lys Gly Asp Tyr Val
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: (d-N-Benzylcarbamoyl)
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
<223> OTHER INFORMATION: Xaa = ornithine
<220> FEATURE:
<221> NAME/KEY: MISC_FEATURE
```

```
<222> LOCATION: (4)..(4)
<223> OTHER INFORMATION: D amino acid
<220> FEATURE:
<221> NAME/KEY: MISC_FEATURE
<222> LOCATION: (4)..(4)
<223> OTHER INFORMATION: (N-[2-[[[5-[carbonyl]-2-
      pyridinyl]hydrazono]methyl]-benzenesulfonic acid]-3-aminopropyl)

<400> SEQUENCE: 26

Xaa Gly Asp Tyr Val
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: (b-(2-benzimidazolylacetyl)
<220> FEATURE:
<221> NAME/KEY: MISC_FEATURE
<222> LOCATION: (1)..(1)
<223> OTHER INFORMATION: Xaa = 2,3-diaminopropionic acid
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: (N-[2-[[[5-[carbonyl]-2-
      pyridinyl]hydrazono]methyl]-benzenesulfonic acid]-3-aminopropyl)
<220> FEATURE:
<221> NAME/KEY: MISC_FEATURE
<222> LOCATION: (4)..(4)
<223> OTHER INFORMATION: D amino acid

<400> SEQUENCE: 27

Xaa Gly Asp Tyr Val
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: (d-N-2-Imidazolinyl)
<220> FEATURE:
<221> NAME/KEY: MISC_FEATURE
<222> LOCATION: (1)..(1)
<223> OTHER INFORMATION: Xaa = ornithine
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (5)..(5)
<223> OTHER INFORMATION: (N-[2-[[[5-[carbonyl]-2-
      pyridinyl]hydrazono]methyl]-benzensulfonic acid])

<400> SEQUENCE: 28

Xaa Gly Asp Phe Lys
```

1           5

<210> SEQ ID NO 29
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: (d-N-Benzylcarbamoyl)
<220> FEATURE:
<221> NAME/KEY: MISC_FEATURE
<222> LOCATION: (1)..(1)
<223> OTHER INFORMATION: Xaa = ornithine
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: (N-[2-[[[5-carbonyl]-2-
      pyridinyl]hydrazono]methyl]-benzenesulfonic acid])
<220> FEATURE:
<221> NAME/KEY: MISC_FEATURE
<222> LOCATION: (4)..(4)
<223> OTHER INFORMATION: D amino acid

<400> SEQUENCE: 29

Xaa Gly Asp Phe Lys
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (2)..(4)
<223> OTHER INFORMATION: D amino acid
<220> FEATURE:
<221> NAME/KEY: MISC_FEATURE
<222> LOCATION: (3)..(3)
<223> OTHER INFORMATION: (N-[2-[[[5-[carbonyl]-2-
      pyridinyl]hydrazono]methyl]-benzenesulfonic acid]-3-aminopropyl)

<400> SEQUENCE: 30

Lys Val Tyr Asp Gly
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: (d-N-Benzylcarbamoyl)
<220> FEATURE:
<221> NAME/KEY: MISC_FEATURE
<222> LOCATION: (1)..(1)
<223> OTHER INFORMATION: Xaa = ornithine
<220> FEATURE:
<221> NAME/KEY: MISC_FEATURE

```
<222> LOCATION: (1)..(5)
<223> OTHER INFORMATION: cyclic amino acid
<220> FEATURE:
<221> NAME/KEY: MISC_FEATURE
<222> LOCATION: (2)..(4)
<223> OTHER INFORMATION: D amino acid
<220> FEATURE:
<221> NAME/KEY: MISC_FEATURE
<222> LOCATION: (3)..(3)
<223> OTHER INFORMATION: (N-[2-[[[5-[carbonyl]-2-
      pyridinyl]hydrazono]methyl]-benzenesulfonic acid]-3-aminopropyl)

<400> SEQUENCE: 31

Xaa Val Tyr Asp Gly
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: (d-N-2-Imidazolinyl)
<220> FEATURE:
<221> NAME/KEY: MISC_FEATURE
<222> LOCATION: (1)..(1)
<223> OTHER INFORMATION: Xaa = ornithine
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (2)..(4)
<223> OTHER INFORMATION: D amino acid
<220> FEATURE:
<221> NAME/KEY: MISC_FEATURE
<222> LOCATION: (3)..(3)
<223> OTHER INFORMATION: (N-[2-[[[5-[carbonyl]-2-
      pyridinyl]hydrazono]methyl]-benzenesulfonic acid]-3-aminopropyl)

<400> SEQUENCE: 32

Xaa Val Tyr Asp Gly
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 99mTc (tricine) (TPPTS)
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: (N-[[5-[carbonyl]-2-pyridinyl]diazenido]-3-
      aminopropyl)
<220> FEATURE:
<221> NAME/KEY: MISC_FEATURE
<222> LOCATION: (4)..(4)
<223> OTHER INFORMATION: D amino acid

<400> SEQUENCE: 33

Arg Gly Asp Tyr Val
```

```
<210> SEQ ID NO 34
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 99mTc (tricine) (TPPMS)
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (2)..(4)
<223> OTHER INFORMATION: D amino acid
<220> FEATURE:
<221> NAME/KEY: MISC_FEATURE
<222> LOCATION: (3)..(3)
<223> OTHER INFORMATION: (N-[[5-[carbonyl]-2-pyridinyl]diazenido]-3-
      aminopropyl)

<400> SEQUENCE: 34

Arg Val Tyr Asp Gly
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 99mTc (tricine) (TPPDS)
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (2)..(4)
<223> OTHER INFORMATION: D amino acid
<220> FEATURE:
<221> NAME/KEY: MISC_FEATURE
<222> LOCATION: (3)..(3)
<223> OTHER INFORMATION: (N-[[5-[carbonyl]-2-pyridinyl]diazenido]-3-
      aminopropyl)

<400> SEQUENCE: 35

Arg Val Tyr Asp Gly
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 99mTc (tricine) (TPPTS)
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
```

```
<222> LOCATION: (2)..(4)
<223> OTHER INFORMATION: D amino acid
<220> FEATURE:
<221> NAME/KEY: MISC_FEATURE
<222> LOCATION: (3)..(3)
<223> OTHER INFORMATION: (N-[[5-carbonyl]-2-pyridinyl]diazenido]-3-
      aminopropyl)

<400> SEQUENCE: 36

Arg Val Tyr Asp Gly
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 99mTc (tricine) (TPPTS)
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (5)..(5)
<223> OTHER INFORMATION: (N-[[5-[carbonyl]-2-pyridinyl]diazenido])

<400> SEQUENCE: 37

Arg Gly Asp Phe Lys
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 99mTc (tricine) (TPPTS)
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (5)..(5)
<223> OTHER INFORMATION: (N-[[5-[carbonyl]-2-pyridinyl]diazenido])

<400> SEQUENCE: 38

Arg Gly Asp Tyr Lys
1               5

<210> SEQ ID NO 39
<211> LENGTH: 12
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: MISC_FEATURE
<222> LOCATION: (1)..(1)
<223> OTHER INFORMATION: 99mTc (tricine) (TPPTS)
<220> FEATURE:
<221> NAME/KEY: MISC_FEATURE
<222> LOCATION: (1)..(1)
<223> OTHER INFORMATION: ([2-[[[5-[carbonyl]-2-
      pyridinyl]hydrazono]methyl]-benzenesulfonic acid]
<220> FEATURE:
<221> NAME/KEY: MISC_FEATURE
<222> LOCATION: (3)..(7)
<223> OTHER INFORMATION: cyclic amino acid
<220> FEATURE:
<221> NAME/KEY: MISC_FEATURE
<222> LOCATION: (7)..(7)
<223> OTHER INFORMATION: D amino acid
<220> FEATURE:
<221> NAME/KEY: MISC_FEATURE
<222> LOCATION: (8)..(12)
<223> OTHER INFORMATION: cyclic amino acid
<220> FEATURE:
<221> NAME/KEY: MISC_FEATURE
<222> LOCATION: (12)..(12)
<223> OTHER INFORMATION: D amino acid

<400> SEQUENCE: 39

Phe Glu Lys Arg Gly Asp Phe Lys Arg Gly Asp Phe
1               5                   10

<210> SEQ ID NO 40
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 99mTc (tricine) (TPPTS)
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: Xaa = naphthyl alanine
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (5)..(5)
<223> OTHER INFORMATION: ([2-[[[5-[carbonyl]-2-
      pyridinyl]hydrazono]methyl]-benzenesulfonic acid])

<400> SEQUENCE: 40

Arg Gly Asp Xaa Lys
1               5

<210> SEQ ID NO 41
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 99mTc (tricine) (TPPTS)
<220> FEATURE:
<221> NAME/KEY: MISC_FEATURE
<222> LOCATION: (1)..(1)
<223> OTHER INFORMATION: ([2-[[[5-[carbonyl]-2-
```

```
            pyridinyl]hydrazono]methyl]-benzenesulfonic acid]
<220> FEATURE:
<221> NAME/KEY: MISC_FEATURE
<222> LOCATION: (2)..(6)
<223> OTHER INFORMATION: cyclic amino acid
<220> FEATURE:
<221> NAME/KEY: MISC_FEATURE
<222> LOCATION: (6)..(6)
<223> OTHER INFORMATION: Xaa = naphthyl alanine
<220> FEATURE:
<221> NAME/KEY: MISC_FEATURE
<222> LOCATION: (6)..(6)
<223> OTHER INFORMATION: D amino acid
<220> FEATURE:
<221> NAME/KEY: MISC_FEATURE
<222> LOCATION: (7)..(11)
<223> OTHER INFORMATION: cyclic amino acid
<220> FEATURE:
<221> NAME/KEY: MISC_FEATURE
<222> LOCATION: (11)..(11)
<223> OTHER INFORMATION: Xaa = naphthyl alanine
<220> FEATURE:
<221> NAME/KEY: MISC_FEATURE
<222> LOCATION: (11)..(11)
<223> OTHER INFORMATION: D amino acid

<400> SEQUENCE: 41

Glu Lys Arg Gly Asp Xaa Lys Arg Gly Asp Xaa
1               5                   10

<210> SEQ ID NO 42
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 99mTc (tricine) (TPPTS)
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: (N-[[5-[carbonyl]-2-pyridinyl]diazenido]-18-
      amino-14-aza-4,7,10-oxy-15-oxo-octadecoyl)-3-aminopropyl)
<220> FEATURE:
<221> NAME/KEY: MISC_FEATURE
<222> LOCATION: (4)..(4)
<223> OTHER INFORMATION: D amino acid

<400> SEQUENCE: 42

Arg Gly Asp Tyr Val
1               5

<210> SEQ ID NO 43
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 99mTc (tricine) (TPPTS)
<220> FEATURE:
<221> NAME/KEY: MISC_FEATURE
<222> LOCATION: (1)..(1)
<223> OTHER INFORMATION: (N-[[5-[carbonyl]-2-pyridinyl]diazenido]
<220> FEATURE:
<221> NAME/KEY: MISC_FEATURE
<222> LOCATION: (2)..(6)
```

```
<223> OTHER INFORMATION: O cyclic amino acid
<220> FEATURE:
<221> NAME/KEY: MISC_FEATURE
<222> LOCATION: (6)..(6)
<223> OTHER INFORMATION: D amino acid
<220> FEATURE:
<221> NAME/KEY: MISC_FEATURE
<222> LOCATION: (7)..(11)
<223> OTHER INFORMATION: O cyclic amino acid
<220> FEATURE:
<221> NAME/KEY: MISC_FEATURE
<222> LOCATION: (11)..(11)
<223> OTHER INFORMATION: D amino acid

<400> SEQUENCE: 43

Glu Lys Arg Gly Asp Phe Lys Arg Gly Asp Phe
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 99mTc (tricine) (TPPTS)
<220> FEATURE:
<221> NAME/KEY: MISC_FEATURE
<222> LOCATION: (1)..(1)
<223> OTHER INFORMATION: N-[[5-[carbonyl]-2-pyridinyl]diazenido]
<220> FEATURE:
<221> NAME/KEY: MISC_FEATURE
<222> LOCATION: (2)..(2)
<223> OTHER INFORMATION: (3-aminopropyl)
<220> FEATURE:
<221> NAME/KEY: MISC_FEATURE
<222> LOCATION: (2)..(2)
<223> OTHER INFORMATION: D amino acid
<220> FEATURE:
<221> NAME/KEY: MISC_FEATURE
<222> LOCATION: (2)..(6)
<223> OTHER INFORMATION: O cyclic amino acid
<220> FEATURE:
<221> NAME/KEY: MISC_FEATURE
<222> LOCATION: (7)..(7)
<223> OTHER INFORMATION: (3-aminopropyl)
<220> FEATURE:
<221> NAME/KEY: MISC_FEATURE
<222> LOCATION: (7)..(7)
<223> OTHER INFORMATION: D amino acid
<220> FEATURE:
<221> NAME/KEY: MISC_FEATURE
<222> LOCATION: (7)..(11)
<223> OTHER INFORMATION: O cyclic amino acid

<400> SEQUENCE: 44

Glu Tyr Val Arg Gly Asp Tyr Val Arg Gly Asp
1               5                   10

<210> SEQ ID NO 45
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 99mTc (tricine) (TPPTS)
<220> FEATURE:
<221> NAME/KEY: MISC_FEATURE
<222> LOCATION: (1)..(5)
<223> OTHER INFORMATION: cyclic amino acid
```

```
<220> FEATURE:
<221> NAME/KEY: MISC_FEATURE
<222> LOCATION: (4)..(4)
<223> OTHER INFORMATION: (N-[[5-[carbonyl]-2-pyridinyl]diazenido])
<220> FEATURE:
<221> NAME/KEY: MISC_FEATURE
<222> LOCATION: (5)..(5)
<223> OTHER INFORMATION: D amino acid

<400> SEQUENCE: 45

Arg Gly Asp Lys Val
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 99mTc (tricine) (TPPTS)
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(3)
<223> OTHER INFORMATION: D amino acid
<220> FEATURE:
<221> NAME/KEY: MISC_FEATURE
<222> LOCATION: (2)..(2)
<223> OTHER INFORMATION: ([2-[[[5-[carbonyl]-2-
     pyridinyl]hydrazono]methyl]-benzenesulfonic acid])

<400> SEQUENCE: 46

Lys Phe Asp Gly Arg
1               5

<210> SEQ ID NO 47
<211> LENGTH: 11
<212> TYPE: PRT
<213> ORGANISM: Artificial Sequence
<220> FEATURE:
<223> OTHER INFORMATION: Synthethic Construct
<220> FEATURE:
<221> NAME/KEY: MISC_FEATURE
<222> LOCATION: (1)..(1)
<223> OTHER INFORMATION: 99mTc (tricine) (TPPTS)
<220> FEATURE:
<221> NAME/KEY: MISC_FEATURE
<222> LOCATION: (1)..(1)
<223> OTHER INFORMATION: [2-[[[5-carbonyl]-2-
     pyridinyl]hydrazono]methyl]-benzenesulfonic acid]
<220> FEATURE:
<221> NAME/KEY: MISC_FEATURE
<222> LOCATION: (2)..(4)
<223> OTHER INFORMATION: D amino acid
<220> FEATURE:
<221> NAME/KEY: MISC_FEATURE
<222> LOCATION: (2)..(6)
<223> OTHER INFORMATION: cyclic amino acid
<220> FEATURE:
<221> NAME/KEY: MISC_FEATURE
<222> LOCATION: (7)..(11)
<223> OTHER INFORMATION: cyclic amino acid
<220> FEATURE:
<221> NAME/KEY: MISC_FEATURE
<222> LOCATION: (7)..(9)
<223> OTHER INFORMATION: D amino acid

<400> SEQUENCE: 47
```

```
Glu Lys Phe Asp Gly Arg Lys Phe Asp Gly Arg
1               5                   10
```

```
<210> SEQ ID NO 48
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 99mTc (tricine) (TPPTS)
<220> FEATURE:
<221> NAME/KEY: MISC_FEATURE
<222> LOCATION: (1)..(3)
<223> OTHER INFORMATION: D amino acid
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (2)..(2)
<223> OTHER INFORMATION: [2-[[[5-[carbony]-2-
      pyridinyl]hydrazono]methyl]-benzenesulfonic acid]

<400> SEQUENCE: 48

Phe Lys Asp Gly Arg
1               5
```

```
<210> SEQ ID NO 49
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 99mTc (tricine) (TPPTS)
<220> FEATURE:
<221> NAME/KEY: MISC_FEATURE
<222> LOCATION: (1)..(1)
<223> OTHER INFORMATION: a-N-methyl
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: Xaa = 2-aminothiazole-5-acetic acid or 2-
      aminothiazole-5-acetyl group
<220> FEATURE:
<221> NAME/KEY: MISC_FEATURE
<222> LOCATION: (5)..(5)
<223> OTHER INFORMATION: (N-[[5-[carbonyl]-2-pyridinyl]diazenido])
<220> FEATURE:
<221> NAME/KEY: MISC_FEATURE
<222> LOCATION: (5)..(5)
<223> OTHER INFORMATION: D amino acid

<400> SEQUENCE: 49

Arg Gly Asp Xaa Lys
1               5
```

```
<210> SEQ ID NO 50
<211> LENGTH: 5
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: MISC_FEATURE
<222> LOCATION: (1)..(1)
<223> OTHER INFORMATION: Xaa = citrulline
<220> FEATURE:
<221> NAME/KEY: MISC_FEATURE
<222> LOCATION: (1)..(1)
<223> OTHER INFORMATION: 99mTc (tricine) (TPPTS)
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (5)..(5)
<223> OTHER INFORMATION: ([2-[[[5-carbonyl]-2-
     pyridinyl]hydrazono]methyl]-benzenesulfonic acid])

<400> SEQUENCE: 50

Xaa Gly Asp Phe Lys
1               5

<210> SEQ ID NO 51
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 99mTC (tricine) (1,2,4-triazole)
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: (N-[[5-[carbonyl]-2-pyridinyl]diazenido]-3-
     aminopropyl)
<220> FEATURE:
<221> NAME/KEY: MISC_FEATURE
<222> LOCATION: (4)..(4)
<223> OTHER INFORMATION: D amino acid

<400> SEQUENCE: 51

Arg Gly Asp Tyr Val
1               5

<210> SEQ ID NO 52
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: (DOTA-111In)
<220> FEATURE:
<221> NAME/KEY: MISC_FEATURE
<222> LOCATION: (2)..(6)
<223> OTHER INFORMATION: cyclic amino acid
<220> FEATURE:
<221> NAME/KEY: MISC_FEATURE
<222> LOCATION: (6)..(6)
<223> OTHER INFORMATION: D amino acid
<220> FEATURE:
<221> NAME/KEY: MISC_FEATURE
<222> LOCATION: (7)..(11)
<223> OTHER INFORMATION: cyclic amino acid
```

```
<220> FEATURE:
<221> NAME/KEY: MISC_FEATURE
<222> LOCATION: (11)..(11)
<223> OTHER INFORMATION: D amino acid

<400> SEQUENCE: 52

Glu Lys Arg Gly Asp Phe Lys Arg Gly Asp Phe
1               5                   10

<210> SEQ ID NO 53
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (5)..(5)
<223> OTHER INFORMATION: (DTPA-111In)

<400> SEQUENCE: 53

Arg Gly Asp Phe Lys
1               5

<210> SEQ ID NO 54
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (5)..(5)
<223> OTHER INFORMATION: 2 (DTPA-111In)

<400> SEQUENCE: 54

Arg Gly Asp Phe Lys
1               5

<210> SEQ ID NO 55
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (5)..(5)
<223> OTHER INFORMATION: (DTPA-153Sm)
```

```
<400> SEQUENCE: 55

Arg Gly Asp Phe Lys
1               5

<210> SEQ ID NO 56
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (5)..(5)
<223> OTHER INFORMATION: 2 (DTPA-153Sm)

<400> SEQUENCE: 56

Arg Gly Asp Phe Lys
1               5

<210> SEQ ID NO 57
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: (N-DTPA(153Sm)-3-aminopropyl)
<220> FEATURE:
<221> NAME/KEY: MISC_FEATURE
<222> LOCATION: (4)..(4)
<223> OTHER INFORMATION: D amino acid

<400> SEQUENCE: 57

Arg Gly Asp Tyr Val
1               5

<210> SEQ ID NO 58
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (5)..(5)
<223> OTHER INFORMATION: (DTPA-177Lu)

<400> SEQUENCE: 58

Arg Gly Asp Phe Lys
```

<210> SEQ ID NO 59
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: (DOTA-177Lu)
<220> FEATURE:
<221> NAME/KEY: MISC_FEATURE
<222> LOCATION: (2)..(6)
<223> OTHER INFORMATION: cyclic amino acid
<220> FEATURE:
<221> NAME/KEY: MISC_FEATURE
<222> LOCATION: (6)..(6)
<223> OTHER INFORMATION: D amino acid
<220> FEATURE:
<221> NAME/KEY: MISC_FEATURE
<222> LOCATION: (7)..(11)
<223> OTHER INFORMATION: cyclic amino acid
<220> FEATURE:
<221> NAME/KEY: MISC_FEATURE
<222> LOCATION: (11)..(11)
<223> OTHER INFORMATION: D amino acid

<400> SEQUENCE: 59

Glu Lys Arg Gly Asp Phe Lys Arg Gly Asp Phe
1               5                   10

<210> SEQ ID NO 60
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (5)..(5)
<223> OTHER INFORMATION: 2 (DTPA-177Lu)

<400> SEQUENCE: 60

Arg Gly Asp Phe Lys
1               5

<210> SEQ ID NO 61
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: (N-DTPA(177Lu)-3-aminopropyl
<220> FEATURE:
<221> NAME/KEY: MISC_FEATURE
<222> LOCATION: (4)..(4)
<223> OTHER INFORMATION: D amino acid

```
<400> SEQUENCE: 61

Arg Gly Asp Tyr Val
1               5

<210> SEQ ID NO 62
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: (DOTA-90Y)
<220> FEATURE:
<221> NAME/KEY: MISC_FEATURE
<222> LOCATION: (2)..(6)
<223> OTHER INFORMATION: cyclic amino acid
<220> FEATURE:
<221> NAME/KEY: MISC_FEATURE
<222> LOCATION: (6)..(6)
<223> OTHER INFORMATION: D amino acid
<220> FEATURE:
<221> NAME/KEY: MISC_FEATURE
<222> LOCATION: (7)..(11)
<223> OTHER INFORMATION: cyclic amino acid
<220> FEATURE:
<221> NAME/KEY: MISC_FEATURE
<222> LOCATION: (11)..(11)
<223> OTHER INFORMATION: D amino acid

<400> SEQUENCE: 62

Glu Lys Arg Gly Asp Phe Lys Arg Gly Asp Phe
1               5                   10

<210> SEQ ID NO 63
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: (N-DTPA(Gd(III)-3-aminopropyl)
<220> FEATURE:
<221> NAME/KEY: MISC_FEATURE
<222> LOCATION: (4)..(4)
<223> OTHER INFORMATION: D amino acid

<400> SEQUENCE: 63

Arg Gly Asp Tyr Val
1               5

<210> SEQ ID NO 64
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 1-(1,2-Dipalmitoyl-sn-glycero-3-
      phosphoethanolamino)-12
<220> FEATURE:
<221> NAME/KEY: MISC_FEATURE
<222> LOCATION: (1)..(5)
```

-continued

```
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (5)..(5)
<223> OTHER INFORMATION: dodecane-1,12-dione

<400> SEQUENCE: 64

Arg Gly Asp Phe Lys
1               5

<210> SEQ ID NO 65
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 1-(1,2-Dipalmitoyl-sn-glycero-3-
      phosphoethanolamino)-12-(omega-amino-PEG3400-alpha-carbonyl)
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (5)..(5)
<223> OTHER INFORMATION: dodecane-1,12-dione

<400> SEQUENCE: 65

Arg Gly Asp Phe Lys
1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 1-(1,2-Dipalmitoyl-sn-glycero-3-
      phosphoethanolamino)-12-(omega-amino-PEG3400-alpha-carbonyl)
<220> FEATURE:
<221> NAME/KEY: MISC_FEATURE
<222> LOCATION: (2)..(6)
<223> OTHER INFORMATION: cyclic amino acid
<220> FEATURE:
<221> NAME/KEY: MISC_FEATURE
<222> LOCATION: (5)..(5)
<223> OTHER INFORMATION: D amino acid
<220> FEATURE:
<221> NAME/KEY: MISC_FEATURE
<222> LOCATION: (6)..(6)
<223> OTHER INFORMATION: 2)-Dodecane-1,12-dione

<400> SEQUENCE: 66

Glu Arg Gly Asp Phe Lys
1               5

<210> SEQ ID NO 67
<211> LENGTH: 16
<212> TYPE: PRT
```

```
<213> ORGANISM: Artificial Sequence
<220> FEATURE:
<223> OTHER INFORMATION: Synthetic Construct

<400> SEQUENCE: 67

Met Trp Tyr Arg Pro Asp Leu Asp Glu Arg Lys Gln Gln Lys Arg Glu
1               5                   10                  15

<210> SEQ ID NO 68
<211> LENGTH: 18
<212> TYPE: PRT
<213> ORGANISM: Artificial Sequence
<220> FEATURE:
<223> OTHER INFORMATION: Synthetic Construct

<400> SEQUENCE: 68

Ala Gln Leu Ala Gly Glu Cys Arg Glu Asn Val Cys Met Gly Ile Glu
1               5                   10                  15

Gly Arg

<210> SEQ ID NO 69
<211> LENGTH: 8
<212> TYPE: PRT
<213> ORGANISM: Artificial Sequence
<220> FEATURE:
<223> OTHER INFORMATION: Synthetic Construct

<400> SEQUENCE: 69

Ala Pro Ser Gly His Tyr Lys Gly
1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic Construct

<400> SEQUENCE: 70

Lys Arg Thr Gly Gln Tyr Lys Leu
1               5

<210> SEQ ID NO 71
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid

<400> SEQUENCE: 71

Arg Gly Asp Arg Gly Asp
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(6)
<223> OTHER INFORMATION: cyclic amino acid
<220> FEATURE:
```

```
<221> NAME/KEY: MISC_FEATURE
<222> LOCATION: (6)..(6)
<223> OTHER INFORMATION: D amino acid

<400> SEQUENCE: 72

Arg Gly Asp Arg Gly Asp
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic Construct

<400> SEQUENCE: 73

Arg Gly Asp Arg Gly Asp
1               5

<210> SEQ ID NO 74
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (5)..(5)
<223> OTHER INFORMATION: Xaa = methoxy-trimethylbenzenesulfonyl

<400> SEQUENCE: 74

Ala Arg Gly Asp Xaa
1               5

<210> SEQ ID NO 75
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(11)
<223> OTHER INFORMATION: cyclic amino acid
<220> FEATURE:
<221> NAME/KEY: MISC_FEATURE
<222> LOCATION: (7)..(7)
<223> OTHER INFORMATION: Xaa = beta-turn dipeptide

<400> SEQUENCE: 75

Arg Gly Asp Val Gly Ser Xaa Ser Gly Val Ala
1               5                   10

<210> SEQ ID NO 76
<211> LENGTH: 9
<212> TYPE: PRT
<213> ORGANISM: Artificial Sequence
<220> FEATURE:
<223> OTHER INFORMATION: Synthetic Construct

<400> SEQUENCE: 76

Cys Asp Cys Arg Gly Asp Cys Phe Cys
1               5

<210> SEQ ID NO 77
```

```
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid

<400> SEQUENCE: 77

Cys Asn Gly Asp Cys
1               5

<210> SEQ ID NO 78
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: tosyl
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (3)..(3)
<223> OTHER INFORMATION: O-benzyl
<220> FEATURE:
<221> NAME/KEY: MISC_FEATURE
<222> LOCATION: (4)..(4)
<223> OTHER INFORMATION: (N-Cbz-3-aminopropyl)
<220> FEATURE:
<221> NAME/KEY: MISC_FEATURE
<222> LOCATION: (4)..(4)
<223> OTHER INFORMATION: D amino acid

<400> SEQUENCE: 78

Arg Gly Asp Tyr Val
1               5

<210> SEQ ID NO 79
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = t-butyloxycarbonyl
<220> FEATURE:
<221> NAME/KEY: MISC_FEATURE
<222> LOCATION: (2)..(2)
<223> OTHER INFORMATION: O-benzyl
<220> FEATURE:
<221> NAME/KEY: MISC_FEATURE
<222> LOCATION: (3)..(3)
<223> OTHER INFORMATION: (N-Cbz-aminopropyl)
<220> FEATURE:
<221> NAME/KEY: MISC_FEATURE
<222> LOCATION: (3)..(3)
<223> OTHER INFORMATION: D amino acid
<220> FEATURE:
<221> NAME/KEY: MISC_FEATURE
<222> LOCATION: (5)..(5)
<223> OTHER INFORMATION: tosyl

<400> SEQUENCE: 79

Xaa Asp Tyr Val Arg Gly
```

1               5

<210> SEQ ID NO 80
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: (3-aminopropyl)
<220> FEATURE:
<221> NAME/KEY: MISC_FEATURE
<222> LOCATION: (4)..(4)
<223> OTHER INFORMATION: D amino acid

<400> SEQUENCE: 80

Arg Gly Asp Tyr Val
1               5

<210> SEQ ID NO 81
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (4)..(4)
<223> OTHER INFORMATION: (3-aminopropyl)

<400> SEQUENCE: 81

Arg Gly Asp Tyr Val
1               5

<210> SEQ ID NO 82
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (4)..(4)
<223> OTHER INFORMATION: (3-(3-(N-(3-(2-(2-(3-
      (amino)propoxy)ethoxy)ethoxy)propyl)carbamoyl)-propanamido)propyl)

<400> SEQUENCE: 82

Arg Gly Asp Tyr Val
1               5

```
<210> SEQ ID NO 83
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (4)..(4)
<223> OTHER INFORMATION: ((N-[2-[[[5-carbonyl]-2-
      pyridinyl]hydrazono]methyl]-benzenesulfonic acid]-18-amino-14-aza-
      4,7,10-oxy-15-oxo-octadecoyl)-3-aminopropyl)

<400> SEQUENCE: 83

Arg Gly Asp Tyr Val
1               5

<210> SEQ ID NO 84
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = t-butyloxycarbonyl
<220> FEATURE:
<221> NAME/KEY: MISC_FEATURE
<222> LOCATION: (3)..(3)
<223> OTHER INFORMATION: D amino acid
<220> FEATURE:
<221> NAME/KEY: MISC_FEATURE
<222> LOCATION: (3)..(3)
<223> OTHER INFORMATION: (3-aminopropyl)
<220> FEATURE:
<221> NAME/KEY: MISC_FEATURE
<222> LOCATION: (3)..(7)
<223> OTHER INFORMATION: cyclic amino acid
<220> FEATURE:
<221> NAME/KEY: MISC_FEATURE
<222> LOCATION: (8)..(12)
<223> OTHER INFORMATION: cyclic amino acid
<220> FEATURE:
<221> NAME/KEY: MISC_FEATURE
<222> LOCATION: (8)..(8)
<223> OTHER INFORMATION: D amino acid
<220> FEATURE:
<221> NAME/KEY: MISC_FEATURE
<222> LOCATION: (8)..(8)
<223> OTHER INFORMATION: (3-aminopropyl)

<400> SEQUENCE: 84

Xaa Glu Tyr Val Arg Gly Asp Tyr Val Arg Gly Asp
1               5                   10

<210> SEQ ID NO 85
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
```

```
<221> NAME/KEY: MISC_FEATURE
<222> LOCATION: (1)..(1)
<223> OTHER INFORMATION: D amino acid
<220> FEATURE:
<221> NAME/KEY: MISC_FEATURE
<222> LOCATION: (1)..(1)
<223> OTHER INFORMATION: (3-aminopropyl)

<400> SEQUENCE: 85

Tyr Val Arg Gly Asp
1               5

<210> SEQ ID NO 86
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(6)
<223> OTHER INFORMATION: cyclic amino acid
<220> FEATURE:
<221> NAME/KEY: MISC_FEATURE
<222> LOCATION: (2)..(2)
<223> OTHER INFORMATION: D amino acid
<220> FEATURE:
<221> NAME/KEY: MISC_FEATURE
<222> LOCATION: (2)..(2)
<223> OTHER INFORMATION: (3-aminopropyl)
<220> FEATURE:
<221> NAME/KEY: MISC_FEATURE
<222> LOCATION: (7)..(11)
<223> OTHER INFORMATION: cyclic amino acid
<220> FEATURE:
<221> NAME/KEY: MISC_FEATURE
<222> LOCATION: (7)..(7)
<223> OTHER INFORMATION: D amino acid
<220> FEATURE:
<221> NAME/KEY: MISC_FEATURE
<222> LOCATION: (7)..(7)
<223> OTHER INFORMATION: (3-aminopropyl)

<400> SEQUENCE: 86

Glu Tyr Val Arg Gly Asp Tyr Val Arg Gly Asp
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = t-butyloxycarbonyl
<220> FEATURE:
<221> NAME/KEY: MISC_FEATURE
<222> LOCATION: (3)..(7)
<223> OTHER INFORMATION: cyclic amino acid
<220> FEATURE:
<221> NAME/KEY: MISC_FEATURE
<222> LOCATION: (3)..(3)
<223> OTHER INFORMATION: D amino acid
<220> FEATURE:
<221> NAME/KEY: MISC_FEATURE
<222> LOCATION: (3)..(3)
<223> OTHER INFORMATION: (3-aminopropyl)
<220> FEATURE:
<221> NAME/KEY: MISC_FEATURE
<222> LOCATION: (8)..(12)
<223> OTHER INFORMATION: cyclic amino acid
<220> FEATURE:
<221> NAME/KEY: MISC_FEATURE
```

```
<222> LOCATION: (8)..(8)
<223> OTHER INFORMATION: D amino acid
<220> FEATURE:
<221> NAME/KEY: MISC_FEATURE
<222> LOCATION: (8)..(8)
<223> OTHER INFORMATION: (3-aminopropyl)

<400> SEQUENCE: 87

Xaa Glu Tyr Val Arg Gly Asp Tyr Val Arg Gly Asp
 1               5                  10

<210> SEQ ID NO 88
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: D amino acid
<220> FEATURE:
<221> NAME/KEY: MISC_FEATURE
<222> LOCATION: (2)..(2)
<223> OTHER INFORMATION: (3-aminopropyl)
<220> FEATURE:
<221> NAME/KEY: MISC_FEATURE
<222> LOCATION: (2)..(6)
<223> OTHER INFORMATION: cyclic amino acid
<220> FEATURE:
<221> NAME/KEY: MISC_FEATURE
<222> LOCATION: (7)..(7)
<223> OTHER INFORMATION: D amino acid
<220> FEATURE:
<221> NAME/KEY: MISC_FEATURE
<222> LOCATION: (7)..(7)
<223> OTHER INFORMATION: (3-aminopropyl)
<220> FEATURE:
<221> NAME/KEY: MISC_FEATURE
<222> LOCATION: (7)..(11)
<223> OTHER INFORMATION: cyclic amino acid

<400> SEQUENCE: 88

Glu Tyr Val Arg Gly Asp Tyr Val Arg Gly Asp
 1               5                  10

<210> SEQ ID NO 89
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
<223> OTHER INFORMATION: tosyl
<220> FEATURE:
<221> NAME/KEY: MISC_FEATURE
<222> LOCATION: (3)..(3)
<223> OTHER INFORMATION: O-benzyl
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (4)..(4)
<223> OTHER INFORMATION: Benzyl
<220> FEATURE:
<221> NAME/KEY: MISC_FEATURE
<222> LOCATION: (5)..(5)
```

```
<223> OTHER INFORMATION: Carbobenzyloxy

<400> SEQUENCE: 89

Arg Gly Asp Tyr Lys
1               5

<210> SEQ ID NO 90
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = t-butyloxycarbonyl
<220> FEATURE:
<221> NAME/KEY: MISC_FEATURE
<222> LOCATION: (2)..(2)
<223> OTHER INFORMATION: O-benzyl
<220> FEATURE:
<221> NAME/KEY: MISC_FEATURE
<222> LOCATION: (3)..(3)
<223> OTHER INFORMATION: D amino acid
<220> FEATURE:
<221> NAME/KEY: MISC_FEATURE
<222> LOCATION: (3)..(3)
<223> OTHER INFORMATION: Benzyl
<220> FEATURE:
<221> NAME/KEY: MISC_FEATURE
<222> LOCATION: (4)..(4)
<223> OTHER INFORMATION: Carbobenzyloxy
<220> FEATURE:
<221> NAME/KEY: MISC_FEATURE
<222> LOCATION: (5)..(5)
<223> OTHER INFORMATION: tosyl

<400> SEQUENCE: 90

Xaa Asp Tyr Lys Arg Gly
1               5

<210> SEQ ID NO 91
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid

<400> SEQUENCE: 91

Arg Gly Asp Tyr Lys
1               5

<210> SEQ ID NO 92
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
```

```
<223> OTHER INFORMATION: tosyl
<220> FEATURE:
<221> NAME/KEY: MISC_FEATURE
<222> LOCATION: (3)..(3)
<223> OTHER INFORMATION: O-benzyl
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (5)..(5)
<223> OTHER INFORMATION: Carbobenzyloxy

<400> SEQUENCE: 92

Arg Gly Asp Phe Lys
1               5

<210> SEQ ID NO 93
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = t-butyloxycarbonyl
<220> FEATURE:
<221> NAME/KEY: MISC_FEATURE
<222> LOCATION: (2)..(2)
<223> OTHER INFORMATION: O-benzyl
<220> FEATURE:
<221> NAME/KEY: MISC_FEATURE
<222> LOCATION: (3)..(3)
<223> OTHER INFORMATION: D amino acid
<220> FEATURE:
<221> NAME/KEY: MISC_FEATURE
<222> LOCATION: (4)..(4)
<223> OTHER INFORMATION: Carbobenzyloxy
<220> FEATURE:
<221> NAME/KEY: MISC_FEATURE
<222> LOCATION: (5)..(5)
<223> OTHER INFORMATION: tosyl

<400> SEQUENCE: 93

Xaa Asp Phe Lys Arg Gly
1               5

<210> SEQ ID NO 94
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid

<400> SEQUENCE: 94

Arg Gly Asp Phe Lys
1               5

<210> SEQ ID NO 95
<211> LENGTH: 12
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = t-butyloxycarbonyl
<220> FEATURE:
<221> NAME/KEY: MISC_FEATURE
<222> LOCATION: (3)..(7)
<223> OTHER INFORMATION: cyclic amino acid
<220> FEATURE:
<221> NAME/KEY: MISC_FEATURE
<222> LOCATION: (7)..(7)
<223> OTHER INFORMATION: D amino acid
<220> FEATURE:
<221> NAME/KEY: MISC_FEATURE
<222> LOCATION: (8)..(12)
<223> OTHER INFORMATION: cyclic amino acid
<220> FEATURE:
<221> NAME/KEY: MISC_FEATURE
<222> LOCATION: (12)..(12)
<223> OTHER INFORMATION: D amino acid

<400> SEQUENCE: 95

Xaa Glu Lys Arg Gly Asp Phe Lys Arg Gly Asp Phe
1               5                   10

<210> SEQ ID NO 96
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (5)..(5)
<223> OTHER INFORMATION: D amino acid

<400> SEQUENCE: 96

Lys Arg Gly Asp Phe
1               5

<210> SEQ ID NO 97
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(6)
<223> OTHER INFORMATION: cyclic amino acid
<220> FEATURE:
<221> NAME/KEY: MISC_FEATURE
<222> LOCATION: (6)..(6)
<223> OTHER INFORMATION: D amino acid
<220> FEATURE:
<221> NAME/KEY: MISC_FEATURE
<222> LOCATION: (7)..(11)
<223> OTHER INFORMATION: cyclic amino acid
<220> FEATURE:
<221> NAME/KEY: MISC_FEATURE
<222> LOCATION: (11)..(11)
<223> OTHER INFORMATION: D amino acid

<400> SEQUENCE: 97

Glu Lys Arg Gly Asp Phe Lys Arg Gly Asp Phe
1               5                   10

<210> SEQ ID NO 98
```

```
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(7)
<223> OTHER INFORMATION: cyclic amino acid
<220> FEATURE:
<221> NAME/KEY: MISC_FEATURE
<222> LOCATION: (7)..(7)
<223> OTHER INFORMATION: D amino acid
<220> FEATURE:
<221> NAME/KEY: MISC_FEATURE
<222> LOCATION: (8)..(12)
<223> OTHER INFORMATION: cyclic amino acid
<220> FEATURE:
<221> NAME/KEY: MISC_FEATURE
<222> LOCATION: (12)..(12)
<223> OTHER INFORMATION: D amino acid

<400> SEQUENCE: 98

Phe Glu Lys Arg Gly Asp Phe Lys Arg Gly Asp Phe
1               5                   10

<210> SEQ ID NO 99
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: methoxy-trimethylbenzenesulfonyl
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (3)..(3)
<223> OTHER INFORMATION: t-butyl ester
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (4)..(4)
<223> OTHER INFORMATION: Xaa = naphthyl alanine
<220> FEATURE:
<221> NAME/KEY: MISC_FEATURE
<222> LOCATION: (5)..(5)
<223> OTHER INFORMATION: t-butyloxycarbonyl

<400> SEQUENCE: 99

Arg Gly Asp Xaa Lys
1               5

<210> SEQ ID NO 100
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: t-butyl ester
<220> FEATURE:
<221> NAME/KEY: MISC_FEATURE
<222> LOCATION: (2)..(2)
<223> OTHER INFORMATION: D amino acid
```

```
<220> FEATURE:
<221> NAME/KEY: MISC_FEATURE
<222> LOCATION: (2)..(2)
<223> OTHER INFORMATION: Xaa = naphthyl alanine
<220> FEATURE:
<221> NAME/KEY: MISC_FEATURE
<222> LOCATION: (3)..(3)
<223> OTHER INFORMATION: t-butyloxycarbonyl
<220> FEATURE:
<221> NAME/KEY: MISC_FEATURE
<222> LOCATION: (4)..(4)
<223> OTHER INFORMATION: methoxy-trimethylbenzenesulfonyl

<400> SEQUENCE: 100

Asp Xaa Lys Arg Gly
1               5

<210> SEQ ID NO 101
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: Xaa = naphthyl alanine
<220> FEATURE:
<221> NAME/KEY: MISC_FEATURE
<222> LOCATION: (4)..(4)
<223> OTHER INFORMATION: D amino acid

<400> SEQUENCE: 101

Arg Gly Asp Xaa Lys
1               5

<210> SEQ ID NO 102
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = t-butyloxycarbonyl
<220> FEATURE:
<221> NAME/KEY: MISC_FEATURE
<222> LOCATION: (3)..(7)
<223> OTHER INFORMATION: cyclic amino acid
<220> FEATURE:
<221> NAME/KEY: MISC_FEATURE
<222> LOCATION: (7)..(7)
<223> OTHER INFORMATION: Xaa = naphthyl alanine
<220> FEATURE:
<221> NAME/KEY: MISC_FEATURE
<222> LOCATION: (7)..(7)
<223> OTHER INFORMATION: D amino acid
<220> FEATURE:
<221> NAME/KEY: MISC_FEATURE
<222> LOCATION: (8)..(12)
<223> OTHER INFORMATION: cyclic amino acid
<220> FEATURE:
<221> NAME/KEY: MISC_FEATURE
<222> LOCATION: (12)..(12)
<223> OTHER INFORMATION: Xaa = naphthyl alanine
<220> FEATURE:
<221> NAME/KEY: MISC_FEATURE
<222> LOCATION: (12)..(12)
<223> OTHER INFORMATION: D amino acid
```

```
<400> SEQUENCE: 102

Xaa Glu Lys Arg Gly Asp Xaa Lys Arg Gly Asp Xaa
1               5                   10

<210> SEQ ID NO 103
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (5)..(5)
<223> OTHER INFORMATION: D amino acid
<220> FEATURE:
<221> NAME/KEY: MISC_FEATURE
<222> LOCATION: (5)..(5)
<223> OTHER INFORMATION: Xaa = naphthyl alanine

<400> SEQUENCE: 103

Lys Arg Gly Asp Xaa
1               5

<210> SEQ ID NO 104
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(6)
<223> OTHER INFORMATION: cyclic amino acid
<220> FEATURE:
<221> NAME/KEY: MISC_FEATURE
<222> LOCATION: (6)..(6)
<223> OTHER INFORMATION: Xaa = naphthyl alanine
<220> FEATURE:
<221> NAME/KEY: MISC_FEATURE
<222> LOCATION: (6)..(6)
<223> OTHER INFORMATION: D amino acid
<220> FEATURE:
<221> NAME/KEY: MISC_FEATURE
<222> LOCATION: (7)..(11)
<223> OTHER INFORMATION: cyclic amino acid
<220> FEATURE:
<221> NAME/KEY: MISC_FEATURE
<222> LOCATION: (11)..(11)
<223> OTHER INFORMATION: Xaa = naphthyl alanine
<220> FEATURE:
<221> NAME/KEY: MISC_FEATURE
<222> LOCATION: (11)..(11)
<223> OTHER INFORMATION: D amino acid

<400> SEQUENCE: 104

Glu Lys Arg Gly Asp Xaa Lys Arg Gly Asp Xaa
1               5                   10

<210> SEQ ID NO 105
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
```

<221> NAME/KEY: MISC_FEATURE
<222> LOCATION: (1)..(1)
<223> OTHER INFORMATION: tosyl
<220> FEATURE:
<221> NAME/KEY: MISC_FEATURE
<222> LOCATION: (3)..(3)
<223> OTHER INFORMATION: O-benzyl
<220> FEATURE:
<221> NAME/KEY: MISC_FEATURE
<222> LOCATION: (4)..(4)
<223> OTHER INFORMATION: Carbobenzyloxy
<220> FEATURE:
<221> NAME/KEY: MISC_FEATURE
<222> LOCATION: (5)..(5)
<223> OTHER INFORMATION: D amino acid

<400> SEQUENCE: 105

Arg Gly Asp Lys Val
1               5

<210> SEQ ID NO 106
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = t-butyloxycarbonyl
<220> FEATURE:
<221> NAME/KEY: MISC_FEATURE
<222> LOCATION: (2)..(2)
<223> OTHER INFORMATION: O-benzyl
<220> FEATURE:
<221> NAME/KEY: MISC_FEATURE
<222> LOCATION: (3)..(3)
<223> OTHER INFORMATION: Carbobenzyloxy
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (5)..(5)
<223> OTHER INFORMATION: tosyl

<400> SEQUENCE: 106

Xaa Asp Lys Val Arg Gly
1               5

<210> SEQ ID NO 107
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (5)..(5)
<223> OTHER INFORMATION: D amino acid

<400> SEQUENCE: 107

Arg Gly Asp Lys Val
1               5

<210> SEQ ID NO 108
<211> LENGTH: 12
<212> TYPE: PRT

```
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = t-butyloxycarbonyl
<220> FEATURE:
<221> NAME/KEY: MISC_FEATURE
<222> LOCATION: (3)..(7)
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (8)..(12)
<223> OTHER INFORMATION: cyclic amino acid
<220> FEATURE:
<221> NAME/KEY: MISC_FEATURE
<222> LOCATION: (9)..(9)
<223> OTHER INFORMATION: D amino acid

<400> SEQUENCE: 108

Xaa Glu Lys Val Arg Gly Asp Lys Val Arg Gly Asp
1               5                   10

<210> SEQ ID NO 109
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (2)..(2)
<223> OTHER INFORMATION: D amino acid

<400> SEQUENCE: 109

Lys Val Arg Gly Asp
1               5

<210> SEQ ID NO 110
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(6)
<223> OTHER INFORMATION: cyclic amino acid
<220> FEATURE:
<221> NAME/KEY: MISC_FEATURE
<222> LOCATION: (3)..(3)
<223> OTHER INFORMATION: D amino acid
<220> FEATURE:
<221> NAME/KEY: MISC_FEATURE
<222> LOCATION: (7)..(11)
<223> OTHER INFORMATION: cyclic amino acid
<220> FEATURE:
<221> NAME/KEY: MISC_FEATURE
<222> LOCATION: (8)..(8)
<223> OTHER INFORMATION: D amino acid

<400> SEQUENCE: 110

Glu Lys Val Arg Gly Asp Lys Val Arg Gly Asp
1               5                   10
```

```
<210> SEQ ID NO 111
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = t-butyloxycarbonyl
<220> FEATURE:
<221> NAME/KEY: MISC_FEATURE
<222> LOCATION: (3)..(7)
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (8)..(12)
<223> OTHER INFORMATION: cyclic amino acid
<220> FEATURE:
<221> NAME/KEY: MISC_FEATURE
<222> LOCATION: (9)..(9)
<223> OTHER INFORMATION: D amino acid

<400> SEQUENCE: 111

Xaa Glu Lys Val Arg Gly Asp Lys Val Arg Gly Asp
1               5                   10

<210> SEQ ID NO 112
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
<223> OTHER INFORMATION: tosyl
<220> FEATURE:
<221> NAME/KEY: MISC_FEATURE
<222> LOCATION: (2)..(4)
<223> OTHER INFORMATION: D amino acid
<220> FEATURE:
<221> NAME/KEY: MISC_FEATURE
<222> LOCATION: (3)..(3)
<223> OTHER INFORMATION: N-Carbobenzyloxy-3-aminopropyl
<220> FEATURE:
<221> NAME/KEY: MISC_FEATURE
<222> LOCATION: (4)..(4)
<223> OTHER INFORMATION: O-benzyl

<400> SEQUENCE: 112

Arg Val Tyr Asp Gly
1               5

<210> SEQ ID NO 113
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = t-butyloxycarbonyl
<220> FEATURE:
<221> NAME/KEY: MISC_FEATURE
```

```
<222> LOCATION: (2)..(2)
<223> OTHER INFORMATION: tosyl
<220> FEATURE:
<221> NAME/KEY: MISC_FEATURE
<222> LOCATION: (3)..(5)
<223> OTHER INFORMATION: D amino acid
<220> FEATURE:
<221> NAME/KEY: MISC_FEATURE
<222> LOCATION: (4)..(4)
<223> OTHER INFORMATION: N-Carbobenzyloxy-aminopropyl
<220> FEATURE:
<221> NAME/KEY: MISC_FEATURE
<222> LOCATION: (5)..(5)
<223> OTHER INFORMATION: O-benzyl

<400> SEQUENCE: 113

Xaa Arg Val Tyr Asp Gly
1               5

<210> SEQ ID NO 114
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (2)..(4)
<223> OTHER INFORMATION: D amino acid
<220> FEATURE:
<221> NAME/KEY: MISC_FEATURE
<222> LOCATION: (3)..(3)
<223> OTHER INFORMATION: 3-aminopropyl

<400> SEQUENCE: 114

Arg Val Tyr Asp Gly
1               5

<210> SEQ ID NO 115
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
<223> OTHER INFORMATION: Carbobenzyloxy
<220> FEATURE:
<221> NAME/KEY: MISC_FEATURE
<222> LOCATION: (1)..(3)
<223> OTHER INFORMATION: D amino acid
<220> FEATURE:
<221> NAME/KEY: MISC_FEATURE
<222> LOCATION: (3)..(3)
<223> OTHER INFORMATION: O-benzyl
<220> FEATURE:
<221> NAME/KEY: MISC_FEATURE
<222> LOCATION: (5)..(5)
<223> OTHER INFORMATION: tosyl

<400> SEQUENCE: 115

Lys Phe Asp Gly Arg
1               5
```

```
<210> SEQ ID NO 116
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = t-butyloxycarbonyl
<220> FEATURE:
<221> NAME/KEY: MISC_FEATURE
<222> LOCATION: (2)..(2)
<223> OTHER INFORMATION: tosyl
<220> FEATURE:
<221> NAME/KEY: MISC_FEATURE
<222> LOCATION: (3)..(5)
<223> OTHER INFORMATION: D amino acid
<220> FEATURE:
<221> NAME/KEY: MISC_FEATURE
<222> LOCATION: (3)..(3)
<223> OTHER INFORMATION: Carbobenzyloxy
<220> FEATURE:
<221> NAME/KEY: MISC_FEATURE
<222> LOCATION: (5)..(5)
<223> OTHER INFORMATION: O-benzyl

<400> SEQUENCE: 116

Xaa Arg Lys Phe Asp Gly
1               5

<210> SEQ ID NO 117
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(3)
<223> OTHER INFORMATION: D amino acid

<400> SEQUENCE: 117

Lys Phe Asp Gly Arg
1               5

<210> SEQ ID NO 118
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = t-butyloxycarbonyl
<220> FEATURE:
<221> NAME/KEY: MISC_FEATURE
<222> LOCATION: (3)..(7)
<223> OTHER INFORMATION: cyclic amino acid
<220> FEATURE:
<221> NAME/KEY: MISC_FEATURE
<222> LOCATION: (3)..(5)
<223> OTHER INFORMATION: D amino acid
<220> FEATURE:
<221> NAME/KEY: MISC_FEATURE
<222> LOCATION: (8)..(12)
<223> OTHER INFORMATION: cyclic amino acid
<220> FEATURE:
<221> NAME/KEY: MISC_FEATURE
<222> LOCATION: (8)..(10)
```

```
<223> OTHER INFORMATION: D amino acid

<400> SEQUENCE: 118

Xaa Glu Lys Phe Asp Gly Arg Lys Phe Asp Gly Arg
1               5                   10

<210> SEQ ID NO 119
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(6)
<223> OTHER INFORMATION: cyclic amino acid
<220> FEATURE:
<221> NAME/KEY: MISC_FEATURE
<222> LOCATION: (2)..(4)
<223> OTHER INFORMATION: D amino acid
<220> FEATURE:
<221> NAME/KEY: MISC_FEATURE
<222> LOCATION: (7)..(12)
<223> OTHER INFORMATION: cyclic amino acid
<220> FEATURE:
<221> NAME/KEY: MISC_FEATURE
<222> LOCATION: (8)..(10)
<223> OTHER INFORMATION: D amino acid

<400> SEQUENCE: 119

Glu Lys Phe Asp Gly Arg Lys Phe Asp Gly Arg
1               5                   10

<210> SEQ ID NO 120
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(3)
<223> OTHER INFORMATION: D amino acid
<220> FEATURE:
<221> NAME/KEY: MISC_FEATURE
<222> LOCATION: (2)..(2)
<223> OTHER INFORMATION: Carbobenzyloxy
<220> FEATURE:
<221> NAME/KEY: MISC_FEATURE
<222> LOCATION: (3)..(3)
<223> OTHER INFORMATION: O-benzyl
<220> FEATURE:
<221> NAME/KEY: MISC_FEATURE
<222> LOCATION: (5)..(5)
<223> OTHER INFORMATION: tosyl

<400> SEQUENCE: 120

Phe Lys Asp Gly Arg
1               5

<210> SEQ ID NO 121
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
```

```
<223> OTHER INFORMATION: Xaa = t-butyloxycarbonyl
<220> FEATURE:
<221> NAME/KEY: MISC_FEATURE
<222> LOCATION: (2)..(2)
<223> OTHER INFORMATION: tosyl
<220> FEATURE:
<221> NAME/KEY: MISC_FEATURE
<222> LOCATION: (3)..(5)
<223> OTHER INFORMATION: D amino acid
<220> FEATURE:
<221> NAME/KEY: MISC_FEATURE
<222> LOCATION: (4)..(4)
<223> OTHER INFORMATION: Carbobenzyloxy
<220> FEATURE:
<221> NAME/KEY: MISC_FEATURE
<222> LOCATION: (5)..(5)
<223> OTHER INFORMATION: O-benzyl

<400> SEQUENCE: 121

Xaa Arg Phe Lys Asp Gly
1               5

<210> SEQ ID NO 122
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(3)
<223> OTHER INFORMATION: D amino acid

<400> SEQUENCE: 122

Phe Lys Asp Gly Arg
1               5

<210> SEQ ID NO 123
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
<223> OTHER INFORMATION: a-N-methyl arginine
<220> FEATURE:
<221> NAME/KEY: MISC_FEATURE
<222> LOCATION: (1)..(1)
<223> OTHER INFORMATION: tosyl
<220> FEATURE:
<221> NAME/KEY: MISC_FEATURE
<222> LOCATION: (3)..(3)
<223> OTHER INFORMATION: O-benzyl
<220> FEATURE:
<221> NAME/KEY: MISC_FEATURE
<222> LOCATION: (4)..(4)
<223> OTHER INFORMATION: Xaa = 2-aminothiazole-5-acetic acid or 2-
      aminothiazole-t-acetyl group
<220> FEATURE:
<221> NAME/KEY: MISC_FEATURE
<222> LOCATION: (5)..(5)
<223> OTHER INFORMATION: D amino acid
<220> FEATURE:
<221> NAME/KEY: MISC_FEATURE
<222> LOCATION: (5)..(5)
```

```
<223> OTHER INFORMATION: Carbobenzylxy

<400> SEQUENCE: 123

Arg Gly Asp Xaa Lys
1               5

<210> SEQ ID NO 124
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = t-butyloxycarbonyl
<220> FEATURE:
<221> NAME/KEY: MISC_FEATURE
<222> LOCATION: (2)..(2)
<223> OTHER INFORMATION: O-benzyl
<220> FEATURE:
<221> NAME/KEY: MISC_FEATURE
<222> LOCATION: (3)..(3)
<223> OTHER INFORMATION: Xaa = 2-aminothiazole-5-acetic acid or 2-
      aminothiazole-t-acetyl group
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (4)..(4)
<223> OTHER INFORMATION: Carbobenzyloxy
<220> FEATURE:
<221> NAME/KEY: MISC_FEATURE
<222> LOCATION: (5)..(5)
<223> OTHER INFORMATION: a-N-methyl
<220> FEATURE:
<221> NAME/KEY: MISC_FEATURE
<222> LOCATION: (5)..(5)
<223> OTHER INFORMATION: tosyl

<400> SEQUENCE: 124

Xaa Asp Xaa Lys Arg Gly
1               5

<210> SEQ ID NO 125
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: a-N-methyl
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: Xaa = 2-aminothiazole-5-acetic acid or 2-
      aminothiazole-t-acetyl group
<220> FEATURE:
<221> NAME/KEY: MISC_FEATURE
<222> LOCATION: (5)..(5)
<223> OTHER INFORMATION: D amino acid

<400> SEQUENCE: 125

Arg Gly Asp Xaa Lys
1               5
```

```
<210> SEQ ID NO 126
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
<223> OTHER INFORMATION: Xaa = citrulline
<220> FEATURE:
<221> NAME/KEY: MISC_FEATURE
<222> LOCATION: (3)..(3)
<223> OTHER INFORMATION: t-butyl ester
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (5)..(5)
<223> OTHER INFORMATION: t-butyloxycarbonyl

<400> SEQUENCE: 126

Xaa Gly Asp Phe Lys
1               5

<210> SEQ ID NO 127
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: t-butyl ester
<220> FEATURE:
<221> NAME/KEY: MISC_FEATURE
<222> LOCATION: (2)..(2)
<223> OTHER INFORMATION: D amino acid
<220> FEATURE:
<221> NAME/KEY: MISC_FEATURE
<222> LOCATION: (3)..(3)
<223> OTHER INFORMATION: t-butyloxycarbonyl
<220> FEATURE:
<221> NAME/KEY: MISC_FEATURE
<222> LOCATION: (4)..(4)
<223> OTHER INFORMATION: Xaa = citrulline

<400> SEQUENCE: 127

Asp Phe Lys Xaa Gly
1               5

<210> SEQ ID NO 128
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
<223> OTHER INFORMATION: Xaa = citrulline
<220> FEATURE:
<221> NAME/KEY: MISC_FEATURE
```

```
<222> LOCATION: (4)..(4)
<223> OTHER INFORMATION: D amino acid

<400> SEQUENCE: 128

Xaa Gly Asp Phe Lys
1               5

<210> SEQ ID NO 129
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: 2-(1,4,7,10-tetraaza-4,7,10-tris(t-
      butoxycarbonylmethyl)-1-cyclododecyl)acetyl
<220> FEATURE:
<221> NAME/KEY: MISC_FEATURE
<222> LOCATION: (2)..(6)
<223> OTHER INFORMATION: cyclic amino acid
<220> FEATURE:
<221> NAME/KEY: MISC_FEATURE
<222> LOCATION: (6)..(6)
<223> OTHER INFORMATION: D amino acid
<220> FEATURE:
<221> NAME/KEY: MISC_FEATURE
<222> LOCATION: (7)..(12)
<223> OTHER INFORMATION: cyclic amino acid
<220> FEATURE:
<221> NAME/KEY: MISC_FEATURE
<222> LOCATION: (12)..(12)
<223> OTHER INFORMATION: D amino acid

<400> SEQUENCE: 129

Glu Lys Arg Gly Asp Phe Lys Arg Gly Asp Phe
1               5                   10

<210> SEQ ID NO 130
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(6)
<223> OTHER INFORMATION: cyclic amino acid
<220> FEATURE:
<221> NAME/KEY: MISC_FEATURE
<222> LOCATION: (6)..(6)
<223> OTHER INFORMATION: D amino acid
<220> FEATURE:
<221> NAME/KEY: MISC_FEATURE
<222> LOCATION: (7)..(11)
<223> OTHER INFORMATION: cyclic amino acid
<220> FEATURE:
<221> NAME/KEY: MISC_FEATURE
<222> LOCATION: (11)..(11)
<223> OTHER INFORMATION: D amino acid

<400> SEQUENCE: 130

Glu Lys Arg Gly Asp Phe Lys Arg Gly Asp Phe
1               5                   10

<210> SEQ ID NO 131
<211> LENGTH: 5
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid

<400> SEQUENCE: 131

Arg Gly Asp Phe Lys
1               5

<210> SEQ ID NO 132
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (4)..(4)
<223> OTHER INFORMATION: 3-aminopropyl

<400> SEQUENCE: 132

Arg Gly Asp Tyr Val
1               5

<210> SEQ ID NO 133
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
<223> OTHER INFORMATION: Xaa = ornithine
<220> FEATURE:
<221> NAME/KEY: MISC_FEATURE
<222> LOCATION: (1)..(1)
<223> OTHER INFORMATION: d-N-1-Tos-2-Imadazolinyl
<220> FEATURE:
<221> NAME/KEY: MISC_FEATURE
<222> LOCATION: (3)..(3)
<223> OTHER INFORMATION: O-benzyl
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (4)..(4)
<223> OTHER INFORMATION: N-Carbobenzyloxy-3-aminopropyl

<400> SEQUENCE: 133

Xaa Gly Asp Tyr Val
1               5

<210> SEQ ID NO 134
<211> LENGTH: 6
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = t-butyloxycarbonyl
<220> FEATURE:
<221> NAME/KEY: MISC_FEATURE
<222> LOCATION: (2)..(2)
<223> OTHER INFORMATION: O-benzyl
<220> FEATURE:
<221> NAME/KEY: MISC_FEATURE
<222> LOCATION: (3)..(3)
<223> OTHER INFORMATION: D amino acid
<220> FEATURE:
<221> NAME/KEY: MISC_FEATURE
<222> LOCATION: (3)..(3)
<223> OTHER INFORMATION: N-Carbobenzyloxy-aminopropyl
<220> FEATURE:
<221> NAME/KEY: MISC_FEATURE
<222> LOCATION: (5)..(5)
<223> OTHER INFORMATION: Xaa = ornithine
<220> FEATURE:
<221> NAME/KEY: MISC_FEATURE
<222> LOCATION: (5)..(5)
<223> OTHER INFORMATION: d-N-1-Tos-2-Imadazolinyl

<400> SEQUENCE: 134

Xaa Asp Tyr Val Xaa Gly
 1               5

<210> SEQ ID NO 135
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
<223> OTHER INFORMATION: Xaa = ornithine
<220> FEATURE:
<221> NAME/KEY: MISC_FEATURE
<222> LOCATION: (1)..(1)
<223> OTHER INFORMATION: d-N-2-Imidazolinyl
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (4)..(4)
<223> OTHER INFORMATION: 3-aminopropyl

<400> SEQUENCE: 135

Xaa Gly Asp Tyr Val
 1               5

<210> SEQ ID NO 136
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
```

```
<222> LOCATION: (1)..(1)
<223> OTHER INFORMATION: Tfa
<220> FEATURE:
<221> NAME/KEY: MISC_FEATURE
<222> LOCATION: (3)..(3)
<223> OTHER INFORMATION: O-benzyl
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (4)..(4)
<223> OTHER INFORMATION: N-Carbobenzyloxy-3-aminopropyl

<400> SEQUENCE: 136

Lys Gly Asp Tyr Val
1               5

<210> SEQ ID NO 137
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = t-butyloxycarbonyl
<220> FEATURE:
<221> NAME/KEY: MISC_FEATURE
<222> LOCATION: (2)..(2)
<223> OTHER INFORMATION: O-benzyl
<220> FEATURE:
<221> NAME/KEY: MISC_FEATURE
<222> LOCATION: (3)..(3)
<223> OTHER INFORMATION: D amino acid
<220> FEATURE:
<221> NAME/KEY: MISC_FEATURE
<222> LOCATION: (3)..(3)
<223> OTHER INFORMATION: N-Carbobenzyloxy-aminopropyl
<220> FEATURE:
<221> NAME/KEY: MISC_FEATURE
<222> LOCATION: (5)..(5)
<223> OTHER INFORMATION: Tfa

<400> SEQUENCE: 137

Xaa Asp Tyr Val Lys Gly
1               5

<210> SEQ ID NO 138
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
<223> OTHER INFORMATION: Tfa
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (4)..(4)
<223> OTHER INFORMATION: 3-aminopropyl

<400> SEQUENCE: 138
```

Lys Gly Asp Tyr Val
1               5

<210> SEQ ID NO 139
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
<223> OTHER INFORMATION: 2-N-Tfa-aminoethyl
<220> FEATURE:
<221> NAME/KEY: MISC_FEATURE
<222> LOCATION: (3)..(3)
<223> OTHER INFORMATION: O-benzyl
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (4)..(4)
<223> OTHER INFORMATION: N-Carbobenzyloxy-3-aminopropyl

<400> SEQUENCE: 139

Cys Gly Asp Tyr Val
1               5

<210> SEQ ID NO 140
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = t-butyloxycarbonyl
<220> FEATURE:
<221> NAME/KEY: MISC_FEATURE
<222> LOCATION: (2)..(2)
<223> OTHER INFORMATION: O-benzyl
<220> FEATURE:
<221> NAME/KEY: MISC_FEATURE
<222> LOCATION: (3)..(3)
<223> OTHER INFORMATION: D amino acid
<220> FEATURE:
<221> NAME/KEY: MISC_FEATURE
<222> LOCATION: (3)..(3)
<223> OTHER INFORMATION: N-Carbobenzyloxy-aminopropyl
<220> FEATURE:
<221> NAME/KEY: MISC_FEATURE
<222> LOCATION: (5)..(5)
<223> OTHER INFORMATION: 2-N-Tfa-aminoethyl

<400> SEQUENCE: 140

Xaa Asp Tyr Val Cys Gly
1               5

<210> SEQ ID NO 141
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)

<223> OTHER INFORMATION: cyclic amino acid
<220> FEATURE:
<221> NAME/KEY: MISC_FEATURE
<222> LOCATION: (1)..(1)
<223> OTHER INFORMATION: 2-N-Tfa-aminoethyl
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (4)..(4)
<223> OTHER INFORMATION: 3-aminopropyl

<400> SEQUENCE: 141

Cys Gly Asp Tyr Val
1               5

<210> SEQ ID NO 142
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
<223> OTHER INFORMATION: Homo
<220> FEATURE:
<221> NAME/KEY: MISC_FEATURE
<222> LOCATION: (1)..(1)
<223> OTHER INFORMATION: Tfa
<220> FEATURE:
<221> NAME/KEY: MISC_FEATURE
<222> LOCATION: (3)..(3)
<223> OTHER INFORMATION: O-benzyl
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (4)..(4)
<223> OTHER INFORMATION: N-Carbobenzyloxy-3-aminopropyl

<400> SEQUENCE: 142

Lys Gly Asp Tyr Val
1               5

<210> SEQ ID NO 143
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = t-butyloxycarbonyl
<220> FEATURE:
<221> NAME/KEY: MISC_FEATURE
<222> LOCATION: (2)..(2)
<223> OTHER INFORMATION: O-benzyl
<220> FEATURE:
<221> NAME/KEY: MISC_FEATURE
<222> LOCATION: (3)..(3)
<223> OTHER INFORMATION: D amino acid
<220> FEATURE:
<221> NAME/KEY: MISC_FEATURE
<222> LOCATION: (3)..(3)
<223> OTHER INFORMATION: N-Carbobenzyloxy-aminopropyl

```
<220> FEATURE:
<221> NAME/KEY: MISC_FEATURE
<222> LOCATION: (5)..(5)
<223> OTHER INFORMATION: Homo
<220> FEATURE:
<221> NAME/KEY: MISC_FEATURE
<222> LOCATION: (5)..(5)
<223> OTHER INFORMATION: Tfa

<400> SEQUENCE: 143

Xaa Asp Tyr Val Lys Gly
1               5

<210> SEQ ID NO 144
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Homo
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
<223> OTHER INFORMATION: Tfa
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (4)..(4)
<223> OTHER INFORMATION: 3-aminopropyl

<400> SEQUENCE: 144

Lys Gly Asp Tyr Val
1               5

<210> SEQ ID NO 145
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
<223> OTHER INFORMATION: Homo
<220> FEATURE:
<221> NAME/KEY: MISC_FEATURE
<222> LOCATION: (1)..(1)
<223> OTHER INFORMATION: Tfa
<220> FEATURE:
<221> NAME/KEY: MISC_FEATURE
<222> LOCATION: (3)..(3)
<223> OTHER INFORMATION: O-benzyl
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (4)..(4)
<223> OTHER INFORMATION: N-Carbobenzyloxy-3-aminopropyl
```

```
<400> SEQUENCE: 145

Lys Gly Asp Tyr Val
1               5

<210> SEQ ID NO 146
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
<223> OTHER INFORMATION: Xaa = ornithine
<220> FEATURE:
<221> NAME/KEY: MISC_FEATURE
<222> LOCATION: (1)..(1)
<223> OTHER INFORMATION: d-N-Benzylcarbamoyl
<220> FEATURE:
<221> NAME/KEY: MISC_FEATURE
<222> LOCATION: (3)..(3)
<223> OTHER INFORMATION: O-benzyl
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (4)..(4)
<223> OTHER INFORMATION: N-Carbobenzyloxy-3-aminopropyl

<400> SEQUENCE: 146

Xaa Gly Asp Tyr Val
1               5

<210> SEQ ID NO 147
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = t-butyloxycarbonyl
<220> FEATURE:
<221> NAME/KEY: MISC_FEATURE
<222> LOCATION: (2)..(2)
<223> OTHER INFORMATION: O-benzyl
<220> FEATURE:
<221> NAME/KEY: MISC_FEATURE
<222> LOCATION: (3)..(3)
<223> OTHER INFORMATION: D amino acid
<220> FEATURE:
<221> NAME/KEY: MISC_FEATURE
<222> LOCATION: (3)..(3)
<223> OTHER INFORMATION: N-Carbobenzyloxy-aminopropyl
<220> FEATURE:
<221> NAME/KEY: MISC_FEATURE
<222> LOCATION: (5)..(5)
<223> OTHER INFORMATION: Xaa = ornithine
<220> FEATURE:
<221> NAME/KEY: MISC_FEATURE
<222> LOCATION: (5)..(5)
<223> OTHER INFORMATION: d-N-Benzylcarbamoyl

<400> SEQUENCE: 147

Xaa Asp Tyr Val Xaa Gly
1               5
```

```
<210> SEQ ID NO 148
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
<223> OTHER INFORMATION: Xaa = ornithine
<220> FEATURE:
<221> NAME/KEY: MISC_FEATURE
<222> LOCATION: (1)..(1)
<223> OTHER INFORMATION: d-N-Benzylcarbamoyl
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (5)..(5)
<223> OTHER INFORMATION: 3-aminopropyl

<400> SEQUENCE: 148

Xaa Gly Asp Tyr Val
1               5

<210> SEQ ID NO 149
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
<223> OTHER INFORMATION: Xaa = 2,3-diaminoropionic acid
<220> FEATURE:
<221> NAME/KEY: MISC_FEATURE
<222> LOCATION: (1)..(1)
<223> OTHER INFORMATION: (b-(1-Tos-2-benzimidazolylacetyl))
<220> FEATURE:
<221> NAME/KEY: MISC_FEATURE
<222> LOCATION: (3)..(3)
<223> OTHER INFORMATION: O-benzyl
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (4)..(4)
<223> OTHER INFORMATION: N-Carbobenzyloxy-3-aminopropyl

<400> SEQUENCE: 149

Xaa Gly Asp Tyr Val
1               5

<210> SEQ ID NO 150
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
```

```
<222> LOCATION: (1)..(1)
<223> OTHER INFORMATION: Xaa = t-butyloxycarbonyl
<220> FEATURE:
<221> NAME/KEY: MISC_FEATURE
<222> LOCATION: (2)..(2)
<223> OTHER INFORMATION: O-benzyl
<220> FEATURE:
<221> NAME/KEY: MISC_FEATURE
<222> LOCATION: (3)..(3)
<223> OTHER INFORMATION: D amino acid
<220> FEATURE:
<221> NAME/KEY: MISC_FEATURE
<222> LOCATION: (3)..(3)
<223> OTHER INFORMATION: N-Carbobenzyloxy-aminopropyl
<220> FEATURE:
<221> NAME/KEY: MISC_FEATURE
<222> LOCATION: (5)..(5)
<223> OTHER INFORMATION: Xaa = 2,3-diaminopropionic acid
<220> FEATURE:
<221> NAME/KEY: MISC_FEATURE
<222> LOCATION: (5)..(5)
<223> OTHER INFORMATION: (b-(1-Tos-2-benzimidazolylacetyl))

<400> SEQUENCE: 150

Xaa Asp Tyr Val Xaa Gly
1               5

<210> SEQ ID NO 151
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = 2,3-diaminopropionic acid
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
<223> OTHER INFORMATION: (b-(2-benzimidazolylacetyl))
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (4)..(4)
<223> OTHER INFORMATION: 3-aminopropyl

<400> SEQUENCE: 151

Xaa Gly Asp Tyr Val
1               5

<210> SEQ ID NO 152
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
<223> OTHER INFORMATION: Xaa = ornithine
<220> FEATURE:
<221> NAME/KEY: MISC_FEATURE
<222> LOCATION: (1)..(1)
```

```
<223> OTHER INFORMATION: (d-N-1-Tos-2-Imidazolinyl)
<220> FEATURE:
<221> NAME/KEY: MISC_FEATURE
<222> LOCATION: (3)..(3)
<223> OTHER INFORMATION: O-benzyl
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (5)..(5)
<223> OTHER INFORMATION: Carbobenzyloxy

<400> SEQUENCE: 152

Xaa Gly Asp Phe Lys
1               5

<210> SEQ ID NO 153
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = t-butyloxycarbonyl
<220> FEATURE:
<221> NAME/KEY: MISC_FEATURE
<222> LOCATION: (2)..(2)
<223> OTHER INFORMATION: O-benzyl
<220> FEATURE:
<221> NAME/KEY: MISC_FEATURE
<222> LOCATION: (3)..(3)
<223> OTHER INFORMATION: D amino acid
<220> FEATURE:
<221> NAME/KEY: MISC_FEATURE
<222> LOCATION: (4)..(4)
<223> OTHER INFORMATION: Carbobenzyloxy
<220> FEATURE:
<221> NAME/KEY: MISC_FEATURE
<222> LOCATION: (5)..(5)
<223> OTHER INFORMATION: Xaa = ornithine
<220> FEATURE:
<221> NAME/KEY: MISC_FEATURE
<222> LOCATION: (5)..(5)
<223> OTHER INFORMATION: (d-N-1-Tos-2-Imidazolinyl)

<400> SEQUENCE: 153

Xaa Asp Phe Lys Xaa Gly
1               5

<210> SEQ ID NO 154
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
<223> OTHER INFORMATION: Xaa = ornithine
<220> FEATURE:
<221> NAME/KEY: MISC_FEATURE
<222> LOCATION: (1)..(1)
<223> OTHER INFORMATION: (d-N-2-Imidazolinyl)
<220> FEATURE:
<221> NAME/KEY: MISC_FEATURE
<222> LOCATION: (4)..(4)
<223> OTHER INFORMATION: D amino acid
```

<400> SEQUENCE: 154

Xaa Gly Asp Phe Lys
1               5

<210> SEQ ID NO 155
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
<223> OTHER INFORMATION: Xaa = ornithine
<220> FEATURE:
<221> NAME/KEY: MISC_FEATURE
<222> LOCATION: (1)..(1)
<223> OTHER INFORMATION: (d-N-Benzylcarbamoyl)
<220> FEATURE:
<221> NAME/KEY: MISC_FEATURE
<222> LOCATION: (3)..(3)
<223> OTHER INFORMATION: O-benzyl
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (5)..(5)
<223> OTHER INFORMATION: Carbobenzyloxy

<400> SEQUENCE: 155

Xaa Gly Asp Phe Lys
1               5

<210> SEQ ID NO 156
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = t-butyloxycarbonyl
<220> FEATURE:
<221> NAME/KEY: MISC_FEATURE
<222> LOCATION: (2)..(2)
<223> OTHER INFORMATION: O-benzyl
<220> FEATURE:
<221> NAME/KEY: MISC_FEATURE
<222> LOCATION: (3)..(3)
<223> OTHER INFORMATION: D amino acid
<220> FEATURE:
<221> NAME/KEY: MISC_FEATURE
<222> LOCATION: (4)..(4)
<223> OTHER INFORMATION: Carbobenzyloxy
<220> FEATURE:
<221> NAME/KEY: MISC_FEATURE
<222> LOCATION: (5)..(5)
<223> OTHER INFORMATION: Xaa = ornithine
<220> FEATURE:
<221> NAME/KEY: MISC_FEATURE
<222> LOCATION: (5)..(5)
<223> OTHER INFORMATION: (d-N-Benzylcarbamoyl)

<400> SEQUENCE: 156

Xaa Asp Phe Lys Xaa Gly
1               5

```
<210> SEQ ID NO 157
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
<223> OTHER INFORMATION: Xaa = ornithine
<220> FEATURE:
<221> NAME/KEY: MISC_FEATURE
<222> LOCATION: (1)..(1)
<223> OTHER INFORMATION: (d-N-Benzylcarbamoyl)
<220> FEATURE:
<221> NAME/KEY: MISC_FEATURE
<222> LOCATION: (4)..(4)
<223> OTHER INFORMATION: D amino acid

<400> SEQUENCE: 157

Xaa Gly Asp Phe Lys
1               5

<210> SEQ ID NO 158
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
<223> OTHER INFORMATION: Tfa
<220> FEATURE:
<221> NAME/KEY: MISC_FEATURE
<222> LOCATION: (2)..(4)
<223> OTHER INFORMATION: D amino acid
<220> FEATURE:
<221> NAME/KEY: MISC_FEATURE
<222> LOCATION: (3)..(3)
<223> OTHER INFORMATION: N-Carbobenzyloxy-3-aminopropyl
<220> FEATURE:
<221> NAME/KEY: MISC_FEATURE
<222> LOCATION: (4)..(4)
<223> OTHER INFORMATION: O-benzyl

<400> SEQUENCE: 158

Lys Val Tyr Asp Gly
1               5

<210> SEQ ID NO 159
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = t-butyloxycarbonyl
<220> FEATURE:
<221> NAME/KEY: MISC_FEATURE
<222> LOCATION: (2)..(2)
<223> OTHER INFORMATION: Tfa
<220> FEATURE:
```

```
<221> NAME/KEY: MISC_FEATURE
<222> LOCATION: (3)..(5)
<223> OTHER INFORMATION: D amino acid
<220> FEATURE:
<221> NAME/KEY: MISC_FEATURE
<222> LOCATION: (4)..(4)
<223> OTHER INFORMATION: N-Carbobenzyloxy-aminopropyl
<220> FEATURE:
<221> NAME/KEY: MISC_FEATURE
<222> LOCATION: (5)..(5)
<223> OTHER INFORMATION: O-benzyl

<400> SEQUENCE: 159

Xaa Lys Val Tyr Asp Gly
1               5

<210> SEQ ID NO 160
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (2)..(4)
<223> OTHER INFORMATION: D amino acid
<220> FEATURE:
<221> NAME/KEY: MISC_FEATURE
<222> LOCATION: (3)..(3)
<223> OTHER INFORMATION: 3-aminopropyl

<400> SEQUENCE: 160

Lys Val Tyr Asp Gly
1               5

<210> SEQ ID NO 161
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = ornithine
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
<223> OTHER INFORMATION: (d-N-Benzylcarbamoyl)
<220> FEATURE:
<221> NAME/KEY: MISC_FEATURE
<222> LOCATION: (2)..(4)
<223> OTHER INFORMATION: D amino acid
<220> FEATURE:
<221> NAME/KEY: MISC_FEATURE
<222> LOCATION: (3)..(3)
<223> OTHER INFORMATION: (N-Carbobenzyloxy-3-aminopropyl)
<220> FEATURE:
<221> NAME/KEY: MISC_FEATURE
<222> LOCATION: (4)..(4)
<223> OTHER INFORMATION: O-benzyl

<400> SEQUENCE: 161

Xaa Val Tyr Asp Gly
1               5
```

```
<210> SEQ ID NO 162
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = t-butyloxycarbonyl
<220> FEATURE:
<221> NAME/KEY: MISC_FEATURE
<222> LOCATION: (2)..(2)
<223> OTHER INFORMATION: (d-N-Benzylcarbamoyl)
<220> FEATURE:
<221> NAME/KEY: MISC_FEATURE
<222> LOCATION: (2)..(2)
<223> OTHER INFORMATION: Xaa = ornithine
<220> FEATURE:
<221> NAME/KEY: MISC_FEATURE
<222> LOCATION: (3)..(5)
<223> OTHER INFORMATION: D amino acid
<220> FEATURE:
<221> NAME/KEY: MISC_FEATURE
<222> LOCATION: (4)..(4)
<223> OTHER INFORMATION: (N-Carbobenzyloxy-aminopropyl
<220> FEATURE:
<221> NAME/KEY: MISC_FEATURE
<222> LOCATION: (5)..(5)
<223> OTHER INFORMATION: O-benzyl

<400> SEQUENCE: 162

Xaa Xaa Val Tyr Asp Gly
1               5

<210> SEQ ID NO 163
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
<223> OTHER INFORMATION: Xaa = ornithine
<220> FEATURE:
<221> NAME/KEY: MISC_FEATURE
<222> LOCATION: (1)..(1)
<223> OTHER INFORMATION: (d-N-Benzylcarbamoyl)
<220> FEATURE:
<221> NAME/KEY: MISC_FEATURE
<222> LOCATION: (2)..(4)
<223> OTHER INFORMATION: D amino acid
<220> FEATURE:
<221> NAME/KEY: MISC_FEATURE
<222> LOCATION: (3)..(3)
<223> OTHER INFORMATION: 3-aminopropyl

<400> SEQUENCE: 163

Xaa Val Tyr Asp Gly
1               5

<210> SEQ ID NO 164
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
```

```
<222> LOCATION: (1)..(1)
<223> OTHER INFORMATION: Xaa = ornithine
<220> FEATURE:
<221> NAME/KEY: MISC_FEATURE
<222> LOCATION: (1)..(1)
<223> OTHER INFORMATION: (d-N-1-Tos-2-Imidazolinyl)
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (2)..(4)
<223> OTHER INFORMATION: D amino acid
<220> FEATURE:
<221> NAME/KEY: MISC_FEATURE
<222> LOCATION: (3)..(3)
<223> OTHER INFORMATION: (N-Carbobenzyloxy-3-aminopropyl)
<220> FEATURE:
<221> NAME/KEY: MISC_FEATURE
<222> LOCATION: (4)..(4)
<223> OTHER INFORMATION: O-benzyl

<400> SEQUENCE: 164

Xaa Val Tyr Asp Gly
1               5

<210> SEQ ID NO 165
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = t-butyloxycarbonyl
<220> FEATURE:
<221> NAME/KEY: MISC_FEATURE
<222> LOCATION: (2)..(2)
<223> OTHER INFORMATION: Xaa = ornithine
<220> FEATURE:
<221> NAME/KEY: MISC_FEATURE
<222> LOCATION: (2)..(2)
<223> OTHER INFORMATION: (d-N-1-Tos-2-Imidazolinyl)
<220> FEATURE:
<221> NAME/KEY: MISC_FEATURE
<222> LOCATION: (3)..(5)
<223> OTHER INFORMATION: D amino acid
<220> FEATURE:
<221> NAME/KEY: MISC_FEATURE
<222> LOCATION: (4)..(4)
<223> OTHER INFORMATION: (N-Carbobenzyloxy-aminopropyl)
<220> FEATURE:
<221> NAME/KEY: MISC_FEATURE
<222> LOCATION: (5)..(5)
<223> OTHER INFORMATION: O-benzyl

<400> SEQUENCE: 165

Xaa Xaa Val Tyr Asp Gly
1               5

<210> SEQ ID NO 166
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (1)..(1)
```

```
<223> OTHER INFORMATION: Xaa = ornithine
<220> FEATURE:
<221> NAME/KEY: MISC_FEATURE
<222> LOCATION: (1)..(1)
<223> OTHER INFORMATION: (d-N-2-Imidazolinyl)
<220> FEATURE:
<221> NAME/KEY: MISC_FEATURE
<222> LOCATION: (2)..(4)
<223> OTHER INFORMATION: D amino acid
<220> FEATURE:
<221> NAME/KEY: MISC_FEATURE
<222> LOCATION: (3)..(3)
<223> OTHER INFORMATION: (3-aminopropyl)

<400> SEQUENCE: 166

Xaa Val Tyr Asp Gly
1               5

<210> SEQ ID NO 167
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: (omega-amino-PEG3400-alpha-carbonyl)
<220> FEATURE:
<221> NAME/KEY: MISC_FEATURE
<222> LOCATION: (1)..(5)
<223> OTHER INFORMATION: cyclic amino acid
<220> FEATURE:
<221> NAME/KEY: MISC_FEATURE
<222> LOCATION: (4)..(4)
<223> OTHER INFORMATION: D amino acid

<400> SEQUENCE: 167

Arg Gly Asp Phe Lys
1               5

<210> SEQ ID NO 168
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: (omega-amino-PEG3400-alpha-carbonyl)
<220> FEATURE:
<221> NAME/KEY: MISC_FEATURE
<222> LOCATION: (2)..(6)
<223> OTHER INFORMATION: cyclic amino acid
<220> FEATURE:
<221> NAME/KEY: MISC_FEATURE
<222> LOCATION: (5)..(5)
<223> OTHER INFORMATION: D amino acid

<400> SEQUENCE: 168

Glu Arg Gly Asp Phe Lys
1               5

<210> SEQ ID NO 169
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(6)
```

```
-continued

<223> OTHER INFORMATION: cyclic amino acid
<220> FEATURE:
<221> NAME/KEY: MISC_FEATURE
<222> LOCATION: (5)..(5)
<223> OTHER INFORMATION: D amino acid

<400> SEQUENCE: 169

Glu Arg Gly Asp Phe Lys
1               5
```